US008298545B2

(12) United States Patent
Payne et al.

(10) Patent No.: US 8,298,545 B2
(45) Date of Patent: Oct. 30, 2012

(54) ANTI-AUTOIMMUNE ANTIBODIES FOR TREATMENT OF PEMPHIGUS

(75) Inventors: Aimee S. Payne, Merion Station, PA (US); John R. Stanley, Gladwyne, PA (US); Donald L. Siegel, Lansdale, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 433 days.

(21) Appl. No.: 12/525,269

(22) PCT Filed: Jan. 25, 2008

(86) PCT No.: PCT/US2008/001023
§ 371 (c)(1),
(2), (4) Date: Dec. 2, 2009

(87) PCT Pub. No.: WO2008/097439
PCT Pub. Date: Aug. 14, 2008

(65) Prior Publication Data
US 2010/0135948 A1 Jun. 3, 2010

Related U.S. Application Data

(60) Provisional application No. 60/899,877, filed on Feb. 7, 2007.

(51) Int. Cl.
*A61K 39/00* (2006.01)
(52) U.S. Cl. .................................................. 424/185.1
(58) Field of Classification Search ........................ None
See application file for complete search history.

(56) References Cited

U.S. PATENT DOCUMENTS 5,891,438 A * 4/1999 Silverman .................. 424/185.1
2005/0025760 A1 2/2005 Tsunoda et al.

FOREIGN PATENT DOCUMENTS

WO    WO 2004/035732    *    4/2004

OTHER PUBLICATIONS

Payne, et al., "*Genetic and functional characterization of human pemphigus vulgaris monoclonal autoantibodies isolated by phage display.*" 2005, J Clin Invest 115(4):888-899.

* cited by examiner

*Primary Examiner* — Albert Navarro
(74) *Attorney, Agent, or Firm* — Riverside Law LLP

(57) ABSTRACT

This invention relates to compositions and methods for the use of anti-autoimmune reagents that specifically bind to anti-desmoglein antibodies, which are responsible for both pemphigus vulgaris and pemphigus foliaceus. In addition, the invention relates to methods and compositions for inhibiting the expression or function of a variable region of an anti-desmoglein (anti-Dsg) pathogenic autoantibody.

7 Claims, 48 Drawing Sheets

| Clone | Sequence |
|---|---|
| P4 | ANKTSPFLMWRL |
| P5 | WANKQPTIWRS |
| P7 | YSNKTPHLQWRL |
| P8 | TDKTPFLMWRVH |
| P9 | AKNPPTLMWKHT |
| P10 | QHNKSPNLYWRS |
| P14 | TILTLRH |

Consensus: P-L-WK/R

| Pathogenic | Nonpathogenic |
|---|---|
| YYCAR---GGDYSGWYNFDYWGQ | YYCARDKAAYYESGYYYIGDFWGQ |
| YYCAS-GGVVDFDHWGQ | YYCARGWHRTGFRGYPSHWYFDLWGR |
| YYCVRGPAYYDIDYWGQ | YYCARESFYYGSGTYFDFWGQ |
| YYCAR--DRVEGYVWGGTFDHWGQ | YYCARGYGSGNWDYWGG |
| YYCAR--GGYDGYPWGQ | YYCAKDGITVFGVGDGLDIWGQ |
| | YYCARSFGFGRYEPADDAFDIWGR |
| D/E - - - W | YYCARQGWVIETSGIRASGFDVWGQ |
| | YYCAKDGITVFGVGDGLDIWGQ |
| | YYCAKDGSRVFGVGGGFDFWGQ |

| scFv Name(s) | Desmoglein Specificity | Heavy Chain Identifier | Light Chain Identifier |
|---|---|---|---|
| | | | |
| D(3)4-1, D(3)1a/4a | Dsg-3 | 1a | 4a |
| D(3)4-11, D(3)1b/1 | Dsg-3 | 1b | 1 |
| D(3)4-6, D(3)3-7, D(3)1b/3a, PV4B6 | Dsg-3 | 1b | 3a |
| D(3)4-2, D(3)1b/3b | Dsg-3 | 1b | 3b |
| D(3)4-4, D(3)4-8, D(3)4-9, D(3)4-12, D(3)3-2, D(3)1c/2a | Dsg-3 | 1c | 2a |
| D(3)4-7, D(3)3-4, D(3)2-7, D(3)1d/2c, PV2B7, NP2 | Dsg-3 | 1d | 2c |
| D(3)3-8, D(3)1e/2d | Dsg-3 | 1e | 2d |
| D(3)4-5, D(3)1f/4b | Dsg-3 | 1f | 4b |
| D(3)4-10, D(3)3-6, D(3)3-10, D(3)1f/4c | Dsg-3 | 1f | 4c |
| D(3)3-9, D(3)1h/2b | Dsg-3 | 1g | 2e |
| D(3)3-3, D(3)1h/2b | Dsg-3 | 1h | 2b |
| D(3)2-4, D(3)1i/4d | Dsg-3 | 1i | 4d |
| D(3)3-1, D(3)3a/9 | Dsg-3 | 3a | 9 |
| D(3)3-5, 3b/8 | Dsg-3 | 3b | 8 |
| D(3)4-3, D(3)3-11, D(3)3c/9, PV4B3, P2 | Dsg-3 | 3c | 9 |
| D(3)3-12, D(3)4/30 | Dsg-3 | 4 | 30 |
| | | | |
| D(1)3-6, D(1)5a/22 | Dsg-1 | 5a | 22 |
| D(1)4-3, D(1)5b/16a | Dsg-1 | 5b | 16a |
| D(1)4-4, D(1)6a/16b | Dsg-1 | 6a | 16b |
| D(1)4-6, D(1)6a/17 | Dsg-1 | 6a | 17 |
| D(1)3-1, D(1)6a/19 | Dsg-1 | 6a | 19 |
| D(1)3-4, D(1)6a/21 | Dsg-1 | 6a | 21 |

Figure 14A-2

| scFv Name(s) | Desmoglein Specificity | Heavy Chain Identifier | Light Chain Identifier |
|---|---|---|---|
| D(1)3-7, D(1)6a/23 | Dsg-1 | 6a | 23 |
| D(1)2-2, D(1)6a/24 | Dsg-1 | 6a | 24 |
| D(1)2-4, D(1)6a/26 | Dsg-1 | 6a | 26 |
| D(1)3-2, D(1)2-1, D(1)2-8, D(1)6b/14 | Dsg-1 | 6b | 14 |
| D(1)4-2, D(1)6c/15 | Dsg-1 | 6c | 15 |
| D(1)2-3, D(1)6d/25 | Dsg-1 | 6d | 25 |
| D(1)4-1, D(1)6e/11 | Dsg-1 | 6e | 11 |
| D(1)4-5, D(1)7a/13a | Dsg-1 | 7a | 13a |
| D(1)4-7, D(1)7a/13b | Dsg-1 | 7a | 13b |
| D(1)3-3, D(1)7b/20 | Dsg-1 | 7b | 20 |
| D(1)4-8, D(1)7c/18 | Dsg-1 | 7c | 18 |
| D(1)3-5, D(1)8/12a | Dsg-1 | 8 | 12a |
| D(1)2-5, D(1)8/12c | Dsg-1 | 8 | 12c |
| D(1)2-6, D(1)9/12b | Dsg-1 | 9 | 12b |
| D(1)2-7, D(1)10/27 | Dsg-1 | 10 | 27 |
| D(1)3-8, D(1)11/10, PF3-8 | Dsg-1 | 11 | 10 |
| | | | |
| D(31)4-1, D(31)4-6, D(31)4-8, D(31)2/28, PX4-1 | Dsg-1 and Dsg-3 | 2 | 28 |
| D(31)4-3, D(31)2/29, Px4-3, P1 | Dsg-1 and Dsg-3 | 2 | 29 |
| D(31)4-2, D(31)3-1, D(31)3-7, D(31)12a/5 | Dsg-1 and Dsg-3 | 12a | 5 |
| D(31)4-4, D(31)4-5, D(31)4-7, D(31)3-4, D(31)3-6, D(31)12b/6, PX4-4, NP1 | Dsg-1 and Dsg-3 | 12b | 6 |
| D(31)3-2, D(31)12c/7 | Dsg-1 and Dsg-3 | 12c | 7 |

Figure 14B-1

| Chain Identifier | Nucleotide Sequence | Amino Acid Sequence |
|---|---|---|
| Heavy Chains | | |
| 1a | SEQ ID NO 1 | SEQ ID NO 74 |
| 1b | SEQ ID NO 2 | SEQ ID NO 75 |
| 1c | SEQ ID NO 3 | SEQ ID NO 76 |
| 1d | SEQ ID NO 4 | SEQ ID NO 77 |
| 1e | SEQ ID NO 5 | SEQ ID NO 78 |
| 1f | SEQ ID NO 6 | SEQ ID NO 79 |
| 1g | SEQ ID NO 7 | SEQ ID NO 80 |
| 1h | SEQ ID NO 8 | SEQ ID NO 81 |
| 1i | SEQ ID NO 9 | SEQ ID NO 82 |
| 2 | SEQ ID NO 10 | SEQ ID NO 83 |
| 3a | SEQ ID NO 11 | SEQ ID NO 84 |
| 3b | SEQ ID NO 12 | SEQ ID NO 85 |
| 3c | SEQ ID NO 13 | SEQ ID NO 86 |
| 4 | SEQ ID NO 14 | SEQ ID NO 87 |
| 5a | SEQ ID NO 15 | SEQ ID NO 88 |
| 5b | SEQ ID NO 16 | SEQ ID NO 89 |
| 6a | SEQ ID NO 17 | SEQ ID NO 90 |
| 6b | SEQ ID NO 18 | SEQ ID NO 91 |
| 6c | SEQ ID NO 19 | SEQ ID NO 92 |
| 6d | SEQ ID NO 20 | SEQ ID NO 93 |
| 6e | SEQ ID NO 21 | SEQ ID NO 94 |
| 7a | SEQ ID NO 22 | SEQ ID NO 95 |
| 7b | SEQ ID NO 23 | SEQ ID NO 96 |
| 7c | SEQ ID NO 24 | SEQ ID NO 97 |
| 8 | SEQ ID NO 25 | SEQ ID NO 98 |

Figure 14B-2

| Chain Identifier | Nucleotide Sequence | Amino Acid Sequence |
|---|---|---|
| Heavy Chains | | |
| 9 | SEQ ID NO 26 | SEQ ID NO 99 |
| 10 | SEQ ID NO 27 | SEQ ID NO 100 |
| 11 | SEQ ID NO 28 | SEQ ID NO 101 |
| 12a | SEQ ID NO 29 | SEQ ID NO 102 |
| 12b | SEQ ID NO 30 | SEQ ID NO 103 |
| 12c | SEQ ID NO 31 | SEQ ID NO 104 |
| Light Chains | | |
| 1 | SEQ ID NO 32 | SEQ ID NO 105 |
| 2a | SEQ ID NO 33 | SEQ ID NO 106 |
| 2b | SEQ ID NO 34 | SEQ ID NO 107 |
| 2c | SEQ ID NO 35 | SEQ ID NO 108 |
| 2d | SEQ ID NO 36 | SEQ ID NO 109 |
| 2e | SEQ ID NO 37 | SEQ ID NO 110 |
| 3a | SEQ ID NO 38 | SEQ ID NO 111 |
| 3b | SEQ ID NO 39 | SEQ ID NO 112 |
| 4a | SEQ ID NO 40 | SEQ ID NO 113 |
| 4b | SEQ ID NO 41 | SEQ ID NO 114 |
| 4c | SEQ ID NO 42 | SEQ ID NO 115 |
| 4d | SEQ ID NO 43 | SEQ ID NO 116 |
| 5 | SEQ ID NO 44 | SEQ ID NO 117 |
| 6 | SEQ ID NO 45 | SEQ ID NO 118 |
| 7 | SEQ ID NO 46 | SEQ ID NO 119 |
| 8 | SEQ ID NO 47 | SEQ ID NO 120 |
| 9 | SEQ ID NO 48 | SEQ ID NO 121 |

Figure 14B-3

| Chain Identifier | Nucleotide Sequence | Amino Acid Sequence |
|---|---|---|
| Light Chains | | |
| 10 | SEQ ID NO 49 | SEQ ID NO 122 |
| 11 | SEQ ID NO 50 | SEQ ID NO 123 |
| 12a | SEQ ID NO 51 | SEQ ID NO 124 |
| 12b | SEQ ID NO 52 | SEQ ID NO 125 |
| 12c | SEQ ID NO 53 | SEQ ID NO 126 |
| 13a | SEQ ID NO 54 | SEQ ID NO 127 |
| 13b | SEQ ID NO 55 | SEQ ID NO 128 |
| 14 | SEQ ID NO 56 | SEQ ID NO 129 |
| 15 | SEQ ID NO 57 | SEQ ID NO 130 |
| 16a | SEQ ID NO 58 | SEQ ID NO 131 |
| 16b | SEQ ID NO 59 | SEQ ID NO 132 |
| 17 | SEQ ID NO 60 | SEQ ID NO 133 |
| 18 | SEQ ID NO 61 | SEQ ID NO 134 |
| 19 | SEQ ID NO 62 | SEQ ID NO 135 |
| 20 | SEQ ID NO 63 | SEQ ID NO 136 |
| 21 | SEQ ID NO 64 | SEQ ID NO 137 |
| 22 | SEQ ID NO 65 | SEQ ID NO 138 |
| 23 | SEQ ID NO 66 | SEQ ID NO 139 |
| 24 | SEQ ID NO 67 | SEQ ID NO 140 |
| 25 | SEQ ID NO 68 | SEQ ID NO 141 |
| 26 | SEQ ID NO 69 | SEQ ID NO 142 |
| 27 | SEQ ID NO 70 | SEQ ID NO 143 |
| 28 | SEQ ID NO 71 | SEQ ID NO 144 |
| 29 | SEQ ID NO 72 | SEQ ID NO 145 |
| 30 | SEQ ID NO 73 | SEQ ID NO 146 |

Figure 14C-1

SEQ ID NO 1

CAGGTGCAGCTGGTGCAGTCTGGGGCTGAGATGAAGAAGCCTGGGGTCCTCGGTGAGGGTCTCCTGCAAGGCTTCTGGAGGC
ACCTTCGACACAAACATGTGTCAGTTGGGTGCGACAGGCCCCAGGACGAGGGCTTGAGTGGGATCATCCCTATGC
TTGGTGCTCCACACTACGCACAGAGAAGTTCCAGGGCAGAGTCACGATCACCGCGGACACATCCACGAGCACAGTCTACATGGA
ACTGAGCAGCCTGGGATCTGAGGACACAGCCGTGTATTACTGTGCGAGAGATAAAGCGGCTTACTATGAAAGTGGTTATTACT
ATATCGGTGACTTCTGGGGCCAGGGAACCCTGGTCACCGTCTCCTCAGCCTCCACCAAGGGCCCATCGGTCACTAGTGGCCA
GGC

SEQ ID NO 2

CAGGTGCAGCTGGTGCAGTCTGGGGCTGAGATGAAGAAGCCTGGGGTCCTCGGTGAGGGTCTCCTGCAAGGCTTCTGGAGGC
ACCTTCGACACAAATATGTGTCAGTTGGGTGCGACAGGCCCCAGGACGAGGGCTTGAGTGGGATCATCCCTATGC
TTGGTGCTCCACACTACGCACAGAAGTTCCAGGGCAGAGTCACGATCACCGCGGACACATCCACGAGCACAGTCTACATGGA
ACTGAGCAGCCTGGGATCTGAGGACACAGCCGTGTATTACTGTGCGAGAGATAAAGCGGCTTACTATGAAAGTGGTTATTACT
ATATCGGTGACTTCTGGGGCCAGGGAACCCTGGTCACCGTCTCCTCAGCCTCCACCAAGGGCCCATCGGTCACTAGTGGCCA
GGC

SEQ ID NO 3

CAGGTGCAGCTGGTGCAGTCTGGGGCTGAGATGAAGAAGCCTGGGGTCCTCGGTGAGGGTCTCCTGCAAGGCTTCTGGAGGC
ACCTTCGACACAAACATGTGTCAGTTGGGTGCGACAGGCCCCAGGACGAGGGCTTGAGTGGGATCATCCCTATGC
TTGGTGCTCCACACTACGCACAGAAGTTCCAGGGCAGAGTCACGATCACCGCGGACAAATCCACGAGCACAGTCTACATGGA
ACTGAGCAGCCTGGGATCTGAGGACACAGCCGTGTATTACTGTGCGAGAGATAAAGCGGCTTACTATGAAAGTGGTTATTACT
ATATCGGTGACTTCTGGGGCCAGGGAACCCTGGTCACCGTCTCCTCAGCTTCCACCAAGGGCCCATCGGTCACTAGTGGCCA
GGC

Figure 14C-2

SEQ ID NO 4

CAGGTGCAGCTGGTGCAGTCTGGGGCTGAGATGAAGAAGCCTGGGGCTTCCTCGGTGAGGGTCTCCTGCAAGGCTTCTGGAGGC
ACCTTCGACAAATATGCTGTCAGTTGGGTGCGACAGGCCCCAGGACAGGGCTTGAGTGGGTGGGAGGGATCATCCCTATGC
TTGGTGCTCCACACTACGCACAGAAGTTCCAGGGCAGAGTCACGATCACCGCGGACAAATCCACGAGCACAATCTACATGGAA
CTGAGCAGCCTGAGATCTGAGGACACAGCCGTGTATTACTGTGCGAGAGATAAAGCGGTTACTATGAAGTGGTTATTACTA
TATCGGTGACTTCTGGGGCCAGGGAACCCTGGTCACCGTCTCCTCAGCTTCCACCAAGGGCCCATCGGTCGGTACTGGCCAG
GC

SEQ ID NO 5

CAGGTGCAGCTGGTGCAGTCTGGGGCTGAGATGAAGAAGCCTGGGGCTTCCTCGGTGAGGGTCTCCTGCAAGGCTTCTGGAGGC
ACCTTCGACAAATATGGTGTCAGTTGGGTGCGACAGGCCCCAGGACAAGGGCTTGAGTGGATGGGAGGCATCATCCCTATGC
TTGGTACTCCACACTACGCACAGAAGTTCCAGGGCAGAGTCACGATCACCGCGGACAAATCCACGAGCACAGTCTACATGGAA
CTGAGCAGCCTGGGATCTGAGGACACAGCCGTGTATTACTGTGCGAGAGATAAAGAGGCTTACTACTATGAAGTGGTTATTACTA
TATCGGTGACTTCTGGGGCCAGGGAACCCTGGTCACCGTCTCCTCAGCCTCCACCAAGGGCCCATCGGTCACTAGTGGCCAG
GC

SEQ ID NO 6

GAGGTGCAGCTGGTGCAGTCTGGGGCTGAGATGAAGAAGCCTGGGGCTCCTCGGTGAGGGTCTCCTGCAAGGCTTCTGGAGGC
ACCTTCGACAAATATGCTGTCAGTTGGGTGCGACAGGCCCCAGGACAGGGCTTGAGTGGGTGGGAGGGATCATCCCTATGC
TTGGTGCTCCACACTACGCACAGAAGTTCCAGGGCAGAGTCACGATCACCGCGGACAAATCCACGAGCACAGTCTACATGGA
ACTGAGCAGCCTGGGATCTGAGGACACAGCCGTGTATTACTGGCGGAGAGATAAAGCGGCTTACTACTATGAAAGTGGTTATTACT
ATATCGGTGACTTCTGGGGCCAGGGAACCCTGGGCCAGGGAACCCTCCTCCACCAAGGCCTCCTCCACCAAGGGCCCATCGGTCACTAGTGGCCA
GGC

Figure 14C-3

SEQ ID NO 7

GAGGTGCAGCTGGTGGAGTCTGGGGCTGAGATGAAGAAGCCTGGGGCCTCCGTGAAGGTCTCCTGCAAGGCTTCTGGAGGC
ACCTTCGACAAATATGGTGTCAGTTGGGTGCGACAGGCCCCAGGACAGAGGCTTGAGTGGATGGGAGGGATCATCCCTATGC
TTGGTGCTCCACACTACGCACAGAAGTTCCAGGGCAGAGTCACGGACACGATCACCGCGGACACGAGCACAGTCTATATGGAA
CTGAGCAGCCTGGGATCTGAGGACACAGCCGTGTATTACTGCGCGAGAGATAAAGCGGCTTACTATGAAAGTGGTTATTACTA
TATCGGTGACTTTCTGGGGCCAGGGAACCCTGGTCACCGTCTCCTCAGCCTCCACCAAGGGCCCATCGGTCACTAGTGGCCAG
GC

SEQ ID NO 8

CAGGTGCAGCTGGTGCAGTCTGGGGCTGAGATGAAGAAGCCTGGGGTCCTGGTGAAGGTCTCCTGCAAGGCTTCTGGAGGC
ACCTTCGACAAATATGCTGTCAGTTGGGTGCGACAGGCCCCAANGACAGAGGCTTGAGTGGGAGGGATCATCCCTATGCC
TTGGTGCTCCACACTACGCACAGAAGTTCCAGGGCAGAGTCACGGACACGATCACCGCGGACACAATNTACATGGAA
CTGAGCAGCCTGGGATCTGAGGACACAGCCGTGTATTACTGCGCGAGAGATAAAGCGGCTTACTATGAAAGTGGTTATTACTA
TATCGGTGARTTCTGGGGCCAGGGAACKCTGGTCWCKGTRTCTTCAGCTTCASTARTSGCCAG
GC

SEQ ID NO 9

CAGGTGCAGCTGGTGCAGTCTGGGGCTGAGATGAAGAAGCCTGGGGTCCTCGGTGAGGGTCTCCTGCAAGGCTTCTGGAGGC
ACCTTCGACAAATATGCTGTCAGTTGGGTGCGACAGGCCCCAGGACAGAGGCTTGAGTGGGGGGATCATCCCTCTG
CTTGGTGCTCCACACTACGCACAGAGTCACCCGGACACAATCCACGAGCACAGTCTACATGG
AACTGAGCAGCAGCCTGGGATCTGAGGACAGCCGTGTATTACTGCGCGAGAGATAAAGCGGCTTACTATGAAAGTGGTTATTAC
TATATCGGTGACTTCTGGGGCCAGGGAACCCTCCACCGTCTCCTCAGCCCTCACCGTCACCCAAGGCCCATCGGTCACTAGTGGCC
AGGC

Figure 14C-4

SEQ ID NO 10
CAGGTGCAGCTGGTGCAGTCTGGGGGCTGAAGTGAAGAAGCCTGGGTCCTCGGTGAAGGTCTCCTGTAAGGCTTCTGGAGGC
ACCTTCGGAAACTATGCTATCAATTGGGTGCGACAGGCCCCTGGACAAGGGCTTGAGTGGATGGGAGGGATCATCCCTACAC
TTGATTATTAAACGACGCACAGAACTTCCAGGACAGAGTCACGATTACCGCGACAAATCCACGAACAGTCTACCTGGAG
CTGACCAGTCTGAGATCTGAGGACACGGCCGTGTATTACTGTGCGAGAGGGCGATTACAGTGGCTGGTATAATTTTGACTA
CTGGGGCCAGGGAACCCTGGTCACCGTCTCCTCAGCCTCCACCAAGGGCCCATCGGTCACTAGTGGCCAGGC

SEQ ID NO 11
CAGGTGCAGCTGGTGCAGTCTGGGGGAGGCTTGGTCCAGCCTGGGGGGTCTCTGAGACTCTCCTGTGCAGCCTCCGGATTG
CCGTTTAATAGCTATTGGATGAGCTGGGTCCGCCAGGCTCCCGGGAAGGGGCTGGAGTGGGTGGCCAACATAAACCAAGATG
GCAATGAGAAACACTATGTGGACTCTGTGAAGGGCCGATTCATCATCTCCAGAGACAACACCAACTACTATTTCTGCAAA
TGAACAGCCTGAGAGCCGAGGACACGGCCGTCTACTACTGTGCGAGCGGTGGGTAGTGGACTTTGACCATTGGGGCCAGG
GATCCCTGGTCACCGTCTCCTCAGCCTCCACCAAGGGCCCATCGGTCACTAGTGGCCAGGC

SEQ ID NO 12
GAGGTGCAGCTGGTGGAGTCTGGGGGAGGCTTGGTCCAGCCTGGGGGGTCTCTGAGACTCTCCTGTGCAGCCTCTGGATTG
CCGTTTAGTAGCTCTTGGATGAGCTGGGTCCGCCAGGCTCCCGGGAAGGGGCTGGAGTGGGTGGCCAACATAAACCAAGAT
GGCAATGAGAAACACTATGTGGACTCTGTGAAGGGCCGATTCATCATCTCCAGAGACAACACCAGAACTCACTATTTCTGCAA
ATGAACAGCCTGAGAGCCGAGGACACGGCCGTCTACTACTGTGCGAGCGGTGGGTAGTGGACTTTGACCATTGGGGCCAG
GGAACCCTGGTCACCGTCTCCCCCAGCTTCTCCCCCAGCGGCCCATCGGTCACTAGTGGCCAGGC

SEQ ID NO 13
GAGGTGCAGCTGTTGGAGTCTGGGGGAGGCTTGGTCAACCCTGGGGGGTCCCTGAGACTCTCCTGTGCAGCCTCTGGATTG
CCGTTTAATAGCTATTGGATGAGCTGGGTCCGCCAGGCTCCGCCAGGGCTCCGCCAGGGCTGGAGTGGGTGGCCAACATAAACCAAGATG
GCAATGAGAAACACTATGTGGACTCTGTGAAGGGCCGATTCATCATCTCCAGAGACAACACCAGAATTCACTATTTCTGCAAA
TGAACAGCCTGAGGGCCGAGGACACGGCCGTCTACTACTGTGCGAGCGGTGGGTAGTGGACTTTGACCATTGGGGCCAGG
GAACCCTGGTCACCGTCTCCCCAGCTTCCACCAAGGGCCCATCGGTCACTAGTGGCCAGGC

Figure 14C-5

SEQ ID NO 14

GAGGTGCAGCTGGTGGAGTCTGGGGGAGGCGTGGTCCAGCCTGGGGAGGTCCCTGAGACTTTCCTGTGCAGCCTCTGGATTC
ACCTTCAGTAACTATGCTATGCACTGGGTCCGCCAGGCTCCAGGCAAGGGGCTGGAGTGGGTGGCAGTTATATCATATGATG
GAAGTAATAAATACTACGCAGACTCCGTGAAGGGCCGATTCACCATCTCCAGAGACAATTCCAAGAACACCCTTTATCTGCAAA
TGAACAGCCTGAGAGCCTGAGGACACGGCTGTGTATTACTGTGCGAGAGAAGCTCTGGTCTACTATGATAGTAGTGGTTACTATA
ANGGGGGATTTGACTACTGGGGNCAGGGAACCCTGGTCACCGTCTCCTCAGCTTCCACCAAGGGNCCATCGGTCACTAGTGG
NCAGGC

SEQ ID NO 15

GAGGTGCAGCTGGTGGAGTCTGGGGGAGGCTTGGTCAAGCCTGGAGGGTCCCTGAGACTCTCCTGTGCAGCCTCTGGATTC
ACCTTCAATGACTACTACATGAGCTGGATTCGCCAGGCTCCAGGGAAGGGGCTGGAGTGGGTTTCATACATCAGTAGTAGTGG
TCCTTACACAGACTACGCAAACTCTGTGAAGGGCCGATTCACCATCTCCAGAGACAACGCCAAGAACTCACTGTATCTGCAAAT
GAACAGCCTGAGAGCCGAGGACACGGCTGTGTATTACTGTGCGAGAGAAATGAGTCCAATTACGACAGCAGGTGCCCACACC
TATGAGTGCTGCTGGGGCCAGGGAACCCTGGTCACCGTCTCCTCAGCCTCCACCAAGGGCCCATCGGTCACTAGTGGCCAGGC

SEQ ID NO 16

GAGGTGCAGCTGGTGGAGTCTGGGGGAGGCGTGGTCCAGCCTGGGGAGGTCCCTGAGACTCTCCTGTGCAGCCTCTGGATTC
ACCTTCAATGACTACTACATGAGCTGGATTCGCCAGGCTCCAGGGAAGGGGCTGGAGTGGGTTTCATACATCAGTAGTAGTGG
TCCTTACACAGACTACGCAAACTCTGTGAAGGGCCGATTCACCATCTCCAGAGACAACGCCAAGAACTCACTGTATCTGCAAAT
GAACAGCCTGAGAGCCGAGGACACGGCTGTGTATTACTGTGCGAGAGAAATGAGTCCAATTACGACAGCAGGTGCCCACACC
TATGAGTGCTGCTGGGGCCAGGGAACCCTGGTCACCGTCTCCTCAGCCTCCACCAAGGGCCCATCGGTCACTAGTGGCCAGGC

SEQ ID NO 17

GAGGTGCAGCTGGTGGTGCAGTCTGGGGGAGGCTTGGTCAAGCCTGGAGGGTCCCTGAGACTCTCCTGTGCAGCCTCTACATTCA
CCTTCAATGACGACTATATGAGTTGGATCCGCCAGGCTCCAGGGAAGGGGCTGGAGTGGGTTTCATACATTAGTAGTAGTAGT
AGTTACACACTACGCAGACTCTGTGAAGGGCCGATTCAGCAGACATCCAAGAACTCACTGTTTCTGCAAAT
GAACAGCCTGAGAGCCGAGGACACGGCTGTTTATTACTGTGCGAGAGAACTCAGTCTTTACAGCAGCAACTGCCCACAGCT
ATGACCCTCTGGGGCCAGGGAACCCTGGTCACCGTCTCTTCAGCTTCCACCAAGGGCCCATCGGTCACTAGTGGCCAGGC

Figure 14C-6

SEQ ID NO 18

GAGGTGCAGCTGGTGGAGTCTGGGGGAGGCTTGGTCAAGCCTGGTCGGGGGGTCCCTGAGACTCTCCTGTGCAGCCTCTGGATTC
ACCTTCAATGACGACTATATGAGTTGGATCCGCCAGGCTCCAGGGAAGGGGCTGGAGTGGGTTTCATACAACTAGTAGTAG
TAGTTACACACATACGCAGACTCTGTGAAGGGCCGATTCAGCATCTCCAGAGACAACGCCAAGAACTCACTGTTTCTGCAAAT
GAACAGCCTGAGAGCCGAGGACACGGCTGTTTATTACTGTGCGAGAGAACTCAGTCCTTTACAGCAGCAACTGCCCACAGCT
ATGACCTCTCTGGGGCCAGGGAACCCTGGTCACCGTCTCTTCAGCTCTTCCACCAAGGGCCCATCGGTCACTAGTGGCCAGGC

SEQ ID NO 19

CAGGTGCAGCTGGTGCAGTCTGGGGGAGGCCTGGTCAAGCCTGGACGGGTCCCTGAGACTCTCCTGTGCAGCCTCTACATTCA
CCTTCAATGACGACTATATGAGTTGGATCCGCCAGGCTCCAGGGAAGGGCTGGAGTGGGTTTCATACATTAGTAGTAGTAGT
AGTTACACACTACGCAGACTCTGTGAAGGGCCGATTCAGCATCAGAGAACAACTCACTGTTTCTGCAAAT
GAACAGCCTGAGAGCCGAGGACACGGCTGTCCTTTTACAGCAGCAACTGCCCACAGCT
ATGACCTCTCTGGGGCCAGGGAACCCTGGTCACCGTCTCCTCAGCTCTTCCACCAAGGGCCCATCGGTCACTAGTGGCCAGGC

SEQ ID NO 20

GAGGTGCAGCTGGTGGAGTCTGGGGGAGGCTTGGTCAAGCCTGGACGGGTCCCTGAGACTCTCCTGTGCAGCCTCTACATTCA
CCTTCAATGACGACTATATGAGTTGGATTGGATCCGCCAGGCTCCAGGGAAGGGGCTGGAGTGGGTTTCATACATTAGTAGTAGT
AGTTACACACTACGCAGACTCTGTGAAGGGCCGTGTTTATTACTGTGCGAGAGAACTCAGTCCTTTTACAGCAGCAACTGCCCACAGCT
GAGCAGCCTGAGAGCCGAGGACACGGCTGTGTTTATTACTGTGCGAGAGAACTCAGTCCTTTTACAGCAGCAACTGCCCACAGCT
ATGACCTCTCTGGGGCCAGGGAACCCTGGTCACCGTCTCTTCAGCTCTTCCACCAAGGGCCCATCGGTCACTAGTGGCCAGGC

SEQ ID NO 21

GAGGTGCAGCTGGTGGAGTCTGGGGGAGGCTTGGTCAAGCCTGGACGGGTCCCTGAGACTCTCCTGTGCAGCCTCTACATTCA
CCTTCAATGACGACTATATGAGTTGGATCCGCCAGGCTCCAGGGAAGGGGCTGGAGTGGGTTTCATACATTAGTAGTAGTAGT
AGTTACACACTACGCAGACTCTGTGAAGGGCCGATTCAGCATCTCCAGAGAACAACGCCAAGAACTCACTGTTTCTGCAAAT
GAACAGCCTGAGAGCCGAGGACACGGCTGTGTTTATTACTGTGCGAGAGAACTCAGTCCTTTTACAGCAGCAACTGCCCACAGCT
ATGACCTCTCTGGGGCCAGGGAACCCTGGTCACCGTCTCTTCAGCTCTTCCACCAAGGGCCCATCGGTCACTAGTGGCCAGGC

Figure 14C-7

SEQ ID NO 22

CAGATCACCTTGAAGGAGTCTGGGGAGGCTTGGTCAAGCCTCCAGCCTCTGTGGAGAGTCCCTGAGACTCTCCTGTGCAGCCTCTGATTTCA
CCTTCAGTGACTACTACATGAGCTGGATCCGCCAGCCTCCAGGGAAGGGGCTGGAGTGGGTTCATACATTAGTAGTAGTGGT
CGTTACACACTACGCAGACTCTGTGAAGGGCCGATTCACCATCTCCAGAGACAACGCCAAGAACTCTGTTTCTGCAAAT
GAACAGCCTGAGAGCCGAGGACACGGCTGTCTATTACTGTGCGAGAGAACTCAGTCCTCTTACAGCAGGTGCTGCCCACACC
TTGGACTACTGGGGCCAGGGAACCCTGGTCACCGTCTCCTCAGCCTCCACCAAGGGCCCATCGGTCACTAGTGGCCAGGC

SEQ ID NO 23

GAGGTGCAGCTGGTGCAGTCTGGGGGCGGCTTGGTCAAGCCTGGAGAGTCCCTGAGACTCTCCTGTGCAGCCTCTGATTTCA
CCTTCGGGGACTACTACATGAGCTGGATCCGCCAGCCTCCAGGGAAGGGGCTGGAGTGGATTCATACATCAGTAGTAGTAG
TCGTTACACAAACTACGCAGACTCTGTGAAGGGCCGATTCACCATCTCCAGAGACAACGCCAAGAATTCTTGTATCTGCAAAT
GAACAGCCTGAGAGCCTGAGGACACGGCTGTCTATTACTGTGCGAGAGAACTCAGTCCTCTTACAGCAGGTGCTGCCCACACC
TTGGACTACTGGGGCCAGGGAACCCTGGTCACCGTCTCCTCAGCCTCCACCAAGGGCCCATCGGTCACTAGTGGCCAGGC

SEQ ID NO 24

GAGGTGCAGCTGGTGGAGTCTGGGGGAGGCTTGGTCAAGCCTCCAGGGTCCCTGAGACTCTCCTGTGCAGCCTCTGATTTCA
CCTTCAGTGACTACTACATGAGCTGGATCCGCCAGCCTCCAGGGAAGGGGCTGGAGTGGATTTCATACATTAGTAGTAATAGT
CGTTTCAGAAACTACGCAGACTCTGTGAAGGGCCGATTCACCATCTCTGTATCTGCAAAT
GAACAGCCTGAGAGCCGAGGACACGGCTGTCTATTACTGTGCGAAAGAACTCAGTCCTCTTACAGCAGGTGCTGCCCACACC
TTGGACTACTGGGGCCAGGGAACCCTGGTCACCGTCTCCTCAGCCTCCACCAAGGGCCCATCGGTCACTAGTGGCCAGGC

SEQ ID NO 25

CAGGTGCAGCTGGTGCAGTCTGGGGGAGGCTTGGTCAAGCCTGGAGGGTCCCTGAGACTCTCCTGTGCAGCCTCTGATTCA
CCTTCAGTGACTACTACATGAACTGGATCCGCCAGCCTCCAGGGAAGGGGCTGGAGTGGATTTCATACATTAGTAGTAGTAGT
TCTTACACTTACTACGCAGACTCTGTGAAGGGCCGATTCACCATCTCCAGAGACAACGCCAAGAACTCACTATATCTGCAAATG
AGCAGCCTGAGAGCCGACGACACGGCTGTTTATTACTGTGCGAGAGAACTCAGTCCTATTACAGCAGGAGATGCCCACACCTT
TGACTCCTGGGGCCAGGGAACCCTGGTCACCGTCTCCTCAGCCTCCACCAAGGGCCCATCGGTCACTAGTGGCCAGGC

Figure 14C-8

SEQ ID NO 26
GAGGTGCAGCTGGTGCAGTCTGGGGGAGGCTTGGTCAAGCCTGGAGGGTCCCTGAGACTCTCCTGTGCAGCCTCTGAATTCA
CCTTCAGTGACTACTACATGTCCTGGATCCGCCAGGCTCCAGGGAAGGGGCTGGAGTGGGTTTCTTACATTAGTAGTAATGGT
CGTTACAGACACTACGCAGACTCTGTGAAGGGCCGATTCACCATCTCCAGAGACAACGCCAAGAACTCACTGTATCTCCAAAT
GAACAGCCTGAGAGCCGAGGACACGGCGGTGTCTATTACTGTGCGAGAGAACTCAGTCAGTTACATCAGCAGATGCCCACACCT
ATGACTACTATTGGGGCCAGGGAACCCTGGTCACCGTCTCCTCAGCCTCCACCAAGGGCCCATCGGTCACTAGTGGCCAGGC

SEQ ID NO 27
GAGGTGCAGCTGGTGGAGTCTGGGGGAGGCTTGGTCAAGCCTGGAGAGTCCCTGCGACTCTCCTGTACAGCCTCTGAATTCA
CCTTCAGTGACTACTACATGAGCTGGATCCGCCAGGCTCCAGGGAAGGGGCTGGAGTGGGTTTCATCATTAGTAGTAGTAGT
CGTTACACACACTACGGAGACTCTGTGAAGGGCCGATTCACCATCTCCAGAGACAACGCCAAAAACTCACTGTATCTGCAAAT
GAACAGCCTGAGAACCGAGGACACGGCTGTCTATTACTGTGCGAGAGAACTCAGTCCTCTTACATCAGCAGGTGCCCACACCT
ATGACTACTGGGGCCAGGGAACCCTGGTCACCGTCTCCTCAGCTTCCACCAAGGGCCCATCGGTCACTAGTGGCCAGGC

SEQ ID NO 28
CAGGTGCAGCTGCAGGAGTCGGGCCCAGGACTGGTGAAGCCTTCGGAGACCCTGTCCCTCACCTGCAGTGTCTCTGGTTACC
CCATCAGCAGTAGTTACTACAATTCGTCCGGCTGGATCCGGCAGCCCCCAGGGAAGGGCAGCTGGAGTATCATCATAG
TGGGAGCACCTACTACAATCCGTCCCTCAAGAGTCGAGTTGACACGTCTAAAAATCAGTTCTCCTGAAGGT
GAGCTCTGTGACCGCCGCAGACACGGCCGTTTATTACTGTGCGAGGACCACTACGGCTACTGGTACTTTGATCTCTGGGGC
CGTGGCACCCTGGTCACTGTCTCCTCAGCTTCCACCAAGGGCCCATCGGTCACTAGTGGCCAGGC

SEQ ID NO 29
GAGGTGCAGCTGTTGGAGTCTGGGCCAGGACTGGTGAAGCCTTCGGGGACCCTGTCCCTCACCTGTGGTGTCTCTGGTGGC
TCCATCAGCACTAATCACTGGTGGACTTGGGTCCGCCAGCCCCCAGGGAAGGGACTGGAGTGGATTGGGGAAATCCATCATA
ATGGGAGCACCTTCTTCAACCCGTCCCTCAAGAGTCGAGTCGATATTCAGTGGACAAGTCCAACAACCAGTTCTCCCTGAAA
CTGACCTCTCTGACCGCCGCGGACACGGCCGTGTATTTCTGTGCGAGAGGGTGGCACCGGACTGGATTTCGTGGCTACCCTT
CCCACTACTTCACTTCGATCTCTGGGGCCGTGGGACCCTGGTCACCGTCTCCTCAGCTTCCTCCACCAAGGGCCCATCGGTCACTAG
TGGCCAGGC

Figure 14C-9

SEQ ID NO 30

CAGGTGCAGCTGCAGGAGTCGGGCCCAGGACTGGGGAAGCCTTCGGGGACCCTGTCCCTCACCTGCGGTGTCTCTGGTGGC
TCCATTAGCAGTAATCACTGGTGGACTTGGGTCCGCCAGCCCCCAGGGAAGGGGCTGGAGTGGATTGGAGAAATCTATCATA
ATGGGAGCACCTTCCTCAACCCGTCCCTCAAGAGTCGAGTCACCATTTCAGTAGACAAGTCCAACAACCAGTTCTCCCTGAAA
CTGACTTCTGTGACCGCCGCGGACACGGCCGTGTATTACTGTGCGAGAGGGTGGCACCGGACTGGATTTCGTGGCTACCCTT
CCCACTGGTACTTCGATCTCTGGGGCCGTGGCACCCTGGTCACCGTCTCCTCAGCCTCCACCAAGGGCCCATCGGTCACTAG
TGGCCAGGC

SEQ ID NO 31

CAGGTGCAGCTGCAGGAGTCGGGCCCAGGACTGGTGAAGCCTTCGGGGACCCTGTCCCTCACCTGTGGTGTCTCTGGTGGC
TCCATCAGCAGTAATCACTGGTGGACTTGGGTCCGCCAGCCCCCAGGGCAGGGGCTGGAGTGGATTGGGGAAGTCCATCATA
ATGGGAGCACCTTCTCAACCCGTCCTCAAGAGTGAGTCACCATTCAGTGACAAGTCCAACAACCAGTTCTCCCTGAAAC
TGACCTCTGTGACCGCCGCGGACACGGCCGTGTATTTCTGTGCGACTGGTGGCACCCTGGTCACTGTCTCCTCAGCCTCCACCAAGGGCCCATCGGTCACTAGT
CCACTGGTACTTCGATCTCTGGGGCCGTGGCACCCTGGTCACTGTCTCCTCAGCCTCCACCAAGGGCCCATCGGTCACTAGT
GGCCAGGC

SEQ ID NO 32

CGGCCGAGCTCGTGCTGACGCAGCCGCCNTCAGCGTCTGAGACGTCTACCAGCAGGTCACCATCTCCTGTTCTGGAAGCA
GCTCCAACATCGCAGTTAATACTGTGTACTGGTACCAGCAGCTCCCAGGAGCAGGCCCCCCAAGCTCCTCATCTATTACAATGAT
CAGCGGCCCTCAGGGGTCCCTGACCGATTCTCTGGCTCCAAGTCTGGCACGTCAGCCTCCCTCGTCCATCAGTGGGCTCCGGT
CCGAGGATGAGGGTGATTATTACTGTTCAGCATGTGGGATGCCAGTCTGTTGGGTGTTCGGCGGAGGCACCAAGCTGACCGT
CCTAGGC

Figure 14C-10

SEQ ID NO 33

CGGCCGAGCTCGTGCTGACTCAGCCACCCTCAGTGTCTGAGACCCGGGCAGAGGGTCACCATCTCCTGTTCTGGAAGCAG
CTCCAACATCGCAGGTAATACTGTGTACTGGTACCAGCAACTCCCAGGAGCGGCCCCCAAGCTCCTCATCTATTACAATGATC
AGCGGCCCTCAGGGGTCCCTGACCGATTCTCTGGCTCCAAGTCTGGCACCTCCTCCTGGCCATCAGTGGGCTCCAGTC
TGAGGATGAGGCTTATTATTACTGTGCAACATGGGATGAAGATGTGAATGGTTGGGTGTTCGGCGGAGGCACCAAGCTGACC
GTCCTAGGC

SEQ ID NO 34

GTGCCCCCAGGCCAGGCCGAGCTTCGTGCTGATTTCAGCCCACCTTCAGGGTCTGAGACCCCCGGCCAGAGGGTCACCAT
CTCCTGTTGCGGAAGCAGAGCTCCAACATGCAGTCCAACATCTGTACTGGTACCAGCAGATCCCAGGGCCCCCCAAGC
TCCTCATCTATTACAATGATCAGCGGCCCTCAGGGTCCCTGACCGATTCTCTGGCTCCAAGTCTGGCACCTCCTCCTTG
GCCATCAGTGGGCTCCAGTCTGAGGATGAGGCTTATTATTACTGTGCAACATGGGATGAAGATGTGAATGGTTGGGTGTTCGG
CGGAGGGACCAAGCTGACCGTCCTAGGC

SEQ ID NO 35

CGGCCGAGCTCGTGCTGACTCAGCCACCTTCAGCGTCTGAGACCCGGGCAGAGGGTCACCATCTCCTGTTCTGGAAGCAG
CTCCAACATCGTAGGTAATACTGTGTACTGGTACCAGCAGCTCCCAAGTCTGGCCACCTCCTCCTCATCTATTACAATGATC
AGCGGCCCTCAGGGTCCCTGACCGATTCTCTGGCTCCAAGTCTGGCCATCAGTCAGTGGGCTCCAGTC
TGAGGATGAGGCTTATTATTACTGTGCAACATGGGATGAAGATGTGAATGGTTGGGTGTTCGGCGGAGGGACCAAGCTGACC
GTCCTAGGC

SEQ ID NO 36

CGGCCGAGCTCGTGGTGACGCAGCCGCCNCTCAGTGTCTGCGNCCCAGGACAGAAGGTCACCATCTCCTGTTCTGGAAGCA
GCTCCAACATCGCAGGTAATACTGTGTACCAGCAGCTCCCAAGTCTCCAAGTCTGGCTCCAAGTCTCCTATTACAATGAT
CAGCGGCCCTCAGGGTCCCTGACCGATTCTCTGGCTCCAAGTCTGGCCACCTCCTCCTTGGCCATCAGTGGGCTCCAGT
CTGAGGATGAGGCTTATTATTACTGTGCAACATGGGATGAAGATGTGAATGGTTGGGTGTTCGGCGGGAGGCACCAAGCTGACC
GTCCTAGGT

Figure 14C-11

SEQ ID NO 37
CGGCCGAGCTCGAGCTGACTCAGCCACCCTCAGTGTCTGGGACCCCCGGGCAGAGGGTCACCATCTCCTGTTCTGGAAGCA
GCTCCAACATCGCAGGTAATACTGTGTACTGGTACCAACAGCTCCAAGTCTCCTCATCTATTACAATGAT
CAGCGGCCCTCAGGGGTCCCTGACCGATTCTCTGGCTCCAAGTCTGGCACCTCCTGCCTCCTTGACCATCAGTGGGCTCCAGT
CTGAGGATGAGGCTTATTATTACTGTGCAACATGGGATGTGAATGGTGTTCGGCGGAGGCACCAAGCTGACC
GTCCTAGGT

SEQ ID NO 38
CGGCCGAGCTCATGCTGACTCAGCCCCACTCAGCGTCTGAGACCCCGGGCAGAGGGTCACCATCTCCTGTTCTGGAAGCAG
CTCCAACATCGCAGGTAATACTGTGTACTGGTACCAGCAGCTCCAAGTCTCCTCATCTATTACAATGATC
AGCGGCCCTCAGGGGTCCCTGACCGATTCTCTGGCTCCAAGTCTGGCACCTCCTGCCTCCAGTC
TGAGGATGAGGCTTATTATTACTGTGCAACATGGGATGAATGGTTGGGTGTTCGGCGGAGGACCGAGCTGACC
GTCCTCGGT

SEQ ID NO 39
CGGCCGAGCTCGTGCTGACTCAGCCACCTTCAGCGTCTGAGACCCCGGGCAGAGGGTCACCATCTCCTGTTCTGGAAGCAG
CTCCAACATCGCAGGTAATACTGTGTACCAGCAGCTCCAAGCAATTCCAGGAGCAATGTACCAAGTCTCCTCATCTATTATAATGATCA
GCGGCCCTCAGGGGTCCCTGACCGATTCTCTGGCTCCACCTCCTCCTTGGCCATCAGTGGTCCAGTCT
GAGGATGAGGCTTATTATTACTGTGCAACATGGGATGAAGATGTTGGGTGTTCGGCGGAGGCACCGAGCTGACCG
TCCTCGGT

SEQ ID NO 40
CGGCCGAGCTCGTGCTGACTCAATCGCCCTCAGCGTCTGAGACCCCGGGCAGAGGGTCACCATCTCCTGTTCTGGAAGCAG
CTCCAACATCGCAGGTAACACTGTGTACTGGTACCAGCAGTTCCAGGAGCAGTCCAAGTCTCCTCATTACAATGATC
AGCGGCCCTCAGGGGTCCCTGACCGATTCTCTGGCTCCAAGTCTGGCCATCAGTGGGCTCCAGTC
TGAGGATGAGGCTTATTATTACTGTGCAACATGGGATGAAGATGTGAATGGTTGGGTGTTCGGCGGAGGCACCAAGGTGACC
GTCCTAGGT

Figure 14C-12

SEQ ID NO 41

CGGCCGAGCTCATGCTGACTCAGCCCCACTCAGCGTCTGGGACCCCGGGCAGAGGGTCACCATCTCTTGTTCTGGAAGCAG
CTCCAACATCGCAGGTAATACTGTGTACTGGTACCAGCAATTCCCAGGAGCGGCCCCAAGCTCCTCCTCATCTATTATGATCA
GGGCCCTCAGGGGTCCCTGACCGATTCTCTGGCTCCAAGTCTGGCACCTCACCTCCTGGCCATCAGTGGGCTCCAGTCT
GAGGATGAGGCTTATTATTACTGTGCAACATGGGATGAAGATGTGAATGGTTCGGCGTGTTCGGCGGAGGCACCAAGGTGACCG
TCCTAGGT

SEQ ID NO 42

CGGCCGAGCTCATGCTGACTCAGCCCCACTCAGCGTCTGAGACCCCGGGCAGAGGGTCACCATCTCTTGTTCTGGAAGCAG
CTCCAACATCGCAGGTAATACTGTGTACTGGTACCAGCAATTCCCAGGAGCGGCCCCAAGCTCCTCCTCATCTATTATGATCA
GGGCCCTCAGGGGTCCCTGACCGATTCTCTGGCTCCAAGTCTGGCACCTCACCTCCTGGCCATCAGTGGGCTCCAGTCT
GAGGATGAGGCTTATTATTACTGTGCAACATGGGATGAAGATGTGAATGGTTCGGCGTGTTCGGCGGAGGCACCAAGGTGACCG
TCCTAGGT

SEQ ID NO 43

GCGGCCGAGCTCGTGCTGACTCAATCGCCCTCAGCGTCTGAGACCCGGGCAGAGGGTCACCATCTCCTGTTCTGGAAGCAGCT
CCAACATCGCAGGTAATACTGTATACTGGTACCAGCAGCAGCTCCCAAGTCTCCTCATCTATTACAATGATCAG
CGGCCCTCAGGGGTCCCTGACCGATTCTCTGGCTCCAAGTCTGGCACCTCACCTCCTGGCCATCAGTGGGCTCCAGTCTG
AGGATGAGGCTTATTATTACTGTGCGACATGAAGATGTGAATGGTTCGGCGGAGGGACCAAGGTGACCGT
CCTAGGC

SEQ ID NO 44

CGGCCGAGCTCGTGTTGACGCAGCCGCCCTCAGTGTCTGGGACCCCAGGACAGAGGGTCACCATCTCTTGTTCTGGAAGCA
GCTCCCACATCGAAATAATTATGTATACCAGCATCTCCCAGGAACGGCCCCAAACTCCTCATCTACAGTAATGATC
AGCGGCCCTCAGGGGTCCTGCCGATTCTCTGCCTCCAAGTCTGCCACCTCAGCCATCAGTGGGCTCCGGTCCGGTC
CGAGGATGAGGCTGATTATTACTGTGCAGCCATGGGATGACAGCCAGGGAGTGTTCGGCGGAGGGACCAAGGTGACCGT
CCTAGGT

Figure 14C-13

SEQ ID NO 45

CGGCCGAGCTCGTGCTGACTCAGCCACCTTCAGTGTCTGGGACTCTGGACAGTGTCACCATCTCTTGTTCTGGAAGCAG
CTCCCACATCGGAAGTAATTATGTGTACTGGTACCAGCAGCTCCCAGGAACGGCCCCCAAAATCCTCATCTACAGTAATGATCA
GCGGCCCGCAGGGGTCCCTGACCGATTCTCTGCCTCCAAGTCTGGCACCTCAGCTCTCCTGGCCCATCAGTGGGCTCCGGTC
CGAGGATGAGGCTGATTATTACTGTGTGCAGCATGGGACATGGGACGGGAGCCAGGGGGGCTTCGGCGGAGGGACCAAGCTGACCGT
CCTAGGC

SEQ ID NO 46

CGGCCGAGCTCGTGCTGACTCAGCCACNTTCAGCGTTCTGGGACCAGAGGGTCACCATCTCTTGTTCTGGAAGCA
GCTCCCACATCGGAAAGAATTATGTATACTGGTACCAACATCTCCCAGGAGCGGCCCCAAACTCCTCATCTTCAGTAATGATC
AGCGGCCCCTCAGGGGTCCCTGACCGATTCTCTGGCTCCAAGTCTGCACCTCCCTGGCCCATCAGTGGGCTCCGGTC
CGAGGATGAGGCTGATTATTACTGTGCAGTATGGGATGACAGCCAGGGGGGTGTTCGGCGGAGGGACCAAGCTGACCGT
CCTAGGT

SEQ ID NO 47

CGGCCGAGCTCGAGCTGACTCAGCCACCCTCAGTGTCTGGGGTCTCCTGGACAGTCGATCACCATCTCCTGCACTGGAAGCAG
CAGTTATATGTTGGAATTTTAACCTTGTCTCCTGGTACCAACAACCCAGGCAACACGGCCCTCCCTGACAATCTCTGGCCTCCAG
ATAAGCGGCCCTCAAACATTCTAATCATTCGCTTCTCTGGCTTCGGCAACACGGCCTCCCTGACAATCTCTGGCCTCCAG
GCTGACGACGAGGCTGATTATTACTGCTACTCATATGTCGCTGGTAGTGTCGCTGGTAGTGATCTTTGGGTGTTCGGGGGAGGCACCAAGCTGAC
CGTCCTAGGC

SEQ ID NO 48

CGGCCGAGCTCGAGCTGACTCAGCCACCCTCAGTGTCTGGGGTCTCCTGGACAGTCGATCACCATCTCCTGCACTGGAAGCAG
CAGTTATATGTTGGAATTTTAACCTTGTCTCCTGGTACCAACAACCCAGGCAACACGGCCCTCCCTGACAATCTCTGGCCTCCAG
ATAAGCGGCCCTCAAACATTCTAATCATTCGCTTCTCTGGCTTCGGCAACACGGCCTCCCTGACAATCTCTGGCCTCCAG
GCTGACGACGAGGCTGATTATTACTGCTACTCATATGTCGCTGGTAGTGATCTTTGGGTGTTCGGGGGAGGCACCAAGCTGAC
CGTCCTAGGC

Figure 14C-14

SEQ ID NO 49

CGGCCGAGCTCGCCCTGACTCAGCCTCCCTCCGTGTCTGGGTCTCCTGGACAGTCGATCACCATCTCCTGCACTGGATTCAG
CAGTGATCTTTCCTGGTACCAACAGGCACCCAAAGCCCCAAACTCATGATTTATGATGTCAATAATCGGCCCTCAGGGG
TTTCTGATCGGTTCTCTGGCTCCAAGTCTGGCAACAGCGACACTTCCCTGATGTTCGGGCGGAGGACCGAGCTGACCGTCCTCGGC

SEQ ID NO 50

CGGCCGAGCTCGCCCTGACTCAGCCTCCCTCCGTGTCTGGGTCTCCTGGACAGTCGATCACCATCTCCTGCACTGGATTCAG
CAGTGATCTTTCCTGGTACCAACAGCACCCAAAGCCCCAAACTCATGATTTATGATGTCAATAATCGGCCCTCAGGGG
TTTCTGATCGGTTCTCTGGCTCCAAGTCTGGCAACAGCAGCACTTCCCTGATGTTCGGGCGGAGGACCGAGCTGACCGTCCTCGGC
TTATTACTGCAGCTCATATACAAGCAGCACTTCCCTGATGTTCGGGCGGAGGACCGAGCTGACCGTCCTCGGC

SEQ ID NO 51

CGGCCGAGCTCGGGGTGACGCAGCCGCCNTCGGGTGTCAGTGNCCCAGGACAGAGACGNCCACGATTACCTGTGGGGGAANC
AACATNGGAAGTAAAGTGTGAACTGGTACCAGCAGAAGCCAGGCCAGGCCCCTGTCGTTGCTGCTCTATCATGATAGCGAAT
GGCCCTCAGGGATCCCTGAGCGATTCTCTGGCTCCAACTCTGGGAACACGGCCACCCTGACCATCAGCAGGGTCGAAGCCG
GGGATGAGGCCGACTATTACTGTCAGGTGTGGGATAGTGATAATGTGATATTCGGCGGAGGCACCGAGCTGACCGT
CCTCGGC

SEQ ID NO 52

CGGCCGAGCTCATGCTGACTCAGCCCCCACTCGGTGTCAGTGNCCCAGGACAGAGACGNCCACGATTACCTGTGGGGGAAACA
ACATNGGAAGTAAAGTGTGAACTGGTACCAGCAGAAGCCAGGCCAGGCCCCTGTCGTTCGTCTATCATGATAGCGAATG
GCCCTCAGGGATCCCTGAGCGATTCTCTGGCTCCAACTCTGGGAACACGGCCACCCTGACCATCAGCAGGGTCGAAGCCGG
GGATGAGGCCGACTATTACTGTCAGGTGTGGGATAGTGATAATGTGATATTCGGCGGAGGCACCGAGCTGACCGTC
CTCGGC

Figure 14C-15

SEQ ID NO 53

CGGCCGAGCTCGTGCTGACTCAGCCACCNTCGGTGTCAGTGCAGAAGACAGACGNCCAGGATTACCTGTGGGGCAAACA
ACATNGGAAGTAAAAGTGTGAACTGGTACCAGCAGCAGAAGCCAGGCCAGGCCCTGTGTCTCATGATAGCGAATG
GCCCTCAGGGATCCCTGAGCGATTCTCTGGCTCCAACTCTGGGAACACGGCCACCCTGACCATCAGCAGGGTCGAAGCCGG
GGATGAGGCCGACTATTACTGTGTCAGGTGTGGGATAGTGTCGTAGTGATAATGTGGTATTGGCGGGAGGCACCGAGCTGACCGTC
CTCGGT

SEQ ID NO 54

ACAGGGCGCCCAGGATTACCTGTGGGGGAAACGACATTGAAAGTAAAAGTGTGCAGTGGTACCAGCAGCAGAAGCCAGGCCAGGCC
CCTGTGTCTGGTCGTCTATAATGATAGTGACGGCCCCTCAGAGATCCCTGAGCGATTCTCTGGCTCCAAGTCTGGAAACACGGC
CACCCTGAGCATCAGCAGGTCGAAGCCGGGGATGAGGCCGACTACTACTGTGTCAGGTGTGTGGGATAGTGTTAATGATCAAGTG
GTATTCGGCGGAGGGACCGAGCTGACCGTCCTCGGC

SEQ ID NO 55

CGGCCGAGCTCGGGCTGACTCAGCCACCNTCAGTGTCAGTGCAGGAGACAGGCCGNCCAGGATTACCTGTGGGGGAAACG
ACATTGAAAGTAAAAGTGTGCAGTGGTACCAGCAGCAGAAGCCAGGCCCCTGTGCTGGTCGTCTATAATGATAGTGACGG
GCCCTCAGAGATCCCTGAGCGATTCTCTGGCTCCAAGTCTGGCTCCAAGTCTGAGCATCAGCAGGTCGAAGCCGGGG
GATGAGGCCGACTACTACTGTGTCAGGTGTGTGGGATAGTGTTAATGATCAAGTGTATTCGGCGGAGGGACCGAGCTGACCGTCC
TCGGC

SEQ ID NO 56

CGGCCGAGCTCGTGCTGACTCAATCGCCCTCGGTGTCAGTGGCCCAGGACAGAGACGGCCAAAGTCACCTGTGGGGGAAATA
ATATTGGAAGTAAGGTGTGCACTGGTACCAGCAGCAGAAGCCAGGCCCCTGTTGTCGTCTTTAATGATAACGACCGG
CCCTCAGGGATCCCTGAGCGATTCTCTGGCTCCAACTCTGGGAACACGGCCACCCTGACCATCAGCAGGTCGAGGCGGG
GATGAGGCCGACTATTACTGTCAGGTGTACGATATTAATAGTGATCTCGTGGTATTCGGCGGAGGGACCGAGCTGACCGTCCT
CGGC

Figure 14C-16

SEQ ID NO 57

CGGCCGAGCTCGAGCTGACTCAGCCACCNTCAGTCGTCCAGTGNCCCAGGACAGACGNCCAAGATTACCTGTGGGGAAAC
AACATTGGAAGTAAAGTGTGCACTGGTACCAGCAGAAGCCAGGCCAGGCCCCTGTACTGGTCGTGTATGATGATAGCGACC
GGCCCTCAGGGATCCCTGAGAGATTCTGGCTCCAAGTCTGGCTCCAAGTCTGGGAAAACGGCCACCCTGACCATCAGCAGGGTCGAAGCCG
GGGATGAGGCCGACTATTACTGTCAGGTGTGTGGGATAGTAGTAGTGATGATGTGATATTCGGCGGAGGCACCAAGCTGACCGT
CCTAGGC

SEQ ID NO 58

CGGCCGAGCTCGCCCTGACTCAGCCTCCNTCCGTGTCAGTGNCCCAGGACAGACGNCCAGGATTACCTGTGGGGAAACA
ACATNGGAAGTAAAGTGTGCACTGGTACCAGCAGAAGCCAGGCCCCTGTGTGCTGTGTCTATGATGATAGCGACCG
GCCCTCAGGGATCCCTGAGCGATTCTGCTCCAACTCTGGGAACACGGCCACCCTGACCATCAGCAGGGTCGAAGCCGG
GATGAGGCCGACTATTACTGTCAGGTGTGGGATAGTAGTGATCATGTGATTCGGCGGAGGACCAAGGTGACCGTC
CTAGGT

SEQ ID NO 59

CGNCCGAGCTCGTGTTGACGCAGCCGCCCTTCGGTGTCAGTGNCCCAGGACAGACGNCCAGGATTACCTGTGGGNAANC
ACCATNGGAAGTAAAAGTGTGCACTGGTACCAGCAGAAGCCCAGNCCAGGCCCCTGTGCTGTGTCTATGATGATAGCGACC
GGCCNTCAGGGATCCCTGAGCGATTCTCTGGCTCCAATTCTGGGAATACGGCCACCCTGTCCATCACCAGGGTCGAAGCCGG
GGATGAGGCCGACTATTACTGTCAGGTGTGGGATAGTAGTGATCATGTGGTATTCGGCGGAGGACCAAGGTGACCGTC
CTAGGC

SEQ ID NO 60

CGGCCGAGCTCGTGTTGACGCAGCCGCCCTCGGTGTCAGTGCCCCAGGACAGTCGGCCAGGATTACTTGTGGGGAAAGCA
ACATTGGATTTCAAAGTGTGCACTGGTACCAGCAGAAGCCAGGCCCCTGTGTTACTCGTCTATGATGATAGTGACCGG
CCCTCAGAGATCCCTGGCTCCAATTCTGGGACACGGCCACCCTGACCATCAGCAGGTCGAAGCCGGGG
ATGAGGCCGACTATTACTGTCAGGTTTGGGAGTAGTAGTGATCATCCGGTTTCGGCGGAGGCACCCAGCTGACCGTCCTC
GGC

Figure 14C-17

SEQ ID NO 61

CGGCCGAGCTCGTGCTGACTCAGCCACCNTCGGTGTCAGTGCCAGGACAGAGCGNCCAGGATTACCTGTGGGGAAACA
ACATNGGAAGTAAAAGTGTGCAGTGGTACCAGCAGAAGCCAGGCCAGGTCCCTGTCCTGGTCGTCTATAATGATAGCGACGG
GCCCTCAGAGATCCCTGAGCGATTCTCTGGCTCCAACTCTGGAACACGGCCACCCTGACCATCAGCAGGGTCGAAGCCGGG
GATGAGGCCGACTATTACTGTGCAGGTGTGGGATAGTAGTTATGATCATGTGGTATTCGGCGGAGGGACCGAGCTGACCGTCC
TCGGC

SEQ ID NO 62

CGGCCGAGCTCGTGCTGACTCAGCCACCTTCGGTGTCAGTGGCCCCAGGACAGACGGCCAGGATTCCCTGTGGGGAAACA
ACATTGGAAGTAAAAGTGTGCACTGGTACCAGCAGAAGCCAGGCCAGGTCCCTGTCGTCGTCTATGATGATAGCGACCG
GCCCTCAGGGATCCCTGAGCGATTCTCTGGCTCCAACTCAGGGAACACGGCCACCCTGACCATCAGCAGGGTCGAAGTCGG
GGATGAGGCCGACTATTACTGTCAGGTGTGGGATCATCTTAGTAGTAGTGATCATGTGGTATTCGGCGGAGGGACCAAGGTGACCGTC
CTAGGC

SEQ ID NO 63

CGGCCGAGCTCGTGCTGACTCAGCCACCTTCGGTGTCAGTGNCCCAGGACAGACGGCCACGATTACCTGTGGGGAAACA
ACATTGGAAGTAAAAGTGTGAACTGGTACCAGCAGAAGCCAGGCCCCTGTCGTCGTCTATCATGATAGCGAATG
GCCCTCAGGGATCCCTGAGCGATTCTCTGGCTCCAACTCTGGGGATAGTAGTCGTAGTAGTGATAATGTGGTCTTCGGCGGAGGGACCAAGGTGACCGTC
CTAGGT

SEQ ID NO 64

CGGCCGAGCTCGTGCTGACTCAGCCACCCTCGGTGTCAGTGNCCCAGGACAGACGGCCAGGATTACCTGTGGGCAAACA
ACATTGGAGGTAAACGTGTGCACTGGTACCAGCAGAAGCCAGGCCCCCTATACTGGTCGTCTATGATGATACCGACCG
GCCCTCAGGGATCCCTGAGCGATTCTCTGGCTCCAACACTGGGAACACGGCCACACTGACCATCAGCAGGGTCGAAGCCGG
GGATGAGGCCGACTATTACTGTCAGGTGTGGGATAGTGGTAGTGATCATGGTCTTCGGCGGAGGGACCGAGCTGACCGTC
CTAGGC

Figure 14C-18

SEQ ID NO 65

CGGCNGAGCTCGTGCTGACTCAGCCACNTTCGGTCTGTCCAGTGNCCCAGGACAGAGACGNCCAGGATTACCTGTGGGGAAAC
AACATTGGAAGTAAAAGTGCACTGGTACCAGCAGCAGGCCAGGCCAGGCCCCTGTGCTGTCTATGATGATAGGAGCC
GGCCCTCAGGATCCCTGAGCGATTCTCTGGCTCCAACTCTGGGAACACGGCCACCCTGACCATCAGCAGGGTCGAAGCCG
GGGATGAGGCCGACTATTACTGTCAGGTGTGGGATAGTAGTGATCATGTGGTATTCGGCGGAGGGACCCAGCTGACCGT
CCTCGGT

SEQ ID NO 66

CGGCCGAGCTCATGCTGACTCAGCCCCACTCGGTGTCCGTGCCCCAGGACAGAGACGNCCAGGATCACTTGTGGGGAAACG
GCATTGGACGTAAAAGTGTTCACTGGTACCAGCAGAAGCCAGGCCAGGCCCCTGTTCTGTCTGTCTATGATGATGTTTCCCGG
CCCTCAGGGATCCCTGAGCGATTCTCTGGCTCCAACTCTGGGAACACGGCCACCCTGATCATCACCAGGGTCGAAGTCGGGG
ATGAGGCCGACTATTACTGTCAGGCTTGGGACATTTCTAGTGATCATGTGATATTCGGCGAAGGGACCAAGGTGACCGTCCTC
GGT

SEQ ID NO 67

CGNCNGAGCTCGTGCTGACTCAGCCACNTTCGGTCTGTGTCGTGTCAGTGGCCCAGGACAGAGACGNCCACGATTACCTGTGGGGAAGCA
ACATNGGAGGTATGCGTACACTGTGAGCGNTTCTCTGGCTCCAACTNGGGCAGACTCCAAGGCAGATCTGTCGTCTATGATGACAGCAGCCG
GCCCTCAGAGATCCCTGAGCGNTTCTCTGGCTCCAACTCTGGCTCCAACTCAGCAGGGTCGAAGCCGG
GGATGAGGCCGACTATTACTGTCAGGTGTGGGAAAGTACTAGTGATCATGTGGTATTCGGCGGAGGGACCAAGCTGACCGTC
CTAGGC

SEQ ID NO 68

CGGCCGAGCTCGTGCTGACTCAGCCACNTTCGGTCTGTCCGTGNCCCAGGACAGAGACGNCCAGTATCACGTGTGGGGAGACG
GCATTGGACGTAAGAGTGCACTGGTACCAGCAGAAGCCAGGCCAGGCCCCTGTCTGTCTATGATGATATTGGCCG
GCCCTCAGGGATCCCTGAGCGCTTCTCTGGCTCCAACATGGCCACCCTGACCATCAGCAGGGTCGAAGCCGG
GGATGAGGCCGACTTTTTTGTCAGGTGTGGGATAGTATTAGTGATCATGTGGTCTTCGGCGGAGGGACCAAGCTGACCGTCC
TAGGC

Figure 14C-19

SEQ ID NO 69

CGGCCGAGCTCGTGCTGACTCAGCCACCNTCGGTGTCCAGTGNCCCAGGACAGAGACGCCCAGGATTACCTGTGGGGGAANC
ACCATNGGAAGTAAAAGTGCACTGGTACCAGCAGAAGCCAGGCCAGGCCAGCAGACATCAGCAGGTCGAAGCCG
GGCCCTCAGGAATCCCTGAGCGATTCTCTGGCTCCAACTCTGGGACACGGCCACGCTGAACATCAGCAGGTCGAAGCCG
GGGATGAGGCCGACTATTACTGTGTCAGGTGTGGGATAGTAGTCGTGATCATGTGTATTCGGCGGAGGCACCAAGCTGACCGT
CCTAGGC

SEQ ID NO 70

CGGCNGAGCTCGTGCTGACTCAGCCACCTTCGGTGTCAGTGCCCCCAGGACAGAGACGNCCAGGATTACCTGTGGGGAAACA
ACATNGGAACTAAAGTGCACTGGTACCAGCAGAAGCCAGGCCAGGCCCCTGTGCTGTCGTCTATGATGATAGCGACCG
GCCCTCAGGGATCCCTGAGCGATTCTCTGGCTCCAACTCTGGGAACACGGCCACCATCAGCAGGTCGAAGCCGG
GATGAGGCCGACTATTACTGTCAGGTGTGGGATAGTAGTAGTGATCTTGTGATTCGGCGGAGGGACCCAGCTGACCGTC
CTCGGC

SEQ ID NO 71

CGGCCGAGCTCATGCTGACTCAGCCCCACTCGGTGTCAGTGGCCCTGGGACAGAGACGCCCAGGATTACCTGTGGGGGAGACA
ACATTGGAACTAAGAATGTTCACTGGTACCAGCAGAAGCCAGGCCAGGCCCCTGTGGTTGCATTTATCGGGATACCAATCG
GCCCTCTGGGATCCCTGAGCGATTCTCTGGCTCCAACTCTGGGACCATCAATAGAGCCCAAGCCCGGG
GATGAGGCTGACTATCACTGTCAGGTGTGGGATAGTGCGATATTCGGCGGAGGCACCAAGCTGACCGTCCTAGGT

SEQ ID NO 72

CTGGTTTCGCTACCGTGCCCCAGGCGCCGAGCTCGTGTTGACGCAGTCGTCAGTGTCCCAGGACAGAGACAGCC
AGCATCACCTGCTCTGGAGATAAATTGGGGATAAATATGCTTCCTGGTATCAGCAGAAGGCAGCCAGTCCCTGTGCTGGT
CATCTATCAAGATAGGAAGCGGCCCTCAGGGATCCCTGAGCGATTCTCTGGCTCCAACAGCCACTCTGACCA
TCAGCGGGACCCAGGCTATGATGAGGCTGACTATTACTGTGTCAGGGCGTGGGAACAGCAGCACTGCGGTGTTCGGGGAGGGA
CCAAGGTGACCGTCCTAGGC

Figure 14C-20

SEQ ID NO 73
CGGCCGAGCTCGTGTNGACGCAGTCTCCAGACACCCTGTCTTCTCTCCAGGGGAAAGAGCCACCNTCTCCTGCCAGGTCCA
GTCAGAATGTTAGCAGCTACTTAGCCTGGTATCAACAGAAACCTGGCCAGGCTCCCAGGCTCCTCCTCACCTATGACACATCCAAC
AATGGGCGTCTTTGCCAGGTTCAGTAGCAGCTAGCAGTGGGTCTGGGACAGACTTCACTCTCACCATCACCAGGTTAGAGCCTGAAGATT
TGCAATTTATTACTGTGAGCAGCGTAATAATTGGCCTCCGGAATTCACTTTCGGCCCTGGGACCAAAGTGATATCAAA

SEQ ID NO 74
QVQLVQSGAEMKKPGSSVRVSCKASGGTFDKYAVSWVRQAPGRGLEWVGGIIPMLGAPHYAQKFQGRVTITADKSTSTVYMELSS
LGSEDTAVYYCARDKAAYYESGYYYIGDFWGQGTLVTVSSASTKGPSVTSGQ

SEQ ID NO 75
QVQLVQSGAEMKKPGSSVRVSCKASGGTFDKHAVSWVRQAPGRGLEWVGGIIPMLGAPHYAQKFQGRVTITADKSTSTVYMELSS
LGSEDTAVYYCARDKAAYYESGYYYIGDFWGQGTLVTVSSASTKGPSVTSGQ

SEQ ID NO 76
QVQLVQSGAEMKKPGSSVRVSCKASGGTFDKHAVSWVRQAPGRGLEWVGGIIPMLGAPHYAQKFQGRVTITADKSTSTVYMELSS
LGSEDTAVYYCARDKAAYYESGYYYIGDFWGQGTLVTVSSASTKGPSVTSGQ

SEQ ID NO 77
QVQLVQSGAEMKKPGSSVRVSCKASGGTFDKYAVSWVRQAPGRGLEWVGGIIPMLGAPHYAQKFQGRVTITADKSTSTIYMELSSL
GSEDTAVYYCARDKAAYYESGYYYIGDFWGQGTLVTVSSASTKGPSVTSGQ

SEQ ID NO 78
QVQLVQSWAEMKKPGSSVRVSCKASGGTFDKYGVSWVRQAPGQGLEWMGGIIPMLGTPHYAQKFQGRVTITADKSTSTVYMELS
SLGSEDTAVYYCARDKEAYYESGYYYIGDFWGQGTLVTVSSASTKGPSVTSGQ

Figure 14C-21

SEQ ID NO 79
EVQLVQSGAEMKKPGSSVRVSCKASGGTFDKYAVSWVRQAPGRGLEWVGGIIPMLGAPHYAQKFQGRVTITADKSTSTVYMELSS
LGSEDTAVYYCARDKAAYYESGYYYIGDFWGQGTLVTVSSASTKGPSVTSGQ

SEQ ID NO 80
EVQLVESGAEMKKPGSSVRVSCKASGGTFDKYGVSWVRQAPGRGLEWVGGIIPMLGAPHYAQKFQGRVTITADKSTSTVYMELSS
LGSEDTAVYYCARDKAAYYESGYYYIGDFWGQGTLVTVSSASTKGPSVTSGQ

SEQ ID NO 81
QVQLVQSGAEMKKPGSSVRXSCKASGGTFDKYAVSWVRQAPXRGLEWVGGIIPMLGAPHYAQKFQGRVTITADKSTSTXYMELSS
LGSEDTAVYYCARDKAAYYESGYYYIGEFWGQGTLVXVSSASTKGPSVXXXQ

SEQ ID NO 82
QVQLVQSGAEMKRPGSSVRVSCKASGGTFDKYAVSWVRQAPGRGLEWVGGIIPLLGAPHYAQKFQGRVTITADKSTSTVYMELSS
LGSEDTAVYYCARDKAAYYESGYYYIGDFWGQGTLVTVSSASTKGPSVTSGQ

SEQ ID NO 83
QVQLVQSGAEVKKPGSSVKVSCKASGGTFGNYAINWVRQAPGQGLEWMGGIIPTLDLLNDAQNFQDRVTITADKSTNTVYLELTSL
RSEDTAVYYCARGGDYSGWYNFDYWGQGTLVTVSSASTKGPSVTSGQ

SEQ ID NO 84
QVQLVQSGGGLVQPGGSLRLSCAASGLPFNSYWMSWVRQAPGKGLEWVANINQDGNEKHYVDSVKGRFIISRDNTHNSLFLQMN
SLRAEDAAVYYCASGGVVDFDHWGQGSLVTVSSASTKGPSVTSGQ

SEQ ID NO 85
EVQLVESGGGLVQPGGSLRLSCAASGLPFSSSWMSWVRQAPGKGLEWVANINQDGNEKHYVDSVKGRFIISRDNTQNSLFLQMN
SLRAEDAAVYYCASGGVVDFDHWGQGTLVTVSPASTKGPSVTSGQ

Figure 14C-22

SEQ ID NO 86
EVQLLESGGGLVNPGGSLRLSCAASGLPFNSYWMSWVRQAPGKGLEWVANINQDGNEKHYVDSVKGRFIISRDNTQNSLFLQMNS
LRAEDAAVYYCASGGVVDFDHWGQGTLVTVSPASTKGPSVTSGQ

SEQ ID NO 87
EVQLVESGGGVVQPGRSLRLSCAASGFTFSNYAMHWVRQAPGKGLEWVAVISYDGGNKYYADSVKGRFTISRDDSKNTLYLQMN
SLRPEDTAVYYCAREALVYYDSSGYYXGGFDYWGQGTLVTVSSASTKGPSVTSGQ

SEQ ID NO 88
EVQLVESGGGLVKPGGSLRLSCAASGFTFNDYYMSWFRQAPGKGLEWISYISSSGPYTNYANSVKGRFTISRDNAENSLYLQMNSL
RAEDTAVYYCAREMSPITAAGAHTYECWGQGTLVTVSSASTKGPSVTSGQ

SEQ ID NO 89
EVQLVESGGGVVQPGRSLRLSCAASGFTFNDYYMSWFRQAPGKGLEWISYISSSGPYTNYANSVKGRFTISRDNAENSLYLQMNSL
RAEDTAVYYCAREMSPITAAGAHTYECWGQGTLVTVSSASTKGPSVTSGQ

SEQ ID NO 90
EVQLVESGGGLVKPGGSLRLSCAASTFTFNDDYMSWIRQAPGKGLEWVSYISSSSSYTHYADSVKGRFSISRDNAKNSLFLQMNSL
RAEDTAVYYCARELSPFTAATAHSYDLWGQGTLVTVSSASTKGPSVTSGQ

SEQ ID NO 91
EVQLVESGGGLVKPGGSLRLSCAASGFTFNDDYMSWIRQAPGKGLEWVSYISSSSSYTHYADSVKGRFSISRDNAKNSLFLQMNSL
RAEDTAVYYCARELSPFTAATAHSYDLWGQGTLVTVSSASTKGPSVTSGQ

SEQ ID NO 92
QVQLVQSGGGLVKPGGSLRLSCAASTFTFNDDYMSWIRQAPGKGLEWVSYISSSSSYTHYADSVKGRFSISRDNAKNSLFLQMNSL
RAEDTAVYYCARELSPFTAATAHSYDLWGQGTLVTVSSASTKGPSVTSGQ

Figure 14C-23

SEQ ID NO 93
EVQLVESGGGLVKPGGSLRLSCAASTFTFNDDYMSWIRQAPGKGLEWVSYISSSSSYTHYADSVKGRFSISRDNAKNSLFLQMSSL
RAEDTAVYYCARELSPFTAATAHSYDLWGQGTLVTVSSASTKGPSVTSGQ

SEQ ID NO 94
EVQLVESGGGLVKPGGSLRLSCAASTFTFNDDYMSWIRQAPGKGLEWVSYISSSSSYTHYADSVKGRFSISRDNAKNSLFLQMNSL
RAEDTAVYYCARELSPFTAATAHSYDLWGQGTLVTVSSASTKGPSVTSGQ

SEQ ID NO 95
QITLKESGGGLVKPGESLRLSCAASDFTFSDYYMSWIRQPPGKGLEWVSYISSSGRYTHYADSVKGRFTISRDNAKNSLFLQMNSLR
AEDTAVYYCARELSPLTAGAAHTLDYWGQGTLVTVSSASTKGPSVTSGQ

SEQ ID NO 96
EVQLVESGGGLVKPGESLRLSCAASDFTFGDYYMSWIRQPPGKGLEWISYISSSSRYTNYADSVKGRFTISRDNARNSLYLQMNSL
RAEDTAVYYCARELSPLTAGAAHTLDYWGQGTLVTVSSASTKGPSVTSGQ

SEQ ID NO 97
EVQLVESGGGLVKPGESLRLSCAASDFTFSDYYMSWIRQPPGKGLEWISYISSNSRFRNYADSVKGRFTISRDNAKNSLYLQMNSL
RGEDTAVYYCAKELSPLTAGAAHTLDYWGQGTLVTVSSASTKGPSVTSGQ

SEQ ID NO 98
QVQLVQSGGGLVKPGGSLRLSCAASGFTFSDYYMNWIRQAPGKGLEWISYISGSSSSYTYYADSVKGRFTISRDNAKNSLYLQMSSL
RADDTAVYYCARELSPITAGDAHTFDSWGQGTLVTVSSASTKGPSVTSGQ

SEQ ID NO 99
EVQLVQSGGGLVKPGGSLRLSCAASEFTFSDYYMSWIRQAPGKGLEWVSYISSNGRYRHYADSVKGRFTISRDNAKNSLYLQMNS
LRAEDTAVYYCARELSPLTSADAHTYDYWGQGTLVTVSSASTKGPSVTSGQ

Figure 14C-24

SEQ ID NO 100
EVQLVESGGGLVKPGESLRLSCTASEFTFSDYYMSWIRQAPGKGLEWVSYISSSSRYTHYGDSVKGRFTISRDNAKNSLYLQMNSL
RTEDTAVYYCARELSPLTSAGAHTYDYWGQGTLVTVSSASTKGPSVTSGQ

SEQ ID NO 101
QVQLQESGPGLVKPSETLSLTCSVSGYPISSGYYWGWIRQPPGKGLEWIGSIHHSGSTYYNSSLKSRVTLSVDTSKNQFSLKVSSVT
AADTAVYYCARTTTAYWYFDLWGRGTLVTVSSASTKGPSVTSGQ

SEQ ID NO 102
EVQLLESGPGPVKPSGTLSLTCGVSGGSISTNHWWTWVRQPPGQGLEWIGEIHHNGSTFFNPSLKSRVTISVDKSNNQFSLKLTSL
TAADTAVYYCARGWHRTGFRGYPSHWYFDLWGRGTLVTVSSASTKGPSVTSGQ

SEQ ID NO 103
QVQLQESGPGPVKPSGTLSLTCGVSGGSISSNHWWTWVRQPPGKGLEWIGEIYHNGSTFLNPSLKSRVTISVDKSNNQFSLKLTSV
TAADTAVYYCARGWHRTGFRGYPSHWYFDLWGRGTLVSVSSASTKGPSVTSGQ

SEQ ID NO 104
QVQLQESGPGLVKPSGTLSLTCGVSGGSISSNHWWTWVRQPPGQGLEWIGEVHHNGSTFFNPSLKSRVTISVDKSNNQFSLKLTS
VTAADTAVYFCARGWHRTGFRGYPSHWYFDLWGRGTLVTVSSASTKGPSVTSGQ

SEQ ID NO 105
AELVLTQPPSASETPGQRVTISCSGSSNIAGNTVYWYQQLPGAAPKLLIYYNDQRPSGVPDRFSGSKSGTSASLSISGLRSEDEGD
YYCSAWDASLSWVFGGGTKLTVLG

SEQ ID NO 106
AELVLTQPPSVSETPGQRVTISCSGSSNIAGNTVYWYQQLPGAAPKLLIYYNDQRPSGVPDRFSGSKSGTSSSLAISGLQSEDEAY
YYCATWDEDVNGWVFGGGTKLTVLG

Figure 14C-25

SEQ ID NO 107
APRPGRASCFQPTFRVDPPARGSPSPVAEAAPTSQVILCTGTSSSPGAAPQAPHLLQSAALRGPPILWLQVWHLLLLGHQWAPVGG
LLLLCNMGRCEWLGVRRRDQADRPR

SEQ ID NO 108
AELVLTQPPSASETPGQRVTISCSGSSSNIAGNTVYWYQQLPGAAPKLLIYYNDQRPSGVPDRFSGSKSGTSSSLAISGLQSEDEAY
YYCATWDEDVNGWVFGGGTKLTVLG

SEQ ID NO 109
AELVVTQPPSVSAXPGQKVTISCSGSSSNIAGNTVYWYQQLPGAAPKLLIYYNDQRPSGVPDRFSGSKSGTSSSLAISGLQSEDEAY
YYCATWDEDVNGWVFGGGTKLTVLG

SEQ ID NO 110
AELELTQPPSVSGTPGQRVTISCSGSSSNIAGNTVYWYQQLPGAAPKLLIYYNDQRPSGVPDRFSGSKSGTSSSLTISGLQSEDEAY
YYCATWDEDVNGWVFGGGTKLTVLG

SEQ ID NO 111
AELMLTQPHSASETPGQRVTISCSGSSSNIAGNTVYWYQQLPGAAPKLLIYYNDQRPSGVPDRFSGSKSGTSSSLAISGLQSEDEAY
YYCATWDEDVNGWVFGGGTELTVLG

SEQ ID NO 112
AELVLTQPPSASETPGQRVTISCSGSSSNIAGNTVYWYQQFPGAAPKLLIYYNDQRPSGVPDRFSGSKSGTSSSLAISGLQSEDEAY
YYCATWDEDVNGWVFGGGTELTVLG

SEQ ID NO 113
AELVLTQSPSASETPGQRVTISCSGSSSNIAGNTVYWYQQFPGAAPKLLIYYNDQRPSGVPDRFSGSKSGTSSSLAISGLQSEDEAY
YYCATWDEDVNGWVFGGGTKVTVLG

Figure 14C-26

SEQ ID NO 114
AELMLTQPHSASGTPGQRVTISCSGSSSNIAGNTVYWYQQFPGAAPKLLIYYNDQRPSGVPDRFSGSKSGTSSSLAISGLQSEDEAYYYCATWDEDVNGWVFGGGTKVTVLG

SEQ ID NO 115
AELMLTQPHSASETPGQRVTISCSGSSSNIAGNTVYWYQQFPGAAPKLLIYYNDQRPSGVPDRFSGSKSGTSSSLAISGLQSEDEAYYYCATWDEDVNGWVFGGGTKVTVL

SEQ ID NO 116
AELVLTQSPSASETPGQRVTISCSGSSSNIAGNTVYWYQQLPGAAPKLLIYYNDQRPSGVPDRFSGSKSGTSSSLAISGLQSEDEAYYYCATWDEDVNGWVFGGGTKVTVLG

SEQ ID NO 117
AELVLTQPPSVSGTPGQRVTISCSGSSSHIGNNYVYWYQHLPGTAPKLLIYSNDQRPSGVPDRFSASKSATSASLAISGLRSEDEADYYCAAWDDSQGGVFGGGTKVTVLG

SEQ ID NO 118
AELVLTQPPSVSGTPGQRVTISCSGSSSHIGSNYVYWYQQLPGTAPKILIYSNDQRPAGVPDRFSASKSGTSASLAISGLRSEDEADYYCAAWDDGQGGVFGGGTKLTVLG

SEQ ID NO 119
AELVLTQPXSAFWDPRAEGHHLLFWKQLPHRKELCILVPTSPRSGPQTPHLQSAALRGPPILWLQVWHLSLPGHQWAPVRGGLLLCSMGQPGGGVRRRDQADRPR

SEQ ID NO 120
AELELTQPPSVSGSPGQSITISCTGSSSYVGIFNLVSWYQQHPGTAPRRVIYEGDKRPSNISNRFSGSKSGNTASLTISGLQADDEADYYCYSYVAGSDLWVFGGGTKLTVLG

Figure 14C-27

SEQ ID NO 121
AELELTQPPSVSGSPGQSITISCTGSSSYVGIFNLVSWYQQHPGTAPRRVIYEGDKRPSNISNRFSGSKSGNTASLTISGLQADDEAD YYCYSYVAGSDLWVFGGGTKLTVLG

SEQ ID NO 122
AELALTQPPSVSGSPGQSITISCTGFSSDLSWYQQHPGKAPKLMIYDVNNRPSGVSDRFSGSKSGNTASLTISGLQAEDEADYYCSS YTSSSTSLMFGGGTELTVLG

SEQ ID NO 123
AELGVTQPPSVSVXPGQTXTITCGGXNXGSKSVNWYQQKPGQAPVLVVYHDSEWPSGIPERFSGSNSGNTATLTISRVEAGDEAD YYCQVWDSRSDNVVFGGGTELTVLG

SEQ ID NO 124
AELMLTQPHSVSVXPGQTXTITCGGNNXGSKSVNWYQQKPGQAPVLVVYHDSEWPSGIPERFSGSNSGNTATLTISRVEAGDEAD YYCQVWDSRSDNVVFGGGTELTVLG

SEQ ID NO 125
AELMLTQPHS VSVXPGQTXT ITCGGNNXGS KSVNWYQQKP GQAPVLVVYH DSEWPSGIPERFSGSNSGNT ATLTISRVEA GDEADYYCQV WDSRSDNVVF GGGTELTVLG

SEQ ID NO 126
AELVLTQPPSVSVXPGQTXRITCGANNXGSKSVNWYQQKPGQAPVLVVYHDSEWPSGIPERFSGSNSGNTATLTISRVEAGDEADY YCQVWDSRSDNVVFGGGTELTVLG

SEQ ID NO 127
RRPGLPVGETTLKVKVCSGTSRSQARPLCWSSIMIVTAPQRSLSDSLAPSLETRPPASAGSKPGMRPTTTVRCGIVLMIKWYSAEGP SPSS

Figure 14C-28

AELGLTQPPSVSVXPGQAXRITCGGNDIESKSVQWYQQKPGQAPVLVVYNDSDGPSEIPERFSGSKSGNTATLSISRVEAGDEADY
YCQVWDSVNDQVVFGGGTELTVLG
SEQ ID NO 128

AELVLTQSPSVSVAPGQTAKVTCGGNNIGSKGVHWYQQKPGQAPVLVVFNDNDRPSGIPERFSGSNSGNTATLTISRVEAGDEADY
YCQVYDINSDLVFGGGTELTVLG
SEQ ID NO 129

AELELTQPPSVSSXPRTDXQDYLWGKQHWKKCALVPAEARPGPCTGRVRPALRDPEILWLQVWENGHPDHQQGRSRGGRLLLSG
VGYCDIRRRHQADRPR
SEQ ID NO 130

AELALTQPPSVSVXPGQTXRITCGGNNXGSKSVHWYQQKPGQAPVLVVYDDSDRPSGIPERFSGSNSGNTATLTISRVEAGDEADY
YCQVWDSSSDHVVFGGGTKVTVLG
SEQ ID NO 131

XELVLTQPPFGVSXPRTDXQDYLWGXHHXKKCALVPAEAXPGPCAGRLRPAXRDPAILWLQFWEYGHPVHHQGRSRGGRLLLSG
VGSCGIRRRDQGDRPR
SEQ ID NO 132

AELVLTQPPSVSVAPGQSARITCGESNIGFQSVHWYQQKPGQAPVLLVYDDSDRPSEIPERFSGSNSGDTATLTISRVEAGDEADYY
CQVWSSSSDHPVFGGGTQLTVLG
SEQ ID NO 133

AELVLTQPPSVSVXPGQTXRITCGGNNXGSKSVQWYQQKPGQVPVLVVYNDSDGPSEIPERFSGSNSGNTATLTISKVEAGDEADY
YCQVWDSSYDHVVFGGGTELTVLG
SEQ ID NO 134

Figure 14C-29

SEQ ID NO 135
AELVLTQPPSVSVAPGQTARIPCGGNNIGSKSVHWYQQKPGQAPVLVVYDDSDRPSGIPERFSGSNSGNTATLTISRVEVGDEADY
YCQVWDLSSDHVVFGGGTKVTVLG

SEQ ID NO 136
AELVLTQPPSVSVXPGQTATITCGGNNIGSKSVNWYQQKPGQAPVLVVYHDSEWPSGIPERFSGSNSGNTATLTISRVEAGDEADY
YCQVWDSRSDNVVFGGGTKVTVLG

SEQ ID NO 137
AELVLTQPPSVSVXPGQTARITCGANNIGGKRVHWYQQKPGQAPILVVYDDTDRPSGIPERFSGSNTGNTATLTISRVEAGDEADYY
CQVWDSGSDHVVFGGGTELTVLG

SEQ ID NO 138
AELVLTQPXSVSSXPRTDXQDYLWGKQHWKKCALVPAAARPGPCAGRLRPALRDPAILWLQLWEHGHPDHQQGRSRGGRLLLSG
VGSCGIRRRDPADRPR

SEQ ID NO 139
AELMLTQPHSVSVPPGQTXRITCGGNGIGRKSVHWYQQKPGQAPVLVVYDDVSRPSGIPERFSGSNSGNTATLIITRVEVGDEADY
YCQAWDISSDHVIFGEGTKVTVLG

SEQ ID NO 140
XELVLTQPXSLSVAPGQTXTITCGGSNXGGMRVHWYXQTPGQAPVLVVYDDSDRPSEIPERFSGSNWGNSATLTISRVEAGDEADY
YCQVWESTSDHVVFGGGTKLTVLG

SEQ ID NO 141
AELVLTQPXSVSVXPGQTXSITCGGDGIGRKSVHWYQQKPGQAPALVVYDDIGRPSGIPERFSGSNSGNMATLTISRVEAGDEADFF
CQVWDSISDHVVFGGGTKLTVLG

Figure 14C-30

SEQ ID NO 142
AELVLTQPPSVSSXPRTDAQDYLWGXHHXKKCALVPAEARPGPCLGRLRPALRNPAILWLQLWGHGHAEHQQGRSRGGRLLLSGV
GSSCGIRRRHQADRPR

SEQ ID NO 143
AELVLTQPPSVSVPPGQTXRITCGGNNXGSKSVHWYQQKPGQAPVLVYDDSDRPSGIPERFSGSNSGNTATLTISRVEAGDEADY
YCQVWDSSSDLVVFGGGTQLTVLG

SEQ ID NO 144
AELMLTQPHSVSVALGQTPRITCGGDNIGTKNVHWYQQKPGQAPCVGHLSGYQSALWDPAILWLQLGEHGHPDHQSPSRGGLSLS
GVGQFYCDIRRRHQADRPR

SEQ ID NO 145
GFATVPQAPSSCRSRPQCRVPRTDSQHHLLWRIGGICFLVSAEGRPVPCAGHLSREAALRDPAILWLQLWEHSHSDHQRDPGYGG
LLLSGVGQQHCGVRRRDQGDRPR

SEQ ID NO 146
AELVXTQSPDTLSFSPGERATXSCQVQSECQLLSLVPTETWPGSQAPHLHIQQWRLCQVQQWVVWDRLHSHHHQVRARFCNLLLA
ALASGIHFRPWDQSDIK under US 8,298,545 B2

ANTI-AUTOIMMUNE ANTIBODIES FOR TREATMENT OF PEMPHIGUS

STATEMENT REGARDING FEDERALLY SPONSORED RESEARCH OR DEVELOPMENT

This research was supported, in part, by U.S. Government funds (National Institutes of Health Grant No. R01-AR052672), and therefore the U.S. Government has certain rights in the invention.

CROSS-REFERENCE TO RELATED APPLICATIONS

This is a National Stage application of PCT International Application No. PCT/US2008/001023, filed Jan. 25, 2008, which in turn claims the benefit pursuant to 35 U.S.C. §119(e) of U.S. Provisional Application No. 60/899,877, filed on Feb. 7, 2007 which is hereby incorporated by reference in its entirety herein.

BACKGROUND OF THE INVENTION

Pemphigus is an autoimmune blistering disease of the skin and mucous membranes characterized by antibodies against the keratinocyte cell surface adhesion proteins desmoglein (Dsg) 1 and 3 (Stanley, 2003 Pemphugus. In: Fitzpatrick's dermatology in general medicine, New York: McGraw-Hill, 558-67). There are two primary forms of pemphigus, pemphigus foliaceus (PF) and pemphigus vulgaris (PV) to PF is characterized by autoantibodies against Dsg1, which cause blistering of the skin, but not mucous membranes, due to loss of cell adhesion in the superficial epidermis. Mucosal PV is characterized by autoantibodies against Dsg3, which cause suprabasilar blistering of the mucous membranes. Mucocutaneous PV patients, who demonstrate both mucous membrane and skin involvement, usually develop additional autoantibodies against Dsg1. In both PV and PF, anti-Dsg antibodies are responsible for the positive direct and indirect immunofluorescence tests that are the pathognomonic feature of these diseases.

Experiments using passive transfer of autoantibodies to neonatal mice have demonstrated that the anti-Dsg antibodies in patients' sera are pathogenic. However, not all anti-Dsg antibodies cause disease. Epitope mapping studies have shown that the more pathogenic autoantibodies tend to bind the amino-terminal extracellular domain of Dsgs that is predicted to form the trans-adhesive interface between cells, while the less or non-pathogenic antibodies bind more membrane-proximal extracellular domains.

Before the advent of corticosteroids, PV was a uniformly fatal disease due to severe blistering of the skin and oropharynx, with resulting malnutrition and sepsis. Currently, therapy for pemphigus relies on general immunosuppression, typically with corticosteroids, steroid-sparing agents, and/or adjunctive treatments such as intravenous immunoglobulin or plasmapheresis, most of which target the total antibody pool. Although mortality from pemphigus has decreased due to these therapies, a significant amount of patient morbidity and rarely mortality now results from side effects of these treatments. Therefore, there has been a long felt need in the field for more specific antibody-targeted therapies for pemphigus that would suppress or eliminate only the anti-Dsg autoantibodies. The present invention satisfies this need.

SUMMARY OF THE INVENTION

The present invention provides an anti-autoimmune reagent capable of binding to an antibody associated with a disease. A non-limiting antibody associated with a disease is an anti-desmoglein (Dsg) autoantibody.

In one embodiment, the invention includes an isolated anti-autoimmune reagent, wherein the anti-autoimmune reagent specifically binds to an anti-desmoglein autoantibody. Preferably, the anti-desmoglein autoantibody binds to a target molecule selected from the group consisting of Dsg1, Dsg3, and any combination thereof. In another embodiment, the anti-desmoglein autoantibody is associated with the pathology of pemphigus vulgaris (PV), or pemphigus foliaceus (PF).

In another embodiment, the anti-autoimmune reagent is selected from the group consisting of a peptide, a small molecule, an antibody, a humanized antibody, a recombinant antibody, and any combination thereof.

In one embodiment, the anti-autoimmune reagent is an antibody that specifically binds to the variable region of the heavy chain ($V_H$) of the anti-desmoglein pathogenic autoantibody. In another embodiment, the heavy chain ($V_H$) of the anti-desmoglein autoantibody is encoded by the gene selected from the group consisting of VH3-8, VH3-07, VH1-4M28, and any combination thereof. In another embodiment, the heavy chain has an amino acid sequence selected from the group consisting of SEQ ID NOs: 74-104. In yet another embodiment, the heavy chain has an amino acid encoded by the nucleic acid sequence selected from the group consisting of SEQ ID NOs: 1-31.

In another embodiment, the anti-autoimmune reagent is an antibody that specifically binds to the variable region of the light chain ($L_H$) of the anti-desmoglein pathogenic autoantibody. In another embodiment, the light chain has an amino acid sequence selected from the group consisting of SEQ ID NOs: 105-146. In yet another embodiment, the light chain has an amino acid encoded by the nucleic acid sequence selected from the group consisting of SEQ ID NOs: 32-73.

In one embodiment, the anti-autoimmune reagent is a peptide comprising an amino acid sequence selected from the group consisting of the sequence set forth in SEQ ID NOs: 174, 175, 176, 177, 178, 179, 180, and any combination thereof. In another embodiment, the peptide comprises an amino acid sequence selected from the group consisting of the sequence set forth in SEQ ID NOs: 170, 171, 172, 173, and any combination thereof. In yet another embodiment, the peptide comprises a nucleic acid sequence encoding an amino acid sequence selected from the group consisting of SEQ ID NOs: 170, 171, 172, 173, and any combination thereof. In another embodiment the invention includes a peptidomimetic compound of any one or more of the aforementioned peptides. In yet another embodiment, the invention includes a plasmapheresis affinity column comprising any one or more of to the aforementioned peptides.

The invention also includes an isolated nucleic acid sequence having at least 85% complementarity to any one of the nucleic acid sequences set forth in SEQ ID NOs: 1-70 or any combination there. In another embodiment, the invention includes an isolated nucleic acid sequence having at least 85% homology to any one of the nucleic acid sequences set forth in SEQ ID NOs: 1-70 or any combination thereof.

The invention also includes an isolated polypeptide having at least 85% homology to any one of the amino acid sequence set forth in SEQ ID NOs:74-146 or any combination thereof.

The invention also includes an inhibitor of an anti-desmoglein pathogenic autoantibody, wherein the inhibitor inhibits at least one of the sequences set for in SEQ ID NOs: 1-73. In one embodiment, the inhibitor is selected from the group consisting a small interfering RNA (siRNA), a microRNA, an antisense nucleic acid, a ribozyme, a polyamide, a triplehelix-forming agent, a synthetic peptide nucleic acids (PNAs), an agRNA, a LNA/DNA copolymer, and any combination thereof.

The invention also includes a composition comprising an anti-autoimmune reagent, wherein the anti-autoimmune reagent specifically binds to an anti-desmoglein autoantibody.

The invention also includes B-cell superantigen linked to an anti-autoimmune reagent, wherein the anti-autoimmune reagent specifically binds to an anti-desmoglein autoantibody.

The invention also includes a method of inhibiting the binding of an anti-desmoglein autoantibody to desmoglein, comprising contacting the anti-desmoglein autoantibody with a composition comprising an anti-autoimmune reagent that specifically binds to a variable region of the anti-desmoglein autoantibody.

The invention also includes a method of modulating the expression of an anti-desmoglein autoantibody, comprising contacting a nucleotide sequence encoding an anti-desmoglein autoantibody or fragment thereof with an inhibitor of an anti-desmoglein autoantibody, wherein the inhibitor is capable of inhibiting the expression of said anti-desmoglein autoantibody. Preferably, the nucleotide sequence encoding an anti-desmoglein autoantibody or fragment thereof is at least 85% homology with the nucleotide sequence selected from the group consisting of to sequences set forth in SEQ ID NOs: 1-73 and any combination thereof. In another embodiment, the sequence encoding the anti-desmoglein autoantibody or fragment thereof is encoded by a gene selected from the group consisting of VH3-8, VH3-07, VH1-4M28, and any combination thereof.

The invention also includes a method of treating an autoimmune pathology associated with desmoglein in a subject, comprising administering to a subject in need thereof a composition comprising an anti-autoimmune reagent that specifically binds to a variable region of an anti-desmoglein autoantibody, thereby inhibiting the binding of the anti-desmoglein autoantibody to desmoglein.

The invention also includes a method of treating an autoimmune pathology associated with desmoglein in a subject, comprising contacting a nucleotide sequence of the subject encoding an anti-desmoglein autoantibody or fragment thereof with an inhibitor capable of inhibiting the expression of the nucleotide sequence encoding the anti-desmoglein autoantibody, thereby inhibiting the expression of the anti-desmoglein autoantibody.

The invention also includes a method of depleting a biological sample from an anti-desmoglein antibody, comprising contacting the sample with an immobile composition comprising an anti-autoimmune reagent capable of specifically binding to an anti-desmoglein autoantibody; and removing the biological sample without the bound anti-desmoglein autoantibody, thereby depleting the biological sample of anti-desmoglein autoantibody. In one embodiment, the biological sample is selected from the group consisting of blood, sera, plasma, and any combination thereof. In yet another embodiment, the immobile composition comprises an affinity column. In another embodiment, the step of contacting the sample with an immobile composition is carried out during a plasmapheresis procedure performed on a subject.

The invention includes a method of diagnosing pemphigus in a subject, comprising the step of contacting a biological sample of the subject with a composition comprising an anti-autoimmune reagent that specifically binds to an anti-desmoglein autoantibody; and analyzing the biological sample for the presence of antibody-antigen complex, whereby the presence of antibody-antigen complex indicates the subject has or is predisposed to pemphigus. In one embodiment, the step of contacting the biological sample with the composition comprising an anti-autoimmune reagent is evaluated using a radio-immunoassay (RIA), an enzyme linked immunosorbent assay (ELISA), a western blot, an immunohistochemical analysis, or a combination thereof.

The invention also includes an isolated anti-autoimmune reagent comprising the sequence represented by Asp-X-X-X-Trp (SEQ ID NO: 181) or Glu-X-X-X-Trp (SEQ ID NO: 182).

The invention includes a method of treating an autoimmune disorder in a subject, comprising administering to a subject having an autoimmune disorder, an effective amount of a therapeutic composition comprising an anti-autoimmune reagent capable of binding to an antibody present on the cell surface of a B cell, wherein the antibody comprises the sequence represented by Asp-X-X-X-Trp (SEQ ID NO: 181) or Glu-X-X-X-Trp (SEQ ID NO: 182). In another embodiment, the antibody comprises the sequence selected from the group consisting of SEQ ID NOs: 74-146 and any combination thereof. In another embodiment, the anti-autoimmune reagent is conjugated or fused to a therapeutic moiety.

The invention includes a method of contacting a B cell that produces a disease-associated antibody with a therapeutic moiety, comprising contacting the B cell with a composition comprising an anti-autoimmune reagent capable of binding to an antibody present on the cell surface of said B cell, wherein the anti-autoimmune reagent is conjugated or fused to a therapeutic moiety, thereby contacting said B cell with a therapeutic moiety. In one embodiment, the disease-associated antibody comprises the sequence represented by Asp-X-X-X-Trp (SEQ ID NO: 181) or Glu-X-X-X-Trp (SEQ ID NO: 182). In yet another embodiment, the disease-associated antibody comprises the sequence selected from the group consisting of SEQ ID NOs: 74-146 and any combination thereof.

The invention includes a method of identifying a molecule capable of binding to a pathogenic antibody, comprising screening a library, wherein the screening comprises providing a library comprising a plurality of molecule members, contacting the pathogenic antibody with the library, and isolating those bound molecules which are bound by the pathogenic antibody, wherein the bound molecules being molecules that are capable of binding to the pathogenic antibody, thereby identifying a molecule capable of binding to a pathogenic antibody. In one embodiment, the library is a phage display peptide library.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 3 is an image depicting peptide sequences identified by peptide phage display screening using (D31)2/29 pathogenic PV mAb. The consensus binding sequence is shown in red.

FIGS. 5A through 5O, is a series of images showing that pooled antisera depletes pathogenic activity from PV(1) serum and binds pathogenic antibodies from different PV patients' sera. Preimmune IgG and pooled antisera IgG were coupled to solid phase matrix and used to deplete various PV patients' sera, including PV(1), the patient from whom the PV(1) phage display library was produced. Due to the low anti-Dsg1 titer of PV3210 and PV3274 sera, ETA was added to incubations using these sera. Both the depleted sera, as well as antibodies eluted from the rabbit preimmune and antisera columns, were evaluated by keratinocyte dissociation assay for pathogenic activity. The number of cell sheet fragments is shown as a mean (standard deviation).

FIG. 7 is an image depicting how peptide phage pools selectively bound pathogenic PV mAbs. PV monoclonal IgG or an unrelated IgG1 lambda mAb were adsorbed to ELISA plates and incubated with varying dilutions of PhD-C7C peptide phage pools from the third round of selection, followed by HRP-coupled anti-M13 secondary antibody.

Figure 8:
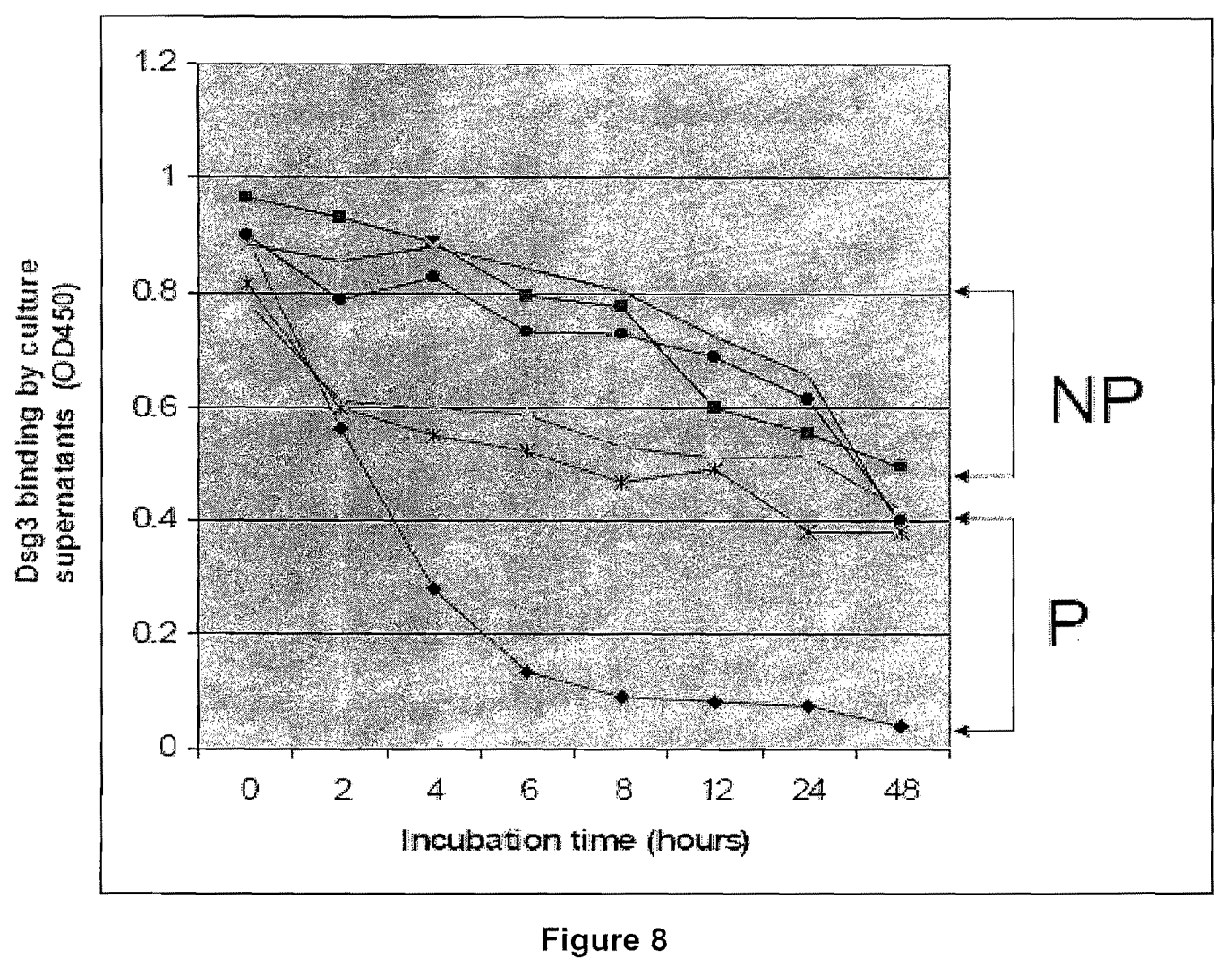

FIG. 8 is an image demonstrating that pathogenic monoclonal antibodies are rapidly cleared relative to non-pathogenic monoclonal antibodies from keratinocyte culture supernatants.

FIG. 9 shows that both Dsg3 and desmoplakin (DP) exhibit a diffused pattern of ER/cytoplasmic staining when cultured in the presence of low calcium media. However, Dsg3 and DP localize to the cell membrane when the cells are cultured in the presence of high calcium media.

FIG. 13 is an image depicting representative sequences that demonstrate the presence and absence of consensus CDR3 sequences in pathogenic and nonpathogenic antibodies. The consensus sequence shared among the pathogenic antibodies reside in the CDR3 region of the antibody is shown in red.

FIG. 14, comprising FIGS. 14A through 14C, is a series of charts showing representative scFvs. FIG. 14A is a chart depicting the makeup of anti-Dsg scFv clones, including the desmoglein specificity, heavy chain identifier, and light chain identifier. FIG. 14B is a chart depicting the identification of each heavy chain and light chain to the corresponding sequence identifier. FIG. 14C is a chart depicting the nucleic acid (SEQ ID NOs 1-73) and amino acid (SEQ ID NOs 74-146) sequence of the representative heavy and light chains.

DETAILED DESCRIPTION OF THE INVENTION

Figure 1:
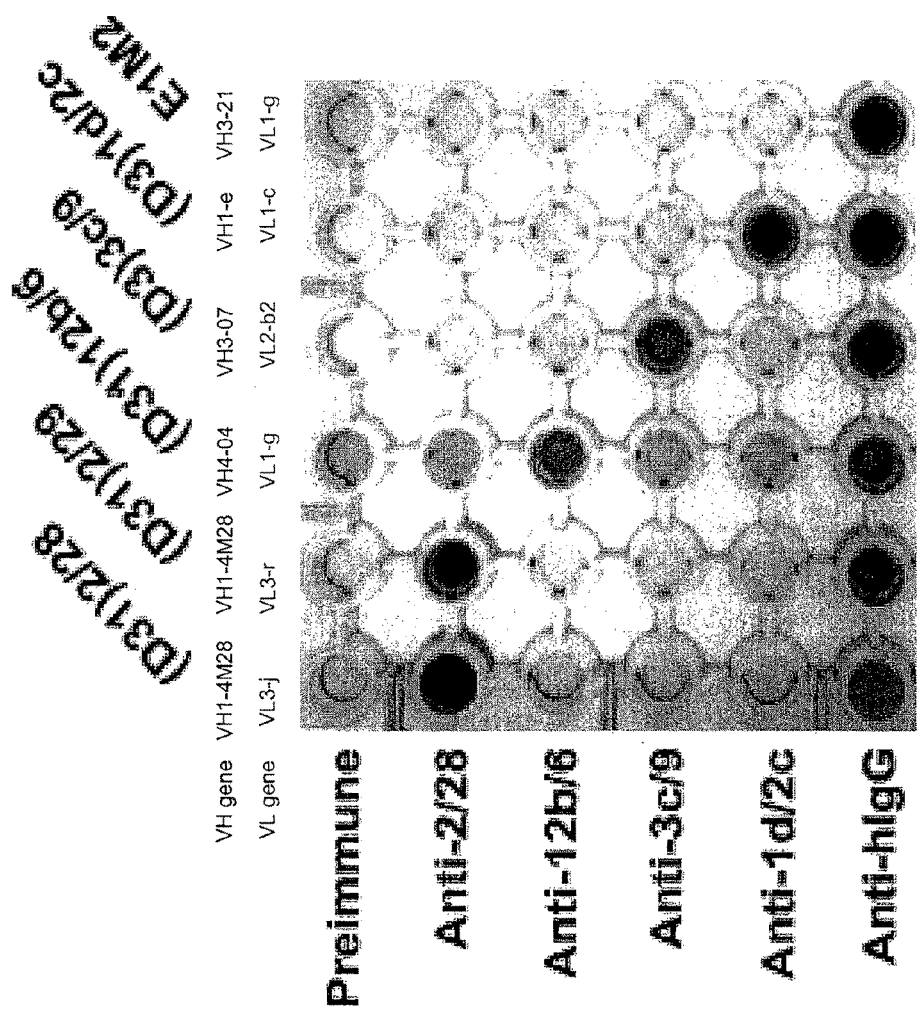
FIG. 1 is an image demonstrating the binding of PV mAbs by anti-idiotype antisera. Recombinant PV monoclonal IgG or E1M2 negative control IgG (an anti-red blood cell antibody) were adsorbed directly to ELISA plates and incubated with dilutions of preimmune sera or anti-idiotype antisera (1:1000), followed by development with HRP-coupled anti-rabbit IgG. The bottom row was incubated only with HRP-coupled anti-human IgG as a control for IgG adsorption to the plate.

The present invention provides an anti-autoimmune reagent capable of binding to an antibody associated with a disease. A non-limiting antibody associated with a disease is an anti-desmoglein antibody.

The present invention includes anti-desmoglein antibodies (e.g., pathogenic or non pathogenic) as well as compositions and methods of identifying an anti-autoimmune reagent capable of binding to the anti-desmoglein antibody.

The invention also includes compositions and methods for modulating anti-desmoglein pathogenic antibodies using an inhibitor of anti-desmoglein pathogenic antibodies. The inhibitor of anti-desmoglein pathogenic antibodies is able to alleviate the pathology associated with an anti-desmoglein pathogenic antibody. In one aspect, the inhibitor is able to specifically bind to an anti-desmoglein pathogenic antibody and inhibit the biological activity of the anti-desmoglein pathogenic to antibody. Inhibition of anti-desmoglein pathogenic antibodies can be achieved on the protein level, for example by contacting the pathogenic antibody with a binding partner. The binding partner can sequester, inhibit activity, or prevent the pathogenic antibody from otherwise binding to its cognate binding partner. For example, the pathogenic antibody can be inhibited with an anti-idiotypic antibody or a peptide (or other small molecule) that is capable of binding to the pathogenic antibody and inhibiting the biological activity of the pathogenic antibody.

In another aspect, the inhibition of the pathogenic antibody can be achieved at the genetic level. For example, inhibition of the pathogenic desmoglein reactive antibody can be achieved by inhibiting gene expression using for example small interfering RNA (siRNA), a microRNA, an antisense nucleic acid, a ribozyme, a polyamide, a triple-helix-forming agent, a synthetic peptide nucleic acids (PNAs), an agRNA, a LNA/DNA copolymer, and any combination thereof.

The invention includes any method capable of inhibiting the biological activity of pathogenic desmoglein reactive antibodies. For example, any method of negatively regulating the expression or activity of the pathogenic desmoglein antibody, including but not limited to transcription of the pathogenic antibody mRNA, stability of the pathogenic antibody mRNA, translation of the pathogenic antibody mRNA, stability of the pathogenic antibody, post-translational modifications of the pathogenic antibody, or any combination thereof, is encompassed in the invention.

This invention relates in one embodiment to compositions and methods for the use of an anti-idiotypic antibody, peptide, or small molecule that is specific against an autoantibody whereby the autoantibody is responsible for pemphigus vulgaris and pemphigus foliaceus or both conditions.

The invention also provides a method of using an autoantibody associated with a disease or condition to screen peptides or other small molecules for specific binding to the disease associated autoantibodies. Preferably, the autoantibody associated with a disease or condition is an anti-desmoglein antibody. Accordingly, the invention also provides an anti-autoimmune reagent capable of binding to an autoantibody, for example an anti-desmoglein antibody. In some instances, the anti-autoimmune reagent is an antibody that can bind to a desired autoantibody. In another aspect, the anti-autoimmune reagent is a peptide or a small molecue that can bind to a desired autoantibody.

The anti-autoimmune reagents of the invention are at least useful for targeting a B cell by way of contacting the anti-autoimmune reagent with the desired autoantibody (e.g., an anti-desmoglein antibody) expressed on a B cell.

The invention also includes the use of the anti-autoimmune reagents for diagnosing the pathology of pemphigus. In one aspect, the anti-autoimmune reagents are able to specifically bind to pathogenic antibodies and therefore reduce the number of false positive identification of pemphigus patients. This is because in some instances, the anti-autoimmune reagents of the present invention are more specific to pathogenic antibodies than the prior art reagents.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

The articles "a" and "an" are used herein to refer to one or to more than one (i.e., to at least one) of the grammatical object of the article. By way of example, "an element" means one element or more than one element.

The term "about" as used herein means in quantitative terms plus or minus 5%, or in another embodiment plus or minus 10%, or in another embodiment plus or minus 15%, or in another embodiment plus or minus 20%.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Some antibodies are typically tetramers of immunoglobulin molecules. The antibodies in the present invention may exist in a variety of forms including, for example, is polyclonal antibodies, monoclonal antibodies, chimeric, hybrid, Fv, Fab and $F(ab)_2$, as well as single chain antibodies, primatized, and humanized antibodies. Antibody fragments refer to antigen-binding immunoglobulin peptides which are at least about 5 to about 15 amino acids or more in length, and which retain the capacity to bind to the antigen. (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, an "autoantibody" or an "autoimmune antibody" is an antibody produced by the immune system that is directed against one or more of the host's own proteins. Autoantibodies may be produced by a host's immune system when it fails to distinguish between "self" and "non-self" proteins. Usually the immune system is able to discriminate by recognizing foreign substances ("non-self") and ignoring the host's own cells ("self"). When the immune system ceases to recognize one or more of the host's normal constituents as "self", it may produce to autoantibodies that attack its own cells, tissues, and/or organs.

As used herein, an "anti-autoimmune reagent" refers to an agent that is capable of binding to an autoimmune antibody. An example of an autoimmune antibody is an anti-desmoglein antibody. Therefore, an anti-autoimmune reagent can be any agent that can bind to an anti-desmoglein antibody. In some instances, the anti-autoimmune reagent is an antibody that can bind to an anti-desmoglein antibody. In another aspect, the anti-autoimmune reagent is a peptide, polypeptide or other small molecule that can bind to an anti-desmoglein antibody.

By the term “Fab/phage” as used herein, is meant a phage particle which expresses the Fab portion of an antibody.

By the term “scFv/phage” as used herein, is meant a phage particle which expresses the Fv portion of an antibody as a single chain.

“Phage,” or “phage particle,” as these terms are used herein, include bacteriophage that contain phage nucleic acid encoding, inter alia, an antibody. This is because, as would be appreciated by the skilled artisan, unlike peptide phage display (where the peptide DNA insert is small and it is actually cloned into the phage DNA), the larger scFv or Fab DNA inserts are actually cloned into, among other things, a plasmid. Thus, the nucleic acid encoding the antibody, e.g., a plasmid such as, but not limited to, pComb3X, not only comprises a plasmid origin of replication, but also a phage (e.g., M13) origin of replication sequence and an M13 packaging sequence, so that when the nucleic acid is produced, a helper phage can be used to provide the required phage (e.g., M13) proteins in trans to make “phage-like” particles. That is, these particles resemble phage on the outside, but on the inside they contain plasmid (also referred to as a “phagemid”) DNA. In other words, the phagemid DNA need not encode any M13 phage proteins, except a piece of M13 gene III fused to the DNA for antibody or peptide. Thus, it should be understood that the terms “phage,” “phage particle,” “phage-like particle” and “phagemid” are used interchangeably herein.

As used herein, to “alleviate” a disease, disorder or condition means reducing the severity of one or more symptoms of the disease, disorder or condition.

“Derivative” in the context of proteins and peptides includes any purposefully generated amino acid sequence that in its entirety, or in part, comprises a substantially similar amino acid sequence to a desired protein. The term derivative can also be applied to the antibodies described herein such that “derivative” includes any purposefully generated peptide, which in its entirety, or in part, comprises a substantially similar amino acid sequence to an anti-desmoglein antibody or an anti-idiotypic antibody that is capable of specifically bindng to an anti-desmoglein antibody. Derivatives of the antibodies may be characterized by single or multiple amino acid substitutions, deletions, additions, or replacements. Derivatives may include: (a) derivatives in which one or more amino acid residues are substituted with conservative or non-conservative amino acids; (b) derivatives in which one or more amino acids are added; (c) derivatives in which one or more of the amino acids of the amino acid sequence includes a substituent group; (d) derivatives in which amino acid sequences or a portion thereof is fused to another peptide (e.g., serum albumin or protein transduction domain); (e) derivatives in which one or more nonstandard amino acid residues (e.g., those other than the 20 standard L-amino acids found in naturally occurring proteins) are incorporated or substituted into the amino acid sequences; (f) derivatives in which one or more non-amino acid linking groups are incorporated into or replace a portion of the amino acids; and (g) derivatives in which one or more amino acid is modified by glycosylation, acetylation, myristoylation, and the like.

“Immunization” is the process of administering an immunogenic composition and stimulating an immune response to an antigen in a host (i.e., rodents and rabbits). Preferred hosts are mammals, such as primates (e.g., humans) as well as veterinary animals and agricultural animals. An “immunogen” is an immunogenic composition used to immunized the host. “Immunogen” also refers to a substance that is able to stimulate or induce a humoral antibody and/or cell-mediated immune response in a mammal. In some instances, the immunogen comprises an anti-desmoglein pathogenic antibody or any fragment thereof.

An “immune response” refers to the activities of the immune system, including activation and proliferation of specific cytotoxic T-cells and B-cells resulting in antigen-specific antibody production, after contact with an antigen.

The term “expression” as used herein is defined as the transcription and/or translation of a particular nucleotide sequence driven by its promoter.

The term “expression vector” as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

As used herein, the term “fragment,” as applied to a nucleic acid, refers to a subsequence of a larger nucleic acid. A “fragment” of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between).

As used herein, the term “fragment,” as applied to a protein or peptide, refers to a subsequence of a larger protein or peptide. A “fragment” of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

As used herein, the terms “gene” and “recombinant gene” refer to nucleic acid molecules comprising an open reading frame encoding a polypeptide. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins from other species (homologs), which have a nucleotide sequence which differs from that of the human proteins described herein are within the scope of the invention. Nucleic acid molecules corresponding to natural allelic variants and homologs of a cDNA of the invention can be isolated based on their identity to human nucleic acid molecules using the human cDNAs, or a portion thereof, as a hybridization probe according to standard hybridization techniques under stringent hybridization conditions.

An “isolated nucleic acid” refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a is genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

As used herein, the term "modulate" is meant to refer to any change in biological state, i.e. increasing, decreasing, and the like. For example, the term "modulate" refers to the ability to regulate positively or negatively the expression or activity of, for example, an anti-desmoglein pathogenic antibody, including but not limited to transcription of the desired anti-desmoglein pathogenic antibody mRNA, stability of the desired anti-desmoglein pathogenic antibody mRNA, translation of the desired anti-desmoglein pathogenic antibody mRNA, stability of the desired anti-desmoglein pathogenic antibody polypeptide, post-translational modifications of the desired anti-desmoglein pathogenic antibody, or any combinations thereof. Further, the term modulate can be used to refer to an increase, decrease, masking, altering, overriding or restoring of activity of an anti-desmoglein pathogenic antibody.

A "portion" of a polynucleotide means at least about twenty sequential nucleotide residues of the polynucleotide. It is understood that a portion of a polynucleotide may include every nucleotide residue of the polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides. Conventional notation is used herein to portray polypeptide sequences: the left-hand end of a polypeptide sequence is the amino-terminus; the right-hand end of a polypeptide sequence is the carboxyl-terminus. As used herein the term polypeptide is mutually inclusive of the terms "peptides" and "proteins".

A "recombinant polypeptide" is one which is produced upon expression of a recombinant nucleic acid.

By the term "specifically binds," as used herein, is meant a compound, e.g., a protein, a nucleic acid, an antibody, and the like, which recognizes and binds a specific molecule, but does not substantially recognize or bind other molecules in a sample.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

As used herein, to "treat" means reducing the frequency with which symptoms of a disease, disorder, or adverse condition, and the like, are experienced by a patient. Such non-limiting conditions include bona fide illness as well as cosmetic or other conditions for example removal of unwanted hair or treating baldness where hair growth is desired.

A molecule (e.g., a ligand, a receptor, an antibody, and the like) "specifically binds with" or "is specifically immunoreactive with" another molecule where it binds preferentially with the compound and does not bind in a significant amount to other compounds present in the sample.

As used herein, a "therapeutic agent" is a molecule or atom, which is conjugated to an anti-autoimmune reagent to produce a conjugate which is useful for therapy. Examples of therapeutic agents include drugs, toxins, enzymes, hormones, cytokines, immunomodulators, anti-tumor agents, chemotherapeutic agents, anti-cell proliferation agents, boron compounds, and therapeutic radioisotopes.

DESCRIPTION OF THE INVENTION

The ability of the immune system to discriminate between "self" and "non-self" antigens is vital to the functioning of the immune system as a specific defense against invading microorganisms. "Non-self" antigens are those antigens on substances entering or present in the body which are detectably different or foreign from the animal's own constituents, whereas "self" antigens are those which, in the healthy animal, are not detectably different or foreign from its own constituents. However, under certain conditions, including in certain disease states, an individual's immune system will identify its own constituents as "non-self," and initiate an immune response against "self" material, at times causing more damage or discomfort as from an invading microbe or foreign material, and often producing serious illness in an individual. Autoimmune disease results when an individual's immune system attacks his own organs or tissues, producing a clinical condition associated with the destruction of that organ or tissue. Pemphigus is an autoimmune blistering disease of the skin in one embodiment, or the mucous membranes in another embodiment, or both in yet another embodiment, characterized in certain embodiments by antibodies against the keratinocyte cell surface adhesion proteins desmoglein (Dsg) 1 and 3.

There are two primary forms of pemphigus, pemphigus foliaceus (PF) and pemphigus vulgaris (PV). PF is characterized in one embodiment by autoantibodies against Dsg1, which cause blistering of the skin, but not mucous membranes, due to loss of cell adhesion in the superficial epidermis. Mucosal PV is characterized in another embodiment by autoantibodies against Dsg3, which cause suprabasilar blistering of the mucous membranes. Mucocutaneous PV patients, who demonstrate both mucous membrane and skin involvement, develop in another embodiment, additional autoantibodies against Dsg1. Anti-Dsg antibodies are responsible in one embodiment, for both PV and PF, as well as in another embodiment, for the positive direct and indirect immunofluorescence tests that are the pathognomonic feature of these diseases.

Anti-Desmoglein Pathogenic Antibodies:

The present invention relates, in part, to the isolation of an anti-desmoglein pathogenic antibody. In one aspect, an anti-desmoglein pathogenic antibody can bind to Dsg3, but not to Dsg1. In another aspect, an anti-desmoglein pathogenic binds to Dsg1, but not to Dsg3. In yet another aspect, an anti-desmoglein pathogenic binds to both Dsg1 and Dsg3.

In one embodiment, antibodies are classified into different classes based on the structure of their heavy chains. These include IgG, IgM, IgA and IgE. Antibodies having the same heavy chain structure are in one embodiment, of the same "isotype". Antibodies of the same isotype having different antigenic determinants as a result of the inheritance of different alleles are referred to in another embodiment as "allotypes". Antigenic determinants found primarily (but not exclusively) in the hypervariable region of the antigen binding site of the antibody are referred to in one embodiment as "idiotypes". In another embodiment, antibodies having common or shared idiotypes are considered as members of the same idiotype.

In one embodiment, antigenic determinants on the variable regions of L chain or in another embodiment, of the H chain, which are associated with antigen-binding site of an antibody are referred to in certain embodiments as "idiotypes". In another embodiment, antibodies raised, or which react in certain embodiments against to an idiotype (idiotope) are referred to as "anti-idiotypic antibodies".

In one embodiment, the term "antibody" includes complete antibodies (e.g., bivalent IgG, pentavalent IgM) or fragments of antibodies which contain an antigen binding site in other embodiments. Such fragments include in one embodiment Fab, F(ab')$_2$, Fv and single chain Fv (scFv) fragments. In one embodiment, such fragments may or may not include antibody constant domains. In another embodiment, Fab's lack constant domains which are required for complement fixation. ScFvs are composed of an antibody variable light chain ($V_L$) linked to a variable heavy chain ($V_H$) by a flexible hinge. ScFvs are able to bind antigen and can be rapidly produced in bacteria or other systems. The invention includes antibodies and antibody fragments which are produced in bacteria and in mammalian cell culture. An antibody obtained from a bacteriophage library can be a complete antibody or an antibody fragment. In one embodiment, the domains present in such a library are heavy chain variable domains ($V_H$) and light chain variable domains ($V_L$) which together comprise Fv or scFv, with the addition, in another embodiment, of a heavy chain constant domain ($C_{H1}$) and a light chain constant domain ($C_L$). The four domains (i.e., $V_H$-$C_{H1}$ and $V_L$-$C_L$) comprise an Fab. Complete antibodies are obtained in one embodiment, from such a library by replacing missing constant domains once a desired $V_H$-$V_L$ combination has been identified.

Antibodies of the invention can be monoclonal antibodies (mAb) in one embodiment, or polyclonal antibodies in another embodiment. Antibodies of the invention which are useful for the compositions, methods and kits of the invention can be from any source, and in addition may be chimeric. In one embodiment, sources of antibodies can be from a mouse, or a rat, a plant, or a human in other embodiments. Antibodies of the invention which are useful for the compositions, and methods of the invention have reduced antigenicity in humans (to reduce or eliminate the risk of formation of anti-human antibodies), and in another embodiment, are not antigenic in humans. Chimeric antibodies for use the invention contain in one embodiment, human amino acid sequences and include humanized antibodies which are non-human antibodies substituted with sequences of human origin to reduce or eliminate immunogenicity, but which retain the antigen binding characteristics of the non-human antibody.

In one embodiment, not all anti-Dsg antibodies cause PV or PF. In another embodiment, epitope mapping show that the more pathogenic autoantibodies to bind the amino-terminal extracellular domain of Dsgs, which form in another embodiment, the trans-adhesive interface between cells, while less or non-pathogenic antibodies bind more membrane-proximal extracellular domains.

In another embodiment, the anti-desmoglein (Dsg) pathogenic autoantibody used in the methods and compositions provided herein, is an anti-Dsg1 autoantibody. In another embodiment the anti-desmoglein (Dsg) pathogenic autoantibody is an anti-Dsg3 autoantibody. In another embodiment the anti-desmoglein (Dsg) pathogenic autoantibody is an anti-$Dsg_1$ and anti-$Dsg_3$ autoantibody (Anti-$Dsg_{1,3}$ autoantibody). In one embodiment, the anti-desmoglein pathogenic autoantibody is pathognomonic of pemphigus vulgaris (PV), or pemphigus foliaceus (PF).

In one embodiment, the genetic analysis of cloned antibodies from the PV(1) library show a restriction of autoantibody $V_H$ gene usage, with different $V_H$ gene usage by pathogenic and non-pathogenic antibodies (Table 1). In another embodiment, PV mAb $V_H$ gene usage correlates with antibody function, with respect to Dsg antigen binding in one embodiment, or its pathogenicity in another embodiment. In one embodiment, genetic restriction in the light chain repertoire indicates functional importance (Table 2A). In one embodiment, limited genetic diversity in PV mAbs indicates it is feasible to improve the specificity and safety of pemphigus therapies by targeting the anti-Dsg antibodies, as opposed to generally suppressing the immune system.

In one embodiment, the heavy chain ($V_H$) of the anti-desmoglein pathogenic autoantibody, against which the anti-idiotypic antibodies described in the methods and compositions provided herein are used, is encoded by VH3-8, VH3-07, or VH1-4M28 genes, or the combinations thereof.

In one embodiment, the pathogenic antibodies share a conserved sequence at the amino acid level. The consensus sequence shared among the pathogenic antibodies resides in the CDR3 region of the antibody. The consensus sequence shared among the pathogenic antibodies is D/E-X-X-X-W, wherein X can represent any amino acid.

The consensus sequence of D/E-X-X-X-W identified with the pathogenic cloned antibodies represents a structural binding motif that is believed to be a candidate for targeted therapy. Without wishing to be bound by any particular theory, it is believed that the consensus sequence of D/E-X-X-X-W may mimic the desmosomal cadherin tertiary structure, thereby directly (sterically) interfering with desmosomal trans-adhesion between cells.

Thus, the invention encompasses small molecules or peptidomimetic compounds that are able to inhibit the binding of an antibody comprising the D/E-X-X-X-W consensus sequence to its target sequence. Accordingly, the invention includes inhibitors based on the peptide sequences of D/E-X-X-X-W, as well as to methods of making them.

A preferred peptide interferes with at least the activity of a pathogenic anti-desmoglein antibody mediated by the D/E-X-X-X-W consensus sequence. The skilled person is aware that a peptidomimetic compound can be made in which one or more amino acid residues is replaced by its corresponding D-amino acid, substitutions or modifications are made to one or more amino acids in the sequence, peptide bonds can be replaced by a structure more resistant to metabolic degradation and different cyclizing constraints and dimerization groups can be incorporated.

With respect to compounds in which one or more amino acids is replaced by its corresponding D-amino acid, the skilled person is aware that retro-inverso amino acid sequences can be synthesized by standard methods; see, for example, Chorev and Goodman, 1993 Acc. Chem. Res. 26: 266. Olson et al., 1993 J. Med. Chem. 36: 3039 provides an example of replacing a peptide bond with a structure more resistant to metabolic degradation.

Peptidomimetic compounds can also be made where individual amino acids are replaced by analogous structures, for example gem-diaminoalkyl groups or alkylmalonyl groups, with or without modified termini or alkyl, acyl or amine substitutions to modify their charge. The use of such alternative structures can provide significantly longer half-life in the body, since they are more resistant to breakdown under physiological conditions.

Methods for combinatorial synthesis of peptide analogs and for screening of peptides and peptide analogs are well known in the art (see, for example, Gallop et al., 1994 J. Med. Chem. 37: 1233). It is particularly contemplated that the compounds of the invention are useful as templates for design and synthesis of compounds of improved activity, stability and bioavailability. Preferably where amino acid substitution is used, the substitution is conservative, i.e. an amino acid is replaced by one of similar size and with similar charge properties. As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted amino acid in place of an unsubstituted parent amino acid.

The antibodies of the present invention include those cloned from a phage antibody library, as described in detail elsewhere herein. For example, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab or scFv fragments on their surface. Phage which display the antibody of interest are selected by antigen binding and are propagated in bacteria to produce soluble human Fab or scFv immunoglobulin. Thus, in contrast to conventional monoclonal antibody synthesis, this procedure immortalizes DNA encoding human immunoglobulin rather than cells which express human immunoglobulin.

In one aspect of the invention, the antibody comprises a heavy chain sequence selected from the amino acid sequence selection from the group consisting of SEQ ID NOs: 74-104, and any combination thereof. In another aspect, the antibody comprises a heavy chain encoded by the nucleic acid sequence selected from the group consisting of SEQ ID NOs: 1-31, and any combination thereof. In another aspect of the invention, the antibody comprises a light chain sequence selected from the amino acid sequence selection from the group consisting of SEQ ID NOs: 105-146, and any combination thereof. In another aspect, the antibody comprises a light chain encoded by the nucleic acid sequence selected from the group consisting of SEQ ID NOs: 32-73, and any combination thereof.

Using the information provided herein, the antibodies of the present invention can be produced recombinantly using standard techniques well known to those of skill in the art. For example, the sequences provided herein can be used to to identify and clone appropriate nucleic acid sequences encoding the antibodies. These nucleic acid sequences can then be used to express one or more antibodies. The nucleic acid sequence may be optimized to reflect particular codon "preferences" for various expression systems according to standard methods well known to those of skill in the art.

Using the sequence information provided herein, the nucleic acids may be synthesized according to a number of standard methods known to those of skill in the art. Oligonucleotide synthesis, is preferably carried out on commercially available solid phase oligonucleotide synthesis machines or manually synthesized using the solid phase phosphoramidite triester method described by Beaucage et. al., 1981, Tetrahedron Letts. 22:1859-1862.

Once a nucleic acid encoding an antibody is synthesized, it may be amplified and/or cloned according to standard methods in order to produce recombinant antibodies of the invention. Molecular cloning techniques to achieve these ends are known in the art. A wide variety of cloning and in vitro amplification methods suitable for the construction of recombinant nucleic acids are known to those skilled in the art. Examples of these techniques and instructions sufficient to direct the skilled artisan are found in Berger and Kimmel, Guide to Molecular Cloning Techniques, Methods in Enzymology volume 152 Academic Press, Inc., San Diego, Calif. (Berger); Sambrook et al., 2002 Molecular Cloning. A Laboratory Manual Vol. 1-3, Cold Spring Harbor Laboratory, Cold Spring Harbor Press, NY, (Sambrook). Methods of producing recombinant immunoglobulins are also known in the art. See, Cabilly, U.S. Pat. No. 4,816,567; and Queen et al., 1989 Proc. Nat'l Acad. Sci. USA Examples of techniques sufficient to direct persons of skill through in vitro amplification methods, including the polymerase chain reaction (PCR), the ligase chain reaction (LCR), and other DNA or RNA polymerase-mediated techniques are found in Berger, Sambrook, and Ausubel, as well as U.S. Pat. No. 4,683,202 and U.S. Pat. No. 5,426,039.

Once the nucleic acid encoding a desired antibody is isolated and cloned, a skilled artisan may express the recombinant gene(s) in a variety of engineered cells known to those of skill in the art. Examples of such cells include bacteria, yeast, filamentous fungi, insect (especially employing baculoviral vectors), and mammalian cells. It is expected that those of skill in the art are knowledgeable in the numerous expression systems available for expression of the desired antibodies.

For some uses, including in vivo use of antibodies in humans and in vitro detection assays, it may be preferable to use chimeric, hybrid, primatized, humanized, or human antibodies. Methods for producing chimeric and hybrid is antibodies are known in the art. See e.g., Morrison, 1985 Science 229: 1202-1207; U.S. Pat. Nos. 6,965,024, 5,807,715; 4,816, 567; and 4,816,397. Humanized antibodies are antibody molecules from non-human species that bind the desired antigen having one or more complementarity determining regions (CDRs) from the non-human species and framework regions and constant domains from a human immunoglobulin molecule. Often, framework residues in the human framework regions are substituted with the corresponding residue from the CDR donor antibody to alter and in some instances improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089. Antibodies can be humanized using a variety of techniques known in the art including, for example, CDR-grafting and chain shuffling. Humanized antibodies may be generated using any of the methods disclosed in U.S. Pat. No. 5,693,762, U.S. Pat. No. 5,693,761, U.S. Pat. No. 5,585,089, U.S. Pat. No. 6,180,370.

Screening for Anti-Autoimmune Reagents

The present invention is partly based on the identification of peptides or small molecules that bind a desired autoimmune antibody. In some instances, the autoimmune antibody is a disease associate-pathogenic antibody, for example a pathogentic anti-desmoglein antibody. Accordingly, a peptide that binds to a disease associated-pathogenic antibody is an example of an anti-autoimmune reagent. However, the invention also includes peptides or small molecules that bind to non-pathogenic antibodies.

There are several examples of methods that use peptides or nucleotides to develop libraries of potential receptor, enzyme, or antibody interacting peptides. These libraries have been incorporated into systems that allow the expression of random peptides on the surface of different phage or bacteria. The use of phage display technology to produce and screen libraries of polypeptides for binding to a selected target has been widely used. A basic concept of phage display methods is the establishment of a physical association between DNA encoding a polypeptide to be screened and the target polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means.

As discussed elsewhere herein, a phage display library was screened to identify peptides that bind to an anti-desmoglein antibody (e.g., a pathogenic anti-desmoglein antibody). Accordingly, the invention provides peptides that specifically bind pathogenic anti-desmoglein antibodies. For example, the peptide sequence for P4, P5, P7, P8, P9, P10, and P14 is set forth in SEQ ID NO: 174, 175, 176, 177, 178, 179, and 180, respectively. However, the invention should not be limited to only these peptides. Rather, the invention encompasses using any disease-associated pathogenic antibody to screen libraries of peptides or small molecules to identify therapeutic reagents. This is because the disclosure presented herein demonstrate the successful isolation of a disease-associated pathogenic antibody (e.g., pathogenic anti-desmoglein antibody) and the use of the disease-associated pathogenic antibody in a phage display library to identify peptides that bind to the disease-associated pathogenic antibody.

However, the invention also contemplates peptides and small molecules that bind to non-pathogenic antibodies. This is because a non-pathogenic can be used in the phage display library screening procedure to identify the corresponding binding molecule, and in some cases non-pathogenic antibodies when used in combination or under certain conditions may prove to cause pathology.

Inhibitors of Anti-Desmoglein Pathogenic Antibodies:

The invention provides a composition comprising an anti-autoimmune reagent. The anti-autoimmune reagent includes any agent that is capable of binding to an autoimmune antibody. In one aspect, the anti-autoimmune reagent is an antibody that binds to an autoantibody. In another aspect, the anti-autoimmune reagent is a peptide or small molecule that binds to an autoantibody. For example, the anti-autoimmune reagent binds to a pathogenic anti-desmoglein antibody.

The present invention relates to the discovery that inhibition of an anti-desmoglein pathogenic antibody provides a therapeutic benefit. Accordingly, the invention includes an inhibitor of an anti-desmoglein pathogenic antibody. In one aspect, the inhibitor is an agent capable of binding and sequestering an anti-desmoglein pathogenic antibody. In another aspect, the inhibitor can inhibit the function an anti-desmoglein pathogenic autoantibody. In yet another aspect, the inhibitor can inhibit the expression of an anti-desmoglein pathogenic antibody.

In another embodiment, the inhibitor is an anti-autoimmune reagent that is capable of binding to an anti-desmoglein pathogenic antibody. The anti-autoimmune reagent can be an antibody that binds to an anti-desmoglein pathogenic antibody whereby the anti-autoimmune reagent (e.g., an antibody) can be produced by immunizing an animal (i.e., rodents or rabbits) with an immunogen comprising anti-desmoglein pathogenic antibody or any fragment thereof.

In another embodiment, an inhibitor of an anti-desmoglein pathogenic antibody is a peptide that that is capable of binding and sequestering an anti-desmoglein pathogenic antibody. Preferably, the peptide comprises the consensus sequence of Pro-X-Ile-X-Trp-Lys (SEQ ID NO: 170), Pro-X-Leu-X-Trp-Arg (SEQ ID NO: 171), Pro-X-Ile-X-Trp-Arg (SEQ ID NO: 172), or Pro-X-Leu-X-Trp-Lys (SEQ ID NO: 173). In yet another embodiment, an inhibitor of an anti-desmoglein pathogenic antibody is a peptide comprising the amino acid sequence selected from the group of sequences set forth SEQ ID NOs: 174-180, and any combination thereof.

In one embodiment, Dsg antigens are largely conserved among subjects, with the possible exception in certain embodiments of varying Dsg3 and Dsg1 allotypes associated with disease. In one embodiment, autoantibody $V_H$ gene usage is restricted and shared among subjects and thus serves as a therapeutic target. In one embodiment, $V_H$ gene restriction in autoimmune diseases indicates that a limited number of $V_H$ genes may be able to cause disease. In another embodiment, antibody function and the binding and inhibition of anti-autoimmune reagents correlates with $V_H$ gene usage (FIG. 1 and Tables 1 and 3).

Accordingly, and in another embodiment, provided herein is an agent capable of inhibiting the expression or function of a variable region of an anti-desmoglein (anti-Dsg) pathogenic autoantibody wherein the compound is an antibody specific against the variable region of the heavy chain ($V_H$) of an anti-desmoglein pathogenic autoantibody.

Figure 2:
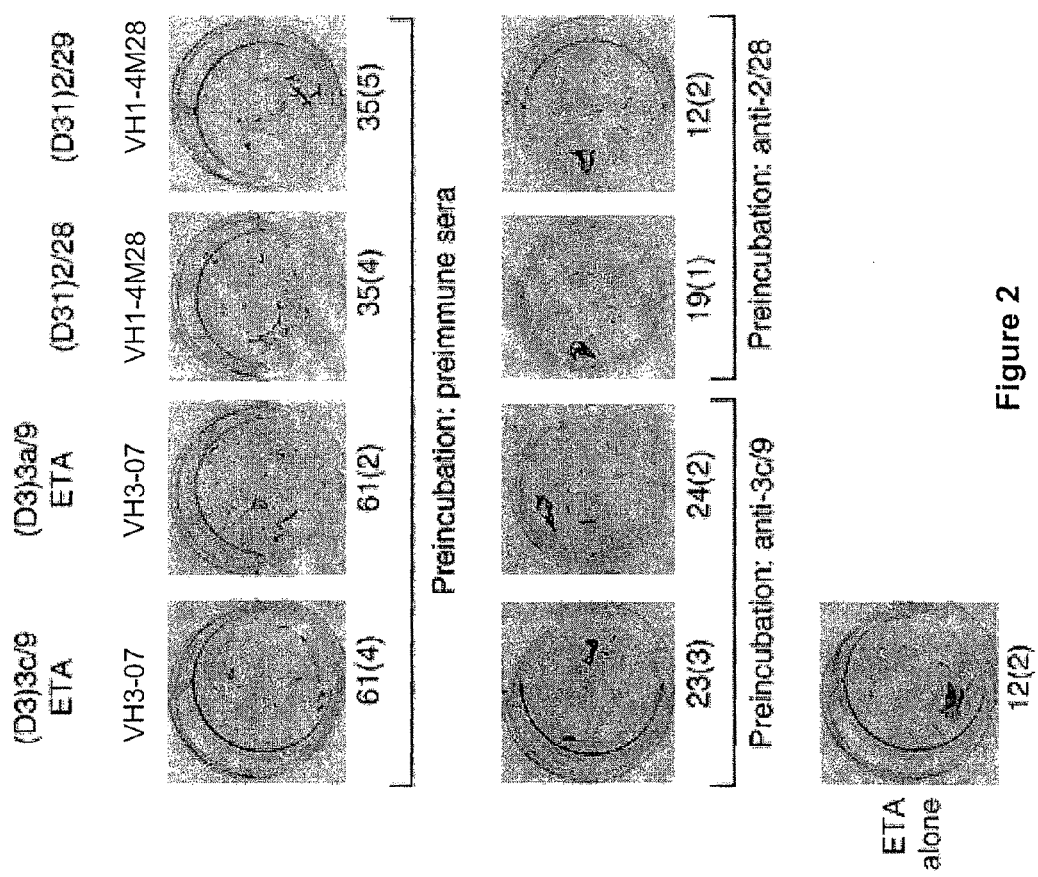
FIG. 2 is an image demonstrating that anti-idiotypic antisera inhibited pathogenicity of PV mAbs according to $V_H$ gene usage. PV mAbs were preincubated with cleared rabbit preimmune sera or antisera prior to incubation with primary human epidermal keratinocytes. ETA was added to (D3) antibody incubations at a final concentration of 1 µg/mL in order to inactivate Dsg1. Intact cell sheets were released from the cell culture plate by treatment with dispase and subjected to mechanical shear stress. The ability of rabbit antisera to inhibit cell sheet dissociation by PV mAbs was quantified by counting the resulting number of cell sheet fragments, shown as a mean (standard deviation).
Figure 4:
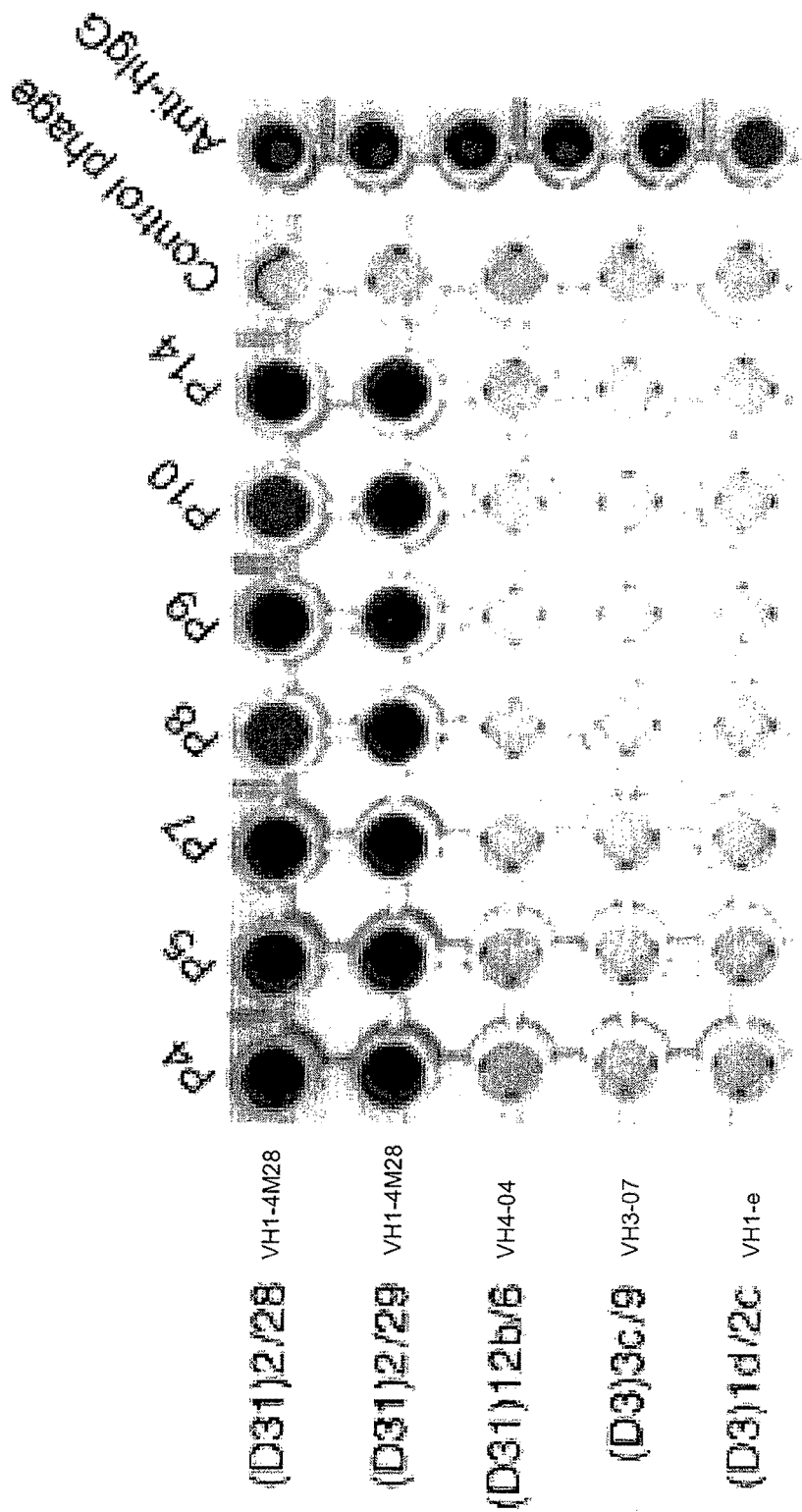
FIG. 4 is an image demonstrating that monoclonal peptide phage bound PV mAbs in a $V_H$ gene-specific manner. PV mAbs were adsorbed to plates and incubated with $10^9$ pfu of various phage-displayed peptides, followed by HRP-coupled anti-M13 secondary antibody. Control phage displayed a non-consensus peptide sequence. As a control for PV mAb adsorption to the plate, the last column was developed with HRP-coupled anti-human IgG.
Figure 5:
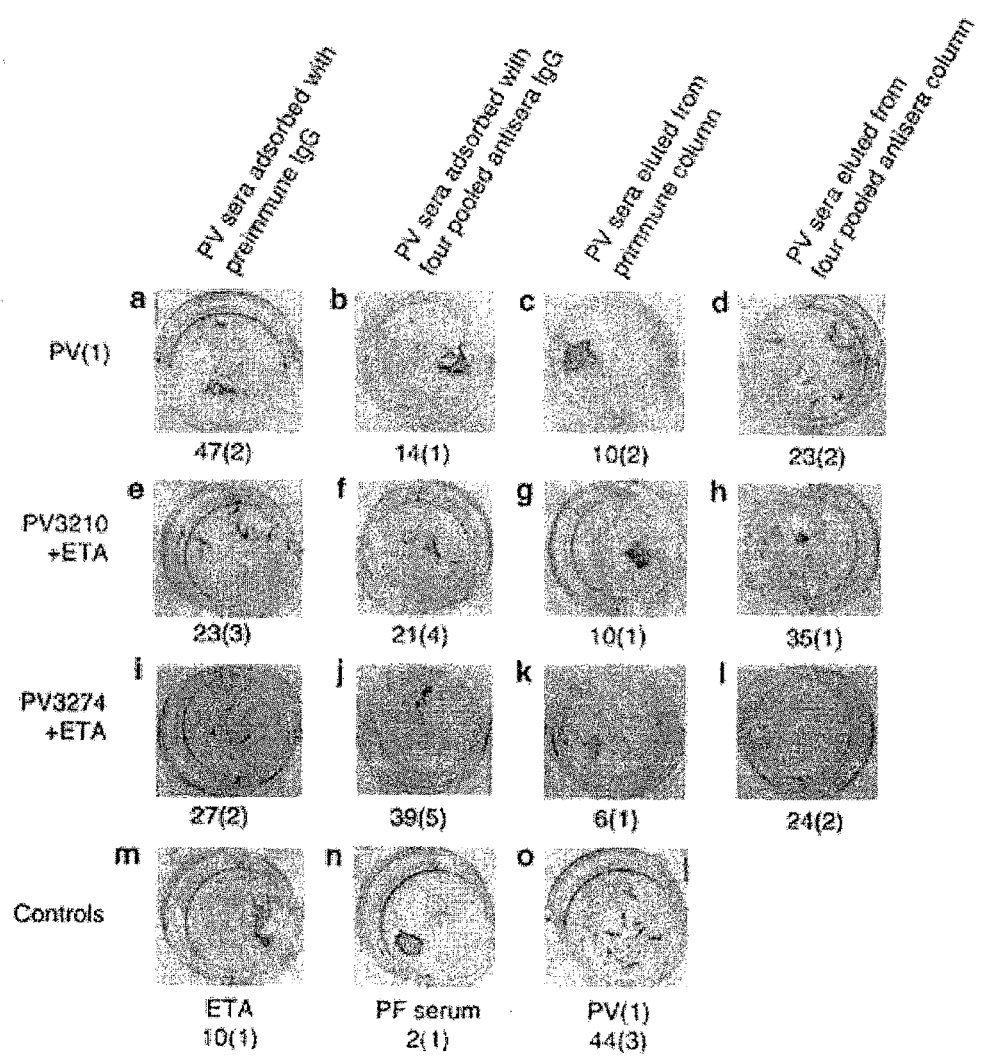
FIG. 5, comprising

In one embodiment, the binding of an anti-autoimmune reagent, for example anti-idiotypic antibodies and peptide reagents to PV mAbs correlates with $V_H$ gene usage (FIG. 1, Table 3, and FIG. 4). In another embodiment, neither different light chains nor somatic mutation of the variable region outside the CDR3 affect the binding or inhibition of anti-idiotypic antisera (FIGS. 1 and 2 and Table 3). In one embodiment, PV mAb $V_H$ genes identified by phage display represent feasible targets for therapy. These genes are VH3-8, VH3-07, or VH1-4M28 genes, or the combinations thereof. In another embodiment, certain combination of otherwise non-pathogenic anti-Dsg antibodies, still induce pathogenic reaction in the subject. Accordingly, in one embodiment PV mAb $V_H$ target gene for therapy using the compositions and methods provided herein is VH4-b, or VH3-30, VH1-e, VH4-04, VH1-46, VH1-69 or their combination in other embodiments.

In one embodiment, heavy and light chains are randomly paired during PCR construction using phage display technique. In one embodiment, the term "phage display" or "phage display technique" refers to a methodology that utilizes fusions of nucleic acid sequences encoding foreign polypeptides of interest to sequences encoding phage coat proteins, in order to display the foreign polypeptides on the surface of bacteriophage particles. In another embodiment, applications of the technology include the use of affinity interactions to select particular clones from a library of polypeptides (such as the agents provided in the compositions described herein), the members of which are displayed on the surfaces of individual phage particles. Display of the polypeptides is due in one embodiment, to expression of sequences encoding them from phage vectors into which the sequences have been inserted. In one embodiment, a library of polypeptide encoding sequences are transferred to individual display phage vectors to form a phage library that can be used in another embodiment, to screen for polypeptides of interest. In one embodiment, the agent capable of inhibiting the expression or function of a variable region of an anti-desmoglein (anti-Dsg) pathogenic autoantibody is a peptide encoding phage, or in another embodiment a phage surface protein.

In one embodiment, the term "phage surface protein" refers to any protein normally found at the surface of a bacteriophage that can be adapted to be expressed as a fusion protein with a heterologous polypeptide and still be assembled into a phage particle such that the polypeptide is displayed on the surface of the phage.

In another embodiment, the term "heterologous polypeptide" refers to a polypeptide that is not normally found as encoded by the phage from which sequences have been used to prepare a phage derived construct of the invention. Heterologous polypeptides are in one embodiment, those encoded by nucleic acid molecules or open reading frames (ORFs) found in eukaryotic or prokaryotic cells, such as in another embodiment, those from human beings, or plants, plant cells, and research organisms and animals. Non-limiting examples include bacteria, mice, rats, fruit flies, yeast, rabbits, non-human primates or zebrafish in other embodiments. Other embodiments of nucleic acid molecules are from other mammals, such as in certain embodiments, those important to agricultural applications (such as, but not limited to, cattle, sheep, horses, and other "farm animals") and for human companionship (such as, but not limited to, dogs and cats). In another embodiment, the source of nucleic acid molecules are those of pests, such as insects, weeds, fungi, viruses and unicellular organisms. In one embodiment, the nucleic acid molecules or ORFs are those encoding, or suspected of encoding, clinically relevant gene products including potential targets for the identification of drugs for PV, PF or both.

In one embodiment, a variety of different phage derived constructs may be used in the practice of the invention. In certain embodiments, the constructs of the compositions described herein, utilised in the methods provided herein, are phage genomes that have been modified to be capable of conditionally expressing a heterologous polypeptide, as a fusion protein with a phage surface protein, as discussed herein. In other embodiments, the ability to express a fusion protein is regulated in part by use of a regulated promoter or other regulatory region like an inducible promoter in one embodiment, such that in the absence of induction, expression controlled by them is low or undetectable. In one embodiment, the inducible promoter with which the expression controlled by it is low or undetectable is the lac promoter. In one embodiment, the inducible promoter with which the expression controlled by it is low or undetectable is the lac UV5 promoter. In one embodiment, the inducible promoter with which the expression controlled by it is low or undetectable is the arabinose promoter. In one embodiment, the inducible promoter with which the expression controlled by it is low or undetectable is the tet promoter.

In one embodiment, the compositions comprising a phage genome contain sequences encoding the phage gene products necessary to package an is infective phage comprising a fusion of a phage surface protein and a heterologous polypeptide. In embodiments where a construct of the invention does not encode the phage gene products necessary for phage propagation, the missing products are provided by expression of sequences present in the cell used to propagate the phage. In other embodiments, a phage comprising the agents described herein contains sequences from a non-phage vector to assist in the propagation and manipulation of the nucleic acid molecule. Selection of appropriate vectors, including phage based vectors, for propagation or transfer of nucleic acids is well known in the art. The requisite techniques for vector construction, introduction of the vector into the host, and propagation or expression in the host are routine to those skilled in the art.

In one embodiment, linear peptide sequences that specifically bind pathogenic PV mAbs (FIGS. 3 and 4) are identified. For example, the peptide sequence for P4 is set forth in SEQ ID NO: 174; the peptide sequence for P5 is set forth in SEQ ID NO: 175; the peptide sequence for P7 is set forth in SEQ ID NO: 176; the peptide sequence for P8 is set forth in SEQ ID NO: 177; the peptide sequence for P9 is set forth in SEQ ID NO: 178; the peptide sequence for P10 is set forth in SEQ ID NO: 179; the peptide sequence for P14 is set forth in SEQ ID NO: 180.

In another embodiment, the identified sequences, similar in another embodiment to the anti-idiotype antisera, are $V_H$-specific in their binding of PV mAbs. In one embodiment, the consensus peptide sequence includes a tryptophan residue (FIG. 4). Surprisingly, membrane distal tryptophan residues form a critical part of the trans-adhesive interface between cells for the classical cadherins, whose extracellular domain structures have been determined. However, the consensus sequence identified does not correlate with any linear sequence in human Dsgs 1-4 or human desmocollins 1-3. In another embodiment, peptide phage displaying the consensus sequence does not demonstrate specific binding directly to Dsg3 by ELISA, and in yet another embodiment, injection of peptides into normal human skin does not result in any tissue pathology In one embodiment, the peptide sequences identified do not mimic the desmosomal cadherin adhesive interface. In one embodiment, the peptide sequences identified encode sequences for direct binding of specific $V_H$ genes. In another embodiment, the identified sequences are modified to optimize pathogenic antibody adsorption from PV sera. In one embodiment, the sequences identified are used to construct a siRNA, or polyamides, triple-helix-forming agents, antisense RNA, synthetic peptide nucleic acids (PNAs), agRNA, LNA/DNA copolymers, small molecule chemical compounds, or a combination thereof in other embodiments, which are capable of inhibiting the expression of the variable region of an anti-desmoglein (anti-Dsg) pathogenic autoantibody.

Accordingly and in another embodiment, the compositions described herein and which are used in the methods provided herein comprise an agent capable of inhibiting the expression or function of a variable region of an anti-desmoglein (anti-Dsg) pathogenic autoantibody is a peptide encoding phage, or in another embodiment a phage surface protein, wherein the phage surface protein comprises a nucleic acid encoding an amino acid sequence represented by Pro-X-Ile-X-Trp-Lys (SEQ ID NO: 170). In another embodiment, the phage surface protein comprises a nucleic acid encoding an amino acid sequence represented by Pro-X-Leu-X-Trp-Arg (SEQ ID NO: 171). In one embodiment, the phage surface protein comprises a nucleic acid encoding an amino acid sequence represented by Pro-X-Ile-X-Trp-Arg (SEQ ID NO: 172). In one embodiment, the phage surface protein comprises a nucleic acid encoding an amino acid sequence represented by Pro-X-Leu-X-Trp-Lys (SEQ ID NO: 173). In one embodiment, the phage surface protein comprises a nucleic acid encoding an amino acid sequence represented by the combination of Pro-X-Ile-X-Trp-Lys (SEQ ID NO: 170), Pro-X-Leu-X-Trp-Arg (SEQ ID NO: 171), Pro-X-Ile-X-Trp-Arg (SEQ ID NO: 172), and Pro-X-Leu-X-Trp-Lys (SEQ ID NO: 173).

In one embodiment, the agent used in the compositions provided herein, which are utilized in the methods provided herein, is capable of inhibiting the expression of a nucleotide sequence encoding the heavy chain ($V_1$) of an anti-desmoglein autoantibody. In another embodiment, the nucleotide sequence to be inhibited is selected from the group consisting of the sequence set forth in SEQ ID NOs: 1-31, and any combination thereof.

In another one embodiment, the agent used in the compositions provided herein, which are utilized in the methods provided herein, is capable of inhibiting the expression of a nucleotide sequence encoding the light chain ($V_L$) of an anti-desmoglein autoantibody. In another embodiment, the nucleotide sequence to be inhibited is selected from the group consisting of the sequence set forth in SEQ ID NOs: 32-73, and any combination, thereof.

In one embodiment, the terms "nucleotide" or "oligonucleotide" refers to a molecule comprised of two or more deoxyribonucleotides or ribonucleotides, or in another embodiment, more than three. In one embodiment, the exact size will of the nucleotide depends on many factors, which in turn depend on the ultimate function or use of the nucleotide. The nucleotide may is derived in one embodiment synthetically or in another embodiment, by cloning.

In one embodiment, the nucleotide has at least 85% homology to the nucleotide sequence selected from the group consisting of the sequence set forth in SEQ ID NOs. 1-73, and any combination thereof. In one embodiment, the terms "homology", "homologue" or "homologous", indicate that the sequence referred to, whether an amino acid sequence, or a nucleic acid sequence, exhibits, in one embodiment at least 70% correspondence with the indicated sequence. In another embodiment, the amino acid sequence or nucleic acid sequence exhibits at least 72% correspondence with the indicated sequence. In another embodiment, the amino acid sequence or nucleic acid sequence exhibits at least 75% correspondence with the indicated sequence. In another embodiment, the amino acid sequence or nucleic acid sequence exhibits at least 80% correspondence with the indicated sequence. In another embodiment, the amino acid sequence or nucleic acid sequence exhibits at least 82% correspondence with the indicated sequence. In another embodiment, the amino acid sequence or nucleic acid sequence exhibits at least 85% correspondence with the indicated sequence. In another embodiment, the amino acid sequence or nucleic acid sequence exhibits at least 87% correspondence with the indicated sequence. In another embodiment, the amino acid sequence or nucleic acid sequence exhibits at least 90% correspondence with the indicated sequence. In another embodiment, the amino acid sequence or nucleic acid sequence exhibits at least 92% correspondence with the indicated sequence. In another embodiment, the amino acid sequence or nucleic acid sequence exhibits at least 95% or more correspondence with the indicated sequence. In another embodiment, the amino acid sequence or nucleic acid sequence exhibits at least 97% correspondence with the indicated sequence. In another embodiment, the amino acid sequence or nucleic acid sequence exhibits at least 99% correspondence with the indicated sequence. In another embodiment, the amino acid sequence or nucleic acid sequence exhibits 95%-100% correspondence with the indicated sequence. Similarly, as used herein, the reference to a correspondence to a particular sequence includes both direct correspondence, as well as homology to that sequence as herein defined.

In another embodiment, homology refers to sequence identity, or in yet another embodiment, may refer to structural identity, or functional identity. By using the term "homology" and other like forms, it is to be understood that any molecule, whether nucleic acid or peptide, that functions similarly, and/or contains sequence identity, and/or is conserved structurally so that it approximates the reference sequence, is to be considered as part of this invention.

Protein and/or peptide homology for any peptide sequence listed herein may be determined by immunoblot analysis, or via computer algorithm analysis of amino acid sequences, utilizing any of a number of software packages available, via methods well known to one skilled in the art. Some of these packages may include the FASTA, BLAST, MPsrch or Scanps packages, and may employ the use of the Smith and Waterman algorithms, and/or globaUlocal or BLOCKS alignments for analysis, for example.

In one embodiment, the agent used in the compositions described herein, which are utilized in the methods provided herein, is a siRNA. In another embodiment, the agent capable of inhibiting the expression of the variable region of an anti-desmoglein (anti-Dsg) pathogenic autoantibody is a polyamide. In another embodiment, the agent capable of inhibiting the expression of the variable region of an anti-desmoglein (anti-Dsg) pathogenic autoantibody is a triple-helix-forming agent. In another embodiment, the agent capable of inhibiting the expression of the variable region of an anti-desmoglein (anti-Dsg) pathogenic autoantibody is an antisense RNA. In another embodiment, the agent capable of inhibiting the expression of the variable region of an anti-desmoglein (anti- Dsg) pathogenic autoantibody is a synthetic peptide nucleic acids (PNAs). In another embodiment, the agent capable of inhibiting the expression of the variable region of an anti-desmoglein (anti-Dsg) pathogenic autoantibody is an agRNA. In another embodiment, the agent capable of inhibiting the expression of the variable region of an anti-desmoglein (anti-Dsg) pathogenic autoantibody is a LNA/DNA copolymer. In another embodiment, the agent capable of inhibiting the expression of the variable region of an anti-desmoglein (anti-Dsg) pathogenic autoantibody is a small molecule chemical compounds, or a combination thereof.

In one embodiment, the term "siRNA" refers to RNA interference, which in another embodiment refers to the process of sequence-specific post-transcriptional gene silencing in animals, mediated by short interfering RNAs (siRNAs). In another embodiment, the process of post-transcriptional gene silencing is an evolutionarily-conserved cellular defense mechanism used to prevent the expression of foreign genes. Such protection from foreign gene expression evolved in one embodiment, in response to the production of double-stranded RNAs (dsRNAs) derived from viral infection or in another embodiment, from the random integration of transposon elements into a host genome via a cellular response that specifically destroys homologous single-stranded RNA of viral genomic RNA. In one embodiment, the presence of dsRNA in cells triggers the RNAi response. In one embodiment, the siRNA used in the compositions and methods provided herein interferes with the expression of a heavy chain ($V_H$) of an anti-desmoglein pathogenic autoantibody, encoded by VH3-8, VH3-07, or VH1-4M28 genes, or the combinations thereof.

In one embodiment, the term "conserved", refers to amino acid sequences comprising the peptides or nucleotides described herein, which remain in one embodiment, essentially unchanged throughout evolution, and exhibit homology among various species producing the protein.

The presence of long dsRNAs in cells stimulates, in another embodiment, the activity of a ribonuclease III enzyme referred to as dicer. Dicer is involved in one embodiment, in the processing of the dsRNA into short pieces of dsRNA known as short interfering RNAs (siRNAs). Short interfering RNAs derived from dicer activity are in another embodiment about 21 to about 23 nucleotides in length and comprise about 19 base pair duplexes. Small RNAs function in one embodiment, by base-pairing to complementary RNA or DNA target sequences. When bound to RNA, small RNAs trigger RNA cleavage in another embodiment, or translational inhibition of the target sequence in another embodiment. When bound to DNA target sequences, small interfering RNAs mediate in one embodiment, DNA methylation of the target sequence. The consequence of these events, in one embodiment, is the inhibition of gene expression, which, in another embodiment is the PV1 gene encoding the variable region of an anti-desmoglein (anti-Dsg) pathogenic autoantibody described herein. In one embodiment, the agent used for reducing the level or function of a gene encoding the variable region of an anti-desmoglein (anti-Dsg) pathogenic autoantibody, is a siRNA specific for the nucleic acid encoding the $V_H$ variable region of an anti-desmoglein (anti-Dsg) pathogenic autoantibody.

In one embodiment, the siRNA of the gene encoding the variable is region of an anti-desmoglein (anti-Dsg) pathogenic autoantibody described herein exhibits substantial complementarity to its target sequence. In another embodiment, "complementarity" refers to an oligonucleotide has a base sequence containing an at least 15 contiguous base region that is at least 70% complementary, or in another embodiment at least 75% complementary, or in another embodiment at least 80% complementary, or in another embodiment at least 85% complementary, or in another embodiment at least 90% complementary, or in another embodiment at least 95% complementary, or in another embodiment 100% complementary to an-at least 15 contiguous base region present of a target gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment, the siRNA of the gene encoding the variable region of an anti-desmoglein (anti-Dsg) pathogenic autoantibody described herein is sufficiently complimentary to its target sequence. In one embodiment, the term "Sufficiently complementary" refers to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including a basic "nucleotides"), but in which the entire complementary base sequence is capable of specifically hybridizing with another base sequence under appropriate hybridization conditions. Contiguous bases are at least about 80% in one embodiment, or at least about 90% in another embodiment, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, $2^{nd}$ ed. (Cold Spring Harbor Laboratory Press, Cold Spring Harbor, N.Y., 1989).

In one embodiment, minor groove-binding N-methylpyrrole (Py) and N-methylimidazole (Im) polyamides (peptides) uniquely recognize each of the four Watson-Crick base pairs. Antiparallel pairing of imidazole with pyrrole (Im/Py) recognizes a GC base pair, whereas in another embodiment, a Py/Py pair recognizes either an AT or TA base pair. The binding constant and sequence-specificity of the Py-Im hairpin polyamides are similar to that of a transcription factor. Therefore, many genes are silenced, in other embodiments, by competitive binding of Py-Im hairpin polyamides to their regulatory sequences. Gene expression is controlled in one embodiment, by a combination of multiple common transcription factors. In one embodiment, inhibition of gene expression through the binding of Py-Im polyamides to regulatory sequences is unique to a specific gene, and contains part of the recognition sequence of the transcription factor together with the unique flanking sequences. In another embodiment, targeting Py-Im polyamide to the coding region is more straightforward when selecting a unique sequence. In one embodiment, the agent used to silence the gene encoding the variable region of an anti-desmoglein (anti-Dsg) pathogenic autoantibody in the methods and compositions described herein, is Py-Im polyamide specific for the gene's coding region, or to regulatory sequences that is unique to the gene encoding the variable region of an anti-desmoglein (anti-Dsg) pathogenic autoantibody in another embodiment. In one embodiment, the agent used to silence the gene encoding the variable region of an anti-desmoglein (anti-Dsg) pathogenic autoantibody in the methods and compositions described herein, is a synthetic polyamide nucleic acid (PNA) specific for the coding region of the gene encoding variable region of an anti-desmoglein (anti-Dsg) pathogenic autoantibody, or to its unique regulatory sequences in another embodiment.

In one embodiment, the polyamides used in the compositions and methods described herein, which, in another embodiment are referred to as "peptide nucleic acid" (PNA) or "synthetic peptide nucleic acids", are alkylating Py-Im polyamides that show sequence-specific DNA alkylation. In another embodiment, alkylation of a template strand in the coding region of Men1, by Py-Im polyamide cyclopropylpyrroloindole (CPI) conjugates with a vinyl linker results in the production of truncated mRNA, effectively inhibiting transcription of Men1 in vitro. In one embodiment, Py-Im tetrahydro-cyclo-propabenzindolone (CBI) conjugates with indole linkers are the alkylating polyamides used as the agent capable of inhibiting the expression or function of the gene encoding the variable region of an anti-desmoglein (anti-Dsg) pathogenic autoantibody, because indole-CBI has increased chemical stability under acidic and basic conditions.

In another embodiment, oligodeoxynucleotides utilized in methods and compositions described herein inhibit cellular transcription by binding to duplex DNA to form a triple helix. Due to the possibility of long-term inhibition of the gene product, oligodeoxynucleotides that can bind duplex DNA have advantages over those that bind mRNA or proteins. These oligodeoxynucleotides are called in one embodiment, triplex forming oligonucleotides (TFOs). By using DNA-specific TFOs, the inhibition of expression of several cellular genes has been demonstrated, including the oncogene, c-myc, the human immunodeficiency virus-1, the alpha chain of the interleukin 2 receptor, the epidermal growth factor receptor, the progesterone responsive gene and the mouse insulin receptor. In one embodiment, the oligonucleotides used in the methods and compositions described herein, can bind to duplex DNA and form triple helices in a sequence-specific manner and will silence expression or function of the gene encoding the variable region of an anti-desmoglein (anti-Dsg) pathogenic autoantibody.

In one embodiment, homopyrimidine DNA strand (triplex forming oligonucleotide, TFO) can bind to a homopurine/homopyrimide DNA duplex in the major groove by forming Hoogsteen base pairs with the homopurine strand. The Hoogsteen base pairing scheme mediates sequence specific recognition of the double stranded DNA by the TFO where in one embodiment, an AT base pair is recognized by a T; and a GC base pair by a C that is protonated at $N3^+$. In another embodiment, homopurine strands specifically form a DNA triplex in which the AT base pair is contacted by an A; and the GC base pair by a G. In one embodiment, the agent capable of inhibiting the expression or function of the gene encoding the variable region of an anti-desmoglein (anti-Dsg) pathogenic autoantibody is a triple-helix-forming agent. In another embodiment, the triple-helix-forming agents are oligonucleotides. In one embodiment, oligonucleotide-mediated triplex formation prevent transcription factor binding to promoter sites and block mRNA synthesis in vitro and in vivo. In another embodiment, DNA intercalating or cross-linking agents are used to prolong oligonucleotide-duplex interactions.

In one embodiment, the term "TFO" or "triplex forming oligonucleotide" refers to the synthetic oligonucleotides of the present invention which are capable of forming a triple helix by binding in the major groove with a duplex DNA structure.

In another embodiment, the term "bases" refers to both the deoxyribonucleic acids and ribonucleic acids. The following abbreviations are used, "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill in this art would readily recognize that these bases may be modified or derivatized to optimize the methods described herein, without changing the scope of the invention.

The term "nucleic acid" as used in connection with siRNA, refers in one embodiment to a polymer or oligomer composed of nucleotide units (ribonucleotides, deoxyribonucleotides or related structural variants or synthetic analogs thereof) linked via phosphodiester bonds (or related structural variants or synthetic analogs thereof). Thus, the term refers to a nucleotide polymer in which the nucleotides and the linkages between them are naturally occurring (DNA or RNA), as well as various analogs, for example and without limitation, peptide-nucleic acids (PNAs), phosphoramidates, phosphorothioates, methyl phosphonates, 2-O-methyl ribonucleic acids, and the like. In one embodiment, the siRNAs used in the compositions and methods of the invention, are nucleic acid sequences.

In one embodiment oligomeric antisense compounds, particularly oligonucleotides, are used in modulating the function of nucleic acid molecules encoding the variable region of an anti-desmoglein (anti-Dsg) pathogenic autoantibody, ultimately modulating the amount of the pathogenic autoantibody produced. This is accomplished by providing antisense compounds which specifically hybridize with one or more nucleic acids encoding the variable region of an anti-desmoglein (anti-Dsg) pathogenic autoantibody. In one embodiment, the terms "target nucleic acid" and "nucleic acid encoding the variable region of an anti-desmoglein (anti-Dsg) pathogenic autoantibody" encompass DNA encoding the variable region of an anti-desmoglein (anti-Dsg) pathogenic autoantibody, RNA (including pre-mRNA and mRNA) transcribed from such DNA, and also cDNA derived from such RNA. The specific hybridization of an oligomeric compound with its target nucleic acid interferes in another embodiment, with the normal function of the nucleic acid. The modulation of function of a target nucleic acid by compounds which specifically hybridize to it, is referred to in one embodiment as "antisense". In one embodiment, the functions of DNA to be interfered with using the antisense oligonucleotides described herein, which are used in the methods and compositions described herein, include replication and transcription. In another embodiment, functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of the variable region of an anti-desmoglein (anti-Dsg) pathogenic autoantibody. In one embodiment, inhibition of gene expression is preferred and mRNA is a preferred target. In one embodiment, since many genes (including VH3-8, VH3-07, or VH1-4M28 genes, or the combinations thereof) have multiple transcripts, "inhibition" also includes an alteration in the ratio between gene products, such as alteration of mRNA splice products.

In one embodiment, specific nucleic acids are targeted for antisense. "Targeting" an antisense compound to a particular nucleic acid, in one embodiment, is a multistep process. The process usually begins with the identification of a nucleic acid sequence whose function is to be inhibited. This may be, for example, a cellular gene (or mRNA transcribed from the gene) whose expression is associated with a particular disorder or disease state, or a nucleic acid molecule from an infectious agent. In one embodiment, the target is a nucleic acid molecule encoding the variable region of an anti-desmoglein (anti-Dsg) pathogenic autoantibody. The targeting process also includes in another embodiment, determination of a site or sites within this gene for the antisense interaction to occur such that the desired effect, e.g., inhibition of expression of the protein such as an anti-desmoglein (anti-Dsg) pathogenic autoantibody, will result. In one embodiment, an intragenic site is the region encompassing the translation initiation or termination codon of the open reading frame (ORF) of the gene. Since, the translation initiation codon is in one embodiment 5'-AUG (in transcribed mRNA molecules; 5'-ATG in the corresponding DNA molecule), the translation initiation codon is referred to in one embodiment as the "AUG codon," the "start codon" or the "AUG start codon". In another embodiment, a minority of genes have a translation initiation codon having the RNA sequence 5'-GUG, 5'-UUG or 5'-CUG, and 5'-AUA, 5'-ACG and 5'-CUG and have been shown to function in vivo. Thus, the terms "translation initiation codon" and "start codon" encompasses in other embodiments, many codon sequences, even though the initiator amino acid in each instance is typically methionine (in eukaryotes) or formylmethionine (in prokaryotes). In another embodiment, "start codon" and "translation initiation codon" refer to the codon or codons that are used in vivo to initiate translation of an mRNA molecule transcribed from a gene encoding the variable region of an anti-desmoglein (anti-Dsg) pathogenic autoantibody, regardless of the sequence(s) of such codons.

In certain embodiments, a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer in one embodiment, to a portion of such a mRNA or gene that encompasses from about 25 to about 50 contiguous nucleotides in either direction (i.e., 5' or 3') from a translation initiation codon. In another embodiment, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," refers in one embodiment to the region between the translation initiation codon and the translation termination codon, is a region which may be targeted effectively. Other target regions include in other embodiments, the 5' untranslated region (5'UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises in one embodiment, an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region is a preferred target region in one embodiment.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be target regions in one embodiment, and are particularly useful in situations where aberrant splicing is implicated in disease, or where an overproduction of a particular mRNA splice product is implicated in disease in other embodiment, such as PV or PF. Aberrant fusion junctions due to rearrangements or deletions are also preferred targets. In one embodiment, introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect. In one embodiment, the term "hybridization" refers to hydrogen bonding, which may be Watson-Crick, Hoogsteen or reversed Hoogsteen hydrogen bonding, between complementary nucleoside or nucleotide bases. In one embodiment, adenine and thymine are complementary nucleotide bases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are used in one embodiment, as research reagents and diagnostics. In another embodiment, antisense oligonucleotides, which are able to inhibit gene expression, such as the gene encoding the variable region of an anti-desmoglein (anti-Dsg) pathogenic autoantibody, with extreme specificity, are used by those of ordinary skill to elucidate the function of particular genes. Antisense compounds are used in another embodiment, to distinguish between functions of various members of a biological pathway. Antisense modulation is, in one embodiment of the agents described in the methods and compositions described herein, being harnessed for research use.

In one embodiment, the specificity and sensitivity of antisense agents described herein, is also harnessed for therapeutic uses. Antisense oligonucleotides are employed in one embodiment, as therapeutic moieties in the treatment of disease states in animals and man. In one embodiment, antisense oligonucleotides are safely and effectively administered to humans. In one embodiment oligonucleotides are useful therapeutic modalities that can be configured to be useful in treatment regimes of cells, tissues and animals, especially humans.

In one embodiment, the term "oligonucleotide" refers to an oligomer or polymer of ribonucleic acid (RNA) or deoxyribonucleic acid (DNA) or mimetics to thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, is enhanced affinity for nucleic acid target and increased stability in the presence of nucleases.

In one embodiment, the oligonucleotides used in the methods and compositions described herein, are synthetic peptide nucleic acids (PNAs) which interact with the nucleotide sequence encoding the variable region of an anti-desmoglein (anti-Dsg) pathogenic autoantibody, in a sequence-specific manner and silence its expression or function. In another embodiment, the oligonucleotides used in the methods and compositions described herein, are locked nucleic acid (LNA), which interact with the nucleotide sequence encoding the variable region of an anti-desmoglein (anti-Dsg) pathogenic autoantibody, forming a LNA/DNA co-polymer, in a sequence-specific manner and substantially silence expression or function of the gene encoding the variable region of an anti-desmoglein (anti-Dsg) pathogenic autoantibody.

In one embodiment, the term "locked nucleic acid" (LNA) refers to a synthetic nucleic acid analogue, incorporating "internally bridged" nucleoside analogues. Synthesis of LNA, and properties thereof, have been described by a number of authors: Nielsen et al, (1997 J. Chem. Soc. Perkin Trans. 1, 3423); Koshkin et al, (1998 Tetrahedron Letters 39, 4381); Singh & Wengel (1998 Chem. Commun. 1247); and Singh et al, (1998 Chem. Commun. 455). As with PNA, LNA exhibits greater thermal stability when paired with DNA, than do conventional DNA/DNA heteroduplexes. In one embodiment, LNA can be joined to DNA molecules by conventional techniques. Therefore, in one embodiment, LNA is to be preferred over PNA, for use in the agents of the methods and compositions described herein. In another embodiment, the target specific regions of the agent that is able to inhibit gene expression of the variable region of an anti-desmoglein (anti-Dsg) pathogenic autoantibody, may comprise LNA and/or PNA and the arm region comprise DNA, with the agent further comprising a destabilizing moiety.

In another embodiment, the agent capable of inhibiting expression or function of the gene encoding the variable region of an anti-desmoglein (anti-Dsg) to pathogenic autoantibody, is an agPNA. In another embodiment, this antibody is referred to as antigenic PNA. In one embodiment, the gene encoding the variable region of an anti-desmoglein (anti-Dsg) pathogenic autoantibody, is VH3-8, VH3-07, or VH1-4M28 genes, or the combinations thereof.

In one embodiment, the agents described hereinabove are used in the compositions described herein. In another embodiment, the compositions described hereinabove are used in the methods described herein.

In one embodiment, the anti-autoimmune reagents, for example anti-idiotypic antibodies provided herein, in the methods and compositions described herein, are linked to a B-cell superantigen. In one embodiment the term "B-cell superantigen (Sag)" refers to proteins or peptides which, unlike conventional antigens, bind to the Fab regions of immunoglobulin (Ig) molecules outside their complementarity-determining regions (CDRs). However, the invention should not be limited to anti-idiotypic antibodies because any anti-autoimmune reagent is applicable. In another embodiment, B-cell Sag's can react with a substantial amount of a host's peripheral B-cells and serum Igs by virtue of their ability to interact with many members of an entire variable region heavy ($V_H$) or variable region light ($V_L$) gene family, such as in one embodiment, those encoded by VH3-8, VH3-07, or VH1-4M28 genes, or the combinations thereof. In another embodiment, Staphylococcal protein A (SpA) is the B-cell Sag used in the methods and compositions described herein. In one embodiment, B-cell Sag's trigger all B cells bearing the appropriate $V_H$ or $V_L$, regardless of the other $J_H$, D, $J_L$, and pairing with $V_H$ or $V_L$ segments. In one embodiment, B-cell Sag induce in vivo deletion of $V_H$-targeted supraclonal sets of B lymphocytes, resulting in effective long-lasting immunologic tolerance to a common antigen such as Dsg in one embodiment.

In one embodiment, the anti-autoimmune reagents, for example anti-idiotypic antibodies used in the methods and compositions provided herein, are specific against the light chain of the variable region VL. In one embodiment, VL2-a2, or in another embodiment, VL2-b2, or in another embodiment, VL3-r, or in another embodiment, VL3-j are genes encoding the variable region of an anti-desmoglein pathogenic autoantibody, which expression is inhibited using a siRNA, polyamide, triple-helix-forming agent, antisense RNA, synthetic peptide nucleic acids (PNAs), agRNA, LNA/DNA copolymers, small molecule chemical compounds, or the combinations thereof as described herein, for the methods provided described hereinabove.

In one embodiment, a combination of otherwise non-pathogenic antibodies with a light chain of variable region of an anti-desmoglein antibody, still induce a pathogenic reaction. In another embodiment, the genes encoding the light chain of the variable region of an anti-desmoglein antibody are targeted using the compositions and methods provided herein, to inhibit the expression or function of VL3h in one embodiment, or VKIII-L6, VL1-c, VL1-g, VL1-g, or the combinations thereof in other embodiments.

In one embodiment, any of the genes described in Tables I and II hereinbelow, or their encoded protein, peptidomimetics or the combinations thereof are used in certain embodiments of the anti-autoimmune reagents, for example anti-idiotypic antibodies provided herein, or in another embodiment, are the target of the siRNA, polyamide, triple-helix-forming agent, antisense RNA, synthetic peptide nucleic acids (PNAs), agRNA, LNA/DNA copolymers, small molecule chemical compounds, or the combinations thereof as described herein, for the methods provided herein.

In one embodiment, the specific antibody-targeted therapy for pemphigus aims to suppress or eliminate only the anti-Dsg autoantibodies. In another embodiment, the methods described herein target only the pathogenic autoantibodies. In one embodiment, antibodies are targeted by their idiotype. In another embodiment, antibodies are targeted based on their variable region gene usage.

In one embodiment, cloning of human PV mAbs provide novel strategies for direct antibody targeting. In another embodiment treatments using the methods provided herein, are designed based on autoantibody $V_H$ gene usage. In another embodiment, the identification of peptides that specifically bind PV mAbs (FIG. 4) indicates that the small molecule reagents described in the compositions described herein, can also discriminate among PV mAbs based on their $V_H$ gene usage. These small molecule reagents are more practical in one embodiment, than rabbit antibodies against PVmAbs for the development of therapeutic intervention strategies.

Accordingly, the invention provides a method of inhibiting the binding of a autoimmune antibody, for example a pathogenic autoimmune antibody to desmoglein (Dsg), comprising contacting the autoimmune antibodies with a composition comprising an agent capable of inhibiting the expression or function of a variable region of an anti-desmoglein pathogenic autoantibody. In another embodiment, the anti-desmoglein (Dsg) pathogenic autoantibody is an anti-Dsg1 autoantibody, an anti-Dsg3 autoantibody, or an anti-$Dsg_1$ and anti-$Dsg_3$ autoantibody (Anti-$Dsg_{1,3}$ autoantibody), which, in yet another embodiment, is pathognomonic of pemphigus vulgaris (PV), or pemphigus foliaceus (PF).

In another embodiment, provided herein is a nucleic acid sequence having at least 85% complementarity to the nucleic acid sequence selected from the group of sequence set forth in SEQ ID NOs. 1-73, and any combination thereof.

In another embodiment, provided herein is a method of inhibiting the binding of a pathogenic autoimmune antibody to desmoglein (Dsg), comprising contacting the autoimmune antibodies with a composition comprising an anti-autoimmune reagent capable of inhibiting the binding of a variable region of an anti-desmoglein pathogenic autoantibody.

In another embodiment, provided herein is a method of inhibiting the binding of a pathogenic autoimmune antibody to desmoglein (Dsg), comprising contacting a nucleotide sequence encoding a heavy chain ($V_H$) of an anti-desmoglein pathogenic autoantibody with a siRNA, a polyamide, a triple-helix-forming agent, an antisense RNA, a synthetic peptide nucleic acids (PNAs), an agRNA, a LNA/DNA copolymers, a small molecule chemical compounds, or a combination thereof capable of inhibiting the expression of the nucleotide sequence encoding the heavy chain ($V_H$) of an anti-desmoglein pathogenic autoantibody, thereby inhibiting the expression of said pathogenic autoimmune antibody to desmoglein (Dsg).

In one embodiment, the gene encoding the variable region of an anti-desmoglein (anti-Dsg) pathogenic autoantibody, is VH3-8, or VH3-07, VH1-4M28, or the combinations thereof in other embodiments.

In one embodiment, the antibody-targeted agents described in the compositions provided herein and utilized in the methods provided herein, could be coupled to columns as an adjunct for plasmapheresis to improve the efficiency of pathogenic antibody removal from subjects' sera. In another embodiment, the antibody-specific agents described in the compositions provided herein and utilized in the methods provided herein, are linked to B cell superantigens as a method of $V_H$-targeted B-cell deletion. In one embodiment, the methods provided herein offer a safer and more effective treatments for pemphigus. In another embodiment, the $V_H$ gene-targeting approach described hereinabove has implications for the treatment of other genetically restricted antibody-mediated diseases.

In one embodiment, the variable region of the heavy chain ($V_H$) of an anti-desmoglein pathogenic autoantibody of a pool of subjects is used to generate the anti autoimmune antibody. In one embodiment, the variable region of the light chain (VL) of an anti-desmoglein pathogenic autoantibody of a pool of subjects is used to generate the anti autoimmune antibody. In one embodiment, the gene encoding the variable region of the heavy chain ($V_H$) of an anti-desmoglein pathogenic autoantibody, is VH3-8, VH3-07, or VH1-4M28 genes, or the combinations thereof. In another embodiment, the variable region of the light chain ($V_L$) of an anti-desmoglein autoantibody used to generate the anti autoimmune antibody is encoded by VL3h, or in another embodiments, by VKIII-L6, VL1-c, VL1-g, VL1-g, VL2-a2, VL2-b2, VL3-r, VL3-j or the combinations thereof.

In one embodiment, provided herein is a method of treating an autoimmune pathology associated with desmoglein in a subject, comprising the step of contacting a biological sample of the subject with a composition comprising an agent capable of inhibiting the expression or function of a variable region of an anti-desmoglein pathogenic autoantibody. In another embodiment, the anti-desmoglein (Dsg) pathogenic autoantibody, which in yet another embodiment is pathognomonic of pemphigus vulgaris (PV), or pemphigus foliaceus (PF), is an anti-Dsg1 autoantibody, an anti-Dsg3 autoantibody, or an anti-$Dsg_1$ and anti-$Dsg_3$ autoantibody (Anti-$Dsg_{1,3}$ autoantibody).

In another embodiment, the anti-autoimmune reagent used in the methods and compositions described herein, is linked to a B cell superantigen, whereby, in another embodiment, linking the anti-autoimmune reagent, for example an anti-idiotypic antibody, to a B cell superantigen affects $V_H$-targeted B-cell deletion, resulting in deletion of B-lymphocytes encoding pathogenic anti-Dsg antibodies and self tolerance of the subject to Dsg, thereby treating pemphigus.

In one embodiment, the variable region of an anti-desmoglein pathogenic autoantibody, is encoded by VH3-8, VH3-07, or VH1-4M28 genes, or the combinations thereof.

In another embodiment, provided herein is a method of treating an autoimmune pathology associated with desmoglein in a subject, comprising contacting a nucleotide sequence of the subject, encoding a heavy chain ($V_H$) of an anti-desmoglein pathogenic autoantibody with a siRNA, a polyamide, a triple-helix-forming agent, an antisense RNA, a synthetic peptide nucleic acids (PNAs), an agRNA, a LNA/DNA copolymers, a small molecule chemical compounds, or a combination thereof capable of inhibiting the expression of the nucleotide sequence encoding the heavy chain ($V_H$) of an anti-desmoglein pathogenic autoantibody, thereby inhibiting the expression of said pathogenic autoimmune antibody to desmoglein (Dsg).

In one embodiment, the term "treatment", or "treating" refers to any process, action, application, therapy, or the like, wherein a subject, including a human being, is subjected to medical aid with the object of improving the subject's condition, directly or indirectly. The term "treating" refers also to reducing incidence, or zo alleviating symptoms, eliminating recurrence, preventing recurrence, preventing incidence, improving symptoms, improving prognosis or combination thereof in other embodiments.

In another embodiment, "treating" comprises reducing incidence, inhibiting or suppressing, whereby inhibiting the expression or function of the gene encoding the variable region of an anti-desmoglein (anti-Dsg) pathogenic autoantibody, by the agents used in the methods and compositions described herein, for the treatment of PV, PF or both, comprises lowering the level of a protein or nucleic acid regulating the expression or function of said gene, or inhibiting function of gene's encoded variable region of an anti-desmoglein (anti-Dsg) pathogenic autoantibody. In one embodiment, the agent used in the compositions and methods described herein, is an anti-autoimmune antibody, a siRNA, polyamides, triple-helix-forming agents, antisense RNA, synthetic peptide nucleic acids (PNAs), agRNA, LNAJDNA copolymers, small molecule chemical compounds, or a combination thereof.

"Treating" embraces in another embodiment, the amelioration of an existing condition. The skilled artisan would understand that treatment does not necessarily result in the complete absence or removal of symptoms. Treatment also embraces palliative effects: that is, those that reduce the likelihood of a subsequent medical condition. The alleviation of a condition that results in a more serious condition is encompassed by this term. Therefore, in one embodiment, the invention provides a method of treating pemphigus in a subject, of either PV or PF, comprising the step of contacting a biological sample of said subject with an effective amount of an agent capable of inhibiting the expression or function of the gene encoding the variable region of an anti-desmoglein (anti-Dsg) pathogenic autoantibody, whereby the inhibition of expression or function that gene or its encoded proteins results in depleting a biological sample from an anti-desmoglein pathogenic antibody.

Accordingly and in one embodiment, provided herein is a method of depleting a biological sample from an anti-desmoglein pathogenic antibody, comprising contacting the sample with an immobile composition comprising an agent capable of binding to a variable region of an anti-desmoglein pathogenic autoantibody; and removing the biological sample without the bound variable region of the heavy chain ($V_H$) of an anti-desmoglein pathogenic autoantibody, thereby depleting the biological sample of anti-desmoglein (Dsg) pathogenic autoantibody. In one embodiment, depletion of the biological sample from an anti-desmoglein pathogenic antibody, is achieved using plsmapheresis.

In another embodiment, provided herein is a method of depleting a biological sample from an anti-desmoglein pathogenic antibody, comprising contacting the sample with an immobile composition comprising an anti-autoimmune reagent capable of binding to a variable region of an anti-desmoglein pathogenic autoantibody; and removing the biological sample without the bound variable region of the heavy chain ($V_H$) of an anti-desmoglein pathogenic autoantibody, thereby depleting the biological sample of anti-desmoglein (Dsg) pathogenic autoantibody. In one embodiment, the heavy chain ($V_H$) of an anti-desmoglein pathogenic autoantibody, is encoded by VH3-8, VH3-07, or VH1-4M28 genes, or the combinations thereof.

In one embodiment, provided herein, is a method of depleting a biological sample from an anti-desmoglein pathogenic antibody, comprising contacting the sample with an immobile composition comprising an anti-autoimmune reagent, for example an anti-idiotypic antibody capable of binding to a variable region of an anti-desmoglein pathogenic autoantibody; and removing the biological sample without the bound variable region of the light chain ($V_H$) of an anti-desmoglein pathogenic autoantibody, thereby depleting the biological sample of anti-desmoglein (Dsg) pathogenic autoantibody. In one embodiment, the light chain ($V_H$) of an anti-desmoglein pathogenic autoantibody, is encoded by VL2-a2, VL2-b2, VL3-r, VL3-j genes, or the combinations thereof in other embodiments.

In one embodiment, it is desirable to deplete the biological sample from all anti-Dsg antibodies, whether pathogenic or not. Accordingly and in another to embodiment, provided herein is a method of depleting a biological sample from an anti-desmoglein antibody, comprising contacting the sample with an immobile composition comprising an anti-autoimmune reagent, for example an anti-idiotypic antibody capable of binding to a variable region of an anti-desmoglein autoantibody; and removing the biological sample without the bound variable region of the anti-desmoglein autoantibody, thereby depleting the biological sample of anti-desmoglein (Dsg) autoantibody. In one embodiment, the variable region of an anti-desmoglein autoantibody, is encoded by the genes provided in tables I and II provided hereinbelow, or the combinations thereof in other embodiments.

In one embodiment, the anti-autoimmune reagents of the invention is useful in removing toxic or unwanted elements, for example, plasma constituents implicated in disease, such as complement or antibodies, from the blood of a patient. The term "plasmapheresis" refers to the separation of a portion of the plasma fraction of the blood from the cellular components thereof. In another embodiment, continuous plasmapheresis is used therapeutically to remove pathologic substances contained in the plasma portion of the blood, such as an anti-Dsg3 autoantibody, or an anti-$Dsg_1$ and anti-$Dsg_3$ autoantibody (Anti-$Dsg_{1,3}$ autoantibody) in certain embodiments. In another embodiment, continuous plasmapheresis is used therapeutically to separate the cellular components from the diseased plasma and returning the cellular components to the patient in admixture with a suitable replacement fluid, or in one embodiment, by further fractionating the patient's plasma to remove the unwanted substances, such as an anti-Dsg3 autoantibody, or an anti-$Dsg_1$ and anti-$Dsg_3$ autoantibody (Anti-$Dsg_{1,3}$ autoantibody) in certain embodiments and returning a major portion of the patient's plasma with the depleted cellular components.

In one embodiment, the plasmapheresis used to remove the autoimuune antibodies, is selective plasmapheresis. In another embodiment, the techniques used is selectively removing only the clinically undesirable plasma proteins while leaving the bulk of the remainder of the plasma components in the donor's circulation, thereby enabling extensive plasmapheresis without the need for any plasma replacement. In one embodiment the plasma fraction, after being separated from the corpuscular element fraction, is treated so as to remove one or more selected plasma proteins therefrom, such as an anti-Dsg3 autoantibody, or an anti-$Dsg_1$ and anti-$Dsg_3$ autoantibody (Anti-$Dsg_{1,3}$ autoantibody) in certain embodiments and the resulting protein-depleted plasma fraction is thereafter recombined with the corpuscular element fraction for return back into the donor's bloodstream. In one embodiment, the protein-depleted plasma fraction is obtained by passing the plasma fraction through an immunoadsorption column to cause adsorption of certain immunoglobulins and/or immune complexes. This technique provides in is another embodiment, a high degree of specificity in the profile of proteins removed. In another embodiment of a selective plasmapheresis technique utilized in conjunction with the methods and compositions provided herein, forced-flow electrophoresis is employed for separating an immunoglobulin-rich fraction from plasma on the basis of differences in electrophoretic mobility. In one embodiment, an anti-Dsg3 autoantibody, or an anti-$Dsg_1$ and anti-$Dsg_3$ autoantibody (Anti-$Dsg_{1,3}$ autoantibody) have different mobilities as compared with other desirable immunoglobulins present in the subjects' biological sample and are thus separated from the bulk.

In one embodiment, the biological sample used in the methods described herein, is blood, sera, plasma or a combination thereof.

"Therapeutic plasmapheresis" is herein meant as a method for removing toxic or unwanted elements, for example, plasma constituents implicated in disease, such as complement or autoantibodies, from the blood of a patient. In one embodiment, the invention provides a method for removing blood from a patient, separating the plasma, filtering the unwanted elements from the plasma, such as plasma constituents implicated in disease, such as complement or autoantibodies, and reinfusing the plasma replacement back to the patient, wherein the filtering step utilizes an anti-autoimmune reagent of the invention to remove pathogenic autoantibodies from the blood sample.

In one aspect, the autoantibody and/or other immunologically active elements are removed from the blood by loading an anti-autoimmune reagent that is specific to the autoantibody and/or immunologically active elements onto a solid support or otherwise immobilized on a solid substrate to allow for separation of the autoantibody. When a sample is passed through a solid substrate containing an anti-autoimmune reagent, the anti-autoimmune reagent binds to the corresponding autoantibody, thereby removing the autoantibody from the sample. For example, beads (e.g., magnetic beads) can be coated with an anti-autoimmune reagent. The beads can easily be removed by passing the cultured cells through a magnetic column. Procedures for separation may include magnetic separation, using anti-autoimmune reagent-coated magnetic beads or dynal beads, affinity chromatography, and "panning" with antibody attached to a solid matrix, e.g., plate, or other convenient technique.

Accordingly, the invention provides a method of treating autoimmune conditions of a patient comprising filtering the patient's blood or otherwise separating a plasma constituent from the blood of the present invention and returning the cellular components back to the patient. In one aspect, the method comprises removing autoantibody from the patient's blood using anti-autoimmune reagents of the present invention.

Peptides:

In one embodiment, provided herein is an isolated nucleic acid encoding an amino acid sequence represented by Pro-X-Ile-X-Trp-Lys (SEQ ID NO: 170), Pro-X-Leu-X-Trp-Arg (SEQ ID NO: 171), Pro-X-Ile-X-Trp-Arg (SEQ ID NO: 172), or Pro-X-Leu-X-Trp-Lys (SEQ ID NO: 173). In another embodiment, provided herein are the polypeptides encoded by the isolated nucleic acid encoding an amino acid sequence represented by Pro-X-Ile-X-Trp-Lys (SEQ ID NO: 170), Pro-X-Leu-X-Trp-Arg (SEQ ID NO: 171), Pro-X-Ile-X-Trp-Arg (SEQ ID NO: 172), or Pro-X-Leu-X-Trp-Lys (SEQ ID NO: 173). In one embodiment, the invention provides a peptidomimetic compound of the peptides encoded by the isolated nucleic acid encoding an amino acid sequence represented by Pro-X-Ile-X-Trp-Lys (SEQ ID NO: 170), Pro-X-Leu-X-Trp-Arg (SEQ ID NO: 171), Pro-X-Ile-X-Trp-Arg (SEQ ID NO: 172), or Pro-X-Leu-X-Trp-Lys (SEQ ID NO: 173).

In one embodiment, the term "peptide" refers to an oligomer in which the monomers are natural amino acids (alpha-amino acids) joined together through amide bonds. in another embodiment, peptides are two or more amino acid monomers long, but more often are between 5 to 10 amino acid monomers long and even longer in other embodiments, i.e. up to 20 amino acids or more, although peptides longer than 20 amino acids are likely to be called "polypeptides." in certain embodiments The term "protein" is well known in the art and in one embodiment refers to a very large polypeptide, or set of associated homologous or heterologous polypeptides, that has some biological function. In one embodiment, the terms "peptide," "polypeptide," to and "protein" are largely interchangeable, as all three types can be synthesized by the translation system, and in another embodiment, are referred to as peptides.

The peptidomimetic compounds described herein are prepared in one embodiment, by the methods for peptide synthesis described in monographs such as ("Principles of Peptide Synthesis, M. Bodanszky, Springer-Verlag, 2nd Ed., 1993; "Synthetic Peptides: A Users Guide", G. A. Grant, Ed, W. H. Freeman and Co., 1992; and references sited therein), or by other methods generally known to one skilled in the art. In another embodiment, the term "peptidomimetic" refers to a peptide analog containing one or more unnatural amino acids (e.g. unnatural side chains, unnatural chiralities, N-substituted amino acids, or beta amino acids), unnatural topologies (e.g. cyclic or branched) or unnatural chemical derivatives (e.g. methylated or terminally blocked), or any molecule, other than a peptide containing natural amino acids, that is synthesized by a ribosome, including those products that have unnatural backbones and even those with partially or totally substituted amide (peptide) bonds with ester, thioester or other linkages.

In another embodiment, the terms "amino acid residue" and "peptide residue" refers to an amino acid or peptide molecule without the —OH of its carboxyl group (C-terminally linked) or the proton of its amino group (N-terminally linked). In general the abbreviations used herein for designating the amino acids and the protective groups are based on recommendations of the IUPAC-IUB Commission on Biochemical Nomenclature (see Biochemistry (1972) 11:1726-1732). Amino acid residues in peptides are abbreviated as follows: Alanine is Ala or A; Cysteine is Cys or C; Aspartic Acid is Asp or D; Glutamic Acid is Glu or E; Phenylalanine is Phe or F; Glycine is Gly or G; Histidine is H is or H; Isoleucine is Ile or I; Lysine is Lys or K; Leucine is Leu or L; Methionine is Met or M; Asparagine is Asn or N; Proline is Pro or P; Glutamine is Gln or Q; Arginine is Arg or R; Serine is Ser or S; Threonine is Thr or T; Valine is Val or V; Tryptophan is Trp or W; and Tyrosine is Tyr or Y. Formylmethionine is abbreviated as fMet or fM. By the term "residue" is meant a radical derived from the corresponding .alpha.-amino acid by eliminating the OH portion of the carboxyl group and the H portion of the .alpha.-amino group. The term "amino acid side chain" is that part of an amino acid exclusive of the —CH(NH.sub.2)COOH portion, as defined by K. D. Kopple, "Peptides and Amino Acids", W. A. Benjamin Inc., New York and Amsterdam, 1966, pages 2 and 33; examples of such side chains of the common amino acids are —$CH_2CH_2SCH_3$ (the side chain of methionine), —$CH_2$ ($CH_3$)—$CH_2CH_3$ (the side chain of isoleucine), —$CH_2CH(CH_3)_2$ (the side chain of leucine) or —H (the side chain of glycine).

In one embodiment, the agent capable of inhibiting the expression or function of a variable region of an anti-desmoglein (anti-Dsg) pathogenic autoantibody is a peptidomimetic encoded by the isolated nucleic acid encoding an amino acid sequence represented by Pro-X-Ile-X-Trp-Lys, or Pro-X-Leu-X-Trp-Arg. In another embodiment, provided herein is a siRNA, polyamides, triple-helix-forming agents, anti-sense RNA, synthetic peptide nucleic acids (PNAs), agRNA, LNA/DNA copolymers, small molecule chemical compounds, or a combination thereof capable of inhibiting the expression the isolated nucleic acid encoding an amino acid sequence represented by Pro-X-Ile-X-Trp-Lys, or Pro-X-

Leu-X-Trp-Arg. In one embodiment, the siRNA, polyamides, triple-helix-forming agents, antisense RNA, synthetic peptide nucleic acids (PNAs), agRNA, LNA/DNA copolymers, small molecule chemical compounds, or a combination thereof capable of inhibiting the expression of the isolated nucleic acid encoding an amino acid sequence represented by Pro-X-Ile-X-Trp-Lys, or Pro-X-Leu-X-Trp-Arg are used in the compositions and methods provided herein.

Targeting B-Cells:

Autoimmune diseases are a class of diseases associated with a B-cell disorder. Examples include including immune-mediated thrombocytopenias, such as acute idiopathic thrombocytopenic purpura and chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis multiple sclerosis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis. The most common treatments are corticosteroids and cytotoxic drugs, which can be very toxic. These drugs also suppress the entire immune system which can result in serious infection have adverse affects on the liver and kidneys. The present invention provides a method of targeting B cells using an anti-autoimmune reagent that is capable of binding to an autoantibody.

B-cell clones that bear autoantibody Ig-receptors are present in normal individuals. Autoimmunity results when these B-cells become overactive, and mature to plasma cells that secrete autoantibody. In accordance with the present invention, autoimmune disorders can be treated by administering an anti-autoimmune reagent (e.g., an antibody or polypeptide) that binds to an autoantibody present on a B-cell, such as an anti-desmoglein antibody. In one embodiment, the anti-autoimmune reagent is conjugated with to a therapeutic moiety including, but not limited to an anti-tumor agent, a chemotherapeutic agent, an anti-cell proliferation agent, a drug, a toxin, a therapeutic radioisotope, and any combination thereof.

The present invention contemplates the use of anti-autoimmune reagents for treatment of autoimmune diseases. For example, preferred anti-autoimmune reagents are antibodies or polypeptides that bind to an anti-desmoglein antibody or fragment thereof such as an anti-desmoglein antibody comprising an amino acid sequence represented by SEQ ID NOs: 74-146 or any combination thereof. In a preferred embodiment, the anti-autoimmune reagents are conjugated or fused to a therapeutic moiety. In some instances, the anti-autoimmune reagent is used to deplete the blood or a biological sample of B-cells that express on their surface anti-desmoglein antibodies.

The anti-autoimmune reagents of the invention can be used in combination with other existing therapies in the art. For example, the anti-autoimmune reagents can be administered to mammal, preferably a human, before, concurrently or after administration of other types of therapy. For example, the anti-autoimmune reagent can be co-administered with therapeutics that target against T-cells, plasma cells or macrophages, such as antibodies directed against T-cell epitopes, more particularly against the CD4 epitopes. Gamma globulins also may be co-administered. In some cases, it may be desirable to co-administer immunosuppressive drugs such as corticosteroids and possibly also cytotoxic drugs. In this case, lower doses of the corticosteroids and cytotoxic drugs can be used as compared to the doses used in conventional therapies, thereby reducing the negative side effects of these therapeutics.

Drugs which are known to act on B-cells, plasma cells and/or T-cells are particularly useful in accordance with the present invention, whether conjugated to an anti-autoimmune reagent, or administered as a separate component in combination with the anti-autoimmune reagent. These include methotrexate, phenyl butyrate, is bryostatin, cyclophosphamide, etoposide, bleomycin, doxorubicin, carmustine, vincristine, procarbazine, dexamethasone, leucovorin, prednisone, maytansinoids such as DM1, calicheamicin, rapamycin, leflunomide, FK506, immuran, fludarabine, azathiopine, mycophenolate, and cyclosporin. Drugs such as immuran, methotrexate, and fludarabine which act on both B-cells and T-cells are particularly preferred. Illustrative of toxins which are suitably employed in accordance with the present invention are ricin, abrin, ribonuclease, DNase I, Staphylococcal enterotoxin-A, pokeweed antiviral protein, gelonin, diphtheria toxin, *Pseudomonas exotoxin*, *Pseudomonas* endotoxin and RNAses, such as onconase. Other suitable drugs and toxins are known to those of skill in the art.

Cytokine agonists and antagonists may also be used in the therapies according to the present invention. Tumor necrosis factor alpha (TNFα) and interleukin-1 (IL-1) are important in mediating inflammation in rheumatoid arthritis. Accordingly, anti-TNFα reagents, such as infliximab and etanercept (Enbrel), are useful in therapy according to the invention, as well as anti-IL-1 reagents. Other useful secondary therapeutics included IL-2 and GM-CSF, which may be conjugated with the anti-autoimmune reagent.

Diagnostic Tools:

In one embodiment, provided herein is a plasmapheresis affinity column comprising the peptide encoded by the isolated nucleic acid encoding an amino acid sequence represented by Pro-X-Ile-X-Trp-Lys (SEQ ID NO: 170), Pro-X-Leu-X-Trp-Arg (SEQ ID NO: 171), Pro-X-Ile-X-Trp-Arg (SEQ ID NO: 172), or Pro-X-Leu-X-Trp-Lys (SEQ ID NO: 173). In another embodiment, provided herein are the polypeptides encoded by the isolated nucleic acid encoding an amino acid sequence represented by Pro-X-Ile-X-Trp-Lys (SEQ ID NO: 170), Pro-X-Leu-X-Trp-Arg (SEQ ID NO: 171), Pro-X-Ile-X-Trp-Arg (SEQ ID NO: 172), or Pro-X-Leu-X-Trp-Lys (SEQ ID NO: 173). In one embodiment, the invention provides a peptidomimetic compound of the peptides encoded by the isolated nucleic acid encoding an amino acid sequence represented by Pro-X-Ile-X-Trp-Lys (SEQ ID NO: 170), Pro-X-Leu-X-Trp-Arg (SEQ ID NO: 171), Pro-X-Ile-X-Trp-Arg (SEQ ID NO: 172), or Pro-X-Leu-X-Trp-Lys (SEQ ID NO: 173). In another embodiment, the affinity column comprises the peptidomimetic of the peptides encoded by the isolated nucleic acid provided herein, or in another embodiment the affinity column used in the columns and methods provided herein comprises a specific antibody to the peptide encoded by the isolated nucleic acid encoding an amino acid sequence represented by Pro-X-Ile-X-Trp-Lys (SEQ ID NO: 170), Pro-X-Leu-X-Trp-Arg (SEQ ID NO: 171), Pro-X-Ile-X-Trp-Arg (SEQ ID NO: 172), or Pro-X-Leu-X-Trp-Lys (SEQ ID NO: 173).

In one embodiment, provided herein is a method of diagnosing pemphigus in a subject, comprising the step of contacting a biological sample of said subject with a composition comprising an anti-autoimmune reagent described herein, for example an antibody that specifically binds to an anti-desmoglein (Dsg) pathogenic autoantibody; and analyzing the biological sample for the presence of antibody-antigen complex, whereby the presence of antibody-antigen complex indicates the subject has or is predisposed to pemphigus.

In another embodiment, the step of contacting a biological sample of said subject with a composition comprising the anti-idiotypic antibody described herein, is affected using a radio-immunoassay (RIA), an enzyme linked immunosorbent assay (ELISA), a western blot, an immunohistochemical analysis, or a combination thereof.

In one embodiment, when using RIA, a labeled anti-idiopathic antibody as described herein is contacted with a sample containing an unknown amount of substrate in varying amounts. The decrease in precipitated counts from the labeled anti-idiotypic antibody is proportional to the amount of anti-Dsg antibodies in the added sample, indicating pemphigus.

In another embodiment, when using ELISA, the anti-idiotypic antibody provided herein, which is coupled to an enzyme is applied and allowed to bind to react with the sample. Presence of the anti-Dsg antibody is then detected and quantitated by a colorimetric reaction employing the enzyme coupled to the anti-idiotypic antibody. In another embodiment, enzymes employed in this method are horseradish peroxidase or in another embodiment alkaline phosphatase. In the dynamic range of response, the amount of anti-Dsg antibodies present in the sample is proportional to the amount of color produced. A substrate standard is employed in one embodiment, to improve quantitative accuracy.

The use of the anti-autoimmune reagents of the present invention are more sensitive in the context of a diagnostic test for pathology of pemphigus because is the anti-autoimmune reagents are able to specifically bind to pathogenic antibodies. Prior to the present invention, the diagnostic tests for pemphigus would sometimes result in false positive identification of pemphigus patients because the reagents used by the prior art would sometimes recognized non-pathogenic antibodies.

Administration

In some embodiments, an effective amount of the compositions of the present invention (e.g., anti-idiotypic antibody or otherwise inhibitors of pathogenic PV antibodies) is administered to a mammal, preferably a mammal. In other embodiments, a therapeutically effective amount of the compositions of the present invention are administered to a mammal, preferably a human, for the treatment of a disease or condition.

The term "effective amount" as used herein is defined as the amount of the compositions of the present invention that is necessary to result in a physiological change in the cell or tissue to which it is administered.

The term "therapeutically effective amount" as used herein is defined as the amount of the compositions of the present invention that eliminates, decreases, delays, or minimizes adverse effects of a disease, such as pemphigus. A skilled artisan readily recognizes that in many cases the compositions may not provide a cure but may only provide partial benefit, such as alleviation or improvement of at least one symptom of the disease.

Pharmaceutical compositions comprising the compositions of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries that facilitate processing of the proteins into preparations which can be used pharmaceutically. Proper formulation is dependent upon the route to of administration chosen.

For topical administration the proteins of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, inhalation, oral or pulmonary administration.

For injection, the compostions of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

Alternatively, the proteins may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the proteins can be readily formulated by combining the proteins with pharmaceutically acceptable carriers well known in the art. Such carriers enable the proteins of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

Alternatively, other pharmaceutical delivery systems may be employed. Liposomes and emulsions are well-known examples of delivery vehicles that may be used to deliver proteins of the invention. Certain organic solvents such as dimethylsulfoxide also may be employed, although usually at the cost of greater toxicity. Additionally, the molecules may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

The compositions of the invention may contain charged side chains or termini. Thus, they may be included in any of the above-described formulations as the free acids or bases or as pharmaceutically acceptable salts. Pharmaceutically acceptable salts are those salts that substantially retain the biologic activity of the free bases and which are prepared by reaction with inorganic acids. Pharmaceutical salts tend to be more soluble in aqueous and other protic solvents than are the corresponding free base forms.

The compostions of the invention will generally be used in an amount effective to achieve the intended purpose. For use to treat or prevent a disease condition, the molecules of the invention, or pharmaceutical compositions thereof, are administered or applied in a therapeutically effective amount.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from about 0.001 to 100 mg/kg/day, preferably from about 0.5 to 1 mg/kg/day and any and all whole or partial integers there between. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of the compositions of the present invention administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs.

The following examples are presented in order to more fully illustrate the preferred embodiments of the invention. They should in no way be construed, however, as limiting the broad scope of the invention.

EXAMPLES

Materials and Methods

Production of Anti-Idiotype Antisera

ScFv mAbs were produced in the Top10F' strain of *E. coli* (Invitrogen) and purified by nickel chelation affinity chromatography as previously described (Payne et al., 2005). Rabbit antisera were commercially produced by Cocalico Biologicals, Inc., according to the vendor's standard protein immunization protocol.

Rabbit antisera were first cleared against an irrelevant human scFv, AM3-13 (encoded by VH1-24 and VKI-O12/O2 genes), along with excess hemagglutinin (HA) peptide. To produce the column, 520 µg of AM3-13 and 60 µg of hemagglutinin peptide (Sigma) were coupled to 500 uL of Affigel 15 matrix (BioRad) according to manufacturer's instructions. Rabbit antiserum (500 ul) was incubated with the coupled beads by end-over-end rotation overnight at 4° C. The flow through from the column was collected and combined with the flow through after washing with one bed volume of PBS, pH 7.4. Clearing was evaluated by testing the antisera for depletion of anti-HA activity by ELISA.

To produce an affinity column comprising normal human IgG, 10 mg of human IgG (Sigma) were coupled to 1 mL of Affigel 10 matrix (BioRad) according to manufacturer's instructions. 1 mL of rabbit antiserum was incubated with the human IgG affinity column by end-over-end rotation for 8-16 hours at 4° C. and the flow through from the column was collected and combined with the flow through after washing with one bed volume of PBS, pH 7.4. The column was then washed with an additional 10 bed volumes of PBS and bound IgG was eluted with six bed volumes of 100 mM glycine, pH 2.5. The elution fractions were neutralized with 1/10 volume of 1 M Tris, pH 7.5, and the column was neutralized by washing with 20 bed volumes of PBS, pH 7.4. Binding and elution steps were repeated for 3-8 times, until the A280 of the eluate from the column stabilized. The flow through fractions (comprising the cleared antisera) were pooled and concentrated by Centricon YM-10 ultrafiltration (Millipore).

To produce rabbit anti-idiotype columns, rabbit IgG was purified from preimmune and immune sera by protein A adsorption and elution with acid glycine. The eluate was dialyzed against PBS, pH 7.4. Purified rabbit preimmune or antisera IgG (2.5 mg) was coupled to 500 µL of Affigel 10 matrix (BioRad) as above. PV sera (250 ul) was adsorbed with the rabbit IgG affinity column overnight at 4° C. and the flow through and eluate were collected as described above.
Production of Bivalent IgG1 from Monovalent scFv mAbs The eukaryotic PIGG expression vector was provided by Carlos Barbas (Scripps Research Institute). Primers used to subclone scFv mAbs into the PIGG vector appear in the online Supplemental Table. PV mAbs, contained in the scFv phagemid expression vector pComb3X, were used as the PCR template for the antibody variable region amplifications. E1M2 Fab in the phagemid expression vector pComb3H (Roark et al., 2002) was used as the PCR template for the constant region of the lambda light chain (CO.

The variable region of the heavy chain ($V_H$) was amplified with a 5' primer based on the sequence of PIGG-A, which introduces a SacI cloning site (Rader et al., 2002), along with 3' primer HSCG1234B (Barbas et al., 2001), which includes the endogenous ApaI restriction sequence at the start of the IgG1 CH1 region. The PCR reaction was purified using the Qiaquick PCR purification kit (Qiagen) and digested with SacI and ApaI (New England BioLabs). The SacI-ApaI fragment was purified by agarose gel electrophoresis using the Qiaquick Gel Extraction Kit (Qiagen) and was subcloned into the SacI-ApaI site in the PIGG vector.

The variable region of the light chain ($V_L$) was amplified with a 5' primer based on the sequence of PIGG-C (Rader et al., 2002), which introduces a HindIII cloning site and abolishes the internal SacI cloning site which would otherwise have been amplified from the pComb3X vector. The 3' primer for the $V_L$ region hybridizes in reverse orientation to the 3' end of the $V_L$ sequence. The $C_L$ region was amplified from E1M2 Fab using 5' primer HLC-F (Barbas et al., 2001) and 3' Lead B reverse primer (Barbas et al., 2001). The $V_L$ and $C_L$ PCR fragments were purified by agarose gel electrophoresis as above and quantitated by relative ethidium bromide fluorescence. The $V_L$-$C_L$ region was produced by overlap PCR, using approximately 50 ng each of the $V_L$ and $C_L$ PCR fragments as the template, and the 5' light chain and 3' Lead B reverse primers. The $V_L$-$C_L$ overlap PCR reaction was PCR purified, digested with HindIII and XbaI (New England BioLabs), and purified by agarose gel electrophoresis prior to subcloning in the HindIII-XbaI site of the PIGG vector. All recombinant constructs were verified by automated sequencing.

The primers used are shown in Table 5.

TABLE 5

Primers used for PV mAb PIGG vector construction

| Antibody | Sequence | SEQ ID NO | Primer name |
|---|---|---|---|
| | 5' primer (heavy chain), SacI site underlined | | |
| | GAGGAGGAGGAGGAGGAGCTCACTCCCAGGTGCAGCTGGTGCAGTCTGG | SEQ ID NO: 147 | PIGG.PX4.Sac |
| | GAGGAGGAGGAGGAGGAGCTCACTCCCAGGTGCAGCTGGTGCAGTCTGG | SEQ ID NO: 148 | PIGG.PX4.Sac |
| (D31)12b/6 | GAGGAGGAGGAGGAGGAGCTCACTCCCAGGTGCAGCTGCAGGAGTCGG | SEQ ID NO: 149 | PIGG.PX44.Sac |
| (D3)3c/9 | GAGGAGGAGCTCACTCCGAGGTGCAGCTGTTGGAGTCTGG | SEQ ID NO: 150 | PIGG.4B3.Sac |
| (D3)1d/2c | GAGGAGGAGCTCACTCCCAGGTGCAGCTGGTGCAGTCTGG | SEQ ID NO: 151 | PIGG.2B7.Sac |
| | 3' primer (heavy chain), endogenous ApaI site underlined | | |
| | CCTGGCCGGCCTGGCCACTAGTGACCGATGGGCCCTTGGTGGARGC | SEQ ID NO: 152 | HSCG1234B |
| | CCTGGCCGGCCTGGCCACTAGTGACCGATGGGCCCTTGGTGGARGC | SEQ ID NO: 153 | HSCG1234B |
| (D31)12b/6 | CCTGGCCGGCCTGGCCACTAGTGACCGATGGGCCCTTGGTGGARGC | SEQ ID NO: 154 | HSCG1234B |
| (D3)3c/9 | CCTGGCCGGCCTGGCCACTAGTGACCGATGGGCCCTTGGTGGARGC | SEQ ID NO: 155 | HSCG1234B |
| (D3)1d/2c | CCTGGCCGGCCTGGCCACTAGTGACCGATGGGCCCTTGGTGGARGC | SEQ ID NO: 156 | HSCG1234B |
| | 5' primer (light chain), HindIII site underlined, mutation to abolish SacI site in lower case | | |
| | GAGGAGAAGCTTGTTGCTCTGGATCTCTGGTGCCTACGGGGCGGCCGAGCTgATGCTGACTCAGCC | SEQ ID NO: 157 | PIGG.Px41.Hind.AA |
| (D31)2/29 | GAGGAGAAGCTTGTTGCTCTGGATCTCTGGTGCCTACGGGGCGGCCGAGCTgGTGTTGACGCAGCC | SEQ ID NO: 158 | PIGG.Px43.Hind.AA |
| (D31)12b/6 | GAGGAGAAGCTTGTTGCTCTGGATCTCTGGTGCCTACGGGGCGGCCGAGCTgATGCTGACTCAGCC | SEQ ID NO: 159 | PIGG.Px41.Hind.AA |
| (D3)3c/9 | GAGGAGAAGCTTGTTGCTCTGGATCTCTGGTGCCTACGGGGCGGCCGAGCTgGAGCTGACTCAGC | SEQ ID NO: 160 | PIGG.4B3.Hind.AA |
| (D3)1d/2c | GAGGAGAAGCTTGTTGCTCTGGATCTCTGGTGCCTACGGGGCGGCCGAGCTgGTGCTGACTCAGCC | SEQ ID NO: 161 | PIGG.2B7.Hind.AA |
| | 3' primer (light chain), overlap to CL 5' primer italicized | | |
| | *GGCAGCCTTGGGCTGACC*ACCTAGGACGGTCAGCTTGG | SEQ ID NO: 162 | PIGG.Px41.HLCF |
| | *GGCAGCCTTGGGCTGACC*GCCTAGGACGGTCAGCTTGG | SEQ ID NO: 163 | PIGG.Px43.HLCF |
| (D31)12b/6 | *GGCAGCCTTGGGCTGACC*GCCTAGGACGGTCAGCTTGG | SEQ ID NO: 164 | PIGG.Px44.HLCF |
| (D3)3c/9 | *GGCAGCCTTGGGCTGACC*GCCTAGGACGGTCAGCTTGG | SEQ ID NO: 165 | PIGG.4B3.HLCF |
| (D3)1d/2c | *GGCAGCCTTGGGCTGACC*GCCTAGGACGGTCAGCTTGG | SEQ ID NO: 166 | PIGG.4B3.HLCF |
| | 5' primer (CL), overlap to light chain 3' primer italicized | | |
| E1M2 | *GGTCAGCCCAAGGCTGCCCCC* | SEQ ID NO: 167 | HLC-F |
| | 3' primer (CL) | | |
| E1M2 | GGCCATGGCTGGTTGGGCAGC | SEQ ID NO: 168 | Lead B reverse |
| | 5' primer (light chain), HindIII site underlined, mutation to abolish SacI site in lower case | | |
| | GAGGAGAAGCTTGTTGCTCTGGATCTCTGGTGCCTACGGGGCGGCCGAGCTgATGCTGACTCAGCC | SEQ ID NO: 157 | PIGG.Px41.Hind.AA |
| (D31)2/29 | GAGGAGAAGCTTGTTGCTCTGGATCTCTGGTGCCTACGGGGCGGCCGAGCTgGTGTTGACGCAGCC | SEQ ID NO: 158 | PIGG.Px43.Hind.AA |
| (D31)12b/6 | GAGGAGAAGCTTGTTGCTCTGGATCTCTGGTGCCTACGGGGCGGCCGAGCTgATGCTGACTCAGCC | SEQ ID NO: 159 | PIGG.Px41.Hind.AA |
| (D3)3c/9 | GAGGAGAAGCTTGTTGCTCTGGATCTCTGGTGCCTACGGGGCGGCCGAGCTgGAGCTGACTCAGC | SEQ ID NO: 160 | PIGG.4B3.Hind.AA |
| (D3)1d/2c | GAGGAGAAGCTTGTTGCTCTGGATCTCTGGTGCCTACGGGGCGGCCGAGCTgGTGCTGACTCAGCC | SEQ ID NO: 161 | PIGG.2B7.Hind.AA |
| | 3' primer (light chain), overlap to CL 5' primer italicized | | |
| | *GGCAGCCTTGGGCTGACC*ACCTAGGACGGTCAGCTTGG | SEQ ID NO: 162 | PIGG.Px41.HLCF |
| | *GGCAGCCTTGGGCTGACC*GCCTAGGACGGTCAGCTTGG | SEQ ID NO: 163 | PIGG.Px43.HLCF |
| (D31)12b/6 | *GGCAGCCTTGGGCTGACC*GCCTAGGACGGTCAGCTTGG | SEQ ID NO: 164 | PIGG.Px44.HLCF |
| (D3)3c/9 | *GGCAGCCTTGGGCTGACC*GCCTAGGACGGTCAGCTTGG | SEQ ID NO: 165 | PIGG.4B3.HLCF |
| (D3)1d/2c | *GGCAGCCTTGGGCTGACC*GCCTAGGACGGTCAGCTTGG | SEQ ID NO: 166 | PIGG.4B3.HLCF |
| Antibody | 5' primer (CL), overlap to light chain 3' primer italicized | | |
| E1M2 | *GGTCAGCCCAAGGCTGCCCCC* | SEQ ID NO: 167 | HLC-F |
| | 3' primer (CL) | | |
| E1M2 | GGCCATGGCTGGTTGGGCAGC | SEQ ID NO: 168 | Lead B reverse |

PIGG Vector Expression

Endo-free plasmid maxipreps (Qiagen) of recombinant PIGG vectors were prepared for eukaryotic cell transfection into 293T cells. PIGG vector transfection was performed using jetPEI reagent (ISC Bioexpress) according to standard protocol, using five 10 cm cell culture plates at approximately 90% cell density and DMEM plus 10% ultra low IgG fetal bovine serum (Gibco) as the harvest media. Expressed antibody was harvested from the cell culture supernatant at 3 days and again at 6 days. Non-adherent cells were removed from the supernatant by centrifugation, and the media was neutralized by the addition of 1/100 volume 1M Tris pH. 7.5. IgG was purified from the culture supernatant by rotation with protein A agarose beads (Invitrogen) for 2 hours at room temperature. The beads were transferred to a disposable chromatography column (BioRad), washed with 20 column volumes of PBS, and eluted with 6 column volumes of 100 mM glycine pH 3. Eluted fractions were neutralized with 1/10 volume 1M Tris pH 7.5, and the approximate IgG concentration was estimated by absorbance at 280 nm using an extinction coefficient of 1.43. Samples were dialyzed into PBS pH 7.4 and concentrated to approximately 1 μg/uL using Centricon YM-3 spin columns (Millipore). Antibody concentration was confirmed by non-reducing SDS-PAGE followed by Coomassie staining, using a known amount of monoclonal lambda IgG1 (Sigma) as a concentration standard for reference. Antibody binding to Dsg was confirmed by ELISA (Rhigene) according to manufacturer's protocols.

Peptide Phage Display and Techniques

PhD-12 and PhD-C7C peptide phage display libraries (New England BioLabs) were screened with PV IgG according to manufacturer's instructions, alternating between protein A and protein G magnetic beads (New England BioLabs) for antibody capture. Phage clones were isolated from round 3 of screening for sequencing according to manufacturer's protocols. Unique clones were subsequently characterized by ELISA binding and inhibition assays.

ELISA Binding and Inhibition Assays

For anti-idiotype antiserum binding assays, PV monoclonal IgG were adsorbed directly to ELISA plates at a concentration of 10 µg/mL in PBS overnight at 4° C. The antigen was discarded, and the plate was blocked for one hour at 37° C. in blocking buffer (0.1 M NaHCO$_3$, pH 8.6, 5 mg/mL BSA, 0.02% NaN$_3$). After blocking, the plate was washed with Tris-buffered saline (TBS) containing 0.1% Tween-20. For antisera evaluation, cleared rabbit preimmune and immune sera were incubated at a dilution of 1:1000 (or varying dilutions) on each well and detected with horseradish peroxidase (HRP)-conjugated goat anti-rabbit antibodies (Dako), which demonstrate minimal cross reactivity with human IgG. As a control for mAb adsorption to microplate wells, HRP-conjugated anti-human IgG (Research Diagnostics) was also reacted with wells. ABTS (2,2'-Azino-di[3-ethylbenzthiazoline-sulfonate], Roche) was used as the substrate for ELISA reactions.

For peptide phage binding assays, 0.5 µg of rabbit anti-human Fc was adsorbed to ELISA plates overnight at 4° C. in 0.1 M NaHCO$_3$, pH 9.6. The antigen was discarded, and the plate was blocked as above. Wells were subsequently incubated with 0.5 µg of various PV mAbs in TBS-0.5% Tween-20 for 2 hours at 37° C. After washing with TBS-0.5% Tween-20, 10$^9$ pfu of monoclonal peptide phage in TBS-0.5% Tween-20 were incubated in each well for one hour at room temperature, followed by HRP-conjugated anti-M13 secondary antibody (Amersham Biosciences) in blocking buffer and development with ABTS substrate. As a control to evaluate PV mAb adsorption to microplate wells, 50 ng of PV mAbs were added to the rabbit anti-human Fc-coated wells, and then detected with HRP-conjugated anti-human IgG.

For ELISA inhibition assays, anti-idiotypic reagents were pre-incubated with PV mAbs for one hour at 37° C. prior to incubation on Dsg3 or Dsg1 ELISA plates (Rhigene/MBL), which were otherwise processed according to manufacturer's instructions. Anti-idiotypic antisera were effective and dose responsive at dilutions ranging from 1:3 to 1:6400, while peptide phage were used in inhibition assays from 10$^8$ to 10$^{10}$ pfu/well. PV scFv binding, detected with HRP-conjugated anti-HA secondary antibody (Roche), was titrated to a final OD450 reading of 0.4-1.0, which was within the linear range of detection.

Keratinocyte Dissociation Assay

The keratinocyte dissociation assay was performed as previously described (Payne et al., 2005), using either PV scFv at 5 µg/mL or PV sera at dilutions of 1:5 to 1:7.5 in 500 µL total volume defined keratinocyte-serum free media (Gibco/Invitrogen). For antibodies that only recognize Dsg3, 1 µg/mL exfoliative toxin A (ETA) was added to wells for the last two hours. For antisera depletion assays, 200 µL of PV sera flowthrough (representing a volume of 100 µL, sera, combined with the first 1-volume fraction of the PBS wash) were incubated with cells in a total volume of 500 µL, with or without ETA treatment. Dissociation assays used the total eluate from the antisera columns, concentrated to a volume of 100 µl (representing a starting volume of 250 µL sera).

Example 1

Genetic Restriction of PV(1) mAb Library

Genetic analysis of 63 sequences from the PV(1) mAb library demonstrated 43 unique mAbs based on V(D)J gene usage, heavy and light chain combinations, and somatic hypermutation. However, these 43 unique mAbs were encoded by a total of only 7 variable heavy chain (VH) genes. When these antibodies were further subdivided by antigenic target and pathogenicity, only one to two $V_H$ genes were identified for each functional category (detailed in Table 1).

TABLE 1

$V_H$ gene restriction in the PV(1) phage display library.

| Antigenic specificity | $V_H$ genes | Pathogenic | Non-pathogenic |
|---|---|---|---|
| Dsg 1 | 2 | VH3-8 | VH4-b |
| Dsg 3 | 3 | VH3-07 | VH3-30 |
|  |  |  | VH1-e |
| Dsg 3 + Dsg 1 | 2 | VH1-4M28 | VH4-04 |
| TOTAL | 7 | 3 | 4 |

Each of the 43 unique mAbs used one of 11 different D genes and one of 2 different $J_H$ genes, but these gene usage patterns did not correlate with antigenic target or pathogenicity. Light chain gene analysis also demonstrated genetic restriction, with 9 different $V_L$ genes (Table 2A) combining with 3 different $J_L$ genes.

TABLE 2A $V_L$ gene restriction in the PV(1) phage display library.

| Antigenic Specificity | $V_L$ genes | Pathogenic | Non-pathogenic |
|---|---|---|---|
| Dsg 1 | 2 | VL2-a2 | VL3h |
| Dsg 3 | 4 | VL2-b2 | VKIII-L6 |
|  |  |  | VL1-c |
|  |  |  | VL1-g |
| Dsg 3 + Dsg 1 | 3 | VL3-r | VL1-g |
|  |  | VL3-j |  |
| TOTAL | 9 | 4 | 5 |

For anti-idiotype reagent production, representative pathogenic and non-pathogenic PV mAbs were chosen, which were selected against Dsg3 alone (D3), or both Dsgs 3 and 1 (D31).

ScFv nomenclature has been previously described. Briefly, the scFv designation includes the target antigens, (D3) or (D31), followed by a numeric designation for the heavy and light chain (i.e., 2/28), which is based on the V(D)J gene usage. Somatic mutation is indicated by small letter suffix; for example, (D3)3a/9 and (D3)3c/9 use the same heavy chain ("3") and light chain ("9") variable region genes, but differ by somatic mutation in the heavy chain variable region ("a" versus "c").

Without wishing to be bound by any particular theory, it is believed that somatic mutation did not change the antigenic target or pathogenicity of PV antibodies (in other words, Dsg1-reactive antibodies do not develop from Dsg3 antibodies, and pathogenic antibodies do not develop from nonpathogenic antibodies), providing direct genetic evidence against the theories of intermolecular or intramolecular epitope spreading in PV.

These findings raised several additional inquires. First, it was hypothesized whether these genes were shared among pemphigus patients. It is believed that some degree of common genes are shared among pemphigus, because genes encode proteins, and it is expected that a limited number of antibody variable region genes would encode an antibody with the ability to bind to a specific pathogenic domain of desmoglein 3. To address this question, libraries from several additional pemphigus patients were characterized. Two PV and two PF libraries were characterized. When only the variable heavy region genes used by desmoglein reactive antibodies were examined, it was observed that there were a number of shared genes, not just among PV or PF patients, but also between PV and PF. An example of shared genes between the two PV libraries includes but is not limited to VH1-46 and VH1-4M28. An example of shared genes between the two PF libraries include but is not limited to VH1-8 and VH3-09. An example of shared genes between the PV and PF libraries include but is not limited to VH3-07 and VH3-30. (Table 2B)

TABLE 2B

Shared gene usage by anti-Dsg autoantibodies among pephuigus patients

| PV1 | PV2 | PF1 | PF2 |
|---|---|---|---|
| VH1-46 | VH1-46 | VH1-8 | VH1-8 |
| VH1-4M28 | VH1-4M28 | VH1-18 | VH3-09 |
| VH1-e | VH1-69 | VH3-07 | VH3-30 |
| VH3-07 |  | VH3-09 | VH3-53 |
| VH3-8 |  | VH3-30 | VH3-66 |
| VH3-30 |  |  | VH4-b |
| VH4-b |  |  |  |
| VH4-04 |  |  |  |

These observations relating to a number of pathogenic antibody associated genes present a potential candidate for targeting these genes as a potential therapeutic strategy.

Characterization of the libraries also demonstrate the presence and absence of consensus CDR3 sequences in pathogenic and nonpathogenic antibodies, respectively. It was observed that a consensus sequence was present by all of the tested pathogenic antibody sequences. However, this sequence was not found in the tested nonpathogenic antibody sequences. The consensus sequence shared among the pathogenic antibodies reside in the CDR3 region of the antibody. The consensus sequence shared among the pathogenic antibodies is D/E-X-X-X-W, wherein X can represent any amino acid. The consensus sequence contains a tryptophan (FIG. 13). A conserved tryptophan has been observed in other molecules for example cadherin. Without wishing to be bound by any particular theory, it is believed that cadherin homophilic interaction is dependent on conserved tryptophan residues in the amino terminal binding pocket. Therefore, it is believed that the tryptophan in the CDR3 region plays a role in the antigen-binding characteristic of the antibody to desmogleins and how the pathogenic antibodies cause a disease state.

Example 2

Production of Anti-Idiotype Antibodies Against Pathogenic and Non-Pathogenic PV mAbs Recombinant pathogenic (D3)3c/9, (D31)2/28 and non-pathogenic (D3)1d/2c, (D31)12b/6 single chain variable fragment (scFv) PV mAbs were produced and purified by nickel chelation chromatography as previously described (Payne et al., 2005). Rabbits were immunized with scFv preparations by a commercial vendor. The resulting rabbit antisera were first cleared against an irrelevant scFv and excess hemagglutinin peptide, followed by exhaustive clearing against polyclonal normal human IgG, in order to eliminate antibodies that reacted against non-idiotypic determinants.

ScFv antibody fragments express the monovalent antigen binding sites of native immunoglobulin molecules. To evaluate the ability of rabbit antisera to bind PV mAbs in their native form, scFv were converted to bivalent full-length IgG1 molecules using the PIGG vector. FIG. 1 demonstrates that the antiserum raised against (D31)2/28 ("Anti-2/28") also bound (D31)2/29, a mAb which uses the same heavy chain (VH1-4M28) but has a different light chain. Anti-2/28 antiserum did not bind to (D31)12b/6, which uses different heavy and light chain genes.

To evaluate for potential cross reactivity of antisera with different PV IgG, PV IgG were directly absorbed to ELISA plate wells and incubated with rabbit preimmune and immune sera. FIG. 1 demonstrates that antisera specifically bound the immunizing mAb, with the exception of anti-2/28 antiserum, which also bound (D31)2/29. Antiserum raised against (D31)12b/6 did not cross react with E1M2 IgG (an anti-red blood cell mAb produced using the same eukaryotic PIGG expression system, which uses the same $V_L$ gene (VL1-g). These data indicate that the epitopes recognized by some antisera are encoded by the heavy chain. Antisera did not recognize the denatured heavy or light chains of the target IgG by immunoblot, suggesting that a conformational epitope was recognized.

Example 3

Anti-Dsg Idiotypes Correlate with PV mAb $V_B$ Gene Usage

The phage display technique randomly pairs heavy and light chains during PCR construction of the scFv library, and thus mAbs isolated by phage display may not accurately reflect heavy and light chain pairings in vivo. If, however, the idiotypes of PV mAbs are displayed predominantly by the heavy chain, then development of anti-idiotypic reagents for pemphigus antibodies could be simplified.

Figure 6:
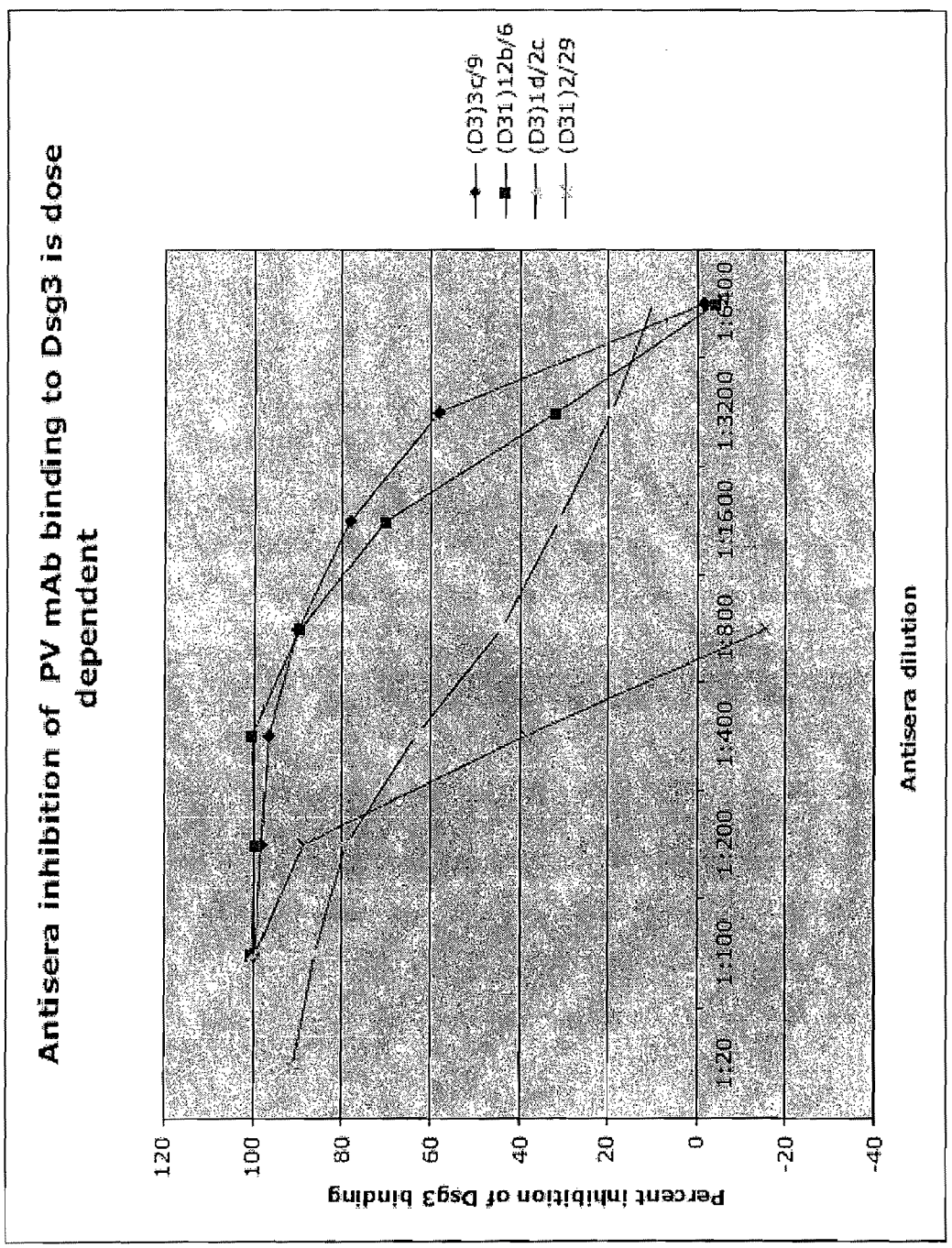
FIG. 6 is an image depicting that antisera inhibition of PV mAb binding to Dsg3 is dose dependent. PV mAbs were preincubated with the corresponding cleared preimmune serum or anti-idiotype antiserum at varying dilutions prior to incubation on Dsg3 ELISA plates.

To further characterize the specificity of anti-idiotypic antisera, each antiserum was tested for its ability to inhibit binding of various PV mAbs to Dsg antigens by ELISA. In initial experiments, dose response curves for anti-idiotypic antisera inhibition were established, using preimmune serum as a control. A dose dependent binding of antisera to bivalent PV IgG was detected by ELISA (FIG. 6). Subsequently, ELISA inhibition assays were performed to evaluate the ability of each antiserum to inhibit binding of various PV mAbs to Dsg 3 and Dsg1. Table 3 summarizes representative inhibition data for all PV mAb inhibition assays, using equivalent dilutions of anti-idiotypic antisera (1:20).

TABLE 3

Antisera inhibition of PV antibody binding to Dsg3/Dsg1 by ELISA.

| VH gene | PV mAb | Anti-2/28 | Anti-12b/6 | Anti-3c/9 | Anti-1d/2c | All 4 |
|---|---|---|---|---|---|---|
| VH1-4M28 | *(D31)2/28 | 84(5)/83(4) | −2 | 11/0.2 | ND | |
|  | *(D31)2/29 | 88(3)/89(7) | −2/1 | 1/5 | ND | |
| VH4-04 | (D31)12b/6 | 3(2)/8(1) | 92(4)/94 | 1(1)/12 | −3 | |
| VH3-07 | *(D3)3c/9 | 2(3) | 2 | 95(3) | 5(1) | |
|  | *(D3)3a/9 | 1(0) | ND | 91(3) | 2(3) | |
|  | *(D3)3b/8 | 3(1) | ND | 89(6) | −3 | |

TABLE 3-continued

Antisera inhibition of PV antibody binding to Dsg3/Dsg1 by ELISA.

| VH gene | PV mAb | Anti-2/28 | Anti-12b/6 | Anti-3c/9 | Anti-1d/2c | All 4 |
|---|---|---|---|---|---|---|
| VH1-e | (D3)1b/3a | 12 | −6(23) | −4(23) | 91(2) | |
| | (D3)1d/2c | 3 | −2 | 0(9) | 94(3) | |
| | (D3)1g/2e | 1 | | 5 | 81 | |
| VH3-30 | (D3)4/30 | 7(1) | 5(1) | 4(0) | 22(4) | |
| poly-clonal | PV(1) serum | 4(1) | 6(1) | 11(2) | 15(3) | 19(2) |

Percent inhibition of PV mAb binding is shown.
Pathogenic mAbs are indicated with an asterisk.

Incubations in which the antisera were raised against a mAb using the same $V_H$ genes as the mAb tested by ELISA are highlighted in gray, demonstrating that antisera specifically inhibited Dsg binding by the original immunizing mAb, as well as mAbs that used the same $V_H$ genes. For example, the anti-2/28 antiserum inhibited (D31)2/28 as well as (D31) 2/29, an antibody using the same $V_H$ but different $V_L$ genes.

Antisera did not inhibit mAbs that used different $V_H$ genes. Notably, the antiserum against (D31)2/28 pathogenic mAb did not inhibit binding of (D3)3c/9 pathogenic mAb to Dsg3, indicating that these two pathogenic antibodies do not share the same idiotype.

Additionally, the presence of somatic mutation did not appear to affect anti-idiotype antisera inhibition. For example, (D3)3c/9 and (D3)3a/9, as well as (D3)1d/2c and (D3)1g/2e, were similarly inhibited by anti-idiotypic antisera.

One non-pathogenic mAb, (D3)4/30, did not effectively immunize rabbits and was not substantially inhibited by any of the other 4 antisera, which were all produced against mAbs using different heavy chain genes. PV(1) serum, obtained from the patient at the same time the phage display library was produced, showed 19% inhibition of total Dsg binding when all 4 antisera were used for inhibition in ELISA assays.

Taken together, these data suggest that the major idiotypes of the PV mAbs studied correlate with $V_H$ gene usage and are not significantly altered by somatic mutation or light chain gene usage, indicating that targeting of either idiotypes or $V_H$ genes may be a viable strategy for therapy.

Example 4

Anti-Idiotype Antibodies Block Pathogenicity of PV mAbs

The question of whether the in vitro inhibition of Dsg binding by ELISA translated into a functional block of antibody pathogenicity was investigated. It was previously shown that neonatal mouse injection is suboptimal for evaluation of pathogenicity of PV mAbs, due to differences in the specificity of mAbs for human versus mouse Dsg substrates. Therefore, the inhibition of mAb pathogenicity was evaluated by a dispase assay using cultured primary human keratinocytes. Pathogenic PV mAbs (D3)3c/9, (D3)3a/9, (D31)2/28, and (D31)2/29 induced cell sheet dissociation in cultured human keratinocytes after pre-incubation with rabbit preimmune serum (top row, FIG. 2). However, after pre-incubation with $V_H$-specific antisera (anti-3c/9 antisera in the case of (D3) 3c/9 and (D3)3a/9, and anti-2/28 antisera in the case of (D31) 2/28 and (D31)2/29), the number of cell sheet fragments induced by PV mAbs was reduced (middle row, FIG. 2). Inhibition of cell sheet fragmentation was not seen after pre-incubation of PV mAbs with antisera raised against PV mAbs using different $V_H$ genes (data not shown). Similar to the findings on ELISA (shown in Example 3), these data demonstrate that anti-idiotype antisera specifically inhibit the pathogenicity of PV mAbs based on their $V_H$ gene usage, despite the presence of different light chains or somatic mutation.

Example 5

Figure 7:
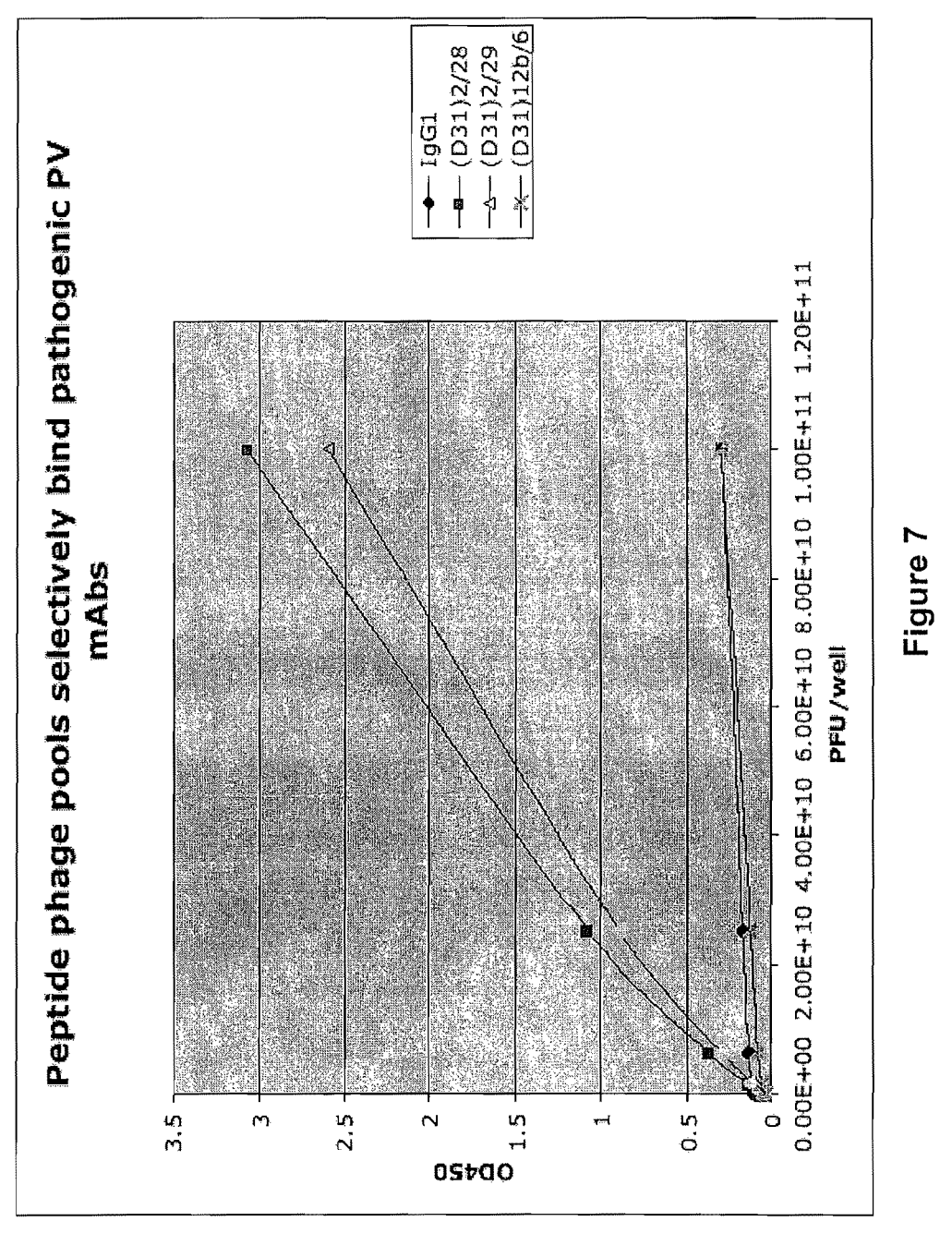

Peptide Phage Display Identifies Sequences that Bind PV mAbs According to $V_H$ Gene Usage Another method that might be used to target antibodies is to develop small peptides that bind pathogenic antibodies. To test the feasibility of this approach, we screened linear 12-mer and disulfide constrained 7-mer peptide phage display libraries with pathogenic (D31)2/29 PV mAb. Pools of phage-displayed peptides from the third round of selection demonstrated specific binding of both (D31)2/28 and (D31)2/29 mAbs, but not the nonpathogenic (D31)12b/6 mAb or an IgG1-A, mAb (Sigma) by ELISA (FIG. 7), suggesting heavy chain specificity of peptide binding. Preparations of individual binding phage clones were isolated and their displayed peptide amino acid sequences were deduced by sequencing phage DNA (FIG. 3). Interestingly, a consensus peptide sequence was identified. Neither the consensus sequence nor the individual peptide sequences aligned with any linear sequence in human desmosomal cadherins. Additionally, monoclonal peptide phage did not demonstrate direct binding to human Dsg3 by ELISA, suggesting that these sequences do not mimic linear or conformational epitopes of desmogleins that may be involved in homo- or hetero-dimerization.

$V_H$-specific binding of individual phage-displayed peptides to PV mAbs was confirmed by ELISA. PV mAbs were immobilized on microplate wells and incubated with peptide phage. Peptide phage demonstrated selective binding of (D31)2/28 and (D31)2/29 mAbs, but not other PV mAbs using different $V_H$ genes (FIG. 4). Control peptide phage displaying a non-consensus sequence (DLNYFTLSSKRE SEQ ID NO. 169), as well as wild type peptide phage displaying pIII coat protein unligated to any additional peptide sequence, did not show significant binding to any PV mAb.

Select peptide phage were tested for their ability to inhibit binding of PV mAbs to Dsg substrates by ELISA (Table 4).

TABLE 4

Inhibition of PV mAb bindinig by monoclonal peptide phase clones

| VH gene | PV mAb | Control | P4 | P7 | P14 |
|---|---|---|---|---|---|
| VH1-4M28 | *(D31)2/28 | 2(6) | 9(3) | 12(7) | 15(3) |
| | *(D31)2/29 | 15(3) | 78(5) | 83(9) | 16(9) |
| VH4-04 | (D31)12b/6 | 11(3) | 10(14) | 8(9) | 13(2) |
| VH3-07 | *(D3)3c/9 | 8(5) | 7(6) | 6(7) | 5(2) |
| VH1-e | (D3)1d/2c | 8(9) | 14(13) | 9(8) | 8(21) |

Percent inhibition is shown as a mean (standard deviation).

Control phage displaying the non-consensus sequence did not demonstrate significant inhibition of PV mAb binding. P14 peptide phage also did not inhibit binding of any PV mAb. However, P4 and P7 peptide phage inhibited binding of (D31)2/29 by 78 and 83 percent, respectively, indicating that these peptides are anti-idiotypic reagents. Again, inhibition was dose dependent. Although P4 and P7 peptide phage bound to (D31)2/28 mAb, they did not inhibit its binding to Dsg3.

Figure 9:
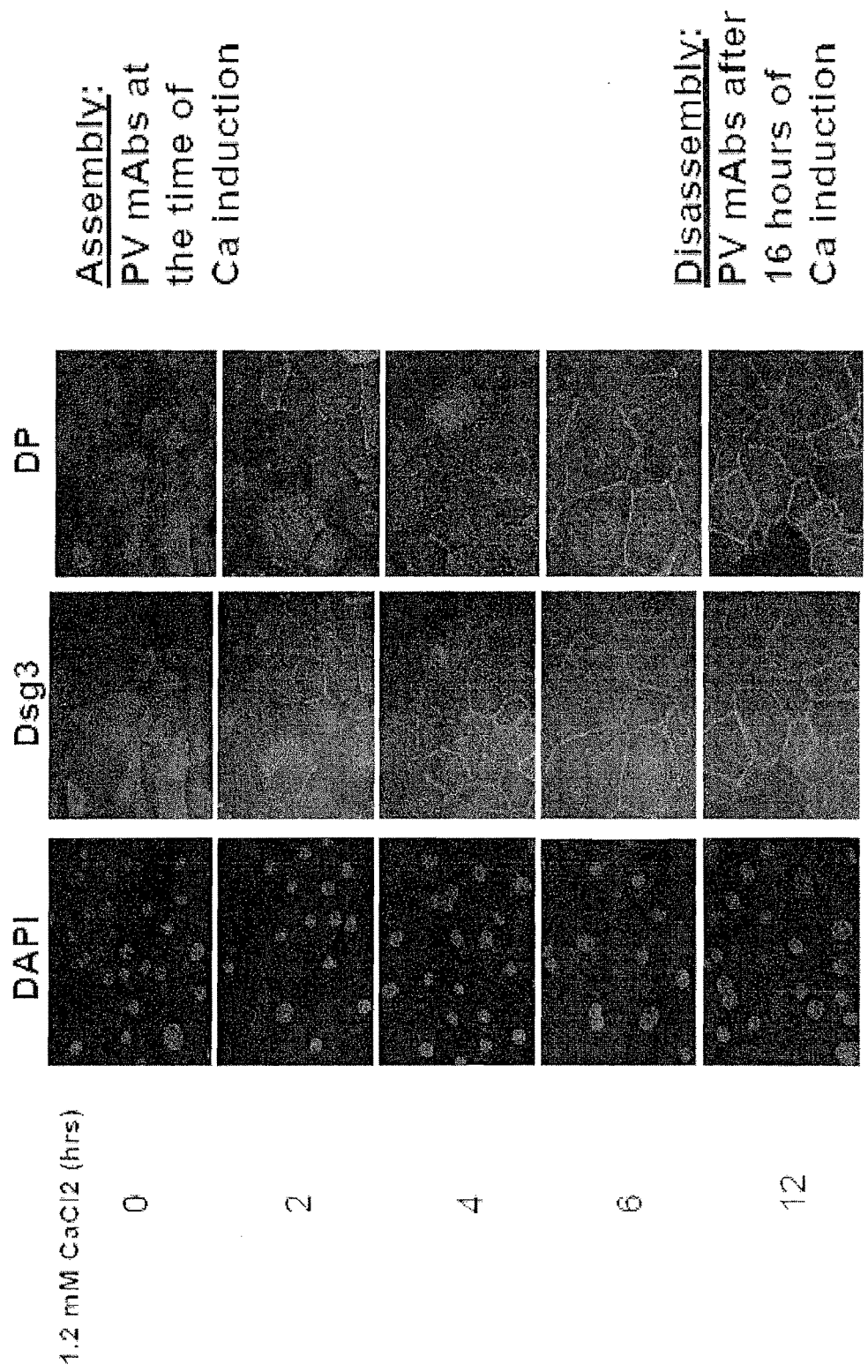
FIG. 9 is an image demonstrating calcium-induced desmosome assembly in keratinocytes.

Thus, as with the anti-idiotypic antibodies, specific binding of peptide phage to PV mAbs was mainly determined by $V_H$ gene usage. However, the binding of peptides to PV mAbs did not correlate with functional inhibition of mAb binding to Dsg3, indicating that the idiotype of PV mAbs may be modified by the light chain.

Example 6

Anti-Idiotypic Antisera Deplete Pathogenic Activity from PV(1) Serum

Although the ELISA inhibition data (Table 3) suggested that the pooled antisera did not inhibit the majority of total anti-Dsg binding in PV(1) serum, many anti-Dsg antibodies do not cause disease. Therefore, the question whether the mAbs targeted by the antisera represented the critical pathogenic antibody populations was tested using the keratinocyte dissociation assay. Collectively, the previous data demonstrate that both anti-idiotypic antibodies and small molecule reagents can specifically bind PV mAbs based on their heavy chain gene usage. Therefore, instead of targeting antibodies based on their idiotype, which may be a more restrictive functional definition and influenced by the light chain, a more general antibody targeting strategy was investigated based on antibody $V_H$ gene usage.

Rabbit preimmune and immune IgG were cleared only against an unrelated scFv (AM3-13, an anti-platelet antibody encoded by VH1-24 and VKI-O12/O2 genes) and excess hemagglutinin peptide (and not against normal human IgG, which could clear antibodies that react against $V_H$ framework regions of the antibody). Antisera against non-pathogenic PV mAbs were included in case these antibodies contributed to pathophysiology when used in combination. Preimmune and immune IgG were immobilized on a solid phase matrix and used to determine whether pathogenic antibodies could be adsorbed from various PV sera. PV(1) serum is pathogenic in the dispase assay (FIG. 5O). After adsorption with rabbit preimmune IgG, PV(1) serum retained pathogenic activity against cultured human keratinocytes (FIG. 5A). However, after adsorption with the 4 pooled PV antisera IgG, pathogenic activity of PV(1) serum was substantially reduced (FIG. 5B). Acid elution of adsorbed proteins followed by neutralization demonstrated that pathogenic antibodies did not bind to the rabbit preimmune column (FIG. 5C). In contrast, PV(1) serum adsorbed by the 4 pooled PV antisera showed increased cell sheet fragmentation activity in the eluate, indicating specific binding of pathogenic antibodies (FIG. 5D). Two other PV patient sera, PV3210 and PV3274, did not show significant depletion of pathogenic activity by the 4 pooled antisera (FIG. 5, compare E to F, and Ito J). However, pathogenic antibodies were eluted from both PV sera after adsorption with the 4 pooled antisera (FIGS. 5, H and L), but not after adsorption with preimmune IgG (FIGS. 5, G and K). Exfoliative toxin A (ETA) (FIG. 5M) or PF serum (FIG. 5N), which only recognize Dsg1, do not demonstrate significant pathogenicity in the keratinocyte dissociation assay, which requires inactivation of both Dsg1 and Dsg3. These data suggest that the 4 $V_H$ gene sets identified from the PV(1) patient library deplete a substantial proportion of the pathogenic activity from the patient's own serum. In addition, pathogenic antibodies using these $V_H$ genes are shared among different PV patients, although additional pathogenic autoantibody $V_H$ genes are likely present in these other patients.

Example 7

Using Pathogenic and Non-Pathogenic Antibodies to Study the Pathology of Pemphigus The following experiments were designed to evaluate the pathology of pemphigus in a cellular model. The experiments were designed to further examine the observation that when pathogenic and nonpathogenic antibodies are incubated with human keratinocytes, the result is the clearing of pathogenic antibodies from culture supernatants relative to the nonpathogenic antibodies (FIG. 8). Without wishing to be bound by any particular theory, it is believed that the pathogenic antibodies can be used to study pathways of desmoglein assembly into and disassembly from desmosomes. Targeting desmosomes and associated proteins can be candidates for therapy against skin fragility or susceptibility to blister formation in pemphigus patients.

Proper cell-cell adhesion is critical during development, tissue morphogenesis, and for the regulation of cell migration and proliferation. Desmosomes are adhesive intercellular junctions that anchor the intermediate filament network to the plasma membrane. By functioning both as an adhesive complex and as a cell-surface attachment site for intermediate filaments, desmosomes link the intermediate filament cytoskeletons between cells and play an important role in maintaining tissue integrity.

A desmosome is a structure that forms a site of adhesion between two adjacent cells, and comprises a dense plate in each adjacent cell separated by a thin layer of extracellular material. The desmosome further comprises a molecular complex of cellular adhesion proteins and linking proteins that append the cell surface adhesion proteins to intracellular keratin cytoskeletal filaments within a cell. Thus, the basic components of the desmosome are the desmosomal plaque and the associated transmembrane adhesion molecules which function to connect neighboring desmosomes. When the desmosomes that connect adjacent epithelial cells do not function properly, epidermal skin layers can pull apart to allow abnormal movements of fluid within the skin, which can result in blisters and other tissue damage.

The results presented herein demonstrate that in human pemphigus vulgaris disorders, pathogenic antibodies bind the desmosomal cadherein protein desmoglein-3 (Dsg3) causing epidermal cell-cell detachment, ultimately resulting in blisters on the associated tissue. The pathology of pemphigus vulgaris can be further studied by examining characteristics of desmosome assembly and dissassembly because desmosomes are adhesive junctions that contain transmembrane desmosomal cadherins, desmoglein and desmocollin. Both cadherins bind plakoglobin. Plakoglobin in turn binds desmoplakin, which links to the keratin intermediate filament (KIF) network. Adapter molecules such as plakophilin are believed to serve to increase the lateral adhesive strength of these junctions.

The experiments disclosed herein were designed to take advantage of the biochemical property of desmosomes. Desmosomes fractionate into the Triton X-100 insoluble fraction of keratinocyte lysates. In contrast, nonKIF linked Dsgs are present in the Triton X-100 soluble fraction of cell lysates. It is believed that Dsg3 may traffic in between these two biochemical fractions, for example it would enter the Triton insoluble fraction during desmosomal assembly, and exit during desmosome disassembly.

Without wishing to be bound by any particular theory, it is believed that pemphigus autoantibodies can act upon non-desmosomal Dsg3, and therefore prevent incorporation of Dsg into the desmosome. Additionally or alternatively, antibodies could bind desmosomal Dsg3, which would be expected to lead to disassembly of Dsg3 from pre-formed desmosomes.

When keratinocytes were examined by immunofluorescence (IF) when grown in the presence of low calcium media, both Dsg3 as well as desmoplakin (DP) exhibited a diffuse pattern of ER/cytoplasmic staining. However, shortly after induction with high calcium media, Dsg3 as well as DP localized to the cell membrane, and the proportion of membrane localized Dsg3 increased over time (FIG. 9). Therefore, when keratinocytes are exposed to PV monoclonal antibodies at the time of the calcium switch, the effects of PV monoclonal antibody during desmosomal assembly can easily be evaluated by examining the localization of Dsg3 and DP. Conversely, if the cells are placed in calcium first, and PV monoclonal antibodies are subsequently added, the effects of PV monoclonal antibodies on desmosomal disassembly can similarly be examined by examining the localization of Dsg3 and DP.

Figure 10:
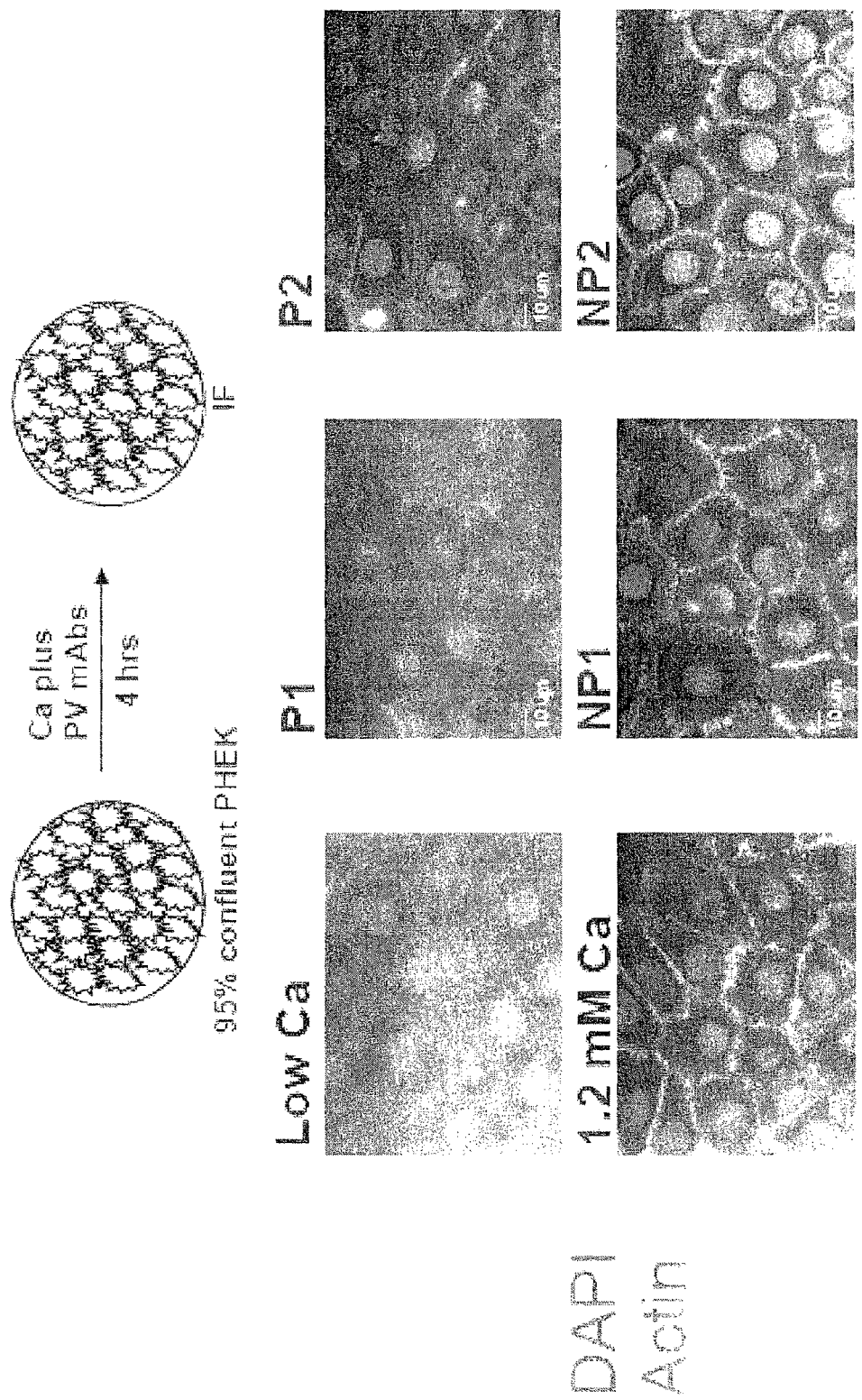
FIG. 10 is an image demonstrating that the effects on Dsg3 parallel the loss of PV monoclonal antibodies from cell culture supernatants. Cells treated with nonpathogenic antibodies exhibit Dsg3 staining at the cell membrane. Cells treated with pathogenic antibodies exhibit diffused cytoplasmic Dsg3 staining.

In order to further examine the clearance of pathogenic antibodies, the next set of experiments were designed to assess whether the effects of Dsg3 parallel the loss of PV monoclonal antibodies from cell culture supernatants. "Assembly" is evaluated by exposing cells to calcium and PV monoclonal antibodies at the same time. The overall cell architecture of a cell in low and high calcium is represented by the cells shown in FIG. 10, where Dsg3 is shown in green, nuclei in blue, and actin in red. In cells treated with two different nonpathogenic antibodies (NP), Dsg3 staining was not disrupted, but in cells treated with two different pathogenic antibodies, Dsg3 staining remained diffusely cytoplasmic.

Figure 11:
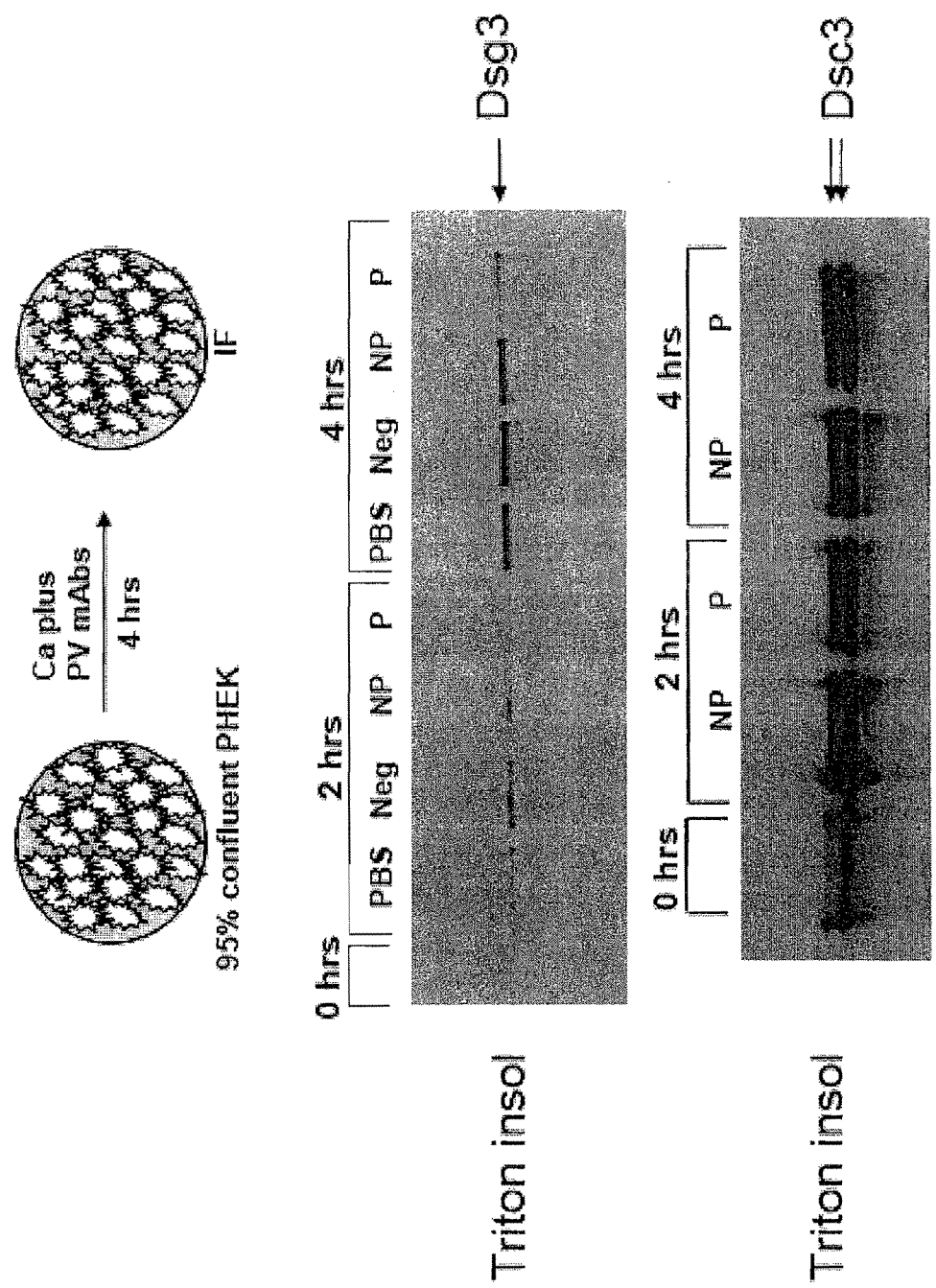
FIG. 11 is an image demonstrating that the effects on Dsg3 parallel the effects of PV monoclonal antibodies from cell culture supernatants as measured by subcellular fractionation. Cells treated with pathogenic antibody exhibited a decrease amount of Dsg3 present in the Triton insoluble fraction.

When cells were examined by subcellular fractionation, it was observed that desmoglein 3 was depleted from the Triton insoluble fraction as early as 2 hrs after pathogenic antibody treatment. At 0 hrs, there was very little Dsg3 in the Triton insoluble fraction, and in control cells treated with PBS, a negative control scFv, or a nonpathogenic PV antibody, the proportion of Dsg3 in the Triton insoluble fraction increased over time. However, in the cells treated with pathogenic antibody, Dsg3 is decreased at 2 hrs, and this effect was more pronounced at 4 hrs. This effect is specific for desmoglein 3, because it was observed that pathogenic antibody had no effects on desmocollin 3 (FIG. 11).

Figure 12:
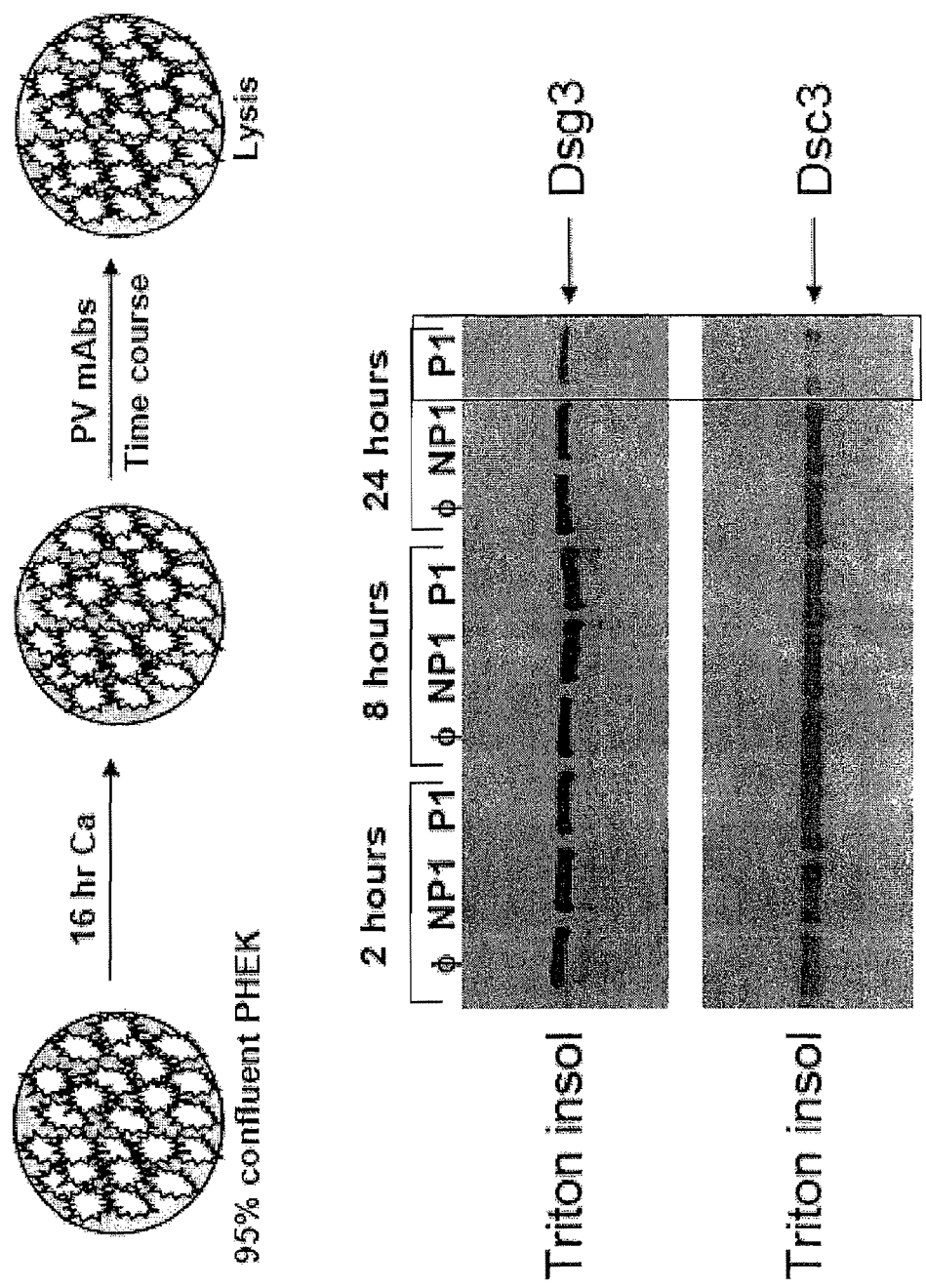
FIG. 12 is an image demonstrating that PV monoclonal antibodies have delayed effects on disassembly of Dsg3. Pathogenic PV monoclonal antibodies cause a moderate decrease in the levels of Dsg3 at early time point. However, at 24 hours after antibody treatment, the decrease in the levels of Dsg3 is more pronounced.

In contrast, pathogenic antibodies did not induce significant disassembly of Dsg3 in keratinocytes. Cells were placed in high calcium overnight, under which conditions approximately 90-95% of total desmoglein are in the form of desmosomal. Either pathogenic or nonpathogenic PV monoclonal antibodies were incubated with the cells for varying lengths of time. It was observed that pathogenic PV monoclonal antibodies caused a moderate decrease in the levels of Dsg3. However, this observation did not take place until 24 hours after antibody treatment, which corresponds to the same time that Dsc3 levels decreased (FIG. 12).

The results presented herein demonstrate that the Dsg3 is preferentially, depleted from the desmosome during calcium-induced desmosome assembly. Without wishing to be bound by any particular theory, the ability of the antibodies to deplete Dsg3 correlates with their pathogenic activity. Thus, it is believed that the level of Dsg3 can be used as diagnosis marker to assess the pathogenic changes associated with pemphigus. The results presented herein also demonstrate that Dsg3 depletion from desmosomes due to anti-Dsg3 antibody activity contained in the pathogenic antibody plays an important role in the skin fragility or susceptibility to blister formation in pemphigus patients.

It is believed that the results demonstrate that advantage of using the pathogenic and nonpathogenic antibodies disclosed herein as preclinical research reagents to determine disease mechanisms. The use of these pathogenic and non-pathogenic antibodies therefore can lead to identification of therapeutic targets.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inhibiting the binding of an anti-desmoglein autoantibody or fragment thereof to desmoglein, said method comprising contacting the anti-desmoglein autoantibody or fragment thereof with a composition comprising an anti-autoimmune reagent that specifically binds to an anti-desmoglein autoantibody or fragment thereof, wherein the anti-autoimmune reagent is a peptide comprising the amino acid sequence of SEQ ID NO: 171.

2. The method of claim 1, wherein the anti-desmoglein (Dsg) autoantibody or fragment thereof binds to a target molecule selected from the group consisting of Dsg1, Dsg3, and any combination thereof 3. The method of claim 1, wherein the anti-desmoglein autoantibody or fragment thereof is associated with the pathology of pemphigus vulgaris (PV), or pemphigus foliaceus (PF).

4. The method of claim 1, wherein the anti-autoimmune reagent specifically binds to a variable region of a heavy chain ($V_H$) of the anti-desmoglein autoantibody or fragment thereof.

5. The method of claim 4, wherein the heavy chain ($V_H$) of the anti-desmoglein autoantibody or fragment thereof is encoded by a gene selected from the group consisting of VH3-8, VH3-07, VH1-4M28, and any combination thereof.

6. The method of claim 1, wherein the anti-autoimmune reagent is linked to a B cell superantigen.

7. The method of claim 6, wherein linking the anti-autoimmune reagent to a B cell superantigen affects $V_H$-targeted B-cell deletion.

* * * * *

SEQUENCE LISTING

<160> NUMBER OF SEQ ID NOS: 182

<210> SEQ ID NO 1
<211> LENGTH: 413
<212> TYPE: DNA
<213> ORGANISM: Homo sapiens

<400> SEQUENCE: 1

```
caggtgcagc tggtgcagtc tggggctgag atgaagaagc ctgggtcctc ggtgagggtc      60
tcctgcaagg cttctggagg caccttcgac aaacatgctg tcagttgggt gcgacaggcc     120
ccaggacgag ggcttgagtg ggtgggaggg atcatcccta tgcttggtgc tccacactac     180
gcacagaagt tccagggcag agtcacgatc accgcggaca aatccacgag cacagtctac     240
atggaactga gcagcctggg atctgaggac acagccgtgt attactgtgc gagagataaa     300
gcggcttact atgaaagtgg ttattactat atcggtgact tctggggcca gggaaccctg     360
gtcaccgtct cctcagcctc caccaagggc ccatcggtca ctagtggcca ggc            413
```

```
<210> SEQ ID NO 2
<211> LENGTH: 413
<212> TYPE: DNA
<213> ORGANISM: Homo sapiens

<400> SEQUENCE: 2
caggtgcagc tggtgcagtc tggggctgag atgaagaagc ctgggtcctc ggtgagggtc      60
tcctgcaagg cttctggagg caccttcgac aaatatgctg tcagttgggt gcgacaggcc     120
ccaggacgag ggcttgagtg ggtgggaggg atcatcccta tgcttggtgc tccacactac     180
gcacagaagt tccagggcag agtcacgatc accgcggaca atccacgag cacagtctac      240 atggaactga gcagcctggg atctgaggac acagccgtgt attactgtgc gagagataaa     300
gcggcttact atgaaagtgg ttattactat atcggtgact tctggggcca ggggaccctg     360
gtcaccgtct cctcagcctc caccaagggc ccatcggtca ctagtggcca ggc            413

<210> SEQ ID NO 3
<211> LENGTH: 413
<212> TYPE: DNA
<213> ORGANISM: Homo sapiens

<400> SEQUENCE: 3
caggtgcagc tggtgcagtc tggggctgag atgaagaagc ctgggtcctc ggtgagggtc      60
tcctgcaagg cttctggagg caccttcgac aaacatgctg tcagttgggt gcgacaggcc     120
ccaggacgag ggcttgagtg ggtgggaggg atcatcccta tgcttggtgc tccacactac     180
gcacagaagt tccagggcag agtcacgatc accgcggaca atccacgag cacagtctac      240 atggaactga gcagcctggg atctgaggac acagccgtgt attactgtgc gagagataaa     300
gcggcttact atgaaagtgg ttattactat atcggtgact tctggggcca ggggaccctg     360
gtcaccgtct cctcagcttc caccaagggc ccatcggtca ctagtggcca ggc            413

<210> SEQ ID NO 4
<211> LENGTH: 413
<212> TYPE: DNA
<213> ORGANISM: Homo sapiens

<400> SEQUENCE: 4
caggtgcagc tggtgcagtc tggggctgag atgaagaagc ctgggtcctc ggtgagggtc      60
tcctgcaagg cttctggagg caccttcgac aaatatgctg tcagctgggt gcgacaggcc     120
ccaggacgag ggcttgagtg ggtgggaggg atcatcccta tgcttggtgc tccacactac     180
gcacagaagt tccagggcag agtcacgatc accgcggaca atccacgag cacaatctac      240 atggaactga gcagcctggg atctgaggac acagccgtgt attactgtgc gagagataaa     300
gcggcttact atgaaagtgg ttattactat atcggtgact tctggggcca ggggaccctg     360
gtcaccgtct cctcagcttc caccaagggc ccatcggtca ctagtggcca ggc            413

<210> SEQ ID NO 5
<211> LENGTH: 413
<212> TYPE: DNA
<213> ORGANISM: Homo sapiens

<400> SEQUENCE: 5
caggtgcagc tggtgcagtc ttgggctgag atgaagaagc ctgggtcctc ggtgagggtc      60
tcctgcaagg cttctggagg caccttcgac aaatatggtg tcagttgggt gcgacaggcc     120
ccaggacaag ggcttgagtg gatgggaggc atcatcccta tgcttggtac tccacactac     180
gcacagaagt tccagggcag agtcacgatc accgcggaca atccacgag cacagtctac      240
```

-continued

```
atggaactga gcagcctggg atctgaggac acagccgtgt attactgtgc gagagataaa      300
gaggcttact atgaaagtgg ttattactat atcggtgact tctggggcca gggaaccctg      360
gtcaccgtct cctcagcctc caccaagggc ccatcggtca ctagtggcca ggc             413
```

<210> SEQ ID NO 6
<211> LENGTH: 413
<212> TYPE: DNA
<213> ORGANISM: Homo sapiens

<400> SEQUENCE: 6

```
gaggtgcagc tggtgcagtc tggggctgag atgaagaagc ctgggtcctc ggtgagggtc       60
tcctgcaagg cttctggagg caccttcgac aaatatgctg tcagttgggt gcgacaggcc      120
ccaggacgag ggcttgagtg ggtgggaggg atcatcccta tgcttggtgc tccacactac      180
gcacagaagt tccagggcag agtcacgatc accgcggaca atccacgag cacagtctac       240 atggaactga gcagcctggg atctgaggac acagccgtgt attactgcgc gagagataaa      300
gcggcttact atgaaagtgg ttattactat atcggtgact tctggggcca gggaaccctg      360
gtcaccgtct cctcagcctc caccaagggc ccatcggtca ctagtggcca ggc             413
```

<210> SEQ ID NO 7
<211> LENGTH: 413
<212> TYPE: DNA
<213> ORGANISM: Homo sapiens

<400> SEQUENCE: 7

```
gaggtgcagc tggtggagtc tggggctgag atgaagaagc ctgggtcctc ggtgagggtc       60
tcctgcaagg cttctggagg caccttcgac aaatatggtg tcagttgggt gcgacaggcc      120
ccaggacgag ggcttgagtg ggtgggaggg atcatcccta tgcttggtgc tccacactac      180
gcacagaagt tccagggcag agtcacgatc accgcggaca atccacgag cacagtctat       240 atggaactga gcagcctggg atctgaggac acagccgtgt attactgcgc gagagataaa      300
gcggcttact atgaaagtgg ttattactat atcggtgact tctggggcca gggaaccctg      360
gtcaccgtct cctcagcctc caccaagggc ccatcggtca ctagtggcca ggc             413
```

<210> SEQ ID NO 8
<211> LENGTH: 413
<212> TYPE: DNA
<213> ORGANISM: Homo sapiens
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t

<400> SEQUENCE: 8

```
caggtgcagc tggtgcagtc tggggctgag atgaagaagc ctgggtcctc ggtgaggntc       60
tcctgcaagg cttctggagg caccttcgac aaatatgctg tcagctgggt gcgacaggcc      120
ccangacgag ggcttgagtg ggtgggaggg atcatcccta tgcttggtgc tccacactac      180
gcacagaagt tccagggcag agtcacgatc accgcggaca atccacgag cacaatntac       240 atggaactga gcagcctggg atctgaggac acagccgtgt attactgtgc gagagataaa      300
```

```
gcggcttact atgaaagtgg ttattactat atcggtgart tctggggcca gggaackctg    360
gtcwckgtrt cttcagcttc caccaagggc ccatcggtca startsgcca ggc           413
```

<210> SEQ ID NO 9
<211> LENGTH: 413
<212> TYPE: DNA
<213> ORGANISM: Homo sapiens

<400> SEQUENCE: 9

```
caggtgcagc tggtgcagtc tggggctgag atgaagaggc ctgggtcctc ggtgagggtc    60
tcctgcaagg cttctggagg caccttcgac aaatatgctg tcagttgggt gcgacaggcc   120
ccaggacgag ggcttgagtg ggtgggggggg atcatccctc tgcttggtgc tccacactac   180
gcacagaagt tccagggcag agtcacgatc accgcggaca atccacgag cacagtctac    240 atggaactga gcagcctggg atctgaggac acagccgtgt attactgcgc gagagataaa   300
gcggcttact atgaaagtgg ttattactat atcggtgact tctggggcca gggaaccctg   360
gtcaccgtct cctcagcctc caccaagggc ccatcggtca ctagtggcca ggc          413
```

<210> SEQ ID NO 10
<211> LENGTH: 401
<212> TYPE: DNA
<213> ORGANISM: Homo sapiens

<400> SEQUENCE: 10

```
caggtgcagc tggtgcagtc tggggctgaa gtgaagaagc ctgggtcctc ggtgaaggtc    60
tcctgtaagg cttctggagg caccttcgga aactatgcta tcaattgggt gcgacaggcc   120
cctggacaag ggcttgagtg gatgggaggg atcatcccta cacttgattt attaaacgac   180
gcacagaact tccaggacag agtcacgatt accgcggaca atccacgaa cacagtctac    240 ctggagctga ccagtctgag atctgaggac acggccgtgt attactgtgc gagaggggggc  300 gattacagtg gctggtataa ttttgactac tggggccagg gaaccctggt caccgtctcc   360
tcagcctcca ccaagggccc atcggtcact agtggccagg c                       401
```

<210> SEQ ID NO 11
<211> LENGTH: 389
<212> TYPE: DNA
<213> ORGANISM: Homo sapiens

<400> SEQUENCE: 11

```
caggtgcagc tggtgcagtc tggggaggc ttggtccagc ctggggggtc tctgagactc     60
tcctgtgcag cctccggatt gccgtttaat agctattgga tgagctgggt ccgccaggct   120
cccgggaagg ggctggagtg ggtggccaac ataaaccaag atggcaatga gaaacactat   180
gtggactctg tgaagggccg attcatcatc tccagagaca cacccacaa ctcactattt   240 ctgcaaatga acagcctgag agccgaggac acggccgtct actactgtgc gagcggtggg   300
gtagtggact ttgaccattg gggccaggga tccctggtca ccgtctcctc agcctccacc   360
aagggcccat cggtcactag tggccaggc                                     389
```

<210> SEQ ID NO 12
<211> LENGTH: 389
<212> TYPE: DNA
<213> ORGANISM: Homo sapiens

<400> SEQUENCE: 12

```
gaggtgcagc tggtggagtc tgggggaggc ttggtccagc ctggggggtc tctgagactc    60
```

```
tcctgtgcag cctctggatt gccgtttagt agctcttgga tgagctgggt ccgccaggct    120
cccgggaagg ggctggagtg ggtggccaac ataaaccaag atggcaatga gaaacactat    180
gtggactctg tgaagggccg attcatcatc tccagagaca cacccagaa ctcactattt     240 ctgcaaatga acagcctgag agccgaggac gcggccgtct actactgtgc gagcggtggg    300
gtagtggact ttgaccattg gggccaggga accctggtca ccgtctcccc agcttccacc    360
aagggcccat cggtcactag tggccaggc                                      389
```

<210> SEQ ID NO 13
<211> LENGTH: 389
<212> TYPE: DNA
<213> ORGANISM: Homo sapiens

<400> SEQUENCE: 13

```
gaggtgcagc tgttggagtc tgggggaggc ctggtcaacc ctgggggtc cctgagactc      60 tcctgtgcag cctctggatt gccgtttaat agctattgga tgagctgggt ccgccaggct    120
cccgggaagg ggctggagtg ggtggccaac ataaaccaag atggcaatga gaaacactat    180
gtggactctg tgaagggccg attcatcatc tccagagaca cacccagaa ttcactattt     240 ctgcaaatga acagcctgag ggccgaggac gcggccgtct actactgtgc gagcggtggg    300
gtagtggact ttgaccattg gggccaggga accctggtca ccgtctcccc agcttccacc    360
aagggcccat cggtcactag tggccaggc                                      389
```

<210> SEQ ID NO 14
<211> LENGTH: 419
<212> TYPE: DNA
<213> ORGANISM: Homo sapiens
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t

<400> SEQUENCE: 14

```
gaggtgcagc tggtggagtc tgggggaggc gtggtccagc ctggggaggtc cctgagactt     60 tcctgtgcag cctctggatt caccttcagt aactatgcta tgcactgggt ccgccaggct    120
ccaggcaagg ggctggagtg ggtggcagtt atatcatatg atggaaggta taaatactac    180
gcagactccg tgaagggccg attcaccatc tccagagacg attccaagaa cacccttta    240 ctgcaaatga acagcctgag acctgaggac acggctgttt attactgtgc gagagaagct    300
ctggtctact atgatagtag tggttactat aangggggat ttgactactg ggncaggga    360 accctggtca ccgtctcctc agcttccacc aagggncccat cggtcactag tggncaggc   419
```

<210> SEQ ID NO 15
<211> LENGTH: 410
<212> TYPE: DNA
<213> ORGANISM: Homo sapiens

<400> SEQUENCE: 15

```
gaggtgcagc tggtggagtc tgggggaggc ttggtcaagc ctggagggtc cctgagactc      60
tcctgtgcag cctctggatt caccttcaat gactactaca tgagctggtt ccgccaggct     120
ccagggaagg ggctggagtg gatttcatac atcagtagta gtggtcctta cacaaactac     180
gcaaactctg tgaagggccg attcaccatc tccagagaca cgccgagaa ctcactgtat      240 ctgcaaatga acagcctgag agccgaggac acggctgtgt attactgtgc gagagaaatg     300
agtccaatta cagcagcagg tgcccacacc tatgagtgct ggggccaggg aaccctggtc     360
accgtctcct cagcctccac caagggccca tcggtcacta gtggccaggc                410

<210> SEQ ID NO 16
<211> LENGTH: 410
<212> TYPE: DNA
<213> ORGANISM: Homo sapiens

<400> SEQUENCE: 16
gaggtgcagc tggtggagtc tgggggaggc gtggtccagc ctgggaggtc cctgagactc      60
tcctgtgcag cctctggatt caccttcaat gactactaca tgagctggtt ccgccaggct     120
ccagggaagg ggctggagtg gatttcatac atcagtagta gtggtcctta cacaaactac     180
gcaaactctg tgaagggccg attcaccatc tccagagaca cgccgagaa ctcactgtat      240 ctgcaaatga acagcctgag agccgaggac acggctgtgt attactgtgc gagagaaatg     300
agtccaatta cagcagcagg tgcccacacc tatgagtgct ggggccaggg aaccctggtc     360
accgtctcct cagcctccac caagggccca tcggtcacta gtggccaggc                410

<210> SEQ ID NO 17
<211> LENGTH: 410
<212> TYPE: DNA
<213> ORGANISM: Homo sapiens

<400> SEQUENCE: 17
gaggtgcagc tggtgcagtc tgggggaggc ttggtcaagc ctggagggtc cctgagactc      60
tcctgtgcag cctctacatt caccttcaat gacgactata tgagttggat ccgccaggct     120
ccagggaagg ggctggagtg ggtttcatac attagtagta gtagtagtta cacacactac     180
gcagactctg tgaagggccg attcagcatc tccagagaca cgccaagaa ctcactgttt      240 ctgcaaatga acagcctgag agccgaggac acggctgttt attactgtgc gagagaactc     300
agtcctttta cagcagcaac tgcccacagc tatgacctct ggggccaggg aaccctggtc     360
accgtctctt cagcttccac caagggccca tcggtcacta gtggccaggc                410

<210> SEQ ID NO 18
<211> LENGTH: 410
<212> TYPE: DNA
<213> ORGANISM: Homo sapiens

<400> SEQUENCE: 18
gaggtgcagc tggtggagtc tgggggaggc ctggtcaagc ctgggggtc cctgagactc      60 tcctgtgcag cctctggatt caccttcaat gacgactata tgagttggat ccgccaggct     120
ccagggaagg ggctggagtg ggtttcatac attagtagta gtagtagtta cacacactac     180
gcagactctg tgaagggccg attcagcatc tccagagaca cgccaagaa ctcactgttt      240 ctgcaaatga acagcctgag agccgaggac acggctgttt attactgtgc gagagaactc     300
agtcctttta cagcagcaac tgcccacagc tatgacctct ggggccaggg aaccctggtc     360
accgtctctt cagcttccac caagggccca tcggtcacta gtggccaggc                410
```

<210> SEQ ID NO 19
<211> LENGTH: 410
<212> TYPE: DNA
<213> ORGANISM: Homo sapiens

<400> SEQUENCE: 19

```
caggtgcagc tggtgcagtc tgggggaggc ctggtcaagc ctggagggtc cctgagactc      60
tcctgtgcag cctctacatt caccttcaat gacgactata tgagttggat ccgccaggct     120
ccagggaagg ggctggagtg ggtttcatac attagtagta gtagtagtta cacacactac     180
gcagactctg tgaagggccg attcagcatc tccagagaca cgccaagaa ctcactgttt      240 ctgcaaatga acagcctgag agccgaggac acggctgttt attactgtgc gagagaactc     300 agtccttta cagcagcaac tgcccacagc tatgacctct ggggccaggg aaccctggtc      360
accgtctcct cagcctccac caagggccca tcggtcacta gtggccaggc                410
```

<210> SEQ ID NO 20
<211> LENGTH: 410
<212> TYPE: DNA
<213> ORGANISM: Homo sapiens

<400> SEQUENCE: 20

```
gaggtgcagc tggtggagtc tgggggaggc ttggtcaagc ctggagggtc cctgagactc      60
tcctgtgcag cctctacatt caccttcaat gacgactata tgagttggat ccgccaggct     120
ccagggaagg ggctggagtg ggtttcatac attagtagta gtagtagtta cacacactac     180
gcagactctg tgaagggccg attcagcatc tccagagaca cgccaagaa ctcactgttt      240 ctgcaaatga gcagcctgag agccgaggac acggctgttt attactgtgc gagagaactc     300 agtccttta cagcagcaac tgcccacagc tatgacctct ggggccaggg aaccctggtc      360
accgtctctt cagcttccac caagggccca tcggtcacta gtggccaggc                410
```

<210> SEQ ID NO 21
<211> LENGTH: 410
<212> TYPE: DNA
<213> ORGANISM: Homo sapiens

<400> SEQUENCE: 21

```
gaggtgcagc tggtggagtc tgggggaggc ttggtcaagc ctggagggtc cctgagactc      60
tcctgtgcag cctctacatt caccttcaat gacgactata tgagttggat ccgccaggct     120
ccagggaagg ggctggagtg ggtttcatac attagtagta gtagtagtta cacacactac     180
gcagactctg tgaagggccg attcagcatc tccagagaca cgccaagaa ctcactgttt      240 ctgcaaatga acagcctgag agccgaggac acggctgttt attactgtgc gagagaactc     300 agtccttta cagcagcaac tgcccacagc tatgacctct ggggccaggg aaccctggtc      360
accgtctctt cagcttccac caagggccca tcggtcacta gtggccaggc                410
```

<210> SEQ ID NO 22
<211> LENGTH: 410
<212> TYPE: DNA
<213> ORGANISM: Homo sapiens

<400> SEQUENCE: 22

```
cagatcacct tgaaggagtc tgggggaggc ttggtcaagc ctggagagtc cctgagactc      60
tcctgtgcag cctctgattt caccttcagt gactactaca tgagctggat ccgccagcct     120
ccagggaagg ggctggagtg ggtttcatac attagtagta gtggtcgtta cacacactac     180
```

```
gcagactctg tgaagggccg attcaccatc tccagagaca acgccaagaa ctctctgttt    240
ctgcaaatga acagcctgag agccgaggac acggctgtct attactgtgc gagagaactc    300
agtcctctta cagcaggtgc tgcccacacc ttggactact ggggccaggg aaccctggtc    360
accgtctcct cagcctccac caagggccca tcggtcacta gtggccaggc                410

<210> SEQ ID NO 23
<211> LENGTH: 410
<212> TYPE: DNA
<213> ORGANISM: Homo sapiens

<400> SEQUENCE: 23
gaggtgcagc tggtgcagtc tgggggcggc ttggtcaagc ctggagagtc cctgagactg     60
tcctgtgcag cctctgattt caccttcggg gactactaca tgagctggat ccgccagcct    120
ccagggaagg ggctggagtg gatttcatac atcagtagta gtagtcgtta cacaaactac    180
gcagactctg tgaagggccg attcaccatc tccagagaca acgccaggaa ttctttgtat    240
ctgcaaatga acagcctgag agccgaggac acggctgtct attactgtgc gagagaactc    300
agtcctctta cagcaggtgc tgcccacacc ttggactact ggggccaggg aaccctggtc    360
accgtctcct cagcctccac caagggccca tcggtcacta gtggccaggc                410

<210> SEQ ID NO 24
<211> LENGTH: 410
<212> TYPE: DNA
<213> ORGANISM: Homo sapiens

<400> SEQUENCE: 24
gaggtgcagc tggtggagtc tggggggaggc ttggtcaagc ctggagagtc cctgagactc     60
tcctgtgcag cctctgattt caccttcagt gactactaca tgagctggat ccgccagcct    120
ccagggaagg ggctggagtg gatttcatac attagtagta atagtcgttt cagaaactac    180
gcagactctg tgaagggccg attcaccatc tccagagaca acgccaagaa ctctctgtat    240
ctgcaaatga acagcctgag aggcgaggac acggctgtct attactgtgc gaaagaactc    300
agtcctctta cagcaggtgc tgcccacacc ttggactact ggggccaggg aaccctggtc    360
accgtctcct cagcctccac caagggccca tcggtcacta gtggccaggc                410

<210> SEQ ID NO 25
<211> LENGTH: 410
<212> TYPE: DNA
<213> ORGANISM: Homo sapiens

<400> SEQUENCE: 25
caggtgcagc tggtgcagtc tggggggaggc ttggtcaagc ctggagggtc cctgagactc     60
tcctgtgcag cctctggatt caccttcagt gactactaca tgaactggat ccgccaggct    120
ccagggaagg ggctggagtg gatttcatac attagtggta gtagttctta cacttactac    180
gcagactctg tgaagggccg attcaccatc tccagagaca acgccaagaa ctcactatat    240
ctgcaaatga gcagcctgag agccgacgac acggctgttt attactgcgc gagagaactc    300
agtcctatta cagcaggaga tgcccacacc tttgactcct ggggccaggg aaccctggtc    360
accgtctcct cagcctccac caagggccca tcggtcacta gtggccaggc                410

<210> SEQ ID NO 26
<211> LENGTH: 410
<212> TYPE: DNA
<213> ORGANISM: Homo sapiens
```

<400> SEQUENCE: 26

```
gaggtgcagc tggtgcagtc tgggggaggc ttggtcaagc ctggagggtc cctgagactc      60
tcctgtgcag cctctgaatt caccttcagt gactactaca tgtcctggat ccgccaggct     120
ccagggaagg ggctggagtg ggtttcttac attagtagta atggtcgtta cagacactac     180
gcagactctg tgaagggccg attcaccatc tccagagaca acgccaagaa ctcactgtat     240
ctccaaatga acagcctgag agccgaggac acggctgtct attactgtgc gagagaactc     300
agtcctctta catcagcaga tgcccacacc tatgactatt ggggccaggg aaccctggtc     360
accgtctcct cagcctccac caagggccca tcggtcacta gtggccaggc                410
```

<210> SEQ ID NO 27
<211> LENGTH: 410
<212> TYPE: DNA
<213> ORGANISM: Homo sapiens

<400> SEQUENCE: 27

```
gaggtgcagc tggtggagtc tgggggaggc ttggtcaagc ctggagagtc cctgcgactc      60
tcctgtacag cctctgaatt caccttcagt gactactaca tgagctggat ccgccaggct     120
ccagggaagg ggctggagtg ggtttcatac attagtagta gtagtcgtta cacacactac     180
ggagactctg tgaagggccg attcaccatc tccagagaca acgccaaaaa ctcactgtat     240
ctgcaaatga acagcctgag aaccgaggac acggctgtct attactgtgc gagagaactc     300
agtcctctta catcagcagg tgcccacacc tatgactact ggggccaggg aaccctggtc     360
accgtctcct cagcctccac caagggccca tcggtcacta gtggccaggc                410
```

<210> SEQ ID NO 28
<211> LENGTH: 395
<212> TYPE: DNA
<213> ORGANISM: Homo sapiens

<400> SEQUENCE: 28

```
caggtgcagc tgcaggagtc gggcccagga ctggtgaagc cttcggagac cctgtccctc      60
acctgcagtg tctctggtta ccccatcagc agtggttact attggggctg gatccggcag     120
cccccaggga aggggctgga gtggattggg agtatccatc atagtgggag cacctactac     180
aattcgtccc tcaagagtcg agtcacccta tcagttgaca cgtctaaaaa tcagttctcc     240
ctgaaggtga gctctgtgac cgccgcagac acggccgttt attactgtgc gaggaccact     300
acggcttact ggtactttga tctctggggc cgtggcaccc tggtcactgt ctcctcagct     360
tccaccaagg gcccatcggt cactagtggc caggc                                 395
```

<210> SEQ ID NO 29
<211> LENGTH: 419
<212> TYPE: DNA
<213> ORGANISM: Homo sapiens

<400> SEQUENCE: 29

```
gaggtgcagc tgttggagtc tggcccagga ccggtgaagc cttcggggac cctgtccctc      60
acctgtggtg tctctggtgg ctccatcagc actaatcact ggtggacttg ggtccgccag     120
cccccagggc aggggctgga gtggattggg gaaatccatc ataatgggag cacccttcttc    180
aacccgtccc tcaagagtcg agtcaccatt tcagtggaca agtccaacaa ccagttctcc     240
ctgaaactga cctctctgac cgccgcggac acggccgtgt atttctgtgc gagagggtgg     300
caccggactg gatttcgtgg ctacccttcc cactggtact cgatctctg gggccgtggc     360
```

-continued

```
accctggtca ctgtctcctc agcttccacc aagggcccat cggtcactag tggccaggc    419
```

<210> SEQ ID NO 30
<211> LENGTH: 419
<212> TYPE: DNA
<213> ORGANISM: Homo sapiens

<400> SEQUENCE: 30

```
caggtgcagc tgcaggagtc gggcccagga ccggtgaagc cttcggggac cctgtccctc    60
acctgcggtg tctctggtgg ctccattagc agtaatcact ggtggacttg ggtccgccag   120
cccccaggga aggggctgga gtggattgga gaaatctatc ataatgggag caccttcctc   180
aacccgtccc tcaagagtcg agtcaccatt tcagtagaca gtccaacaa ccagttctcc    240
ctgaaactga cttctgtgac cgccgcggac acggccgtgt attactgtgc gagagggtgg   300
caccggactg gatttcgtgg ctacccttcc cactggtact tcgatctctg gggccgtggc   360
accctggtct ctgtctcctc agcctccacc aagggcccat cggtcactag tggccaggc    419
```

<210> SEQ ID NO 31
<211> LENGTH: 419
<212> TYPE: DNA
<213> ORGANISM: Homo sapiens

<400> SEQUENCE: 31

```
caggtgcagc tgcaggagtc gggcccagga ctggtgaagc cttcggggac cctgtccctc    60
acctgtggtg tctctggtgg ctccatcagc agtaatcact ggtggacttg ggtccgccag   120
cccccagggc aggggctgga gtggattggg gaagtccatc ataatgggag caccttcttc   180
aacccgtccc tcaagagtcg agtcaccatt tcagtagaca gtccaacaa ccagttctcc    240
ctgaaactga cctctgtgac cgccgcggac acggccgtgt atttctgtgc gagagggtgg   300
caccggactg gatttcgtgg ctacccttcc cactggtact tcgatctctg gggccgtggc   360
accctggtca ctgtctcctc agcctccacc aagggcccat cggtcactag tggccaggc    419
```

<210> SEQ ID NO 32
<211> LENGTH: 335
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, or t

<400> SEQUENCE: 32

```
cggccgagct cgtgctgacg cagccgccnt cagcgtctga accccccggg cagagggtca    60
ccatctcctg ttctggaagc agctccaaca tcgcaggtaa tactgtgtac tggtaccagc   120
agctcccagg agcggccccc aagctcctca tctattacaa tgatcagcgg ccctcagggg   180
tccctgaccg attctctggc tccaagtctg gcacgtcagc ctccctgtcc atcagtgggc   240
tccggtccga ggatgagggt gattattact gttcagcatg ggatgccagt ctgtcttggg   300
tgttcggcgg aggcaccaag ctgaccgtcc taggc                              335
```

<210> SEQ ID NO 33
<211> LENGTH: 338
<212> TYPE: DNA
<213> ORGANISM: Homo sapiens

<400> SEQUENCE: 33

```
cggccgagct cgtgctgact cagccaccct cagtgtctga accccccggg cagagggtca    60
```

```
ccatctcctg ttctggaagc agctccaaca tcgcaggtaa tactgtgtac tggtaccagc    120
aactcccagg agcggccccc aagctcctca tctattacaa tgatcagcgg ccctcagggg    180
tccctgaccg attctctggc tccaagtctg gcacctcctc ctccttggcc atcagtgggc    240
tccagtctga ggatgaggct tattattact gtgcaacatg ggatgaagat gtgaatggtt    300
gggtgttcgg cggaggcacc aagctgaccg tcctaggc                             338
```

<210> SEQ ID NO 34
<211> LENGTH: 357
<212> TYPE: DNA
<213> ORGANISM: Homo sapiens

<400> SEQUENCE: 34

```
gtgcccccag gccaggccga gcttcgtgct gatttcagcc caccttcagg gtctgagacc     60
ccccggccag agggtcacca tctcctgttg cggaagcagc tccaacatcg caggtaatac    120
tgtgtactgg taccagcagc tccccaggag cggccccca agctcctcat ctattacaat    180
gatcagcggc cctcaggggt ccctgaccga ttctctggct ccaagtctgg cacctcctcc    240
tccttggcca tcagtgggct ccagtctgag gatgaggctt attattactg tgcaacatgg    300
gatgaagatg tgaatggttg ggtgttcggc ggagggacca agctgaccgt cctaggc      357
```

<210> SEQ ID NO 35
<211> LENGTH: 338
<212> TYPE: DNA
<213> ORGANISM: Homo sapiens

<400> SEQUENCE: 35

```
cggccgagct cgtgctgact cagccaccttt cagcgtctga gacccccggg cagagggtca     60
ccatctcctg ttctggaagc agctccaaca tcgcaggtaa tactgtgtac tggtaccagc    120
agctcccagg agcggccccc aagctcctca tctattacaa tgatcagcgg ccctcagggg    180
tccctgaccg attctctggc tccaagtctg gcacctcctc ctccttggcc atcagtgggc    240
tccagtctga ggatgaggct tattattact gtgcaacatg ggatgaagat gtgaatggtt    300
gggtgttcgg cggagggacc aagctgaccg tcctaggc                             338
```

<210> SEQ ID NO 36
<211> LENGTH: 338
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 36

```
cggccgagct cgtggtgacg cagccgccnt cagtgtctgc gncccagga cagaaggtca      60 ccatctcctg ttctggaagc agctccaaca tcgcaggtaa tactgtgtac tggtaccagc    120
agctcccagg agcggccccc aagctcctca tctattacaa tgatcagcgg ccctcagggg    180
tccctgaccg attctctggc tccaagtctg gcacctcctc ctccttggcc atcagtgggc    240
tccagtctga ggatgaggct tattattact gtgcaacatg ggatgaagat gtgaatggtt    300
gggtgttcgg cggaggcacc aagctgaccg tcctaggt                             338
```

<210> SEQ ID NO 37

<211> LENGTH: 338
<212> TYPE: DNA
<213> ORGANISM: Homo sapiens

<400> SEQUENCE: 37

| | | | | | | |
|---|---|---|---|---|---|---|
| cggccgagct | cgagctgact | cagccaccct | cagtgtctgg | gaccccggg | cagagggtca | 60 |
| ccatctcctg | ttctggaagc | agctccaaca | tcgcaggtaa | tactgtgtac | tggtaccaac | 120 |
| agctcccagg | agcggccccc | aagctcctca | tctattacaa | tgatcagcgg | ccctcagggg | 180 |
| tccctgaccg | attctctggc | tccaagtctg | gcacctcctc | ctccttgacc | atcagtgggc | 240 |
| tccagtctga | ggatgaggct | tattattact | gtgcaacatg | ggatgaagat | gtgaatggtt | 300 |
| gggtgttcgg | cggaggcacc | aagctgaccg | tcctaggt | | | 338 |

<210> SEQ ID NO 38
<211> LENGTH: 338
<212> TYPE: DNA
<213> ORGANISM: Homo sapiens

<400> SEQUENCE: 38

| | | | | | | |
|---|---|---|---|---|---|---|
| cggccgagct | catgctgact | cagccccact | cagcgtctga | gaccccggg | cagagggtca | 60 |
| ccatctcctg | ttctggaagc | agctccaaca | tcgcaggtaa | tactgtgtac | tggtaccagc | 120 |
| agctcccagg | agcggccccc | aagctcctca | tctattacaa | tgatcagcgg | ccctcagggg | 180 |
| tccctgaccg | attctctggc | tccaagtctg | gcacctcctc | ctccttggcc | atcagtgggc | 240 |
| tccagtctga | ggatgaggct | tattattact | gtgcaacatg | ggatgaagat | gtgaatggtt | 300 |
| gggtgttcgg | cggagggacc | gagctgaccg | tcctcggt | | | 338 |

<210> SEQ ID NO 39
<211> LENGTH: 338
<212> TYPE: DNA
<213> ORGANISM: Homo sapiens

<400> SEQUENCE: 39

| | | | | | | |
|---|---|---|---|---|---|---|
| cggccgagct | cgtgctgact | cagccacctt | cagcgtctga | gaccccggg | cagagggtca | 60 |
| ccatctcctg | ttctggaagc | agctccaaca | tcgcaggtaa | tactgtgtac | tggtaccagc | 120 |
| aattcccagg | agcggccccc | aagctcctca | tctattataa | tgatcagcgg | ccctcagggg | 180 |
| tccctgaccg | attctctggc | tccaagtctg | gcacctcctc | ctccttggcc | atcagtgggc | 240 |
| tccagtctga | ggatgaggct | tattattact | gtgcaacatg | ggatgaagat | gtgaatggtt | 300 |
| gggtgttcgg | cggaggcacc | gagctgaccg | tcctcggt | | | 338 |

<210> SEQ ID NO 40
<211> LENGTH: 338
<212> TYPE: DNA
<213> ORGANISM: Homo sapiens

<400> SEQUENCE: 40

| | | | | | | |
|---|---|---|---|---|---|---|
| cggccgagct | cgtgctgact | caatcgccct | cagcgtctga | gaccccggg | cagagggtca | 60 |
| ccatctcctg | ttctggaagc | agctccaaca | tcgcaggtaa | cactgtgtac | tggtaccagc | 120 |
| agttcccagg | agcggccccc | aagctcctca | tctattacaa | tgatcagcgg | ccctcagggg | 180 |
| tccctgaccg | attctctggc | tccaagtctg | gcacctcctc | ctccttggcc | atcagtgggc | 240 |
| tccagtctga | ggatgaggct | tattattact | gtgcaacatg | ggatgaagat | gtgaatggtt | 300 |
| gggtgttcgg | cggaggcacc | aaggtgaccg | tcctaggt | | | 338 |

<210> SEQ ID NO 41

```
<211> LENGTH: 338
<212> TYPE: DNA
<213> ORGANISM: Homo sapiens

<400> SEQUENCE: 41
cggccgagct catgctgact cagccccact cagcgtctgg accccccggg cagagggtca    60
ccatctcttg ttctggaagc agctccaaca tcgcaggtaa tactgtgtac tggtaccagc   120
aattcccagg agcggccccc aagctcctca tctattataa tgatcagcgg ccctcagggg   180
tccctgaccg attctctggc tccaagtctg gcacctcctc ctccttggcc atcagtgggc   240
tccagtctga ggatgaggct tattattact gtgcaacatg ggatgaagat gtgaatggtt   300
gggtgttcgg cggaggcacc aaggtgaccg tcctaggt                            338

<210> SEQ ID NO 42
<211> LENGTH: 338
<212> TYPE: DNA
<213> ORGANISM: Homo sapiens

<400> SEQUENCE: 42
cggccgagct catgctgact cagccccact cagcgtctga accccccggg cagagggtca    60
ccatctcttg ttctggaagc agctccaaca tcgcaggtaa tactgtgtac tggtaccagc   120
aattcccagg agcggccccc aagctcctca tctattataa tgatcagcgg ccctcagggg   180
tccctgaccg attctctggc tccaagtctg gcacctcctc ctccttggcc atcagtgggc   240
tccagtctga ggatgaggct tattattact gtgcaacatg ggatgaagat gtgaatggtt   300
gggtgttcgg cggaggcacc aaggtgaccg tcctaggt                            338

<210> SEQ ID NO 43
<211> LENGTH: 336
<212> TYPE: DNA
<213> ORGANISM: Homo sapiens

<400> SEQUENCE: 43
gccgagctcg tgctgactca atcgccctca gcgtctgaga ccccccgggca gagggtcacc    60
atctcctgtt ctggaagcag ctccaacatc gcaggtaata ctgtatactg gtaccagcag   120
ctcccaggag cggcccccaa gctcctcatc tattacaatg atcagcggcc ctcaggggtc   180
cctgaccgat tctctggctc caagtctggc acctcctcct ccttggccat cagtgggctc   240
cagtctgagg atgaggctta ttattactgt gcgacatggg atgaagatgt gaatggttgg   300
gtgttcggcg agggaccaa ggtgaccgtc ctaggc                                336

<210> SEQ ID NO 44
<211> LENGTH: 335
<212> TYPE: DNA
<213> ORGANISM: Homo sapiens

<400> SEQUENCE: 44
cggccgagct cgtgttgacg cagccgccct cagtgtctgg accccccggg cagagggtca    60
ccatctcttg ttctggaagc agctcccaca tcggaaataa ttatgtatac tggtaccagc   120
atctcccagg aacggccccc aaactcctca tctacagtaa tgatcagcgg ccctcagggg   180
tccctgaccg attctctgcc tccaagtctg ccacctcagc ctccctggcc atcagtgggc   240
tccggtccga ggatgaggct gattattact gtgcagcatg gatgacagc caggggggag   300
tgttcggcgg agggaccaag gtgaccgtcc taggt                                335

<210> SEQ ID NO 45
```

```
<211> LENGTH: 335
<212> TYPE: DNA
<213> ORGANISM: Homo sapiens

<400> SEQUENCE: 45
cggccgagct cgtgctgact cagccacctt cagtgtctgg acccccggg cagagggtca      60 ccatctcttg ttctggaagc agctcccaca tcggaagtaa ttatgtgtac tggtaccagc    120
agctcccagg aacggccccc aaaatcctca tctacagtaa tgatcagcgg cccgcagggg    180
tccctgaccg attctctgcc tccaagtctg gcacctcagc ctccctggcc atcagtgggc    240
tccggtccga ggatgaggct gattattact gtgcagcatg ggatgacggc caggggggg     300 tcttcggcgg agggaccaag ctgaccgtcc taggc                                335

<210> SEQ ID NO 46
<211> LENGTH: 336
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is a, c, g, or t

<400> SEQUENCE: 46
cggccgagct cgtgctgact cagccacntt cagcgttctg ggaccccgg gcagagggtc      60 accatctctt gttctggaag cagctcccac atcggaaaga attatgtata ctggtaccaa    120
catctcccag gagcggcccc caaactcctc atcttcagta atgatcagcg gccctcaggg    180
gtccctgacc gattctctgg ctccaagtct ggcacctcag cctccctggc catcagtggg    240
ctccggtccg aggatgaggc tgattattac tgtgcagtat gggatgacag ccaggggggg    300
gtgttcggcg gagggaccaa gctgaccgtc ctaggt                               336

<210> SEQ ID NO 47
<211> LENGTH: 341
<212> TYPE: DNA
<213> ORGANISM: Homo sapiens

<400> SEQUENCE: 47
cggccgagct cgagctgact cagccaccct cagtgtctgg gtctcctgga cagtcgatca     60
ccatctcctg cactggaagc agcagttatg ttggaatttt taaccttgtc tcctggtacc    120
aacaacaccc aggcacagcc cccagacgcg tcatttatga gggcgataag cggccctcaa    180
acatttctaa tcgcttctct ggctccaagt ctggcaacac ggcctccctg acaatctctg    240
gcctccaggc tgacgacgag gctgattatt actgctactc atatgtcgct ggtagtgatc    300
tttgggtgtt cggcggaggc accaagctga ccgtcctagg c                        341

<210> SEQ ID NO 48
<211> LENGTH: 341
<212> TYPE: DNA
<213> ORGANISM: Homo sapiens

<400> SEQUENCE: 48
cggccgagct cgagctgact cagccaccct cagtgtctgg gtctcctgga cagtcgatca     60
ccatctcctg cactggaagc agcagttatg ttggaatttt taaccttgtc tcctggtacc    120
aacaacaccc aggcacagcc cccagacgcg tcatttatga gggcgataag cggccctcaa    180
acatttctaa tcgcttctct ggctccaagt ctggcaacac ggcctccctg acaatctctg    240
gcctccaggc tgacgacgag gctgattatt actgctactc atatgtcgct ggtagtgatc    300
```

```
tttgggtgtt cggcggaggc accaagctga ccgtcctagg c                341
```

<210> SEQ ID NO 49
<211> LENGTH: 323
<212> TYPE: DNA
<213> ORGANISM: Homo sapiens

<400> SEQUENCE: 49

```
cggccgagct cgccctgact cagcctccct ccgtgtctgg gtctcctgga cagtcgatca    60
ccatctcctg cactggattc agcagtgatc tttcctggta ccaacagcac ccaggcaaag   120
cccccaaact catgatttat gatgtcaata atcggccctc aggggtttct gatcggttct   180
ctggctccaa gtctggcaac acggcctccc tgaccatctc tgggctccag gctgaggacg   240
aggctgatta ttactgcagc tcatatacaa gcagcagcac ttccctgatg ttcggcggag   300
gcaccgagct gaccgtcctc ggc                                          323
```

<210> SEQ ID NO 50
<211> LENGTH: 323
<212> TYPE: DNA
<213> ORGANISM: Homo sapiens

<400> SEQUENCE: 50

```
cggccgagct cgccctgact cagcctccct ccgtgtctgg gtctcctgga cagtcgatca    60
ccatctcctg cactggattc agcagtgatc tttcctggta ccaacagcac ccaggcaaag   120
cccccaaact catgatttat gatgtcaata atcggccctc aggggtttct gatcggttct   180
ctggctccaa gtctggcaac acggcctccc tgaccatctc tgggctccag gctgaggacg   240
aggctgatta ttactgcagc tcatatacaa gcagcagcac ttccctgatg ttcggcggag   300
gcaccgagct gaccgtcctc ggc                                          323
```

<210> SEQ ID NO 51
<211> LENGTH: 332
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t

<400> SEQUENCE: 51

```
cggccgagct cggggtgacg cagccgccnt cggtgtcagt gncccagga cagacgncca    60
cgattacctg tgggggaanc aacatnggaa gtaaaagtgt gaactggtac cagcagaagc   120
caggccaggc ccctgtgctg gtcgtctatc atgatagcga atggccctca gggatccctg   180
agcgattctc tggctccaac tctgggaaca cggccaccct gaccatcagc agggtcgaag   240
ccggggatga ggccgactat tactgtcagg tgtgggatag tcgtagtgat aatgtggtat   300
```
tcggcggagg caccgagctg accgtcctcg gc                                    332

<210> SEQ ID NO 52
<211> LENGTH: 332
<212> TYPE: DNA
<213> ORGANISM: Homo sapiens
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t

<400> SEQUENCE: 52
cggccgagct catgctgact cagccccact cggtgtcagt gnccccagga cagacgncca    60
cgattacctg tggggaaaac aacatnggaa gtaaaagtgt gaactggtac cagcagaagc   120
caggccaggc ccctgtgctg gtcgtctatc atgatagcga atggccctca gggatccctg   180
agcgattctc tggctccaac tctgggaaca cggccaccct gaccatcagc agggtcgaag   240
ccggggatga ggccgactat tactgtcagg tgtgggatag tcgtagtgat aatgtggtat   300
tcggcggagg caccgagctg accgtcctcg gc                                    332

<210> SEQ ID NO 53
<211> LENGTH: 332
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t

<400> SEQUENCE: 53
cggccgagct cgtgctgact cagccaccnt cggtgtcagt gnccccagga cagacgncca    60
ggattacctg tgggcaaac aacatnggaa gtaaaagtgt gaactggtac cagcagaagc   120
caggccaggc ccctgtgctg gtcgtctatc atgatagcga atggccctca gggatccctg   180
agcgattctc tggctccaac tctgggaaca cggccaccct gaccatcagc agggtcgaag   240
ccggggatga ggccgactat tactgtcagg tgtgggatag tcgtagtgat aatgtggtat   300
tcggcggagg caccgagctg accgtcctcg gt                                    332

<210> SEQ ID NO 54
<211> LENGTH: 283
<212> TYPE: DNA
<213> ORGANISM: Homo sapiens

<400> SEQUENCE: 54
acaggcgccc aggattacct gtgggggaaa cgacattgaa agtaaaagtg tgcagtggta    60

```
ccagcagaag ccaggccagg cccctgtgct ggtcgtctat aatgatagtg acggccctc      120 agagatccct gagcgattct ctggctccaa gtctggaaac acggccaccc tgagcatcag      180
cagggtcgaa gccggggatg aggccgacta ctactgtcag gtgtgggata tgttaatga      240 tcaagtggta ttcggcggag ggaccgagct gaccgtcctc ggc                        283
```

<210> SEQ ID NO 55
<211> LENGTH: 332
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 55

```
cggccgagct cgggctgact cagccaccnt cagtgtcagt gncccagga caggcgncca       60 ggattacctg tggggaaac gacattgaaa gtaaaagtgt gcagtggtac cagcagaagc      120
caggccaggc ccctgtgctg gtcgtctata atgatagtga cgggccctca gagatccctg     180
agcgattctc tggctccaag tctggaaaca cggccaccct gagcatcagc agggtcgaag     240
ccggggatga ggccgactac tactgtcagg tgtgggatag tgttaatgat caagtggtat     300
tcggcggagg gaccgagctg accgtcctcg gc                                    332
```

<210> SEQ ID NO 56
<211> LENGTH: 332
<212> TYPE: DNA
<213> ORGANISM: Homo sapiens

<400> SEQUENCE: 56

```
cggccgagct cgtgctgact caatcgccct cggtgtcagt ggccccagga cagacggcca      60
aagtcacctg tggggaaat aatattggaa gtaaggtgt gcactggtac cagcagaagc      120
caggccaggc ccctgtgttg gtcgtcttta atgataacga ccggccctca gggatccctg     180
agcgattctc tggctccaac tctgggaaca cggccaccct gaccatcagc agggtcgagg     240
ccggggatga ggccgactat tactgtcagg tgtacgatat taatagtgat ctcgtggtat     300
tcggcggagg gaccgagctg accgtcctcg gc                                    332
```

<210> SEQ ID NO 57
<211> LENGTH: 333
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 57

```
cggccgagct cgagctgact cagccaccnt cagtgtccag tgncccagg acagacgncc      60 aagattacct gtgggggaaa caacattgga agtaaaagtg tgcactggta ccagcagaag    120
ccaggccagg ccctgtact ggtcgtgtat gatgatagcg accggccctc agggatccct    180
gagagattct ctggctccaa gtctgggaaa acggccaccc tgaccatcag cagggtcgaa    240
gccggggatg aggccgacta ttactgtcag gtgtgggata gtagtactga tgatgtgata    300
ttcggcggag gcaccaagct gaccgtccta ggc                                  333
```

<210> SEQ ID NO 58
<211> LENGTH: 332
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t

<400> SEQUENCE: 58

```
cggccgagct cgccctgact cagcctccnt ccgtgtcagt gncccagga cagacgncca      60 ggattacctg tgggggaaac aacatnggaa gtaaaagtgt gcactggtac cagcagaagc    120
caggccaggc ccctgtgctg gtcgtctatg atgatagcga accggccctca gggatccctg    180 agcgattctc tggctccaac tctgggaaca cggccaccct gaccatcagc agggtcgaag    240
ccggggatga ggccgactat tactgtcagg tgtgggatag tagtagtgat catgtggtat    300
tcggcggagg gaccaaggtg accgtcctag gt                                   332
```

<210> SEQ ID NO 59
<211> LENGTH: 333
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (125)..(125)

```
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t

<400> SEQUENCE: 59
cgnccgagct cgtgttgacg cagccgccct tcggtgtcag tgnccccagg acagacgncc      60
aggattacct gtggggnaan caccatngga agtaaaagtg tgcactggta ccagcagaag     120
ccagnccagg cccctgtgct ggtcgtctat gatgatagcg accggccntc agggatccct     180
gagcgattct ctggctccaa ttctgggaat acgccaccc tgtccatcac cagggtcgaa      240
gccggggatg aggccgacta ttactgtcag gtgtgggata gtagtagtga tcatgtggta     300
ttcggcggag ggaccaaggt gaccgtccta ggc                                   333

<210> SEQ ID NO 60
<211> LENGTH: 332
<212> TYPE: DNA
<213> ORGANISM: Homo sapiens

<400> SEQUENCE: 60
cggccgagct cgtgttgacg cagccgccct cggtgtcagt ggccccagga cagtcggcca     60
ggattacttg tggggaaagc aacattggat ttcaaagtgt gcactggtac cagcagaagc    120
caggccaggc ccctgtgtta ctcgtctatg atgatagtga ccggccctca gagatccctg    180
agcgattctc tggctccaat tctggggaca cggccaccct gaccatcagc agggtcgaag    240
ccggggatga ggccgactat tactgtcagg tttggagtag tagtagtgat catccggttt    300
tcggcggagg cacccagctg accgtcctcg gc                                   332

<210> SEQ ID NO 61
<211> LENGTH: 332
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t

<400> SEQUENCE: 61
cggccgagct cgtgctgact cagccacccnt cggtgtcagt gnccccagga cagacgncca     60
ggattacctg tgggggaaac aacatnggaa gtaaaagtgt gcagtggtac cagcagaagc    120
caggccaggt ccctgtcctg gtcgtctata atgatagcga cgggccctca gagatccctg    180
agcgattctc tggctccaac tctgggaaca cggccaccct gaccatcagc aaggtcgaag    240
ccggggatga ggccgactat tactgtcagg tgtgggatag tagttatgat catgtggtat    300
tcggcggagg gaccgagctg accgtcctcg gc                                   332

<210> SEQ ID NO 62
<211> LENGTH: 332
<212> TYPE: DNA
```

-continued

<213> ORGANISM: Homo sapiens

<400> SEQUENCE: 62
cggccgagct cgtgctgact cagccacctt cggtgtcagt ggccccagga cagacggcca      60
ggattccctg tgggggaaac aacattggaa gtaaaagtgt gcactggtac cagcagaagc     120
caggccaggc ccctgtgctg gtcgtctatg atgatagcga ccggccctca gggatccctg     180
agcgattctc tggctccaac tcagggaaca cggccaccct gaccatcagc agggtcgaag     240
tcggggatga ggccgactat tactgtcagg tgtgggatct tagtagtgat catgtggtat     300
tcggcggagg gaccaaggtg accgtcctag gc                                    332

<210> SEQ ID NO 63
<211> LENGTH: 332
<212> TYPE: DNA
<213> ORGANISM: Homo sapiens
<220> FEATURE:
<221> NAME/KEY: misc_feature
<222> LOCATION: (42)..(42)
<223> OTHER INFORMATION: n is a, c, g, or t

<400> SEQUENCE: 63
cggccgagct cgtgctgact cagccacctt cggtgtcagt gnccccagga cagacggcca      60
cgattacctg tgggggaaac aacattggaa gtaaaagtgt gaactggtac cagcagaagc     120
caggccaggc ccctgtgctg gtcgtctatc atgatagcga atggccctca gggatccctg     180
agcgattctc tggctccaac tctgggaaca cggccaccct gaccatcagc agggtcgaag     240
ccggggatga ggccgactat tactgtcagg tgtgggatag tcgtagtgat aatgtggtct     300
tcggcggagg gaccaaggtg accgtcctag gt                                    332

<210> SEQ ID NO 64
<211> LENGTH: 332
<212> TYPE: DNA
<213> ORGANISM: Homo sapiens
<220> FEATURE:
<221> NAME/KEY: misc_feature
<222> LOCATION: (42)..(42)
<223> OTHER INFORMATION: n is a, c, g, or t

<400> SEQUENCE: 64
cggccgagct cgtgctgact cagccaccct cggtgtcagt gnccccagga cagacggcca      60
ggattacctg tggggcaaac aacattggag gtaaacgtgt gcactggtac cagcagaagc     120
caggccaggc ccctatactg gtcgtctatg atgataccga ccggccctca gggatccctg     180
agcgattctc tggctccaac actgggaaca cggccacact gaccatcagc agggtcgaag     240
ccggggatga ggccgactat tactgtcagg tgtgggatag tggtagtgat catgtggtct     300
tcggcggagg gaccgagctg accgtcctag gc                                    332

<210> SEQ ID NO 65
<211> LENGTH: 333
<212> TYPE: DNA
<213> ORGANISM: Homo sapiens
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (43)..(43)

<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 65
cggcngagct cgtgctgact cagccacntt cggtgtccag tgnccccagg acagacgncc      60
aggattacct gtgggggaaa caacattgga agtaaaagtg tgcactggta ccagcagcag     120
ccaggccagg ccctgtgct ggtcgtctat gatgatagcg accggccctc agggatccct     180
gagcgattct ctggctccaa ctctgggaac acggccaccc tgaccatcag cagggtcgaa    240
gccggggatg aggccgacta ttactgtcag gtgtgggata gtagtagtga tcatgtggta   300
ttcggcggag ggacccagct gaccgtcctc ggt                                   333

<210> SEQ ID NO 66
<211> LENGTH: 332
<212> TYPE: DNA
<213> ORGANISM: Homo sapiens
<220> FEATURE:
<221> NAME/KEY: misc_feature
<222> LOCATION: (57)..(57)
<223> OTHER INFORMATION: n is a, c, g, or t

<400> SEQUENCE: 66
cggccgagct catgctgact cagccccact cggtgtccgt gccccagga cagacgncca      60 ggatcacttg tgggggaaac ggcattggac gtaaaagtgt tcactggtac cagcagaagc    120
caggccaggc ccctgttctg gtcgtctatg atgatgtttc ccggccctca gggatccctg    180
agcgattctc tggctccaac tctgggaaca cggccaccct gatcatcacc agggtcgaag   240
tcggggatga ggccgactat tactgtcagg cttgggacat ttctagtgat catgtgatat   300
tcggcgaagg gaccaaggtg accgtcctcg gt                                    332

<210> SEQ ID NO 67
<211> LENGTH: 332
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t

<400> SEQUENCE: 67

```
cgncngagct cgtgctgact cagccacntt cgctgtcagt ggccccagga cagacgncca    60
cgattacctg tgggggaagc aacatnggag gtatgcgtgt acactggtac cngcagactc   120
caggccaggc ccctgtactg gtcgtctatg atgacagcga ccggccctca gagatccctg   180
agcgnttctc tggctccaac tgggggaact cggccaccct gaccatcagc agggtcgaag   240
ccggggatga ggccgactat tactgtcagg tgtgggaaag tactagtgat catgtggtat   300
tcggcggagg gaccaagctg accgtcctag gc                                 332
```

<210> SEQ ID NO 68
<211> LENGTH: 332
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 68

```
cggccgagct cgtgctgact cagccacntt cggtgtccgt gnccccagga cagacgncca    60
gtatcacgtg tgggggagac ggcattggac gtaagagtgt gcactggtac cagcagaagc   120
caggccaggc ccctgctctg gtcgtctatg atgatattgg ccggccctca gggatccctg   180
agcgcttctc tggctccaac tctgggaaca tggccaccct gaccatcagc agggtcgaag   240
ccggggatga ggccgacttt ttttgtcagg tgtgggatag tattagtgat catgtggtct   300
tcggcggagg gaccaagctg accgtcctag gc                                 332
```

<210> SEQ ID NO 69
<211> LENGTH: 333
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t

<400> SEQUENCE: 69

```
cggccgagct cgtgctgact cagccaccnt cggtgtccag tgnccccagg acagacgccc    60
aggattacct gtgggggaan caccatngga agtaaaagtg tgcactggta ccagcagaag   120
ccaggccagg ccctgtctt ggtcgtctat gatgatagcg accggccctc aggaatccct   180
gagcgattct ctggctccaa ctctggggac acggccacgc tgaacatcag cagggtcgaa   240
gccggggatg aggccgacta ttactgtcag gtgtgggata gtagtcgtga tcatgtggta   300
ttcggcggag gcaccaagct gaccgtccta ggc                                333
```

```
<210> SEQ ID NO 70
<211> LENGTH: 332
<212> TYPE: DNA
<213> ORGANISM: Homo sapiens
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t

<400> SEQUENCE: 70
cggcngagct cgtgctgact cagccacctt cggtgtcagt gcccccagga cagacgncca      60
ggattacctg tgggggaaac aacatnggaa gtaaaagtgt gcactggtac cagcagaagc     120
caggccaggc ccctgtgctg gtcgtctatg atgatagcga ccggccctca gggatccctg     180
agcgattctc tggctccaac tctgggaaca cggccaccct gaccatcagc agggtcgaag     240
ccggggatga ggccgactat tactgtcagg tgtgggatag tagtagtgat cttgtggtat     300
tcggcggagg gacccagctg accgtcctcg gc                                   332

<210> SEQ ID NO 71
<211> LENGTH: 327
<212> TYPE: DNA
<213> ORGANISM: Homo sapiens

<400> SEQUENCE: 71
cggccgagct catgctgact cagccccact cggtgtcagt ggccctggga cagacgccca      60
ggattacctg tgggggagac aacattggaa ctaagaatgt tcactggtac cagcagaagc     120
caggccaggc ccctgtgtt ggtcatttat cgggatacca atcggccctc tgggatccct     180
gagcgattct ctggctccaa ctcggagaac acggccaccc tgaccatcaa tagagcccaa     240
gccgggatg aggctgacta tcactgtcag gtgtgggtca gttctactgc gatattcggc      300
ggaggcacca agctgaccgt cctaggt                                         327

<210> SEQ ID NO 72
<211> LENGTH: 348
<212> TYPE: DNA
<213> ORGANISM: Homo sapiens

<400> SEQUENCE: 72
ctggtttcgc taccgtgccc caggcgccga gctcgtgttg acgcagccgc cctcagtgtc      60
gtgtccccag gacagacagc cagcatcacc tgctctggag ataaattggg ggataaatat     120
gcttcctggt atcagcagaa ggcaggccag tccctgtgc tggtcatcta tcaagatagg      180
aagcggccct cagggatccc tgagcgattc tctggctcca actctgggaa cacagccact     240
ctgaccatca gcgggaccca ggctatggat gaggctgact attactgtca ggcgtgggac     300
agcagcactg cggtgttcgg cggagggacc aaggtgaccg tcctaggc                  348

<210> SEQ ID NO 73
<211> LENGTH: 326
<212> TYPE: DNA
<213> ORGANISM: Homo sapiens
<220> FEATURE:
<221> NAME/KEY: misc_feature
<222> LOCATION: (16)..(16)
```

<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t

<400> SEQUENCE: 73
cggccgagct cgtgtngacg cagtctccag acaccctgtc tttctctcca ggggaaagag      60
ccaccntctc ctgccaggtc cagtcagaat gttagcagct acttagcctg gtaccaacag     120
aaacctggcc aggctcccag gctcctcacc tatgacacat ccaacaatgg cgtctttgcc     180
aggttcagta gcagtgggtc tgggacagac ttcactctca ccatcaccag gttagagcct     240
gaagattttg caatttatta ctgtgagcag cgtaataatt ggcctccgga attcactttc     300
ggccctggga ccaaagtgat atcaaa                                          326

<210> SEQ ID NO 74
<211> LENGTH: 137
<212> TYPE: PRT
<213> ORGANISM: Homo sapiens

<400> SEQUENCE: 74

Gln Val Gln Leu Val Gln Ser Gly Ala Glu Met Lys Lys Pro Gly Ser
1               5                   10                  15

Ser Val Arg Val Ser Cys Lys Ala Ser Gly Gly Thr Phe Asp Lys Tyr
            20                  25                  30

Ala Val Ser Trp Val Arg Gln Ala Pro Gly Arg Gly Leu Glu Trp Val
        35                  40                  45

Gly Gly Ile Ile Pro Met Leu Gly Ala Pro His Tyr Ala Gln Lys Phe
    50                  55                  60

Gln Gly Arg Val Thr Ile Thr Ala Asp Lys Ser Thr Ser Thr Val Tyr
65                  70                  75                  80

Met Glu Leu Ser Ser Leu Gly Ser Glu Asp Thr Ala Val Tyr Tyr Cys
                85                  90                  95

Ala Arg Asp Lys Ala Ala Tyr Tyr Gly Ser Gly Tyr Tyr Ile Gly
            100                 105                 110

Asp Phe Trp Gly Gln Gly Thr Leu Val Thr Val Ser Ser Ala Ser Thr
        115                 120                 125

Lys Gly Pro Ser Val Thr Ser Gly Gln
    130                 135

<210> SEQ ID NO 75
<211> LENGTH: 137
<212> TYPE: PRT
<213> ORGANISM: Homo sapiens

<400> SEQUENCE: 75

Gln Val Gln Leu Val Gln Ser Gly Ala Glu Met Lys Lys Pro Gly Ser
1               5                   10                  15

Ser Val Arg Val Ser Cys Lys Ala Ser Gly Gly Thr Phe Asp Lys His
            20                  25                  30

Ala Val Ser Trp Val Arg Gln Ala Pro Gly Arg Gly Leu Glu Trp Val
        35                  40                  45

Gly Gly Ile Ile Pro Met Leu Gly Ala Pro His Tyr Ala Gln Lys Phe
    50                  55                  60

Gln Gly Arg Val Thr Ile Thr Ala Asp Lys Ser Thr Ser Thr Val Tyr
65                  70                  75                  80

Met Glu Leu Ser Ser Leu Gly Ser Glu Asp Thr Ala Val Tyr Tyr Cys
                85                  90                  95

Ala Arg Asp Lys Ala Ala Tyr Tyr Glu Ser Gly Tyr Tyr Ile Gly
            100                 105                 110

Asp Phe Trp Gly Gln Gly Thr Leu Val Thr Val Ser Ser Ala Ser Thr
            115                 120                 125

Lys Gly Pro Ser Val Thr Ser Gly Gln
    130                 135

<210> SEQ ID NO 76
<211> LENGTH: 137
<212> TYPE: PRT
<213> ORGANISM: Homo sapiens

<400> SEQUENCE: 76

Gln Val Gln Leu Val Gln Ser Gly Ala Glu Met Lys Lys Pro Gly Ser
1               5                   10                  15

Ser Val Arg Val Ser Cys Lys Ala Ser Gly Gly Thr Phe Asp Lys His
                20                  25                  30

Ala Val Ser Trp Val Arg Gln Ala Pro Gly Arg Gly Leu Glu Trp Val
            35                  40                  45

Gly Gly Ile Ile Pro Met Leu Gly Ala Pro His Tyr Ala Gln Lys Phe
    50                  55                  60

Gln Gly Arg Val Thr Ile Thr Ala Asp Lys Ser Thr Ser Thr Val Tyr
65                  70                  75                  80

Met Glu Leu Ser Ser Leu Gly Ser Glu Asp Thr Ala Val Tyr Tyr Cys
                85                  90                  95

Ala Arg Asp Lys Ala Ala Tyr Tyr Glu Ser Gly Tyr Tyr Ile Gly
            100                 105                 110

Asp Phe Trp Gly Gln Gly Thr Leu Val Thr Val Ser Ser Ala Ser Thr
            115                 120                 125

Lys Gly Pro Ser Val Thr Ser Gly Gln
    130                 135

<210> SEQ ID NO 77
<211> LENGTH: 137
<212> TYPE: PRT
<213> ORGANISM: Homo sapiens

<400> SEQUENCE: 77

Gln Val Gln Leu Val Gln Ser Gly Ala Glu Met Lys Lys Pro Gly Ser
1               5                   10                  15

Ser Val Arg Val Ser Cys Lys Ala Ser Gly Gly Thr Phe Asp Lys Tyr
                20                  25                  30

Ala Val Ser Trp Val Arg Gln Ala Pro Gly Arg Gly Leu Glu Trp Val
            35                  40                  45

Gly Gly Ile Ile Pro Met Leu Gly Ala Pro His Tyr Ala Gln Lys Phe
    50                  55                  60

Gln Gly Arg Val Thr Ile Thr Ala Asp Lys Ser Thr Ser Thr Ile Tyr
65                  70                  75                  80

Met Glu Leu Ser Ser Leu Gly Ser Glu Asp Thr Ala Val Tyr Tyr Cys
                85                  90                  95

Ala Arg Asp Lys Ala Ala Tyr Tyr Glu Ser Gly Tyr Tyr Ile Gly
            100                 105                 110

Asp Phe Trp Gly Gln Gly Thr Leu Val Thr Val Ser Ser Ala Ser Thr
            115                 120                 125

Lys Gly Pro Ser Val Thr Ser Gly Gln
    130                 135

-continued

<210> SEQ ID NO 78
<211> LENGTH: 137
<212> TYPE: PRT
<213> ORGANISM: Homo sapiens

<400> SEQUENCE: 78

Gln Val Gln Leu Val Gln Ser Trp Ala Glu Met Lys Lys Pro Gly Ser
1               5                   10                  15

Ser Val Arg Val Ser Cys Lys Ala Ser Gly Gly Thr Phe Asp Lys Tyr
            20                  25                  30

Gly Val Ser Trp Val Arg Gln Ala Pro Gly Gln Gly Leu Glu Trp Met
        35                  40                  45

Gly Gly Ile Ile Pro Met Leu Gly Thr Pro His Tyr Ala Gln Lys Phe
    50                  55                  60

Gln Gly Arg Val Thr Ile Thr Ala Asp Lys Ser Thr Ser Thr Val Tyr
65                  70                  75                  80

Met Glu Leu Ser Ser Leu Gly Ser Glu Asp Thr Ala Val Tyr Tyr Cys
                85                  90                  95

Ala Arg Asp Lys Glu Ala Tyr Tyr Glu Ser Gly Tyr Tyr Tyr Ile Gly
            100                 105                 110

Asp Phe Trp Gly Gln Gly Thr Leu Val Thr Val Ser Ser Ala Ser Thr
        115                 120                 125

Lys Gly Pro Ser Val Thr Ser Gly Gln
    130                 135

<210> SEQ ID NO 79
<211> LENGTH: 137
<212> TYPE: PRT
<213> ORGANISM: Homo sapiens

<400> SEQUENCE: 79

Glu Val Gln Leu Val Gln Ser Gly Ala Glu Met Lys Lys Pro Gly Ser
1               5                   10                  15

Ser Val Arg Val Ser Cys Lys Ala Ser Gly Gly Thr Phe Asp Lys Tyr
            20                  25                  30

Ala Val Ser Trp Val Arg Gln Ala Pro Gly Arg Gly Leu Glu Trp Val
        35                  40                  45

Gly Gly Ile Ile Pro Met Leu Gly Ala Pro His Tyr Ala Gln Lys Phe
    50                  55                  60

Gln Gly Arg Val Thr Ile Thr Ala Asp Lys Ser Thr Ser Thr Val Tyr
65                  70                  75                  80

Met Glu Leu Ser Ser Leu Gly Ser Glu Asp Thr Ala Val Tyr Tyr Cys
                85                  90                  95

Ala Arg Asp Lys Ala Ala Tyr Tyr Glu Ser Gly Tyr Tyr Tyr Ile Gly
            100                 105                 110

Asp Phe Trp Gly Gln Gly Thr Leu Val Thr Val Ser Ser Ala Ser Thr
        115                 120                 125

Lys Gly Pro Ser Val Thr Ser Gly Gln
    130                 135

<210> SEQ ID NO 80
<211> LENGTH: 137
<212> TYPE: PRT
<213> ORGANISM: Homo sapiens

<400> SEQUENCE: 80

Glu Val Gln Leu Val Glu Ser Gly Ala Glu Met Lys Lys Pro Gly Ser
1               5                   10                  15

```
Ser Val Arg Val Ser Cys Lys Ala Ser Gly Gly Thr Phe Asp Lys Tyr
            20                  25                  30

Gly Val Ser Trp Val Arg Gln Ala Pro Gly Arg Gly Leu Glu Trp Val
            35                  40                  45

Gly Gly Ile Ile Pro Met Leu Gly Ala Pro His Tyr Ala Gln Lys Phe
    50                  55                  60

Gln Gly Arg Val Thr Ile Thr Ala Asp Lys Ser Thr Ser Thr Val Tyr
65                  70                  75                  80

Met Glu Leu Ser Ser Leu Gly Ser Glu Asp Thr Ala Val Tyr Tyr Cys
            85                  90                  95

Ala Arg Asp Lys Ala Ala Tyr Tyr Glu Ser Gly Tyr Tyr Tyr Ile Gly
                100                 105                 110

Asp Phe Trp Gly Gln Gly Thr Leu Val Thr Val Ser Ser Ala Ser Thr
            115                 120                 125

Lys Gly Pro Ser Val Thr Ser Gly Gln
        130                 135

<210> SEQ ID NO 81
<211> LENGTH: 137
<212> TYPE: PRT
<213> ORGANISM: Homo sapiens
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (134)..(136)
<223> OTHER INFORMATION: Xaa can be any naturally occurring amino acid

<400> SEQUENCE: 81

Gln Val Gln Leu Val Gln Ser Gly Ala Glu Met Lys Lys Pro Gly Ser
1               5                   10                  15

Ser Val Arg Xaa Ser Cys Lys Ala Ser Gly Gly Thr Phe Asp Lys Tyr
            20                  25                  30

Ala Val Ser Trp Val Arg Gln Ala Pro Xaa Arg Gly Leu Glu Trp Val
            35                  40                  45

Gly Gly Ile Ile Pro Met Leu Gly Ala Pro His Tyr Ala Gln Lys Phe
    50                  55                  60

Gln Gly Arg Val Thr Ile Thr Ala Asp Lys Ser Thr Ser Thr Xaa Tyr
65                  70                  75                  80

Met Glu Leu Ser Ser Leu Gly Ser Glu Asp Thr Ala Val Tyr Tyr Cys
            85                  90                  95

Ala Arg Asp Lys Ala Ala Tyr Tyr Glu Ser Gly Tyr Tyr Tyr Ile Gly
                100                 105                 110

Glu Phe Trp Gly Gln Gly Thr Leu Val Xaa Val Ser Ser Ala Ser Thr
            115                 120                 125

Lys Gly Pro Ser Val Xaa Xaa Xaa Gln
        130                 135
```

<210> SEQ ID NO 82
<211> LENGTH: 137
<212> TYPE: PRT
<213> ORGANISM: Homo sapiens

<400> SEQUENCE: 82

Gln Val Gln Leu Val Gln Ser Gly Ala Glu Met Lys Arg Pro Gly Ser
1               5                   10                  15

Ser Val Arg Val Ser Cys Lys Ala Ser Gly Gly Thr Phe Asp Lys Tyr
            20                  25                  30

Ala Val Ser Trp Val Arg Gln Ala Pro Gly Arg Gly Leu Glu Trp Val
        35                  40                  45

Gly Gly Ile Ile Pro Leu Leu Gly Ala Pro His Tyr Ala Gln Lys Phe
    50                  55                  60

Gln Gly Arg Val Thr Ile Thr Ala Asp Lys Ser Thr Ser Thr Val Tyr
65                  70                  75                  80

Met Glu Leu Ser Ser Leu Gly Ser Glu Asp Thr Ala Val Tyr Tyr Cys
                85                  90                  95

Ala Arg Asp Lys Ala Ala Tyr Tyr Glu Ser Gly Tyr Tyr Tyr Ile Gly
            100                 105                 110

Asp Phe Trp Gly Gln Gly Thr Leu Val Thr Val Ser Ser Ala Ser Thr
        115                 120                 125

Lys Gly Pro Ser Val Thr Ser Gly Gln
    130                 135

<210> SEQ ID NO 83
<211> LENGTH: 133
<212> TYPE: PRT
<213> ORGANISM: Homo sapiens

<400> SEQUENCE: 83

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Asn Tyr
            20                  25                  30

Ala Ile Asn Trp Val Arg Gln Ala Pro Gly Gln Gly Leu Glu Trp Met
        35                  40                  45

Gly Gly Ile Ile Pro Thr Leu Asp Leu Leu Asn Asp Ala Gln Asn Phe
    50                  55                  60

Gln Asp Arg Val Thr Ile Thr Ala Asp Lys Ser Thr Asn Thr Val Tyr
65                  70                  75                  80

Leu Glu Leu Thr Ser Leu Arg Ser Glu Asp Thr Ala Val Tyr Tyr Cys
                85                  90                  95

Ala Arg Gly Gly Asp Tyr Ser Gly Trp Tyr Asn Phe Asp Tyr Trp Gly
            100                 105                 110

Gln Gly Thr Leu Val Thr Val Ser Ser Ala Ser Thr Lys Gly Pro Ser
        115                 120                 125

Val Thr Ser Gly Gln
    130

<210> SEQ ID NO 84
<211> LENGTH: 129
<212> TYPE: PRT
<213> ORGANISM: Homo sapiens

<400> SEQUENCE: 84

Gln Val Gln Leu Val Gln Ser Gly Gly Gly Leu Val Gln Pro Gly Gly
1               5                   10                  15

```
Ser Leu Arg Leu Ser Cys Ala Ala Ser Gly Leu Pro Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Asn Glu Lys His Tyr Val Asp Ser Val
    50                  55                  60

Lys Gly Arg Phe Ile Ile Ser Arg Asp Asn Thr His Asn Ser Leu Phe
65                  70                  75                  80

Leu Gln Met Asn Ser Leu Arg Ala Glu Asp Ala Ala Val Tyr Tyr Cys
                85                  90                  95

Ala Ser Gly Gly Val Val Asp Phe Asp His Trp Gly Gln Gly Ser Leu
            100                 105                 110

Val Thr Val Ser Ser Ala Ser Thr Lys Gly Pro Ser Val Thr Ser Gly
            115                 120                 125

Gln

<210> SEQ ID NO 85
<211> LENGTH: 129
<212> TYPE: PRT
<213> ORGANISM: Homo sapiens

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Pro Phe Ser Ser Ser
            20                  25                  30

Trp Met Ser Trp Val Arg Gln Ala Pro Gly Lys Gly Leu Glu Trp Val
        35                  40                  45

Ala Asn Ile Asn Gln Asp Gly Asn Glu Lys His Tyr Val Asp Ser Val
    50                  55                  60

Lys Gly Arg Phe Ile Ile Ser Arg Asp Asn Thr Gln Asn Ser Leu Phe
65                  70                  75                  80

Leu Gln Met Asn Ser Leu Arg Ala Glu Asp Ala Ala Val Tyr Tyr Cys
                85                  90                  95

Ala Ser Gly Gly Val Val Asp Phe Asp His Trp Gly Gln Gly Thr Leu
            100                 105                 110

Val Thr Val Ser Pro Ala Ser Thr Lys Gly Pro Ser Val Thr Ser Gly
            115                 120                 125

Gln

<210> SEQ ID NO 86
<211> LENGTH: 129
<212> TYPE: PRT
<213> ORGANISM: Homo sapiens

<400> SEQUENCE: 86

Glu Val Gln Leu Leu Glu Ser Gly Gly Gly Leu Val Asn Pro Gly Gly
1               5                   10                  15

Ser Leu Arg Leu Ser Cys Ala Ala Ser Gly Leu Pro Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Asn Glu Lys His Tyr Val Asp Ser Val
    50                  55                  60

Lys Gly Arg Phe Ile Ile Ser Arg Asp Asn Thr Gln Asn Ser Leu Phe
65                  70                  75                  80
```

Leu Gln Met Asn Ser Leu Arg Ala Glu Asp Ala Ala Val Tyr Tyr Cys
                    85                  90                  95

Ala Ser Gly Gly Val Val Asp Phe Asp His Trp Gly Gln Gly Thr Leu
                100                 105                 110

Val Thr Val Ser Pro Ala Ser Thr Lys Gly Pro Ser Val Thr Ser Gly
            115                 120                 125

Gln

<210> SEQ ID NO 87
<211> LENGTH: 139
<212> TYPE: PRT
<213> ORGANISM: Homo sapiens
<220> FEATURE:
<221> NAME/KEY: misc_feature
<222> LOCATION: (111)..(111)
<223> OTHER INFORMATION: Xaa can be any naturally occurring amino acid

<400> SEQUENCE: 87

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Lys Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Glu Ala Leu Val Tyr Tyr Asp Ser Ser Gly Tyr Tyr Xaa Gly
                100                 105                 110

Gly Phe Asp Tyr Trp Gly Gln Gly Thr Leu Val Thr Val Ser Ser Ala
            115                 120                 125

Ser Thr Lys Gly Pro Ser Val Thr Ser Gly Gln
        130                 135

<210> SEQ ID NO 88
<211> LENGTH: 136
<212> TYPE: PRT
<213> ORGANISM: Homo sapiens

<400> SEQUENCE: 88

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Asp Tyr
            20                  25                  30

Tyr Met Ser Trp Phe Arg Gln Ala Pro Gly Lys Gly Leu Glu Trp Ile
        35                  40                  45

Ser Tyr Ile Ser Ser Ser Gly Pro Tyr Thr Asn Tyr Ala Asn Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Met Ser Pro Ile Thr Ala Ala Gly Ala His Thr Tyr Glu
                100                 105                 110

```
Cys Trp Gly Gln Gly Thr Leu Val Thr Val Ser Ser Ala Ser Thr Lys
        115                 120                 125

Gly Pro Ser Val Thr Ser Gly Gln
    130                 135

<210> SEQ ID NO 89
<211> LENGTH: 136
<212> TYPE: PRT
<213> ORGANISM: Homo sapiens

<400> SEQUENCE: 89

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asp Tyr
            20                  25                  30

Tyr Met Ser Trp Phe Arg Gln Ala Pro Gly Lys Gly Leu Glu Trp Ile
        35                  40                  45

Ser Tyr Ile Ser Ser Ser Gly Pro Tyr Thr Asn Tyr Ala Asn Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Glu Met Ser Pro Ile Thr Ala Gly Ala His Thr Tyr Glu
        100                 105                 110

Cys Trp Gly Gln Gly Thr Leu Val Thr Val Ser Ser Ala Ser Thr Lys
        115                 120                 125

Gly Pro Ser Val Thr Ser Gly Gln
    130                 135

<210> SEQ ID NO 90
<211> LENGTH: 136
<212> TYPE: PRT
<213> ORGANISM: Homo sapiens

<400> SEQUENCE: 90

Glu Val Gln Leu Val Gln Ser Gly Gly Gly Leu Val Lys Pro Gly Gly
1               5                   10                  15

Ser Leu Arg Leu Ser Cys Ala Ala Ser Thr Phe Thr Phe Asn Asp Asp
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Tyr Thr His Tyr Ala Asp Ser Val
    50                  55                  60

Lys Gly Arg Phe Ser Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
            85                  90                  95

Ala Arg Glu Leu Ser Pro Phe Thr Ala Ala Thr Ala His Ser Tyr Asp
        100                 105                 110

Leu Trp Gly Gln Gly Thr Leu Val Thr Val Ser Ser Ala Ser Thr Lys
        115                 120                 125

Gly Pro Ser Val Thr Ser Gly Gln
    130                 135

<210> SEQ ID NO 91
<211> LENGTH: 136
<212> TYPE: PRT
```

<213> ORGANISM: Homo sapiens

<400> SEQUENCE: 91

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Asp Asp
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Tyr Thr His Tyr Ala Asp Ser Val
    50                  55                  60

Lys Gly Arg Phe Ser Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Glu Leu Ser Pro Phe Thr Ala Ala Thr Ala His Ser Tyr Asp
            100                 105                 110

Leu Trp Gly Gln Gly Thr Leu Val Thr Val Ser Ser Ala Ser Thr Lys
        115                 120                 125

Gly Pro Ser Val Thr Ser Gly Gln
    130                 135
```

<210> SEQ ID NO 92
<211> LENGTH: 136
<212> TYPE: PRT
<213> ORGANISM: Homo sapiens

<400> SEQUENCE: 92

```
Gln Val Gln Leu Val Gln Ser Gly Gly Gly Leu Val Lys Pro Gly Gly
1               5                   10                  15

Ser Leu Arg Leu Ser Cys Ala Ala Ser Thr Phe Thr Phe Asn Asp Asp
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Tyr Thr His Tyr Ala Asp Ser Val
    50                  55                  60

Lys Gly Arg Phe Ser Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Glu Leu Ser Pro Phe Thr Ala Ala Thr Ala His Ser Tyr Asp
            100                 105                 110

Leu Trp Gly Gln Gly Thr Leu Val Thr Val Ser Ser Ala Ser Thr Lys
        115                 120                 125

Gly Pro Ser Val Thr Ser Gly Gln
    130                 135
```

<210> SEQ ID NO 93
<211> LENGTH: 136
<212> TYPE: PRT
<213> ORGANISM: Homo sapiens

<400> SEQUENCE: 93

```
Glu Val Gln Leu Val Glu Ser Gly Gly Gly Leu Val Lys Pro Gly Gly
1               5                   10                  15

Ser Leu Arg Leu Ser Cys Ala Ala Ser Thr Phe Thr Phe Asn Asp Asp
            20                  25                  30
```

```
Tyr Met Ser Trp Ile Arg Gln Ala Pro Gly Lys Gly Leu Glu Trp Val
        35                  40                  45

Ser Tyr Ile Ser Ser Ser Ser Tyr Thr His Tyr Ala Asp Ser Val
 50                  55                  60

Lys Gly Arg Phe Ser Ile Ser Arg Asp Asn Ala Lys Asn Ser Leu Phe
 65                  70                  75                  80

Leu Gln Met Ser Ser Leu Arg Ala Glu Asp Thr Ala Val Tyr Tyr Cys
                 85                  90                  95

Ala Arg Glu Leu Ser Pro Phe Thr Ala Ala Thr Ala His Ser Tyr Asp
            100                 105                 110

Leu Trp Gly Gln Gly Thr Leu Val Thr Val Ser Ser Ala Ser Thr Lys
        115                 120                 125

Gly Pro Ser Val Thr Ser Gly Gln
    130                 135

<210> SEQ ID NO 94
<211> LENGTH: 136
<212> TYPE: PRT
<213> ORGANISM: Homo sapiens

<400> SEQUENCE: 94

Glu Val Gln Leu Val Glu Ser Gly Gly Gly Leu Val Lys Pro Gly Gly
 1               5                  10                  15

Ser Leu Arg Leu Ser Cys Ala Ala Ser Thr Phe Thr Phe Asn Asp Asp
             20                  25                  30

Tyr Met Ser Trp Ile Arg Gln Ala Pro Gly Lys Gly Leu Glu Trp Val
        35                  40                  45

Ser Tyr Ile Ser Ser Ser Ser Tyr Thr His Tyr Ala Asp Ser Val
 50                  55                  60

Lys Gly Arg Phe Ser Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                 85                  90                  95

Ala Arg Glu Leu Ser Pro Phe Thr Ala Ala Thr Ala His Ser Tyr Asp
            100                 105                 110

Leu Trp Gly Gln Gly Thr Leu Val Thr Val Ser Ser Ala Ser Thr Lys
        115                 120                 125

Gly Pro Ser Val Thr Ser Gly Gln
    130                 135

<210> SEQ ID NO 95
<211> LENGTH: 136
<212> TYPE: PRT
<213> ORGANISM: Homo sapiens

<400> SEQUENCE: 95

Gln Ile Thr Leu Lys Glu Ser Gly Gly Gly Leu Val Lys Pro Gly Glu
 1               5                  10                  15

Ser Leu Arg Leu Ser Cys Ala Ala Ser Asp Phe Thr Phe Ser Asp Tyr
             20                  25                  30

Tyr Met Ser Trp Ile Arg Gln Pro Pro Gly Lys Gly Leu Glu Trp Val
        35                  40                  45

Ser Tyr Ile Ser Ser Ser Gly Tyr Thr His Tyr Ala Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
```

```
                85                  90                  95
Ala Arg Glu Leu Ser Pro Leu Thr Ala Gly Ala Ala His Thr Leu Asp
            100                 105                 110
Tyr Trp Gly Gln Gly Thr Leu Val Thr Val Ser Ser Ala Ser Thr Lys
        115                 120                 125
Gly Pro Ser Val Thr Ser Gly Gln
    130                 135

<210> SEQ ID NO 96
<211> LENGTH: 136
<212> TYPE: PRT
<213> ORGANISM: Homo sapiens

<400> SEQUENCE: 96

Glu Val Gln Leu Val Gln Ser Gly Gly Gly Leu Val Lys Pro Gly Glu
1               5                   10                  15
Ser Leu Arg Leu Ser Cys Ala Ala Ser Asp Phe Thr Phe Gly Asp Tyr
            20                  25                  30
Tyr Met Ser Trp Ile Arg Gln Pro Pro Gly Lys Gly Leu Glu Trp Ile
        35                  40                  45
Ser Tyr Ile Ser Ser Ser Ser Arg Tyr Thr Asn Tyr Ala Asp Ser Val
    50                  55                  60
Lys Gly Arg Phe Thr Ile Ser Arg Asp Asn Ala Arg Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Leu Ser Pro Leu Thr Ala Gly Ala Ala His Thr Leu Asp
            100                 105                 110
Tyr Trp Gly Gln Gly Thr Leu Val Thr Val Ser Ser Ala Ser Thr Lys
        115                 120                 125
Gly Pro Ser Val Thr Ser Gly Gln
    130                 135

<210> SEQ ID NO 97
<211> LENGTH: 136
<212> TYPE: PRT
<213> ORGANISM: Homo sapiens

<400> SEQUENCE: 97

Glu Val Gln Leu Val Glu Ser Gly Gly Gly Leu Val Lys Pro Gly Glu
1               5                   10                  15
Ser Leu Arg Leu Ser Cys Ala Ala Ser Asp Phe Thr Phe Ser Asp Tyr
            20                  25                  30
Tyr Met Ser Trp Ile Arg Gln Pro Pro Gly Lys Gly Leu Glu Trp Ile
        35                  40                  45
Ser Tyr Ile Ser Ser Asn Ser Arg Phe Arg Asn Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Gly Glu Asp Thr Ala Val Tyr Tyr Cys
                85                  90                  95
Ala Lys Glu Leu Ser Pro Leu Thr Ala Gly Ala Ala His Thr Leu Asp
            100                 105                 110
Tyr Trp Gly Gln Gly Thr Leu Val Thr Val Ser Ser Ala Ser Thr Lys
        115                 120                 125
Gly Pro Ser Val Thr Ser Gly Gln
    130                 135
```

<210> SEQ ID NO 98
<211> LENGTH: 136
<212> TYPE: PRT
<213> ORGANISM: Homo sapiens

<400> SEQUENCE: 98

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Ile
        35                  40                  45

Ser Tyr Ile Ser Gly Ser Ser Tyr Thr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Asp Asp Thr Ala Val Tyr Tyr Cys
                85                  90                  95

Ala Arg Glu Leu Ser Pro Ile Thr Ala Gly Asp Ala His Thr Phe Asp
            100                 105                 110

Ser Trp Gly Gln Gly Thr Leu Val Thr Val Ser Ser Ala Ser Thr Lys
        115                 120                 125

Gly Pro Ser Val Thr Ser Gly Gln
    130                 135

<210> SEQ ID NO 99
<211> LENGTH: 136
<212> TYPE: PRT
<213> ORGANISM: Homo sapiens

<400> SEQUENCE: 99

Glu Val Gln Leu Val Gln Ser Gly Gly Gly Leu Val Lys Pro Gly Gly
1               5                   10                  15

Ser Leu Arg Leu Ser Cys Ala Ala Ser Glu Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Asn Gly Arg Tyr Arg His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Pro Leu Thr Ser Ala Asp Ala His Thr Tyr Asp
            100                 105                 110

Tyr Trp Gly Gln Gly Thr Leu Val Thr Val Ser Ser Ala Ser Thr Lys
        115                 120                 125

Gly Pro Ser Val Thr Ser Gly Gln
    130                 135

<210> SEQ ID NO 100
<211> LENGTH: 136
<212> TYPE: PRT
<213> ORGANISM: Homo sapiens

<400> SEQUENCE: 100

Glu Val Gln Leu Val Glu Ser Gly Gly Gly Leu Val Lys Pro Gly Glu

```
                1               5                  10                 15
Ser Leu Arg Leu Ser Cys Thr Ala Ser Glu Phe Thr Phe Ser Asp Tyr
            20                  25                 30

Tyr Met Ser Trp Ile Arg Gln Ala Pro Gly Lys Gly Leu Glu Trp Val
            35                  40                 45

Ser Tyr Ile Ser Ser Ser Ser Arg Tyr Thr His Tyr Gly Asp Ser Val
            50                  55                 60

Lys Gly Arg Phe Thr Ile Ser Arg Asp Asn Ala Lys Asn Ser Leu Tyr
 65                 70                  75                     80

Leu Gln Met Asn Ser Leu Arg Thr Glu Asp Thr Ala Val Tyr Tyr Cys
                85                  90                 95

Ala Arg Glu Leu Ser Pro Leu Thr Ser Ala Gly Ala His Thr Tyr Asp
            100                 105                110

Tyr Trp Gly Gln Gly Thr Leu Val Thr Val Ser Ser Ala Ser Thr Lys
            115                 120                125

Gly Pro Ser Val Thr Ser Gly Gln
            130                 135

<210> SEQ ID NO 101
<211> LENGTH: 131
<212> TYPE: PRT
<213> ORGANISM: Homo sapiens

<400> SEQUENCE: 101

Gln Val Gln Leu Gln Glu Ser Gly Pro Gly Leu Val Lys Pro Ser Glu
 1               5                  10                 15

Thr Leu Ser Leu Thr Cys Ser Val Ser Gly Tyr Pro Ile Ser Ser Gly
            20                  25                 30

Tyr Tyr Trp Gly Trp Ile Arg Gln Pro Pro Gly Lys Gly Leu Glu Trp
            35                  40                 45

Ile Gly Ser Ile His His Ser Gly Ser Thr Tyr Tyr Asn Ser Ser Leu
            50                  55                 60

Lys Ser Arg Val Thr Leu Ser Val Asp Thr Ser Lys Asn Gln Phe Ser
 65                 70                  75                     80

Leu Lys Val Ser Ser Val Thr Ala Ala Asp Thr Ala Val Tyr Tyr Cys
                85                  90                 95

Ala Arg Thr Thr Thr Ala Tyr Trp Tyr Phe Asp Leu Trp Gly Arg Gly
            100                 105                110

Thr Leu Val Thr Val Ser Ser Ala Ser Thr Lys Gly Pro Ser Val Thr
            115                 120                125

Ser Gly Gln
            130

<210> SEQ ID NO 102
<211> LENGTH: 139
<212> TYPE: PRT
<213> ORGANISM: Homo sapiens

<400> SEQUENCE: 102

Glu Val Gln Leu Leu Glu Ser Gly Pro Gly Pro Val Lys Pro Ser Gly
 1               5                  10                 15

Thr Leu Ser Leu Thr Cys Gly Val Ser Gly Gly Ser Ile Ser Thr Asn
            20                  25                 30

His Trp Trp Thr Trp Val Arg Gln Pro Pro Gly Gln Gly Leu Glu Trp
            35                  40                 45

Ile Gly Glu Ile His His Asn Gly Ser Thr Phe Phe Asn Pro Ser Leu
            50                  55                 60
```

```
Lys Ser Arg Val Thr Ile Ser Val Asp Lys Ser Asn Asn Gln Phe Ser
 65                  70                  75                  80

Leu Lys Leu Thr Ser Leu Thr Ala Ala Asp Thr Ala Val Tyr Phe Cys
                 85                  90                  95

Ala Arg Gly Trp His Arg Thr Gly Phe Arg Gly Tyr Pro Ser His Trp
            100                 105                 110

Tyr Phe Asp Leu Trp Gly Arg Gly Thr Leu Val Thr Val Ser Ser Ala
        115                 120                 125

Ser Thr Lys Gly Pro Ser Val Thr Ser Gly Gln
        130                 135
```

<210> SEQ ID NO 103
<211> LENGTH: 139
<212> TYPE: PRT
<213> ORGANISM: Homo sapiens

<400> SEQUENCE: 103

```
Gln Val Gln Leu Gln Glu Ser Gly Pro Gly Pro Val Lys Pro Ser Gly
  1               5                  10                  15

Thr Leu Ser Leu Thr Cys Gly Val Ser Gly Gly Ser Ile Ser Ser Asn
                 20                  25                  30

His Trp Trp Thr Trp Val Arg Gln Pro Pro Gly Lys Gly Leu Glu Trp
             35                  40                  45

Ile Gly Glu Ile Tyr His Asn Gly Ser Thr Phe Leu Asn Pro Ser Leu
 50                  55                  60

Lys Ser Arg Val Thr Ile Ser Val Asp Lys Ser Asn Asn Gln Phe Ser
 65                  70                  75                  80

Leu Lys Leu Thr Ser Val Thr Ala Ala Asp Thr Ala Val Tyr Tyr Cys
                 85                  90                  95

Ala Arg Gly Trp His Arg Thr Gly Phe Arg Gly Tyr Pro Ser His Trp
            100                 105                 110

Tyr Phe Asp Leu Trp Gly Arg Gly Thr Leu Val Ser Val Ser Ser Ala
        115                 120                 125

Ser Thr Lys Gly Pro Ser Val Thr Ser Gly Gln
        130                 135
```

<210> SEQ ID NO 104
<211> LENGTH: 139
<212> TYPE: PRT
<213> ORGANISM: Homo sapiens

<400> SEQUENCE: 104

```
Gln Val Gln Leu Gln Glu Ser Gly Pro Gly Leu Val Lys Pro Ser Gly
  1               5                  10                  15

Thr Leu Ser Leu Thr Cys Gly Val Ser Gly Gly Ser Ile Ser Ser Asn
                 20                  25                  30

His Trp Trp Thr Trp Val Arg Gln Pro Pro Gly Gln Gly Leu Glu Trp
             35                  40                  45

Ile Gly Glu Val His His Asn Gly Ser Thr Phe Phe Asn Pro Ser Leu
 50                  55                  60

Lys Ser Arg Val Thr Ile Ser Val Asp Lys Ser Asn Asn Gln Phe Ser
 65                  70                  75                  80

Leu Lys Leu Thr Ser Val Thr Ala Ala Asp Thr Ala Val Tyr Phe Cys
                 85                  90                  95

Ala Arg Gly Trp His Arg Thr Gly Phe Arg Gly Tyr Pro Ser His Trp
            100                 105                 110
```

```
Tyr Phe Asp Leu Trp Gly Arg Gly Thr Leu Val Thr Val Ser Ser Ala
        115                 120                 125

Ser Thr Lys Gly Pro Ser Val Thr Ser Gly Gln
        130                 135
```

<210> SEQ ID NO 105
<211> LENGTH: 111
<212> TYPE: PRT
<213> ORGANISM: Homo sapiens

<400> SEQUENCE: 105

```
Ala Glu Leu Val Leu Thr Gln Pro Pro Ser Ala Ser Glu Thr Pro Gly
1               5                   10                  15

Gln Arg Val Thr Ile Ser Cys Ser Gly Ser Ser Ser Asn Ile Ala Gly
            20                  25                  30

Asn Thr Val Tyr Trp Tyr Gln Gln Leu Pro Gly Ala Ala Pro Lys Leu
        35                  40                  45

Leu Ile Tyr Tyr Asn Asp Gln Arg Pro Ser Gly Val Pro Asp Arg Phe
    50                  55                  60

Ser Gly Ser Lys Ser Gly Thr Ser Ala Ser Leu Ser Ile Ser Gly Leu
65                  70                  75                  80

Arg Ser Glu Asp Glu Gly Asp Tyr Tyr Cys Ser Ala Trp Asp Ala Ser
                85                  90                  95

Leu Ser Trp Val Phe Gly Gly Gly Thr Lys Leu Thr Val Leu Gly
            100                 105                 110
```

<210> SEQ ID NO 106
<211> LENGTH: 112
<212> TYPE: PRT
<213> ORGANISM: Homo sapiens

<400> SEQUENCE: 106

```
Ala Glu Leu Val Leu Thr Gln Pro Pro Ser Val Ser Glu Thr Pro Gly
1               5                   10                  15

Gln Arg Val Thr Ile Ser Cys Ser Gly Ser Ser Ser Asn Ile Ala Gly
            20                  25                  30

Asn Thr Val Tyr Trp Tyr Gln Gln Leu Pro Gly Ala Ala Pro Lys Leu
        35                  40                  45

Leu Ile Tyr Tyr Asn Asp Gln Arg Pro Ser Gly Val Pro Asp Arg Phe
    50                  55                  60

Ser Gly Ser Lys Ser Gly Thr Ser Ser Ser Leu Ala Ile Ser Gly Leu
65                  70                  75                  80

Gln Ser Glu Asp Glu Ala Tyr Tyr Tyr Cys Ala Thr Trp Asp Glu Asp
                85                  90                  95

Val Asn Gly Trp Val Phe Gly Gly Gly Thr Lys Leu Thr Val Leu Gly
            100                 105                 110
```

<210> SEQ ID NO 107
<211> LENGTH: 111
<212> TYPE: PRT
<213> ORGANISM: Homo sapiens

<400> SEQUENCE: 107

```
Ala Pro Arg Pro Gly Arg Ala Ser Cys Phe Gln Pro Thr Phe Arg Val
1               5                   10                  15

Asp Pro Pro Ala Arg Gly Ser Pro Ser Pro Val Ala Glu Ala Ala Pro
            20                  25                  30

Thr Ser Gln Val Ile Leu Cys Thr Gly Thr Ser Ser Pro Gly Ala
        35                  40                  45
```

-continued

Ala Pro Gln Ala Pro His Leu Leu Gln Ser Ala Ala Leu Arg Gly Pro
        50                  55                  60

Pro Ile Leu Trp Leu Gln Val Trp His Leu Leu Leu Leu Gly His Gln
 65                  70                  75                  80

Trp Ala Pro Val Gly Gly Leu Leu Leu Cys Asn Met Gly Arg Cys
                85                  90                  95

Glu Trp Leu Gly Val Arg Arg Arg Asp Gln Ala Asp Arg Pro Arg
                100                 105                 110

<210> SEQ ID NO 108
<211> LENGTH: 112
<212> TYPE: PRT
<213> ORGANISM: Homo sapiens

<400> SEQUENCE: 108

Ala Glu Leu Val Leu Thr Gln Pro Pro Ser Ala Ser Glu Thr Pro Gly
 1               5                  10                  15

Gln Arg Val Thr Ile Ser Cys Ser Gly Ser Ser Ser Asn Ile Ala Gly
                20                  25                  30

Asn Thr Val Tyr Trp Tyr Gln Gln Leu Pro Gly Ala Ala Pro Lys Leu
            35                  40                  45

Leu Ile Tyr Tyr Asn Asp Gln Arg Pro Ser Gly Val Pro Asp Arg Phe
 50                  55                  60

Ser Gly Ser Lys Ser Gly Thr Ser Ser Ser Leu Ala Ile Ser Gly Leu
 65                  70                  75                  80

Gln Ser Glu Asp Glu Ala Tyr Tyr Tyr Cys Ala Thr Trp Asp Glu Asp
                85                  90                  95

Val Asn Gly Trp Val Phe Gly Gly Gly Thr Lys Leu Thr Val Leu Gly
                100                 105                 110

<210> SEQ ID NO 109
<211> LENGTH: 112
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa can be any naturally occurring amino acid

<400> SEQUENCE: 109

Ala Glu Leu Val Val Thr Gln Pro Pro Ser Val Ser Ala Xaa Pro Gly
 1               5                  10                  15

Gln Lys Val Thr Ile Ser Cys Ser Gly Ser Ser Ser Asn Ile Ala Gly
                20                  25                  30

Asn Thr Val Tyr Trp Tyr Gln Gln Leu Pro Gly Ala Ala Pro Lys Leu
            35                  40                  45

Leu Ile Tyr Tyr Asn Asp Gln Arg Pro Ser Gly Val Pro Asp Arg Phe
 50                  55                  60

Ser Gly Ser Lys Ser Gly Thr Ser Ser Ser Leu Ala Ile Ser Gly Leu
 65                  70                  75                  80

Gln Ser Glu Asp Glu Ala Tyr Tyr Tyr Cys Ala Thr Trp Asp Glu Asp
                85                  90                  95

Val Asn Gly Trp Val Phe Gly Gly Gly Thr Lys Leu Thr Val Leu Gly
                100                 105                 110

<210> SEQ ID NO 110
<211> LENGTH: 112
<212> TYPE: PRT
<213> ORGANISM: Homo sapiens

<400> SEQUENCE: 110

Ala Glu Leu Glu Leu Thr Gln Pro Pro Ser Val Gly Thr Pro Gly
1               5                   10                  15

Gln Arg Val Thr Ile Ser Cys Ser Gly Ser Ser Ser Asn Ile Ala Gly
            20                  25                  30

Asn Thr Val Tyr Trp Tyr Gln Gln Leu Pro Gly Ala Ala Pro Lys Leu
            35                  40                  45

Leu Ile Tyr Tyr Asn Asp Gln Arg Pro Ser Gly Val Pro Asp Arg Phe
        50                  55                  60

Ser Gly Ser Lys Ser Gly Thr Ser Ser Leu Thr Ile Ser Gly Leu
65                  70                  75                  80

Gln Ser Glu Asp Glu Ala Tyr Tyr Tyr Cys Ala Thr Trp Asp Glu Asp
                85                  90                  95

Val Asn Gly Trp Val Phe Gly Gly Gly Thr Lys Leu Thr Val Leu Gly
            100                 105                 110

<210> SEQ ID NO 111
<211> LENGTH: 112
<212> TYPE: PRT
<213> ORGANISM: Homo sapiens

<400> SEQUENCE: 111

Ala Glu Leu Met Leu Thr Gln Pro His Ser Ala Ser Glu Thr Pro Gly
1               5                   10                  15

Gln Arg Val Thr Ile Ser Cys Ser Gly Ser Ser Ser Asn Ile Ala Gly
            20                  25                  30

Asn Thr Val Tyr Trp Tyr Gln Gln Leu Pro Gly Ala Ala Pro Lys Leu
            35                  40                  45

Leu Ile Tyr Tyr Asn Asp Gln Arg Pro Ser Gly Val Pro Asp Arg Phe
        50                  55                  60

Ser Gly Ser Lys Ser Gly Thr Ser Ser Leu Ala Ile Ser Gly Leu
65                  70                  75                  80

Gln Ser Glu Asp Glu Ala Tyr Tyr Tyr Cys Ala Thr Trp Asp Glu Asp
                85                  90                  95

Val Asn Gly Trp Val Phe Gly Gly Gly Thr Glu Leu Thr Val Leu Gly
            100                 105                 110

<210> SEQ ID NO 112
<211> LENGTH: 112
<212> TYPE: PRT
<213> ORGANISM: Homo sapiens

<400> SEQUENCE: 112

Ala Glu Leu Val Leu Thr Gln Pro Pro Ser Ala Ser Glu Thr Pro Gly
1               5                   10                  15

Gln Arg Val Thr Ile Ser Cys Ser Gly Ser Ser Ser Asn Ile Ala Gly
            20                  25                  30

Asn Thr Val Tyr Trp Tyr Gln Gln Phe Pro Gly Ala Ala Pro Lys Leu
            35                  40                  45

Leu Ile Tyr Tyr Asn Asp Gln Arg Pro Ser Gly Val Pro Asp Arg Phe
        50                  55                  60

Ser Gly Ser Lys Ser Gly Thr Ser Ser Leu Ala Ile Ser Gly Leu
65                  70                  75                  80

Gln Ser Glu Asp Glu Ala Tyr Tyr Tyr Cys Ala Thr Trp Asp Glu Asp
                85                  90                  95

Val Asn Gly Trp Val Phe Gly Gly Gly Thr Glu Leu Thr Val Leu Gly

<210> SEQ ID NO 113
<211> LENGTH: 112
<212> TYPE: PRT
<213> ORGANISM: Homo sapiens

<400> SEQUENCE: 113

Ala Glu Leu Val Leu Thr Gln Ser Pro Ser Ala Ser Glu Thr Pro Gly
1               5                   10                  15

Gln Arg Val Thr Ile Ser Cys Ser Gly Ser Ser Ser Asn Ile Ala Gly
            20                  25                  30

Asn Thr Val Tyr Trp Tyr Gln Gln Phe Pro Gly Ala Ala Pro Lys Leu
        35                  40                  45

Leu Ile Tyr Tyr Asn Asp Gln Arg Pro Ser Gly Val Pro Asp Arg Phe
50                  55                  60

Ser Gly Ser Lys Ser Gly Thr Ser Ser Ser Leu Ala Ile Ser Gly Leu
65                  70                  75                  80

Gln Ser Glu Asp Glu Ala Tyr Tyr Tyr Cys Ala Thr Trp Asp Glu Asp
                85                  90                  95

Val Asn Gly Trp Val Phe Gly Gly Gly Thr Lys Val Thr Val Leu Gly
            100                 105                 110

<210> SEQ ID NO 114
<211> LENGTH: 112
<212> TYPE: PRT
<213> ORGANISM: Homo sapiens

<400> SEQUENCE: 114

Ala Glu Leu Met Leu Thr Gln Pro His Ser Ala Ser Gly Thr Pro Gly
1               5                   10                  15

Gln Arg Val Thr Ile Ser Cys Ser Gly Ser Ser Ser Asn Ile Ala Gly
            20                  25                  30

Asn Thr Val Tyr Trp Tyr Gln Gln Phe Pro Gly Ala Ala Pro Lys Leu
        35                  40                  45

Leu Ile Tyr Tyr Asn Asp Gln Arg Pro Ser Gly Val Pro Asp Arg Phe
50                  55                  60

Ser Gly Ser Lys Ser Gly Thr Ser Ser Ser Leu Ala Ile Ser Gly Leu
65                  70                  75                  80

Gln Ser Glu Asp Glu Ala Tyr Tyr Tyr Cys Ala Thr Trp Asp Glu Asp
                85                  90                  95

Val Asn Gly Trp Val Phe Gly Gly Gly Thr Lys Val Thr Val Leu Gly
            100                 105                 110

<210> SEQ ID NO 115
<211> LENGTH: 111
<212> TYPE: PRT
<213> ORGANISM: Homo sapiens

<400> SEQUENCE: 115

Ala Glu Leu Met Leu Thr Gln Pro His Ser Ala Ser Glu Thr Pro Gly
1               5                   10                  15

Gln Arg Val Thr Ile Ser Cys Ser Gly Ser Ser Ser Asn Ile Ala Gly
            20                  25                  30

Asn Thr Val Tyr Trp Tyr Gln Gln Phe Pro Gly Ala Ala Pro Lys Leu
        35                  40                  45

Leu Ile Tyr Tyr Asn Asp Gln Arg Pro Ser Gly Val Pro Asp Arg Phe
50                  55                  60

```
Ser Gly Ser Lys Ser Gly Thr Ser Ser Leu Ala Ile Ser Gly Leu
 65                  70                  75                  80

Gln Ser Glu Asp Glu Ala Tyr Tyr Tyr Cys Ala Thr Trp Asp Glu Asp
                 85                  90                  95

Val Asn Gly Trp Val Phe Gly Gly Gly Thr Lys Val Thr Val Leu
            100                 105                 110

<210> SEQ ID NO 116
<211> LENGTH: 112
<212> TYPE: PRT
<213> ORGANISM: Homo sapiens

<400> SEQUENCE: 116

Ala Glu Leu Val Leu Thr Gln Ser Pro Ser Ala Ser Glu Thr Pro Gly
 1               5                  10                  15

Gln Arg Val Thr Ile Ser Cys Ser Gly Ser Ser Ser Asn Ile Ala Gly
             20                  25                  30

Asn Thr Val Tyr Trp Tyr Gln Gln Leu Pro Gly Ala Ala Pro Lys Leu
             35                  40                  45

Leu Ile Tyr Tyr Asn Asp Gln Arg Pro Ser Gly Val Pro Asp Arg Phe
 50                  55                  60

Ser Gly Ser Lys Ser Gly Thr Ser Ser Leu Ala Ile Ser Gly Leu
 65                  70                  75                  80

Gln Ser Glu Asp Glu Ala Tyr Tyr Tyr Cys Ala Thr Trp Asp Glu Asp
                 85                  90                  95

Val Asn Gly Trp Val Phe Gly Gly Gly Thr Lys Val Thr Val Leu Gly
            100                 105                 110

<210> SEQ ID NO 117
<211> LENGTH: 111
<212> TYPE: PRT
<213> ORGANISM: Homo sapiens

<400> SEQUENCE: 117

Ala Glu Leu Val Leu Thr Gln Pro Pro Ser Val Ser Gly Thr Pro Gly
 1               5                  10                  15

Gln Arg Val Thr Ile Ser Cys Ser Gly Ser Ser Ser His Ile Gly Asn
             20                  25                  30

Asn Tyr Val Tyr Trp Tyr Gln His Leu Pro Gly Thr Ala Pro Lys Leu
             35                  40                  45

Leu Ile Tyr Ser Asn Asp Gln Arg Pro Ser Gly Val Pro Asp Arg Phe
 50                  55                  60

Ser Ala Ser Lys Ser Ala Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Gln Gly Gly Val Phe Gly Gly Gly Thr Lys Val Thr Val Leu Gly
            100                 105                 110

<210> SEQ ID NO 118
<211> LENGTH: 111
<212> TYPE: PRT
<213> ORGANISM: Homo sapiens

<400> SEQUENCE: 118

Ala Glu Leu Val Leu Thr Gln Pro Pro Ser Val Ser Gly Thr Pro Gly
 1               5                  10                  15

Gln Arg Val Thr Ile Ser Cys Ser Gly Ser Ser Ser His Ile Gly Ser
             20                  25                  30
```

```
Asn Tyr Val Tyr Trp Tyr Gln Gln Leu Pro Gly Thr Ala Pro Lys Ile
         35                  40                  45

Leu Ile Tyr Ser Asn Asp Gln Arg Pro Ala Gly Val Pro Asp Arg Phe
 50                  55                  60

Ser Ala Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp
             85                  90                  95

Gln Gly Gly Val Phe Gly Gly Gly Thr Lys Leu Thr Val Leu Gly
             100                 105                 110

<210> SEQ ID NO 119
<211> LENGTH: 105
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid

<400> SEQUENCE: 119

Ala Glu Leu Val Leu Thr Gln Pro Xaa Ser Ala Phe Trp Asp Pro Arg
 1               5                  10                  15

Ala Glu Gly His His Leu Leu Phe Trp Lys Gln Leu Pro His Arg Lys
             20                  25                  30

Glu Leu Cys Ile Leu Val Pro Thr Ser Pro Arg Ser Gly Pro Gln Thr
         35                  40                  45

Pro His Leu Gln Ser Ala Ala Leu Arg Gly Pro Pro Ile Leu Trp Leu
 50                  55                  60

Gln Val Trp His Leu Ser Leu Pro Gly His Gln Trp Ala Pro Val Arg
 65                  70                  75                  80

Gly Gly Leu Leu Leu Cys Ser Met Gly Gln Pro Gly Gly Val Arg
             85                  90                  95

Arg Arg Asp Gln Ala Asp Arg Pro Arg
             100                 105

<210> SEQ ID NO 120
<211> LENGTH: 113
<212> TYPE: PRT
<213> ORGANISM: Homo sapiens

<400> SEQUENCE: 120

Ala Glu Leu Glu Leu Thr Gln Pro Pro Ser Val Ser Gly Ser Pro Gly
 1               5                  10                  15

Gln Ser Ile Thr Ile Ser Cys Thr Gly Ser Ser Ser Tyr Val Gly Ile
             20                  25                  30

Phe Asn Leu Val Ser Trp Tyr Gln Gln His Pro Gly Thr Ala Pro Arg
         35                  40                  45

Arg Val Ile Tyr Glu Gly Asp Lys Arg Pro Ser Asn Ile Ser Asn Arg
 50                  55                  60

Phe Ser Gly Ser Lys Ser Gly Asn Thr Ala Ser Leu Thr Ile Ser Gly
 65                  70                  75                  80

Leu Gln Ala Asp Asp Glu Ala Asp Tyr Tyr Cys Tyr Ser Tyr Val Ala
             85                  90                  95

Gly Ser Asp Leu Trp Val Phe Gly Gly Gly Thr Lys Leu Thr Val Leu
             100                 105                 110

Gly
```

<210> SEQ ID NO 121
<211> LENGTH: 113
<212> TYPE: PRT
<213> ORGANISM: Homo sapiens

<400> SEQUENCE: 121

Ala Glu Leu Glu Leu Thr Gln Pro Pro Ser Val Ser Gly Ser Pro Gly
1               5                   10                  15

Gln Ser Ile Thr Ile Ser Cys Thr Gly Ser Ser Ser Tyr Val Gly Ile
            20                  25                  30

Phe Asn Leu Val Ser Trp Tyr Gln Gln His Pro Gly Thr Ala Pro Arg
        35                  40                  45

Arg Val Ile Tyr Glu Gly Asp Lys Arg Pro Ser Asn Ile Ser Asn Arg
    50                  55                  60

Phe Ser Gly Ser Lys Ser Gly Asn Thr Ala Ser Leu Thr Ile Ser Gly
65                  70                  75                  80

Leu Gln Ala Asp Asp Glu Ala Asp Tyr Tyr Cys Tyr Ser Tyr Val Ala
                85                  90                  95

Gly Ser Asp Leu Trp Val Phe Gly Gly Gly Thr Lys Leu Thr Val Leu
            100                 105                 110

Gly

<210> SEQ ID NO 122
<211> LENGTH: 107
<212> TYPE: PRT
<213> ORGANISM: Homo sapiens

<400> SEQUENCE: 122

Ala Glu Leu Ala Leu Thr Gln Pro Pro Ser Val Ser Gly Ser Pro Gly
1               5                   10                  15

Gln Ser Ile Thr Ile Ser Cys Thr Gly Phe Ser Ser Asp Leu Ser Trp
            20                  25                  30

Tyr Gln Gln His Pro Gly Lys Ala Pro Lys Leu Met Ile Tyr Asp Val
        35                  40                  45

Asn Asn Arg Pro Ser Gly Val Ser Asp Arg Phe Ser Gly Ser Lys Ser
    50                  55                  60

Gly Asn Thr Ala Ser Leu Thr Ile Ser Gly Leu Gln Ala Glu Asp Glu
65                  70                  75                  80

Ala Asp Tyr Tyr Cys Ser Ser Tyr Thr Ser Ser Ser Thr Ser Leu Met
                85                  90                  95

Phe Gly Gly Gly Thr Glu Leu Thr Val Leu Gly
            100                 105

<210> SEQ ID NO 123
<211> LENGTH: 110
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(28)

-continued

<223> OTHER INFORMATION: Xaa can be any naturally occurring amino acid

<400> SEQUENCE: 123

Ala Glu Leu Gly Val Thr Gln Pro Pro Ser Val Ser Val Xaa Pro Gly
1               5                   10                  15

Gln Thr Xaa Thr Ile Thr Cys Gly Gly Xaa Asn Xaa Gly Ser Lys Ser
            20                  25                  30

Val Asn Trp Tyr Gln Gln Lys Pro Gly Gln Ala Pro Val Leu Val Val
        35                  40                  45

Tyr His Asp Ser Glu Trp Pro Ser Gly Ile Pro Glu Arg Phe Ser Gly
    50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Trp Asp Ser Arg Ser Asp
                85                  90                  95

Asn Val Val Phe Gly Gly Gly Thr Glu Leu Thr Val Leu Gly
            100                 105                 110

<210> SEQ ID NO 124
<211> LENGTH: 110
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 124

Ala Glu Leu Met Leu Thr Gln Pro His Ser Val Ser Val Xaa Pro Gly
1               5                   10                  15

Gln Thr Xaa Thr Ile Thr Cys Gly Gly Asn Asn Xaa Gly Ser Lys Ser
            20                  25                  30

Val Asn Trp Tyr Gln Gln Lys Pro Gly Gln Ala Pro Val Leu Val Val
        35                  40                  45

Tyr His Asp Ser Glu Trp Pro Ser Gly Ile Pro Glu Arg Phe Ser Gly
    50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Trp Asp Ser Arg Ser Asp
                85                  90                  95

Asn Val Val Phe Gly Gly Gly Thr Glu Leu Thr Val Leu Gly
            100                 105                 110

<210> SEQ ID NO 125
<211> LENGTH: 110
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:

```
<221> NAME/KEY: misc_feature
<222> LOCATION: (28)..(28)
<223> OTHER INFORMATION: Xaa can be any naturally occurring amino acid

<400> SEQUENCE: 125

Ala Glu Leu Met Leu Thr Gln Pro His Ser Val Ser Val Xaa Pro Gly
1               5                   10                  15

Gln Thr Xaa Thr Ile Thr Cys Gly Gly Asn Asn Xaa Gly Ser Lys Ser
            20                  25                  30

Val Asn Trp Tyr Gln Gln Lys Pro Gly Gln Ala Pro Val Leu Val Val
        35                  40                  45

Tyr His Asp Ser Glu Trp Pro Ser Gly Ile Pro Glu Arg Phe Ser Gly
50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Trp Asp Ser Arg Ser Asp
                85                  90                  95

Asn Val Val Phe Gly Gly Gly Thr Glu Leu Thr Val Leu Gly
                100                 105                 110

<210> SEQ ID NO 126
<211> LENGTH: 110
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 126

Ala Glu Leu Val Leu Thr Gln Pro Pro Ser Val Ser Val Xaa Pro Gly
1               5                   10                  15

Gln Thr Xaa Arg Ile Thr Cys Gly Ala Asn Asn Xaa Gly Ser Lys Ser
            20                  25                  30

Val Asn Trp Tyr Gln Gln Lys Pro Gly Gln Ala Pro Val Leu Val Val
        35                  40                  45

Tyr His Asp Ser Glu Trp Pro Ser Gly Ile Pro Glu Arg Phe Ser Gly
50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Trp Asp Ser Arg Ser Asp
                85                  90                  95

Asn Val Val Phe Gly Gly Gly Thr Glu Leu Thr Val Leu Gly
                100                 105                 110

<210> SEQ ID NO 127
<211> LENGTH: 91
<212> TYPE: PRT
<213> ORGANISM: Homo sapiens

<400> SEQUENCE: 127

Arg Arg Pro Gly Leu Pro Val Gly Glu Thr Thr Leu Lys Val Lys Val
1               5                   10                  15

Cys Ser Gly Thr Ser Arg Ser Gln Ala Arg Pro Leu Cys Trp Ser Ser
```

-continued

```
                    20                  25                  30
Ile Met Ile Val Thr Ala Pro Gln Arg Ser Leu Ser Asp Ser Leu Ala
                35                  40                  45

Pro Ser Leu Glu Thr Arg Pro Pro Ala Ser Ala Gly Ser Lys Pro Gly
 50                  55                  60

Met Arg Pro Thr Thr Thr Val Arg Cys Gly Ile Val Leu Met Ile Lys
65                  70                  75                  80

Trp Tyr Ser Ala Glu Gly Pro Ser Pro Ser Ser
                85                  90

<210> SEQ ID NO 128
<211> LENGTH: 110
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 128

Ala Glu Leu Gly Leu Thr Gln Pro Pro Ser Val Ser Val Xaa Pro Gly
1               5                   10                  15

Gln Ala Xaa Arg Ile Thr Cys Gly Gly Asn Asp Ile Glu Ser Lys Ser
                20                  25                  30

Val Gln Trp Tyr Gln Gln Lys Pro Gly Gln Ala Pro Val Leu Val Val
            35                  40                  45

Tyr Asn Asp Ser Asp Gly Pro Ser Glu Ile Pro Glu Arg Phe Ser Gly
         50                  55                  60

Ser Lys Ser Gly Asn Thr Ala Thr Leu Ser Ile Ser Arg Val Glu Ala
65                  70                  75                  80

Gly Asp Glu Ala Asp Tyr Tyr Cys Gln Val Trp Asp Ser Val Asn Asp
                85                  90                  95

Gln Val Val Phe Gly Gly Gly Thr Glu Leu Thr Val Leu Gly
                100                 105                 110

<210> SEQ ID NO 129
<211> LENGTH: 110
<212> TYPE: PRT
<213> ORGANISM: Homo sapiens

<400> SEQUENCE: 129

Ala Glu Leu Val Leu Thr Gln Ser Pro Ser Val Ser Val Ala Pro Gly
1               5                   10                  15

Gln Thr Ala Lys Val Thr Cys Gly Gly Asn Asn Ile Gly Ser Lys Gly
                20                  25                  30

Val His Trp Tyr Gln Gln Lys Pro Gly Gln Ala Pro Val Leu Val Val
            35                  40                  45

Phe Asn Asp Asn Asp Arg Pro Ser Gly Ile Pro Glu Arg Phe Ser Gly
         50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Tyr Asp Ile Asn Ser Asp
                85                  90                  95

Leu Val Val Phe Gly Gly Gly Thr Glu Leu Thr Val Leu Gly
                100                 105                 110
```

```
<210> SEQ ID NO 130
<211> LENGTH: 100
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 130

Ala Glu Leu Glu Leu Thr Gln Pro Pro Ser Val Ser Xaa Pro Arg
1               5                   10                  15

Thr Asp Xaa Gln Asp Tyr Leu Trp Gly Lys Gln His Trp Lys Cys
            20                  25                  30

Ala Leu Val Pro Ala Glu Ala Arg Pro Gly Pro Cys Thr Gly Arg Val
        35                  40                  45

Arg Pro Ala Leu Arg Asp Pro Glu Ile Leu Trp Leu Gln Val Trp Glu
    50                  55                  60

Asn Gly His Pro Asp His Gln Gln Gly Arg Ser Arg Gly Gly Arg Leu
65                  70                  75                  80

Leu Leu Ser Gly Val Gly Tyr Cys Asp Ile Arg Arg Arg His Gln Ala
                85                  90                  95

Asp Arg Pro Arg
            100

<210> SEQ ID NO 131
<211> LENGTH: 110
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 131

Ala Glu Leu Ala Leu Thr Gln Pro Pro Ser Val Ser Val Xaa Pro Gly
1               5                   10                  15

Gln Thr Xaa Arg Ile Thr Cys Gly Gly Asn Asn Xaa Gly Ser Lys Ser
            20                  25                  30

Val His Trp Tyr Gln Gln Lys Pro Gly Gln Ala Pro Val Leu Val Val
        35                  40                  45

Tyr Asp Asp Ser Asp Arg Pro Ser Gly Ile Pro Glu Arg Phe Ser Gly
    50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Trp Asp Ser Ser Ser Asp
                85                  90                  95

His Val Val Phe Gly Gly Gly Thr Lys Val Thr Val Leu Gly
            100                 105                 110

<210> SEQ ID NO 132
```

```
<211> LENGTH: 100
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid

<400> SEQUENCE: 132

Xaa Glu Leu Val Leu Thr Gln Pro Pro Phe Gly Val Ser Xaa Pro Arg
1               5                   10                  15

Thr Asp Xaa Gln Asp Tyr Leu Trp Gly Xaa His His Xaa Lys Lys Cys
            20                  25                  30

Ala Leu Val Pro Ala Glu Ala Xaa Pro Gly Pro Cys Ala Gly Arg Leu
        35                  40                  45

Arg Pro Ala Xaa Arg Asp Pro Ala Ile Leu Trp Leu Gln Phe Trp Glu
    50                  55                  60

Tyr Gly His Pro Val His His Gln Gly Arg Ser Arg Gly Gly Arg Leu
65                  70                  75                  80

Leu Leu Ser Gly Val Gly Ser Cys Gly Ile Arg Arg Arg Asp Gln Gly
                85                  90                  95

Asp Arg Pro Arg
            100

<210> SEQ ID NO 133
<211> LENGTH: 110
<212> TYPE: PRT
<213> ORGANISM: Homo sapiens

<400> SEQUENCE: 133

Ala Glu Leu Val Leu Thr Gln Pro Pro Ser Val Ser Val Ala Pro Gly
1               5                   10                  15

Gln Ser Ala Arg Ile Thr Cys Gly Glu Ser Asn Ile Gly Phe Gln Ser
            20                  25                  30

Val His Trp Tyr Gln Gln Lys Pro Gly Gln Ala Pro Val Leu Leu Val
        35                  40                  45

Tyr Asp Asp Ser Asp Arg Pro Ser Glu Ile Pro Glu Arg Phe Ser Gly
    50                  55                  60

Ser Asn Ser Gly Asp Thr Ala Thr Leu Thr Ile Ser Arg Val Glu Ala
65                  70                  75                  80

Gly Asp Glu Ala Asp Tyr Tyr Cys Gln Val Trp Ser Ser Ser Ser Asp
                85                  90                  95
```

His Pro Val Phe Gly Gly Gly Thr Gln Leu Thr Val Leu Gly
                100                 105                 110

<210> SEQ ID NO 134
<211> LENGTH: 110
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 134

Ala Glu Leu Val Leu Thr Gln Pro Pro Ser Val Ser Val Xaa Pro Gly
1               5                   10                  15

Gln Thr Xaa Arg Ile Thr Cys Gly Gly Asn Asn Xaa Gly Ser Lys Ser
            20                  25                  30

Val Gln Trp Tyr Gln Gln Lys Pro Gly Gln Val Pro Val Leu Val Val
        35                  40                  45

Tyr Asn Asp Ser Asp Gly Pro Ser Glu Ile Pro Glu Arg Phe Ser Gly
    50                  55                  60

Ser Asn Ser Gly Asn Thr Ala Thr Leu Thr Ile Ser Lys Val Glu Ala
65                  70                  75                  80

Gly Asp Glu Ala Asp Tyr Tyr Cys Gln Val Trp Asp Ser Ser Tyr Asp
                85                  90                  95

His Val Val Phe Gly Gly Gly Thr Glu Leu Thr Val Leu Gly
                100                 105                 110

<210> SEQ ID NO 135
<211> LENGTH: 110
<212> TYPE: PRT
<213> ORGANISM: Homo sapiens

<400> SEQUENCE: 135

Ala Glu Leu Val Leu Thr Gln Pro Pro Ser Val Ser Val Ala Pro Gly
1               5                   10                  15

Gln Thr Ala Arg Ile Pro Cys Gly Gly Asn Asn Ile Gly Ser Lys Ser
            20                  25                  30

Val His Trp Tyr Gln Gln Lys Pro Gly Gln Ala Pro Val Leu Val Val
        35                  40                  45

Tyr Asp Asp Ser Asp Arg Pro Ser Gly Ile Pro Glu Arg Phe Ser Gly
    50                  55                  60

Ser Asn Ser Gly Asn Thr Ala Thr Leu Thr Ile Ser Arg Val Glu Val
65                  70                  75                  80

Gly Asp Glu Ala Asp Tyr Tyr Cys Gln Val Trp Asp Leu Ser Ser Asp
                85                  90                  95

His Val Val Phe Gly Gly Gly Thr Lys Val Thr Val Leu Gly
                100                 105                 110

<210> SEQ ID NO 136
<211> LENGTH: 110
<212> TYPE: PRT
<213> ORGANISM: Homo sapiens
<220> FEATURE:

<221> NAME/KEY: misc_feature
<222> LOCATION: (14)..(14)
<223> OTHER INFORMATION: Xaa can be any naturally occurring amino acid

<400> SEQUENCE: 136

```
Ala Glu Leu Val Leu Thr Gln Pro Pro Ser Val Ser Val Xaa Pro Gly
1               5                   10                  15

Gln Thr Ala Thr Ile Thr Cys Gly Gly Asn Asn Ile Gly Ser Lys Ser
            20                  25                  30

Val Asn Trp Tyr Gln Gln Lys Pro Gly Gln Ala Pro Val Leu Val Val
        35                  40                  45

Tyr His Asp Ser Glu Trp Pro Ser Gly Ile Pro Glu Arg Phe Ser Gly
    50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Trp Asp Ser Arg Ser Asp
                85                  90                  95

Asn Val Val Phe Gly Gly Gly Thr Lys Val Thr Val Leu Gly
                100                 105                 110
```

<210> SEQ ID NO 137
<211> LENGTH: 110
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa can be any naturally occurring amino acid

<400> SEQUENCE: 137

```
Ala Glu Leu Val Leu Thr Gln Pro Pro Ser Val Ser Val Xaa Pro Gly
1               5                   10                  15

Gln Thr Ala Arg Ile Thr Cys Gly Ala Asn Asn Ile Gly Gly Lys Arg
            20                  25                  30

Val His Trp Tyr Gln Gln Lys Pro Gly Gln Ala Pro Ile Leu Val Val
        35                  40                  45

Tyr Asp Asp Thr Asp Arg Pro Ser Gly Ile Pro Glu Arg Phe Ser Gly
    50                  55                  60

Ser Asn Thr Gly Asn Thr Ala Thr Leu Thr Ile Ser Arg Val Glu Ala
65                  70                  75                  80

Gly Asp Glu Ala Asp Tyr Tyr Cys Gln Val Trp Asp Ser Gly Ser Asp
                85                  90                  95

His Val Val Phe Gly Gly Gly Thr Glu Leu Thr Val Leu Gly
                100                 105                 110
```

<210> SEQ ID NO 138
<211> LENGTH: 100
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 138

```
Ala Glu Leu Val Leu Thr Gln Pro Xaa Ser Val Ser Xaa Pro Arg
1               5                   10                  15

Thr Asp Xaa Gln Asp Tyr Leu Trp Gly Lys Gln His Trp Lys Lys Cys
            20                  25                  30

Ala Leu Val Pro Ala Ala Arg Pro Gly Pro Cys Ala Gly Arg Leu
                35                  40                  45

Arg Pro Ala Leu Arg Asp Pro Ala Ile Leu Trp Leu Gln Leu Trp Glu
        50                  55                  60

His Gly His Pro Asp His Gln Gln Gly Arg Ser Arg Gly Gly Arg Leu
65              70                  75                  80

Leu Leu Ser Gly Val Gly Ser Cys Gly Ile Arg Arg Asp Pro Ala
                85                  90                  95

Asp Arg Pro Arg
            100
```

```
<210> SEQ ID NO 139
<211> LENGTH: 110
<212> TYPE: PRT
<213> ORGANISM: Homo sapiens
<220> FEATURE:
<221> NAME/KEY: misc_feature
<222> LOCATION: (19)..(19)
<223> OTHER INFORMATION: Xaa can be any naturally occurring amino acid

<400> SEQUENCE: 139
```

```
Ala Glu Leu Met Leu Thr Gln Pro His Ser Val Ser Val Pro Pro Gly
1               5                   10                  15

Gln Thr Xaa Arg Ile Thr Cys Gly Gly Asn Gly Ile Gly Arg Lys Ser
            20                  25                  30

Val His Trp Tyr Gln Gln Lys Pro Gly Gln Ala Pro Val Leu Val Val
                35                  40                  45

Tyr Asp Asp Val Ser Arg Pro Ser Gly Ile Pro Glu Arg Phe Ser Gly
        50                  55                  60

Ser Asn Ser Gly Asn Thr Ala Thr Leu Ile Ile Thr Arg Val Glu Val
65              70                  75                  80

Gly Asp Glu Ala Asp Tyr Tyr Cys Gln Ala Trp Asp Ile Ser Ser Asp
                85                  90                  95

His Val Ile Phe Gly Glu Gly Thr Lys Val Thr Val Leu Gly
                100                 105                 110
```

```
<210> SEQ ID NO 140
<211> LENGTH: 110
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
```

```
<400> SEQUENCE: 140

Xaa Glu Leu Val Leu Thr Gln Pro Xaa Ser Leu Ser Val Ala Pro Gly
1               5                   10                  15

Gln Thr Xaa Thr Ile Thr Cys Gly Gly Ser Asn Xaa Gly Gly Met Arg
            20                  25                  30

Val His Trp Tyr Xaa Gln Thr Pro Gly Gln Ala Pro Val Leu Val Val
                35                  40                  45

Tyr Asp Asp Ser Asp Arg Pro Ser Glu Ile Pro Glu Arg Phe Ser Gly
            50                  55                  60

Ser Asn Trp Gly Asn Ser Ala Thr Leu Thr Ile Ser Arg Val Glu Ala
65                  70                  75                  80

Gly Asp Glu Ala Asp Tyr Tyr Cys Gln Val Trp Glu Ser Thr Ser Asp
                85                  90                  95

His Val Val Phe Gly Gly Gly Thr Lys Leu Thr Val Leu Gly
            100                 105                 110

<210> SEQ ID NO 141
<211> LENGTH: 110
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 141

Ala Glu Leu Val Leu Thr Gln Pro Xaa Ser Val Ser Val Xaa Pro Gly
1               5                   10                  15

Gln Thr Xaa Ser Ile Thr Cys Gly Gly Asp Gly Ile Gly Arg Lys Ser
            20                  25                  30

Val His Trp Tyr Gln Gln Lys Pro Gly Gln Ala Pro Ala Leu Val Val
                35                  40                  45

Tyr Asp Asp Ile Gly Arg Pro Ser Gly Ile Pro Glu Arg Phe Ser Gly
            50                  55                  60

Ser Asn Ser Gly Asn Met Ala Thr Leu Thr Ile Ser Arg Val Glu Ala
65                  70                  75                  80

Gly Asp Glu Ala Asp Phe Phe Cys Gln Val Trp Asp Ser Ile Ser Asp
                85                  90                  95

His Val Val Phe Gly Gly Gly Thr Lys Leu Thr Val Leu Gly
            100                 105                 110

<210> SEQ ID NO 142
<211> LENGTH: 101
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
```

```
<220> FEATURE:
<221> NAME/KEY: misc_feature
<222> LOCATION: (29)..(29)
<223> OTHER INFORMATION: Xaa can be any naturally occurring amino acid

<400> SEQUENCE: 142

Ala Glu Leu Val Leu Thr Gln Pro Pro Ser Val Ser Xaa Pro Arg
1               5                   10                  15

Thr Asp Ala Gln Asp Tyr Leu Trp Gly Xaa His His Xaa Lys Lys Cys
            20                  25                  30

Ala Leu Val Pro Ala Glu Ala Arg Pro Gly Pro Cys Leu Gly Arg Leu
        35                  40                  45

Arg Pro Ala Leu Arg Asn Pro Ala Ile Leu Trp Leu Gln Leu Trp Gly
    50                  55                  60

His Gly His Ala Glu His Gln Gln Gly Arg Ser Arg Gly Gly Arg Leu
65                  70                  75                  80

Leu Leu Ser Gly Val Gly Ser Ser Cys Gly Ile Arg Arg Arg His Gln
                85                  90                  95

Ala Asp Arg Pro Arg
            100

<210> SEQ ID NO 143
<211> LENGTH: 110
<212> TYPE: PRT
<213> ORGANISM: Homo sapiens
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 143

Ala Glu Leu Val Leu Thr Gln Pro Pro Ser Val Ser Val Pro Pro Gly
1               5                   10                  15

Gln Thr Xaa Arg Ile Thr Cys Gly Gly Asn Asn Xaa Gly Ser Lys Ser
            20                  25                  30

Val His Trp Tyr Gln Gln Lys Pro Gly Gln Ala Pro Val Leu Val Val
        35                  40                  45

Tyr Asp Asp Ser Asp Arg Pro Ser Gly Ile Pro Glu Arg Phe Ser Gly
    50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Trp Asp Ser Ser Ser Asp
                85                  90                  95

Leu Val Val Phe Gly Gly Gly Thr Gln Leu Thr Val Leu Gly
            100                 105                 110

<210> SEQ ID NO 144
<211> LENGTH: 104
<212> TYPE: PRT
<213> ORGANISM: Homo sapiens

<400> SEQUENCE: 144

Ala Glu Leu Met Leu Thr Gln Pro His Ser Val Ser Val Ala Leu Gly
1               5                   10                  15

Gln Thr Pro Arg Ile Thr Cys Gly Gly Asp Asn Ile Gly Thr Lys Asn
            20                  25                  30
```

Val His Trp Tyr Gln Gln Lys Pro Gly Gln Ala Pro Cys Val Gly His
         35                  40                  45

Leu Ser Gly Tyr Gln Ser Ala Leu Trp Asp Pro Ala Ile Leu Trp Leu
 50                  55                  60

Gln Leu Gly Glu His Gly His Pro Asp His Gln Ser Pro Ser Arg Gly
65                  70                  75                  80

Gly Leu Ser Leu Ser Gly Val Gly Gln Phe Tyr Cys Asp Ile Arg Arg
                 85                  90                  95

Arg His Gln Ala Asp Arg Pro Arg
                100

<210> SEQ ID NO 145
<211> LENGTH: 108
<212> TYPE: PRT
<213> ORGANISM: Homo sapiens

<400> SEQUENCE: 145

Gly Phe Ala Thr Val Pro Gln Ala Pro Ser Cys Arg Ser Arg Pro
1               5                   10                  15

Gln Cys Arg Val Pro Arg Thr Asp Ser Gln His His Leu Leu Trp Arg
                20                  25                  30

Ile Gly Gly Ile Cys Phe Leu Val Ser Ala Glu Gly Arg Pro Val Pro
             35                  40                  45

Cys Ala Gly His Leu Ser Arg Glu Ala Ala Leu Arg Asp Pro Ala Ile
 50                  55                  60

Leu Trp Leu Gln Leu Trp Glu His Ser His Ser Asp His Gln Arg Asp
65                  70                  75                  80

Pro Gly Tyr Gly Gly Leu Leu Leu Ser Gly Val Gly Gln Gln His Cys
                 85                  90                  95

Gly Val Arg Arg Arg Asp Gln Gly Asp Arg Pro Arg
                100                 105

<210> SEQ ID NO 146
<211> LENGTH: 101
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 146

Ala Glu Leu Val Xaa Thr Gln Ser Pro Asp Thr Leu Ser Phe Ser Pro
1               5                   10                  15

Gly Glu Arg Ala Thr Xaa Ser Cys Gln Val Gln Ser Glu Cys Gln Leu
                20                  25                  30

Leu Ser Leu Val Pro Thr Glu Thr Trp Pro Gly Ser Gln Ala Pro His
             35                  40                  45

Leu His Ile Gln Gln Trp Arg Leu Cys Gln Val Gln Gln Trp Val Trp
 50                  55                  60

Asp Arg Leu His Ser His His Gln Val Arg Ala Arg Phe Cys Asn
65                  70                  75                  80

Leu Leu Leu Ala Ala Leu Ala Ser Gly Ile His Phe Arg Pro Trp Asp
                 85                  90                  95

Gln Ser Asp Ile Lys
                100

```
<210> SEQ ID NO 147
<211> LENGTH: 49
<212> TYPE: DNA
<213> ORGANISM: Homo sapiens

<400> SEQUENCE: 147
gaggaggagg aggaggagct cactcccagg tgcagctggt gcagtctgg            49

<210> SEQ ID NO 148
<211> LENGTH: 49
<212> TYPE: DNA
<213> ORGANISM: Homo sapiens

<400> SEQUENCE: 148
gaggaggagg aggaggagct cactcccagg tgcagctggt gcagtctgg            49

<210> SEQ ID NO 149
<211> LENGTH: 48
<212> TYPE: DNA
<213> ORGANISM: Homo sapiens

<400> SEQUENCE: 149
gaggaggagg aggaggagct cactcccagg tgcagctgca ggagtcgg             48

<210> SEQ ID NO 150
<211> LENGTH: 40
<212> TYPE: DNA
<213> ORGANISM: Homo sapiens

<400> SEQUENCE: 150
gaggaggagc tcactccgag gtgcagctgt tggagtctgg                      40

<210> SEQ ID NO 151
<211> LENGTH: 40
<212> TYPE: DNA
<213> ORGANISM: Homo sapiens

<400> SEQUENCE: 151
gaggaggagc tcactcccag gtgcagctgg tgcagtctgg                      40

<210> SEQ ID NO 152
<211> LENGTH: 46
<212> TYPE: DNA
<213> ORGANISM: Homo sapiens

<400> SEQUENCE: 152
cctggccggc ctggccacta gtgaccgatg ggcccttggt ggargc               46

<210> SEQ ID NO 153
<211> LENGTH: 46
<212> TYPE: DNA
<213> ORGANISM: Homo sapiens

<400> SEQUENCE: 153
cctggccggc ctggccacta gtgaccgatg ggcccttggt ggargc               46

<210> SEQ ID NO 154
<211> LENGTH: 46
<212> TYPE: DNA
<213> ORGANISM: Homo sapiens

<400> SEQUENCE: 154
cctggccggc ctggccacta gtgaccgatg ggcccttggt ggargc               46
```

<210> SEQ ID NO 155
<211> LENGTH: 46
<212> TYPE: DNA
<213> ORGANISM: Homo sapiens

<400> SEQUENCE: 155
cctggccggc ctggccacta gtgaccgatg ggcccttggt ggargc             46

<210> SEQ ID NO 156
<211> LENGTH: 46
<212> TYPE: DNA
<213> ORGANISM: Homo sapiens

<400> SEQUENCE: 156
cctggccggc ctggccacta gtgaccgatg ggcccttggt ggargc             46

<210> SEQ ID NO 157
<211> LENGTH: 65
<212> TYPE: DNA
<213> ORGANISM: Homo sapiens

<400> SEQUENCE: 157
gaggagaagc ttgttgctct ggatctctgg tgcctacggg gcggccgagc tgtgctgact    60
cagcc                                                                65

<210> SEQ ID NO 158
<211> LENGTH: 66
<212> TYPE: DNA
<213> ORGANISM: Homo sapiens

<400> SEQUENCE: 158
gaggagaagc ttgttgctct ggatctctgg tgcctacggg gcggccgagc tggtgttgac    60
gcagcc                                                               66

<210> SEQ ID NO 159
<211> LENGTH: 66
<212> TYPE: DNA
<213> ORGANISM: Homo sapiens

<400> SEQUENCE: 159
gaggagaagc ttgttgctct ggatctctgg tgcctacggg gcggccgagc tgatgctgac    60
tcagcc                                                               66

<210> SEQ ID NO 160
<211> LENGTH: 65
<212> TYPE: DNA
<213> ORGANISM: Homo sapiens

<400> SEQUENCE: 160
gaggagaagc ttgttgctct ggatctctgg tgcctacggg gcggccgagc tggagctgac    60
tcagc                                                                65

<210> SEQ ID NO 161
<211> LENGTH: 66
<212> TYPE: DNA
<213> ORGANISM: Homo sapiens

<400> SEQUENCE: 161
gaggagaagc ttgttgctct ggatctctgg tgcctacggg gcggccgagc tggtgctgac    60
tcagcc                                                               66

<210> SEQ ID NO 162
<211> LENGTH: 38
<212> TYPE: DNA
<213> ORGANISM: Homo sapiens

<400> SEQUENCE: 162
ggcagccttg ggctgaccac ctaggacggt cagcttgg                              38

<210> SEQ ID NO 163
<211> LENGTH: 38
<212> TYPE: DNA
<213> ORGANISM: Homo sapiens

<400> SEQUENCE: 163
ggcagccttg ggctgaccgc ctaggacggt caccttgg                              38

<210> SEQ ID NO 164
<211> LENGTH: 38
<212> TYPE: DNA
<213> ORGANISM: Homo sapiens

<400> SEQUENCE: 164
ggcagccttg ggctgaccgc ctaggacggt cagcttgg                              38

<210> SEQ ID NO 165
<211> LENGTH: 38
<212> TYPE: DNA
<213> ORGANISM: Homo sapiens

<400> SEQUENCE: 165
ggcagccttg ggctgaccgc ctaggacggt cagcttgg                              38

<210> SEQ ID NO 166
<211> LENGTH: 38
<212> TYPE: DNA
<213> ORGANISM: Homo sapiens

<400> SEQUENCE: 166
ggcagccttg ggctgaccgc ctaggacggt cagcttgg                              38

<210> SEQ ID NO 167
<211> LENGTH: 21
<212> TYPE: DNA
<213> ORGANISM: Homo sapiens

<400> SEQUENCE: 167
ggtcagccca aggctgcccc c                                                21

<210> SEQ ID NO 168
<211> LENGTH: 21
<212> TYPE: DNA
<213> ORGANISM: Homo sapiens

<400> SEQUENCE: 168
ggccatggct ggttgggcag c                                                21

<210> SEQ ID NO 169
<211> LENGTH: 12
<212> TYPE: PRT
<213> ORGANISM: Homo sapiens

<400> SEQUENCE: 169

Asp Leu Asn Tyr Phe Thr Leu Ser Ser Lys Arg Glu
1               5                   10

```
<210> SEQ ID NO 170
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 170

Pro Xaa Ile Xaa Trp Lys
1               5

<210> SEQ ID NO 171
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 171

Pro Xaa Leu Xaa Trp Arg
1               5

<210> SEQ ID NO 172
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 172

Pro Xaa Ile Xaa Trp Arg
1               5

<210> SEQ ID NO 173
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 173

Pro Xaa Leu Xaa Trp Lys
1               5

<210> SEQ ID NO 174
<211> LENGTH: 12
<212> TYPE: PRT
<213> ORGANISM: Artificial sequence
```

```
<220> FEATURE:
<223> OTHER INFORMATION: P4 peptide sequence

<400> SEQUENCE: 174

Ala Asn Lys Thr Ser Pro Phe Leu Met Trp Arg Leu
1               5                   10

<210> SEQ ID NO 175
<211> LENGTH: 12
<212> TYPE: PRT
<213> ORGANISM: Artificial sequence
<220> FEATURE:
<223> OTHER INFORMATION: P5 peptide sequence

<400> SEQUENCE: 175

Trp Ala Asn Lys Gln Pro Thr Ile Ile Trp Arg Ser
1               5                   10

<210> SEQ ID NO 176
<211> LENGTH: 12
<212> TYPE: PRT
<213> ORGANISM: Artificial sequence
<220> FEATURE:
<223> OTHER INFORMATION: P7 peptide sequence

<400> SEQUENCE: 176

Tyr Ser Asn Lys Thr Pro His Leu Gln Trp Arg Leu
1               5                   10

<210> SEQ ID NO 177
<211> LENGTH: 12
<212> TYPE: PRT
<213> ORGANISM: Artificial sequence
<220> FEATURE:
<223> OTHER INFORMATION: P8 peptide sequence

<400> SEQUENCE: 177

Thr Asp Lys Thr Pro Phe Leu Leu Trp Arg Val His
1               5                   10

<210> SEQ ID NO 178
<211> LENGTH: 12
<212> TYPE: PRT
<213> ORGANISM: Artificial sequence
<220> FEATURE:
<223> OTHER INFORMATION: P9 peptide sequence

<400> SEQUENCE: 178

Ala Lys Asn Pro Pro Thr Leu Ile Trp Lys His Thr
1               5                   10

<210> SEQ ID NO 179
<211> LENGTH: 12
<212> TYPE: PRT
<213> ORGANISM: Artificial sequence
<220> FEATURE:
<223> OTHER INFORMATION: P10 peptide sequence

<400> SEQUENCE: 179

Gln His Asn Lys Ser Pro Asn Leu Tyr Trp Arg Ser
1               5                   10

<210> SEQ ID NO 180
<211> LENGTH: 7
<212> TYPE: PRT
<213> ORGANISM: Artificial sequence
<220> FEATURE:
<223> OTHER INFORMATION: P14 peptide sequence
```

-continued

```
<400> SEQUENCE: 180

Thr Thr Leu Thr Leu Arg His
1               5

<210> SEQ ID NO 181
<211> LENGTH: 5
<212> TYPE: PRT
<213> ORGANISM: Artificial sequence
<220> FEATURE:
<223> OTHER INFORMATION: consensus sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 181

Asp Xaa Xaa Xaa Trp
1               5

<210> SEQ ID NO 182
<211> LENGTH: 5
<212> TYPE: PRT
<213> ORGANISM: Artificial sequence
<220> FEATURE:
<223> OTHER INFORMATION: consensus sequence
<220> FEATURE:
<221> NAME/KEY: misc_feature
<222> LOCATION: (2)..(4)
<223> OTHER INFORMATION: Xaa can be any naturally occurring amino acid

<400> SEQUENCE: 182

Glu Xaa Xaa Xaa Trp
1               5
```